US010390755B2

(12) United States Patent
Goodall et al.

(10) Patent No.: US 10,390,755 B2
(45) Date of Patent: Aug. 27, 2019

(54) MONITORING BODY MOVEMENT OR CONDITION ACCORDING TO MOTION REGIMEN WITH CONFORMAL ELECTRONICS

(71) Applicant: ELWHA LLC, Bellevue, WA (US)

(72) Inventors: Eleanor V. Goodall, Seattle, WA (US); Roderick A. Hyde, Redmond, WA (US); Jordin T. Kare, San Jose, CA (US); Eric C. Leuthardt, St. Louis, MO (US); Mark A. Malamud, Seattle, WA (US); Gary L. McKnight, Bothell, WA (US); Tony S. Pan, Bellevue, WA (US); Katherine E. Sharadin, Redmond, WA (US); Elizabeth A. Sweeney, Seattle, WA (US); Clarence T. Tegreene, Mercer Island, WA (US); Charles Whitmer, North Bend, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 256 days.

(21) Appl. No.: 15/386,434

(22) Filed: Dec. 21, 2016

(65) Prior Publication Data
US 2017/0156662 A1 Jun. 8, 2017

Related U.S. Application Data

(63) Continuation-in-part of application No. 15/361,999, filed on Nov. 28, 2016, and a continuation-in-part of
(Continued)

(51) Int. Cl.
*A61B 5/00* (2006.01)
*A61N 2/00* (2006.01)
(Continued)

(52) U.S. Cl.
CPC .............. *A61B 5/4836* (2013.01); *A61B 5/00* (2013.01); *A61B 5/1121* (2013.01); *A61B 5/45* (2013.01);
(Continued)

(58) Field of Classification Search
CPC ........ A61B 2018/00434; A61B 5/6831; A61B 5/4893; A61B 5/01; A61B 5/02438; A61B 5/0245; A61B 5/05
(Continued)

(56) References Cited

U.S. PATENT DOCUMENTS 4,813,436 A * 3/1989 Au ....................... A61B 5/1038
356/620
5,131,401 A * 7/1992 Westenskow ........ A61B 5/1106
600/554
(Continued)

FOREIGN PATENT DOCUMENTS

WO 2016025468 A2 2/2016
WO WO 2016/019250 A1 2/2016

OTHER PUBLICATIONS

Al-Mulla, Mohammed R. et al., "An Autonomous Wearable System for Predicting and Detecting Localised Muscle Fatigue", Sensors 2011, 11, 1542-1557; doi: 10.3390/s110201542.
(Continued)

*Primary Examiner* — May A Abouelela
(74) *Attorney, Agent, or Firm* — Daniel J. Honz; Advent, LLP

(57) ABSTRACT

Systems and methods are described for monitoring an individual subject and facilitating a motion regimen of the individual subject. In an aspect, a system includes, but is not limited to, a deformable substrate; a sensor assembly configured to generate one or more sense signals based on detection of at least one of a movement of the body portion
(Continued)

or at least one physiological parameter of the body portion; a processor configured to receive the one or more sense signals, the processor including circuitry configured to identify a physiological state of the individual subject based on at least one of the movement of the body portion or the at least one physiological parameter of the body portion; and an effector operably coupled to the processor and configured to effect at least one predetermined motion of the body portion corresponding to a motion regimen responsive to control by the processor.

17 Claims, 44 Drawing Sheets

Related U.S. Application Data application No. 15/361,953, filed on Nov. 28, 2016, and a continuation-in-part of application No. 14/504,954, filed on Oct. 2, 2014, now Pat. No. 10,099,053, and a continuation-in-part of application No. 14/504,944, filed on Oct. 2, 2014, now abandoned, and a continuation-in-part of application No. 14/334,434, filed on Jul. 17, 2014, now abandoned.

(51) Int. Cl.

| | | |
|---|---|---|
| *A61N 5/06* | (2006.01) | |
| *A61B 5/11* | (2006.01) | |
| *A61N 1/36* | (2006.01) | |
| *G16H 50/30* | (2018.01) | |
| *G16H 40/63* | (2018.01) | |
| *G16H 40/67* | (2018.01) | |
| *G16H 20/30* | (2018.01) | |
| *A61N 7/00* | (2006.01) | |
| *A61B 90/00* | (2016.01) | |
| *A61B 5/01* | (2006.01) | |
| *A61B 5/021* | (2006.01) | |
| *A61B 5/024* | (2006.01) | |
| *A61B 5/026* | (2006.01) | |
| *A61B 5/0402* | (2006.01) | |
| *A61B 5/0476* | (2006.01) | |
| *A61B 5/0488* | (2006.01) | |
| *A61B 5/053* | (2006.01) | |
| *A61B 5/08* | (2006.01) | |
| *A61B 5/145* | (2006.01) | |
| *A61N 1/04* | (2006.01) | |
| *B32B 7/12* | (2006.01) | |
| *B32B 25/08* | (2006.01) | |
| *B32B 25/20* | (2006.01) | |
| *B32B 27/08* | (2006.01) | |
| *B32B 3/08* | (2006.01) | |
| *A61N 5/067* | (2006.01) | |
| *A61N 7/02* | (2006.01) | |
| *G16H 40/40* | (2018.01) | |

(52) U.S. Cl.
CPC .......... *A61B 5/4824* (2013.01); *A61B 5/7275* (2013.01); *A61B 5/7282* (2013.01); *A61N 1/36014* (2013.01); *A61N 1/36021* (2013.01); *A61N 2/002* (2013.01); *A61N 2/008* (2013.01); *A61N 5/06* (2013.01); *A61N 5/0625* (2013.01); *G16H 20/30* (2018.01); *G16H 40/63* (2018.01); *G16H 40/67* (2018.01); *G16H 50/30* (2018.01); *A61B 5/0022* (2013.01); *A61B 5/0059* (2013.01); *A61B 5/01* (2013.01); *A61B 5/021* (2013.01); *A61B 5/024* (2013.01); *A61B 5/026* (2013.01); *A61B 5/0402* (2013.01); *A61B 5/0476* (2013.01); *A61B 5/0488* (2013.01); *A61B 5/0537* (2013.01); *A61B 5/0816* (2013.01); *A61B 5/14542* (2013.01); *A61B 5/7455* (2013.01); *A61B 2090/365* (2016.02); *A61B 2562/06* (2013.01); *A61B 2562/164* (2013.01); *A61N 1/0456* (2013.01); *A61N 1/0492* (2013.01); *A61N 1/36003* (2013.01); *A61N 7/00* (2013.01); *A61N 7/02* (2013.01); *A61N 2005/067* (2013.01); *A61N 2005/0659* (2013.01); *A61N 2007/0073* (2013.01); *A61N 2007/0078* (2013.01); *A61N 2007/0095* (2013.01); *B32B 3/08* (2013.01); *B32B 7/12* (2013.01); *B32B 25/08* (2013.01); *B32B 25/20* (2013.01); *B32B 27/08* (2013.01); *B32B 2274/00* (2013.01); *B32B 2307/546* (2013.01); *B32B 2307/7166* (2013.01); *B32B 2307/724* (2013.01); *B32B 2535/00* (2013.01); *G16H 40/40* (2018.01)

(58) Field of Classification Search
USPC ........ 600/300, 301, 557, 587, 595; 128/920; 607/45
See application file for complete search history.

(56) References Cited

U.S. PATENT DOCUMENTS

| | | | |
|---|---|---|---|
| 5,215,100 A | 6/1993 | Spitz et al. | |
| 5,792,025 A | 8/1998 | Kikinis | |
| 5,860,939 A * | 1/1999 | Wofford | A61B 5/0484 600/547 |
| 5,924,999 A | 7/1999 | Agee et al. | |
| 5,938,690 A * | 8/1999 | Law | A61N 1/37235 607/46 |
| 5,941,836 A * | 8/1999 | Friedman | A61B 5/1116 200/61.45 R |
| 6,142,910 A | 11/2000 | Heuvelman | |
| 6,168,569 B1 * | 1/2001 | McEwen | A61B 5/16 600/557 |
| 6,662,032 B1 * | 12/2003 | Gavish | A61B 5/0205 600/300 |
| 7,383,071 B1 | 6/2008 | Russell et al. | |
| 8,057,388 B1 | 11/2011 | Russell et al. | |
| 8,111,165 B2 | 2/2012 | Ortega et al. | |
| 8,416,088 B2 | 4/2013 | Ortega et al. | |
| 8,512,240 B1 * | 8/2013 | Zuckerman-Stark | G16H 50/30 600/301 |
| 8,781,860 B2 * | 7/2014 | Escorcia | A63B 24/0062 705/3 |
| 8,814,791 B2 * | 8/2014 | Sethi | A61B 5/0205 600/300 |
| 8,858,433 B2 * | 10/2014 | Sethi | A61B 5/14551 600/300 |
| 8,886,334 B2 | 11/2014 | Ghaffari et al. | |
| 9,199,096 B2 | 12/2015 | Lewis, Jr. | |
| 9,895,530 B2 * | 2/2018 | Boggs, II | A61N 1/0558 |
| 2002/0052562 A1 * | 5/2002 | Lipman | A61B 5/4824 600/557 |
| 2002/0107434 A1 * | 8/2002 | Lange | A61B 5/0478 600/301 |
| 2003/0236458 A1 | 12/2003 | Hochman | |
| 2004/0133081 A1 * | 7/2004 | Teller | A61B 5/01 600/300 |
| 2004/0225211 A1 | 11/2004 | Gozani et al. | |
| 2004/0267099 A1 * | 12/2004 | McMahon | A61B 5/00 600/300 |
| 2005/0272984 A1 * | 12/2005 | Huiku | A61B 5/0456 600/301 |
| 2006/0022833 A1 * | 2/2006 | Ferguson | A61B 5/1124 340/573.1 |

(56) References Cited

U.S. PATENT DOCUMENTS

| | | | |
|---|---|---|---|
| 2006/0149337 A1* | 7/2006 | John | A61N 1/36082 607/45 |
| 2006/0241356 A1* | 10/2006 | Flaherty | A61B 5/04 600/301 |
| 2006/0241975 A1* | 10/2006 | Brown | A61B 5/0002 705/2 |
| 2007/0010723 A1* | 1/2007 | Uutela | A61B 5/0205 600/301 |
| 2007/0055176 A1 | 3/2007 | Branch et al. | |
| 2007/0118054 A1* | 5/2007 | Pinhas | A61B 5/1102 600/587 |
| 2008/0172104 A1* | 7/2008 | Kieval | A61N 1/0556 607/46 |
| 2008/0183030 A1* | 7/2008 | Shiri | A63F 13/10 600/27 |
| 2008/0300650 A1* | 12/2008 | Gerber | A61B 5/202 607/41 |
| 2009/0036799 A1* | 2/2009 | Sandhu | A61B 5/0476 600/587 |
| 2009/0047644 A1* | 2/2009 | Mensah | G09B 5/06 434/247 |
| 2009/0076418 A1 | 3/2009 | Jung et al. | |
| 2009/0203975 A1* | 8/2009 | Barrett | A61B 17/3417 600/306 |
| 2009/0298650 A1* | 12/2009 | Kutliroff | A63B 71/0622 482/8 |
| 2010/0002402 A1 | 1/2010 | Rogers et al. | |
| 2010/0228315 A1* | 9/2010 | Nielsen | A61B 5/0215 607/42 |
| 2010/0249532 A1* | 9/2010 | Maddess | A61B 5/04842 600/300 |
| 2010/0298895 A1 | 11/2010 | Ghaffari et al. | |
| 2011/0034300 A1* | 2/2011 | Hall | A63B 5/11 482/1 |
| 2011/0118698 A1 | 5/2011 | Eckhoff et al. | |
| 2011/0230745 A1 | 9/2011 | Chandrasekaran et al. | |
| 2012/0053890 A1 | 3/2012 | Van Acht et al. | |
| 2012/0071731 A1* | 3/2012 | Gottesman | A61B 5/6833 600/301 |
| 2012/0108999 A1* | 5/2012 | Leininger | A61B 5/0004 600/546 |
| 2012/0109012 A1* | 5/2012 | Cinbis | A61B 5/1076 600/587 |
| 2012/0123223 A1* | 5/2012 | Freeman | G16H 40/63 600/301 |
| 2012/0143023 A1* | 6/2012 | Costantino | A61B 5/1107 600/309 |
| 2012/0157804 A1 | 6/2012 | Rogers et al. | |
| 2012/0165759 A1 | 6/2012 | Rogers et al. | |
| 2012/0283605 A1 | 11/2012 | Lewis, Jr. | |
| 2012/0302821 A1* | 11/2012 | Burnett | A61N 1/0492 600/14 |
| 2013/0041235 A1 | 2/2013 | Rogers et al. | |
| 2013/0046206 A1* | 2/2013 | Preminger | G09B 7/02 600/595 |
| 2013/0066237 A1 | 3/2013 | Smotrich et al. | |
| 2013/0085348 A1* | 4/2013 | Devenyi | A61B 5/1118 600/301 |
| 2013/0116600 A1* | 5/2013 | Wise | A61N 1/0512 600/587 |
| 2013/0192071 A1 | 8/2013 | Esposito et al. | |
| 2013/0245486 A1* | 9/2013 | Simon | A61N 1/36021 600/546 |
| 2014/0005494 A1* | 1/2014 | Ternes | A61B 5/0028 600/300 |
| 2014/0046416 A1* | 2/2014 | Bennett | A61N 1/0502 607/116 |
| 2014/0070957 A1 | 3/2014 | Longinotti-Buitoni et al. | |
| 2014/0081094 A1* | 3/2014 | Jordan | A61B 5/0476 600/301 |
| 2014/0200487 A1 | 7/2014 | Ramdas et al. | |
| 2014/0206945 A1* | 7/2014 | Liao | A61N 1/0529 600/301 |
| 2014/0228712 A1* | 8/2014 | Elliott | A63B 71/06 600/587 |
| 2014/0256511 A1* | 9/2014 | Smith | G10H 7/00 482/8 |
| 2014/0275821 A1* | 9/2014 | Beckman | A61B 5/1118 600/301 |
| 2014/0275827 A1* | 9/2014 | Gill | A61B 5/4848 600/301 |
| 2014/0296749 A1* | 10/2014 | Reid, Jr. | A61B 5/0053 600/587 |
| 2014/0371544 A1* | 12/2014 | Wu | A61B 5/0077 600/301 |
| 2014/0371547 A1* | 12/2014 | Gartenberg | A61B 5/0048 600/301 |
| 2015/0072326 A1* | 3/2015 | Mauri | A61B 5/0488 434/247 |
| 2015/0080670 A1* | 3/2015 | Osorio | A61B 5/0205 600/301 |
| 2015/0099976 A1 | 4/2015 | Ghaffari et al. | |
| 2015/0142079 A1 | 5/2015 | Pensler et al. | |
| 2015/0224326 A1* | 8/2015 | Toth | A61B 5/042 600/301 |
| 2015/0238259 A1 | 8/2015 | Albeck et al. | |
| 2015/0313533 A1 | 11/2015 | Rapp et al. | |
| 2016/0015280 A1 | 1/2016 | Hyde et al. | |
| 2016/0015972 A1 | 1/2016 | Hyde et al. | |
| 2016/0022167 A1* | 1/2016 | Simon | A61B 5/04842 600/301 |
| 2016/0136462 A1 | 5/2016 | Lewis, Jr. et al. | |

OTHER PUBLICATIONS

Askin, Ayhan et al., "Low dose high frequency ultrasound therapy for stellate ganglion blockage in complex regional pain syndrome type I: a randomised placebo controlled trial", Int. J. Clin. Exp. Med. 2014, 7(12), 5603-5611.

Bandodkar, Amay J. et al., "Tattoo-Based Noninvasive Glucose Monitoring: A Proof-of-Concept Study", Analytical Chemistry 2015, 87, 394-398.

Axisa, F. et al., "Biomedical Stretchable Systems Using Mid Based Stretchable Electronics Technology", Proceedings of the 29th Annual International Conference of the IEEE EMBS, Aug. 23-26, 2007, 5687-5690.

Best, Thomas M. et al., "Sustained acoustic medicine: wearable, long duration ultrasonic therapy for the treatment of tendinopathy", The Physician and Sportsmedicine 2015, 43(4), 366-374.

Fleet, David J., "Motion Models for People Tracking", Visual Analysis of Humans, 2011, 171-198.

Foley, Jessica L. et al., "Image-Guided High-Intensity Focused Ultrasound for Conduction Block of Peripheral Nerves", Annals. of Biomedical Engineering, vol. 35, No. 1, Jan. 2007, 109-119.

Gao, Wei et al., "Fully integrated wearable sensor arrays for multiplexed in situ perspiration analysis", Nature, Jan. 28, 2016, vol. 529, 509-514.

Hamaoka, Takafumi et al., "The use of muscle near-infrared spectroscopy in sport, health and medical sciences: recent developments", Phil. Trans. R. Soc. A (2011) 369, 4591-4604.

Harrison, Adrian P. et al., "Portable acoustic myography—a realistic noninvasive method for assessment of muscle activity and coordination in human subjects in most home and sports settings", Physiological Reports, 2013, vol. 1, Iss. 2, 1-9.

Hodges, Paul W. et al., "Interaction Between Pain, Movement, and Physical Activity Short-term Benefits, Long-term Consequences, and Targets for Treatment", Clin. J. Pain, vol. 31, No. 2, Feb. 2015, 97-107.

Jeong, Jae-Woong et al., "Capacitive Epidermal Electronics for Electrically Safe, Long-Term Electrophysiological Measurements", Adv. Healthcare Mater. 2013, 1-7.

Kim, Dae-Hyeong et al., "Epidermal Electronics", Science, vol. 333, Aug. 12, 2011, 838-843.

(56) References Cited

OTHER PUBLICATIONS

Kim, Jayoung et al., "Noninvasive Alcohol Monitoring Using a Wearable Tattoo-Based Iontophoretic-Biosensing System", ACS Sensors, 2016, A-I.
Kim, Yushin et al., "A Preliminary Study on the Effect of High-Power Pain Threshold Ultrasound to Desensitize Latent Trigger Points: A Double-Blinded Randomized Study", Journal of Musculoskeletal Pain, 2014, Informa Healthcare, 1-7.
Kuehn, Bridget M., "Wearable Biosensors Studied for Clinical Monitoring and Treatment", JAMA, Published Jun. 23, 2016, Medical News and Perspectives, E1-E3.
Langer, Matthew D. et al., "Pilot Clinical Studies of Long Duration, Low Intensity Therapeutic Ultrasound for Osteoarthritis", Proc. IEEE Annu. Northeast Bioeng. Conf. 2014, 1-5.
Lee, Hyunjae et al., "A graphene-based electrochemical device with thermoresponsive microneedles for diabetes monitoring and therapy", Nature Nanotechnology, vol. 11, Jun. 2016, 566-574.
Lee, Seung Min et al., "Self-adhesive epidermal carbon nanotube electronics for tether-free long-term continuous recording of biosignals", Scientific Reports, 4:6074, DOI: 10.1038/srep06074, 1-9.
Lee, Y-F. et al., "Nerve conduction block in diabetic rats using high-intensity focused ultrasound for analgesic applications", British Journal of Anaesthesia, doi: 10.1093/bja/aeu443, 1-7.
Lewis, Jr., George K. et al., "Design and Evaluation of a Wearable Self-Applied Therapeutic Ultrasound Device for Chronic Myofascial Pain", Ultrasound in Med. & Biol., vol. 39, No. 8, 2013, 1429-1439.
Marins, Joao Luis et al., "An Extended Kalman Filter for Quaternion-Based Orientation Estimation Using MARG Sensors", Proceedings of the 2001 IEEE/RSJ International Conference on Intelligent Robots and Systems, 2001, 2003-2011.
Mense, Siegfried, "Muscle Pain: Mechanisms and Clinical Significance" Deutsches Arzteblatt International, Dtsch Arztebl. Int. 2008, 105(12), 214-219.
Middleton, Carolyn, "Understanding the physiological effects of unrelieved pain", Nursing Times, vol. 99, Issue 37, Sep. 16, 2003, 1-7.
Naor, Omer et al., "Ultrasonic neuromodulation", J. Neural Eng. 13, 2016, Mar. 10, 2003, 1-18.
Nyein, Hnin Yin Yin et al., "A Wearable Electrochemical Platform for Noninvasive Simultaneous Monitoring of Ca2+ and pH", ACS Nano 2016, 10, 7216-7224.
Palmer, Keith T., "Carpal tunnel syndrome: The role of occupational factors", Best Pract. Res. Clin. Rheumatol., Feb. 2011, 25(1), 15-29.
Prkachin, Kenneth M., "Assessing pain by facial expression: Facial expression as nexus", Pain Res. Manag. Jan.-Feb. 2009, 14(1), 53-58.
Son, Donghee et al., "Multifunctional wearable devices for diagnosis and therapy of movement disorders", Nature Nanotechnology, 1-8.
Sun, Lei et al., "12-GHz Thin-Film Transistors on Transferrable Silicon Nanomembranes for High-Performance Flexible Electronics", Small 2010, 6, No. 22, 2553-2557.
Taffoni, Fabrizio et al., "Optical Fiber-Based MR-Compatible Sensors for Medical Applications: An Overview", Sensors 2013, 13, 14105-14120.
Tennant, Forest, "The Physiologic Effects of Pain on the Endocrine System", Pain Ther. 2013, 2:75-86.
Walter, Steffen et al., "Automatic pain quantification using autonomic parameters", Psychology & Neuroscience, 2014, 7, 3, 363-380.
Wang, Wei-zhong et al., "Analysis of Filtering Methods for 3D Acceleration Signals in Body Sensor Network", Bulletin of Advanced Technology Research, vol. 5, No. 7, Jul. 2011, 15-18.
Webb, R. Chad et al., "Ultrathin conformal devices for precise and continuous thermal characterization of human skin", Nature Materials, vol. 12, Oct. 2013, 938-945.
Webb, R. Chad et al., "Ultrathin conformal devices for precise and continuous thermal characterization of human skin", Nature Materials, Supplementary Information, 2013, 1-27.
Wells, Jonathon et al., "Biophysical Mechanisms of Transient Optical Stimulation of Peripheral Nerve", Biophysical Journal, vol. 93, Oct. 2007, 2567-2580.
Wolf, K. et al., "The face of pain—a pilot study to validate the measurement of facial pain expression with an Improved electromyogram method", Pain Res. Manag. 2005, 10(1):15-9 (Abstract).
Yeo, Woon-Hong et al., "Multifunctional Epidermal Electronics Printed Directly Onto the Skin", Adv. Mater. 2013, DOI: 10.1002/adma.201204426, 1-6.
Ying, Ming et al., "Silicon Nanomembranes for fingertip electronics", Nanotechnology, 23 (2012), 344004, 1-7.
Ying, Ming et al., Silicon Nanomembranes for Fingertip Electronics, Supplementary Data, 1-11.
Yun, Xiaoping et al., "Design, Implementation, and Experimental Results of a Quaternion-Based Kalman Filter for Human Body Motion Tracking", IEEE Transactions on Robotics, vol. 22, No. 6, Dec. 2006, 1216-1227.
Xu, Sheng et al., "Soft Microfluidic Assemblies of Sensors, Circuits, and Radios for the Skin", Science, vol. 344, Apr. 4, 2014, 70-74.
Lopes, Pedro et al., "Affordance++: allowing objects to communicate dynamic use", Seoul, Republic of Korea, Apr. 2015.
Luan, Song et al., "Neuromodulation: present and emerging methods", Frontiers in Neuroengineering, vol. 7, Article 27, Jul. 2014.
Trenado, Carlos et al., "Broad-band Gaussian noise is most effective in improving motor performance and is most pleasant", Frontiers in Human Neuroscience, vol. 8, Article 22, Feb. 2014.
Leung, Albert et al., "Transcutaneous Magnetic Stimulation (tMS) in Alleviating Post-Traumatic Peripheral Neuropathic Pain States: A Case Series", Pain Medicine, Dec. 2016.
Zhou, Junhong et al., "Sub-sensory vibratory noise augments the physiologic complexity of postural control in older adults", Journal of NeuroEngineering and Rehabilitation, 2016.
PCT International Search Report; International App. No. PCT/US2017/063243; dated Nov. 27, 2017; pp. 1-5.

* cited by examiner

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

> 1900 COMPARING THE ONE OR MORE SENSE SIGNALS TO REFERENCE DATA INDICATIVE OF A STRAIN INJURY TO DETERMINE THE RISK OF INDUCING THE STRAIN INJURY
>
>> 1902 DETERMINING THE ACTION TO EXECUTE BASED UPON COMPARING THE ONE OR MORE SENSE SIGNALS TO REFERENCE DATA INDICATIVE OF A STRAIN INJURY

1808 EXECUTING AN ACTION TO REDUCE THE RISK OF INDUCING THE REPETITIVE STRESS INJURY

FIG. 18

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2000 REPORTING THE DETERMINATION OF THE RISK OF INDUCING THE REPETITIVE STRAIN INJURY TO REDUCE THE RISK

2002 PROVIDING A TACTILE INDICATION OF THE RISK

2004 PROVIDING A VIBRATION-BASED INDICATION OF THE RISK

2006 PROVIDING A TACTILE INDICATION REGARDING A POSITION OF THE BODY PORTION

2008 PROVIDING A TACTILE INDICATION THAT THE POSITION IS A BIOMECHANICALLY DETRIMENTAL POSITION

2010 PROVIDING A TACTILE INDICATION THAT THE BODY PORTION HAS BEEN IN THE POSITION LONGER THAN A THRESHOLD DURATION

FIG. 19

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2000 REPORTING THE DETERMINATION OF THE RISK OF INDUCING THE REPETITIVE STRAIN INJURY TO REDUCE THE RISK

2100 PROVIDING A VISUAL INDICATION OF THE RISK

2102 PROVIDING A VISUAL INDICATION REGARDING A POSITION OF THE BODY PORTION

2104 PROVIDING A VISUAL INDICATION THAT THE POSITION IS A BIOMECHANICALLY DETRIMENTAL POSITION

2106 PROVIDING A VISUAL INDICATION THAT THE BODY PORTION HAS BEEN IN THE POSITION LONGER THAN A THRESHOLD DURATION

FIG. 20

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2000 REPORTING THE DETERMINATION OF THE RISK OF INDUCING THE REPETITIVE STRAIN INJURY TO REDUCE THE RISK

2200 PROVIDING AN AUDITORY INDICATION OF THE RISK

2202 PROVIDING AN AUDITORY INDICATION REGARDING A POSITION OF THE BODY PORTION

2204 PROVIDING AN AUDITORY INDICATION THAT THE POSITION IS A BIOMECHANICALLY DETRIMENTAL POSITION

2206 PROVIDING AN AUDITORY INDICATION THAT THE BODY PORTION HAS BEEN IN THE POSITION LONGER THAN A THRESHOLD DURATION

FIG. 21

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

> 2000 REPORTING THE DETERMINATION OF THE RISK OF INDUCING THE REPETITIVE STRAIN INJURY TO REDUCE THE RISK
>
>> 2300 REPORTING AT LEAST ONE OF AN ACTUATION OF AN EFFECTOR CONFIGURED TO EXECUTE THE ACTION, A DETECTED MOVEMENT OF THE BODY PORTION, OR A DETECTED PHYSIOLOGICAL CONDITION
>>
>> 2302 PROVIDING A WARNING OF A RISK OF A BIOMECHANICALLY DETRIMENTAL POSITIONING OF THE BODY PORTION
>>
>> 2304 PROVIDING AN INSTRUCTION TO MOVE THE BODY PORTION
>>
>> 2306 COMMUNICATING THE DETERMINATION TO A REMOTE LOCATION
>>
>>> 2308 INTERACTING WITH A PROGRAM STORED ON THE COMPUTER SYSTEM
>>>
>>> 2310 MODIFYING A PROGRAM STORED ON THE COMPUTER SYSTEM

FIG. 22

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2400 STIMULATING A NERVE PROXIMATE TO THE BODY PORTION

2402 INDUCING AT LEAST ONE OF A MOVEMENT OR A SENSATION OF THE BODY PORTION BY STIMULATING THE NERVE CONDUCTION OF THE NERVE PROXIMATE TO THE BODY PORTION

2404 INDUCING AT LEAST ONE OF A MOVEMENT OR A SENSATION OF THE BODY PORTION BY STIMULATING A NERVE CONDUCTION OF THE NERVE AFTER A THRESHOLD PERIOD OF TIME DURING WHICH THE BODY PORTION IS RETAINED IN A PARTICULAR POSITION

FIG. 23

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

> 2500 ELECTRICALLY BLOCKING A NERVE CONDUCTION OF A NERVE PROXIMATE TO THE BODY PORTION
>
>> 2502 ELECTRICALLY BLOCKING A NERVE CONDUCTION OF A NERVE PROXIMATE TO THE BODY PORTION TO INHIBIT A PAIN RECEPTOR
>>
>> 2504 ELECTRICALLY BLOCKING A NERVE CONDUCTION OF A NERVE PROXIMATE TO THE BODY PORTION TO INHIBIT A MOVEMENT OF THE BODY PORTION

FIG. 24

1802 DETECTING, VIA AN EPIDERMAL ELECTRONIC SYSTEM (EES), AT LEAST ONE OF A POSITION AND A MOVEMENT OF A BODY PORTION

2600 MEASURING, VIA AN EPIDERMAL ELECTRONIC SYSTEM (EES), A REPEATED MOTION OF THE BODY PORTION

2602 MEASURING, VIA AN EPIDERMAL ELECTRONIC SYSTEM (EES), A NUMBER OF REPETITIONS OF THE MOVEMENT OF THE BODY PORTION

2604 MEASURING, VIA AN EPIDERMAL ELECTRONIC SYSTEM (EES), A SPEED OF THE MOVEMENT OF THE BODY PORTION

2606 MEASURING, VIA AN EPIDERMAL ELECTRONIC SYSTEM (EES), A DURATION OF THE MOVEMENT OF THE BODY PORTION

2608 MEASURING, VIA AN EPIDERMAL ELECTRONIC SYSTEM (EES), A DISPOSITION OF THE BODY PORTION RELATIVE TO A SECOND BODY PORTION

2610 MEASURING, VIA AN EPIDERMAL ELECTRONIC SYSTEM (EES), AN ANGLE OF MOVEMENT OF THE BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

FIG. 25

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2700 DETECTING, VIA AN EPIDERMAL ELECTRONIC SYSTEM (EES), A PHYSIOLOGICAL PARAMETER OF THE BODY PORTION

2702 GENERATING ONE OR MORE SENSE SIGNALS BASED ON DETECTION OF THE PHYSIOLOGICAL PARAMETER OF THE BODY PORTION

FIG. 26

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2700 DETECTING, VIA AN EPIDERMAL ELECTRONIC SYSTEM (EES), A PHYSIOLOGICAL PARAMETER OF THE BODY PORTION

2800 DETECTING A TEMPERATURE OF THE BODY PORTION

2802 DETECTING A STRAIN OF THE BODY PORTION

2804 DETECTING A BLOOD FLOW OF THE BODY PORTION

2806 DETECTING A BLOOD OXYGENATION LEVEL OF THE BODY PORTION

2808 DETECTING AN ELECTRICAL ACTIVITY OF THE BODY PORTION

2702 GENERATING ONE OR MORE SENSE SIGNALS BASED ON DETECTION OF THE PHYSIOLOGICAL PARAMETER OF THE BODY PORTION

FIG. 27

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

2900 DETECTING, VIA AN EPIDERMAL ELECTRONIC SYSTEM (EES), A DISPOSITION OF THE BODY PORTION

2902 DETECTING, VIA AN EPIDERMAL ELECTRONIC SYSTEM (EES), AN ANGLE OF A JOINT PROXIMATE THE BODY PORTION

2904 DETECTING, VIA AN EPIDERMAL ELECTRONIC SYSTEM (EES), A DISPOSITION OF THE BODY PORTION OVER A PERIOD OF TIME

FIG. 28

| 1802 | DETECTING, VIA AN EPIDERMAL ELECTRONIC SYSTEM (EES), AT LEAST ONE OF A POSITION AND A MOVEMENT OF A BODY PORTION |

| 1804 | GENERATING ONE OR MORE SENSE SIGNALS BASED ON DETECTION OF THE AT LEAST ONE OF A POSITION AND A MOVEMENT OF A BODY PORTION |

| 1806 | PROCESSING THE ONE OR MORE SENSE SIGNALS TO DETERMINE A RISK OF INDUCING A REPETITIVE STRESS INJURY |

| 1808 | EXECUTING AN ACTION TO REDUCE THE RISK OF INDUCING THE REPETITIVE STRESS INJURY |

| 3000 | DETECTING, VIA AN EPIDERMAL ELECTRONIC SYSTEM (EES), A DEVICE INTERFACING WITH AT LEAST ONE OF THE BODY PORTION AND ANOTHER BODY PORTION |

| 3002 | TRANSMITTING A COMMUNICATION SIGNAL TO THE DEVICE |

| 3004 | TRANSMITTING THE ONE OR MORE SENSE SIGNALS GENERATED BASED ON DETECTION OF AT LEAST ONE OF THE POSITION AND THE MOVEMENT OF THE BODY PORTION TO THE DEVICE |

FIG. 29

1802 DETECTING, VIA AN EPIDERMAL ELECTRONIC SYSTEM (EES), AT LEAST ONE OF A POSITION AND A MOVEMENT OF A BODY PORTION

1804 GENERATING ONE OR MORE SENSE SIGNALS BASED ON DETECTION OF THE AT LEAST ONE OF A POSITION AND A MOVEMENT OF A BODY PORTION

1806 PROCESSING THE ONE OR MORE SENSE SIGNALS TO DETERMINE A RISK OF INDUCING A REPETITIVE STRESS INJURY

1808 EXECUTING AN ACTION TO REDUCE THE RISK OF INDUCING THE REPETITIVE STRESS INJURY

3100 DETECTING, VIA AN EPIDERMAL ELECTRONIC SYSTEM (EES), AT LEAST ONE OF A POSITION AND A MOVEMENT OF A SECOND BODY PORTION PROXIMATE THE BODY PORTION

FIG. 30

MONITORING BODY MOVEMENT OR CONDITION ACCORDING TO MOTION REGIMEN WITH CONFORMAL ELECTRONICS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation-in-part of U.S. patent application Ser. No. 14/334,434, entitled USE OF EPIDERMAL ELECTRONIC DEVICES TO MEASURE ORIENTATION, naming ALISTAIR K. CHAN, RODERICK A. HYDE, ELIZABETH A. SWEENEY, and DAVID B. TUCKERMAN as inventors, filed 17 Jul. 2014, which is currently co-pending or is an application of which a currently co-pending application is entitled to the benefit of the filing date.

The present application constitutes a continuation-in-part of U.S. patent application Ser. No. 14/504,944, entitled EPIDERMAL ELECTRONICS TO MONITOR REPETITIVE STRESS INJURIES AND ARTHRITIS, naming RODERICK A. HYDE, JORDIN T. KARE, ERIC C. LEUTHARDT, MARK A. MALAMUD, ELIZABETH A. SWEENEY, CLARENCE T. TEGREENE, CHARLES WHITMER, and LOWELL L. WOOD JR. as inventors, filed 2 Oct. 2014, which is currently co-pending or is an application of which a currently co-pending application is entitled to the benefit of the filing date.

The present application constitutes a continuation-in-part of U.S. patent application Ser. No. 14/504,954, entitled EPIDERMAL ELECTRONICS TO MONITOR REPETITIVE STRESS INJURIES AND ARTHRITIS, naming RODERICK A. HYDE, JORDIN T. KARE, ERIC C. LEUTHARDT, MARK A. MALAMUD, ELIZABETH A. SWEENEY, CLARENCE T. TEGREENE, CHARLES WHITMER, and LOWELL L. WOOD JR. as inventors, filed 2 Oct. 2014, which is currently co-pending or is an application of which a currently co-pending application is entitled to the benefit of the filing date.

The present application constitutes a continuation-in-part of U.S. patent application Ser. No. 15/361,953, entitled MONITORING AND TREATING PAIN WITH EPIDERMAL ELECTRONICS, naming RODERICK A. HYDE, JORDIN T. KARE, ERIC C. LEUTHARDT, MARK A. MALAMUD, GARY L. MCKNIGHT, TONY S. PAN, KATHERINE E. SHARADIN, ELIZABETH A. SWEENEY, CLARENCE T. TEGREENE, CHARLES WHITMER, and LOWELL L. WOOD JR. as inventors, filed 28 Nov. 2016, which is currently co-pending or is an application of which a currently co-pending application is entitled to the benefit of the filing date.

The present application constitutes a continuation-in-part of U.S. patent application Ser. No. 15/361,999, entitled MONITORING AND TREATING PAIN WITH EPIDERMAL ELECTRONICS, naming RODERICK A. HYDE, JORDIN T. KARE, ERIC C. LEUTHARDT, MARK A. MALAMUD, GARY L. MCKNIGHT, TONY S. PAN, KATHERINE E. SHARADIN, ELIZABETH A. SWEENEY, CLARENCE T. TEGREENE, CHARLES WHITMER, and LOWELL L. WOOD JR. as inventors, filed 28 Nov. 2016, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a system includes, but is not limited to, a deformable substrate configured to conform to a body portion of an individual subject; a sensor assembly coupled to the deformable substrate, the sensor assembly configured to generate one or more sense signals based on detection of at least one of a movement of the body portion or at least one physiological parameter of the body portion; a processor operably coupled to the sensor assembly and configured to receive the one or more sense signals, the processor including circuitry configured to identify a physiological state of the individual subject based on at least one of the movement of the body portion or the at least one physiological parameter of the body portion; and an effector operably coupled to the processor and configured to effect at least one predetermined motion of the body portion corresponding to a motion regimen responsive to control by the processor.

In an aspect, a method includes, but is not limited to, detecting, via an epidermal electronic system (EES), at least one of a movement of a body portion of an individual subject or a physiological parameter of the body portion; generating one or more sense signals based on detection of at least one of the movement of the body portion or the physiological parameter of the body portion; receiving the one of more sense signals with a computer processor; identifying a physiological state of the individual subject based on at least one of the movement of the body portion or the physiological parameter of the body portion; transmitting a control signal to activate an effector; and effecting at least one predetermined motion of the body portion corresponding to a motion regimen responsive to the control signal.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 18 is a flowchart illustrating aspects of a method such as shown in FIG. 17.

FIG. 19 is a flowchart illustrating aspects of a method such as shown in FIG. 17.

FIG. 20 is a flowchart illustrating aspects of a method such as shown in FIG. 19.

FIG. 21 is a flowchart illustrating aspects of a method such as shown in FIG. 19.

FIG. 22 is a flowchart illustrating aspects of a method such as shown in FIG. 19.

FIG. 23 is a flowchart illustrating aspects of a method such as shown in FIG. 17.

FIG. 24 is a flowchart illustrating aspects of a method such as shown in FIG. 17.

FIG. 25 is a flowchart illustrating aspects of a method such as shown in FIG. 17.

FIG. 26 is a flowchart illustrating aspects of a method such as shown in FIG. 17.

FIG. 27 is a flowchart illustrating aspects of a method such as shown in FIG. 26.

FIG. 28 is a flowchart illustrating aspects of a method such as shown in FIG. 17.

FIG. 29 is a flowchart illustrating aspects of a method such as shown in FIG. 17.

FIG. 30 is a flowchart illustrating aspects of a method such as shown in FIG. 17.

DETAILED DESCRIPTION

Figure 1A:
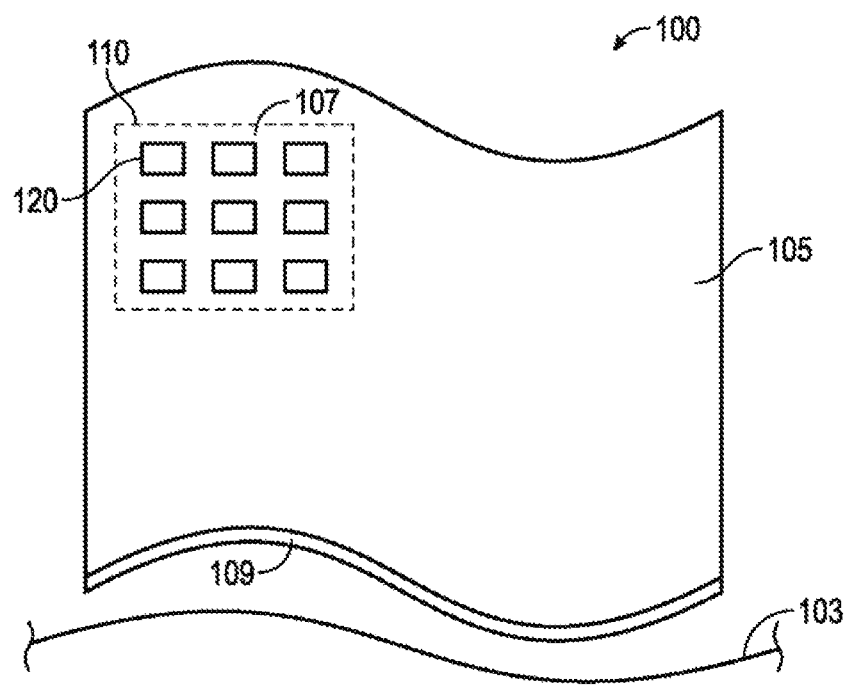
FIG. 1A is a schematic view of an embodiment of an epidermal electronics device showing individual cells of the device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Generally, an epidermal electronics device may include a thin layer of electronic circuits. This thin layer is supported by a barrier layer and optionally encapsulated by a substrate layer. The device is configured to attach to or otherwise engage skin or other tissue, such as by being affixed to the skin via an adhesive material, held in place by an external pressure, such as pressure provided by a material wrapped around or about a body portion (e.g., a fabric, a garment, a glove, a bandage, etc.), affixed in a textile, fabric, garment, accessory (e.g., a glove, a sock, a finger cot, etc.), or so forth. The device is also configured to allow the electronic circuits to flex without being damaged. The epidermal electronics device includes electronics for measuring various parameters. In general, an epidermal electronics device may be used for a variety of medical applications.

Referring to FIG. 1A, an embodiment of epidermal electronics device 100 is shown to include substrate layer 105. Epidermal electronics device 100 further includes electronics layer 107 located between substrate layer 105 and barrier layer 109. Electronics layer 107 is shown through substrate layer 105 with view 110. Included within electronics layer 107 are cells 120. Epidermal electronics device 100 is illustrated as attached to attachment surface 103.

Substrate layer 105 facilitates the transfer of epidermal electronics device 100 to attachment surface 103. For example, substrate layer 105 may provide a backing which is used to transfer electronics layer 107 to attachment surface 103. Substrate layer 105 may then peel away from electronics layer 107 leaving electronics layer 107 attached to attachment surface 103 via barrier layer 109. Substrate layer 107 may also provide protection to electronics layer 107 during the handling of epidermal electronics device 100. Substrate layer 105 also provides support for electronics layer 107. Barrier layer 109 can be an elastomer or polymer suited for use in contact with organic tissue. In some embodiments, the barrier layer 109 is a bio compatible or otherwise inert material. In some embodiments, barrier layer 109 may have a low elastic modulus, e.g., one which is significantly lower (e.g., less than half) of the elastic modulus of attachment surface 103. For example, barrier layer 109 may comprise a low modulus polymeric material such as PDMS or BASF. For example, the substrate layer 105 may be a rubber or silicone material. In some embodiments, substrate layer 105 may be water soluble. Substrate layer 105 may be dissolved following transfer of the epidermal electronics device 100 onto the attachment surface 103. In some embodiments, substrate layer 105 need not be biocompatible as it is removed completely or partially following the transfer of epidermal electronics device 100 onto the attachment surface 103. Substrate layer 105 provides protection to electronics layer 107 from external sources of damage. External sources of damage may include moisture, physical damage (e.g., from a user touching epidermal electronics device 100), electrical interference, magnetic interference, etc.

In one embodiment, attachment surface 103 is the skin of a user. In other embodiments, attachment surface 103 includes other organs. For example, attachment surface 103 may be bone, muscle tissue, the heart, the lungs, etc. In some embodiments, attachment surface 103 is a bandage attached or to be attached to the skin or other organ. In some embodiments, attachment surface 103 is a covering such as a glove, finger cot, or the like.

Epidermal electronics device 100 is held in contact with attachment surface 103 through conformal contact. In some embodiments, epidermal electronics device 100 is held in contact with attachment surface 103 through close-contact atomic forces or van der Waals interactions. In other embodiments, epidermal electronics device 100 is held in contact with attachment surface 103 through the use of an adhesive. The adhesive may be applied after the epidermal electronics device 100 is placed on attachment surface 103. For example, the adhesive may be a spray on bandage or may be adhesive tape. The adhesive may also be included as a component of barrier layer 109.

According to one embodiment, barrier layer 109 at least partially encompasses the electronics layer 107. In some embodiments, barrier layer 109 encompasses the entirety of epidermal electronics layer 107. In other embodiments, barrier layer 109 only coats electronics layer 107 on the surface opposite substrate layer 105. Barrier layer 109 may also partially coat electronics layer 107 to allow for contact between elements or cells of electronics layer 107 and the attachment surface 103.

With continued reference to FIG. 1A, electronics layer 107 is located between substrate layer 105 and barrier layer 109. Barrier layer 109 and/or substrate layer 105 provides support for the elements of electronics layer 107. View 110, illustrated as a dashed line, shows electronics layer 107 through substrate layer 105. In one embodiment, electronics layer 107 includes an array of cells 120. Cells 120 contain individual sensors or components. Cells 120 are also in communication with other components in electronics layer 107. In some embodiments, cells 120 may be in communication with each other or a subset of other cells 120 within epidermal electronics device 100. Cells 120 may also be in communication with other elements. For example, cells 120 may be in communication with a power supply, control circuit, and/or communications device. Cells 120 may also contain connections to allow power delivery to the component in the cell, input/output to and from the component in the cell, and/or multiplexing circuitry. In some embodiments, cells 120 may contain sensors such as accelerometers, inclinometers, magnetometers, or gyroscopes. These sensors may be of the micro electro-mechanical systems (MEMS) type, given the small scale of epidermal electronics device 100 and associated components; MEMS accelerometers, gyroscopes, and inclinometers are commercially available from multiple vendors. The sensors may also be part of or supported by integrated circuits or systems on a chip (SOCs). Cells 120 may also contain interaction devices such as drug delivery systems, electrodes, motion capture markers, etc. Interaction devices may also be MEMS, part of or supported by integrated circuits, or SOCs. According to various alternative embodiments, cells 120 may include circuitry facilitating multiplexing of sensor output, transformers, amplifiers, circuitry for processing data and control signals, one or more transistors, etc.

Figure 1B:
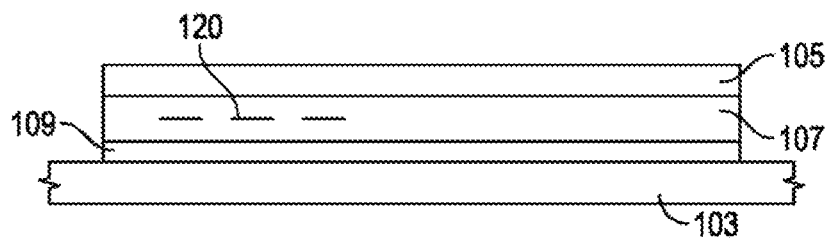
FIG. 1B is a schematic cross section view of an embodiment of an epidermal electronics device showing individual cells of the device.

FIG. 1B illustrates a cross section schematic view of one embodiment of epidermal electronics device 100. Substrate layer 105 is the topmost layer relative to attachment surface 103 and protects electronics layer 107 from the external environment. Barrier layer 109 is in contact with attachment surface 103 and protects electronics layer 107 from attachment surface 103. Electronics layer 107 is between barrier layer 109 and substrate layer 105. Electronics layer 107 is shown with cells 120 located therein.

As previously discussed, attachment surface 103 may be the skin of a user. Barrier layer 109 attaches epidermal electronics device 100 to attachment surface 103. Barrier layer 109 also protects electronic components of epidermal electronics device 100 from damage caused by attachment surface 103. Electronics layer 107, which includes electronic components of epidermal electronics device 100, is coupled to barrier layer 109. Lastly, substrate layer 105 is coupled to electronics layer 107. Substrate layer 105 may provide a surface on which epidermal electronics device 100 is constructed, further protects the electronics components of epidermal electronics device 100, and/or facilitates the attachment of epidermal electronics device 100 to attachment surface 103 (e.g., provides a peel away surface which may be grasped while attaching epidermal electronics device 100.

In alternative embodiments, epidermal electronics device may include a subset of the layers described above. For example, epidermal electronics device 100 may include only barrier layer 109 and the electronic components described herein. Barrier layer 109 may protect the electronic components, attach epidermal electronics device 100 to attachment surface 103, and provide a surface on which epidermal electronics device 100 is constructed. Substrate layer 105 is an optional component of epidermal electronics device 100.

Figure 2A:
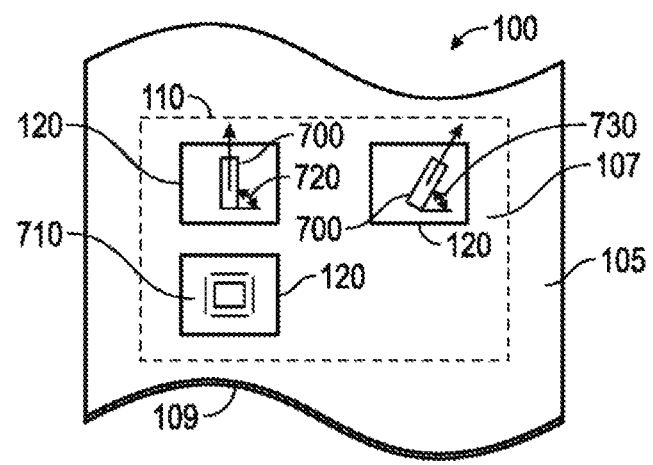
FIG. 2A is a schematic view of an embodiment of an epidermal electronics device showing cells configured to measure orientation using accelerometers.

FIG. 2A illustrates a schematic view of a portion of epidermal electronics device 100 according to one embodiment and shows sensors and sensor combinations which may be used. In some embodiments, epidermal electronics device 100 includes one or more single-axis accelerometers 700. Each accelerometer is located within one of cells 120. Single-axis accelerometers 700 may be positioned at angles such as first angle 720 and second angle 730. Some embodiments of epidermal electronics device 100 include multi-axis accelerometer 710.

In one embodiment, epidermal electronics device 100 includes two or more single-axis accelerometers 700. Each accelerometer is part of a single cell 120. Cell 120 facilitates communication between the single-axis accelerometer 700 and other components of the electronics layer 107. Cell 120 may include one or more transistors. As is shown with view 110, illustrated with a dashed line, the single-axis accelerometers 700 are part of electronics layer 107. Single-axis accelerometer 700 is a MEMS accelerometer measuring acceleration along a single axis. One single-axis accelerometer 700 is shown oriented at a first angle 720. Another single-axis accelerometer 700 is shown oriented at a second angle 730. By orienting two single-axis accelerometers at different angles, 720 and 730, the rotation and orientation of the epidermal electronics device 100 may be determined from the sensor outputs. The different angles 720 and 730 may result in the single-axis accelerometers being oriented along different planes. The single-axis accelerometers may be slightly or fully opposed. Some embodiments of the epidermal electronics device 100 include multi-axis accelerometer 710.

Figure 2B:
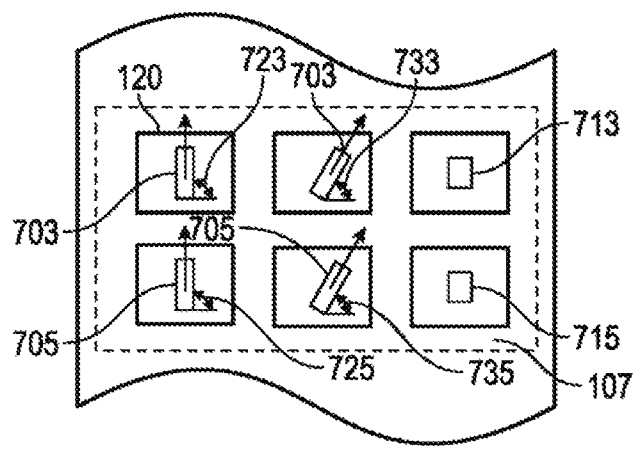
FIG. 2B is a schematic view of an embodiment of the epidermal electronics device showing cells configured to measure orientation using inclinometers and/or gyroscopes.

FIG. 2B illustrates additional sensors which may be included in an embodiment of epidermal electronics device 100. These additional sensors may include one or more of single-axis inclinometers 703, multi-axis inclinometers 713, single-axis gyroscopes 705, and multi-axis gyroscopes 715. Inclinometers may be used to measure an orientation of epidermal electronics device 100 relative to the direction of gravity. One single-axis inclinometer 703 may be oriented at first angle 723. Another single-axis inclinometer 703 may be oriented at second angle 733. By orienting two single-axis inclinometers at different angles, 723 and 733, two components of the orientation of epidermal electronics device 100 relative to the direction of gravity may be determined from the sensor outputs. The different angles 720 and 730 may result in the single-axis inclinometers being oriented along different axes. Single-axis inclinometers may be used to measure pitch or roll relative to the direction of gravity. Some embodiments of epidermal electronics device 100 include a multi-axis inclinometer 713, i.e., to measure both pitch and roll. In some embodiments, electronics layer 107 includes one or more gyroscopes to measure an angular velocity of epidermal electronics device 100. In some embodiments, electronics layer 107 includes one or more single-axis gyroscopes 705 (e.g., a MEMS vibrating structure gyroscope). One single-axis gyroscope 705 may be oriented at first angle 725. Another single-axis gyroscope 705 may be oriented at second angle 735. By orienting two single-axis gyroscopes at different angles, 725 and 735, two components of the angular velocity of epidermal electronics device 100 may be determined from the sensor outputs. The different angles 725 and 735 may result in the single-axis inclinometers being oriented along different axes. Single-axis gyroscopes may be used to measure pitch, roll, and/or yaw. Some embodiments of epidermal electronics device 100 include a multi-axis gyroscope 715.

Figure 2C:
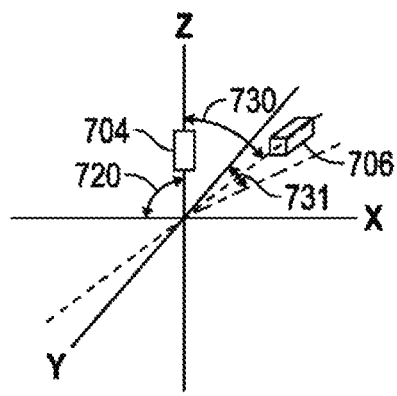
FIG. 2C is an illustration of a sensor configuration according to one embodiment of the epidermal electronics device.

FIG. 2C illustrates an embodiment of epidermal electronics device 100 in which two sensors are arranged to measure the motion (angular and/or translational) of epidermal electronics device 100. Single-axis accelerometer 704 is shown positioned with its axis of measurement parallel to and along the Z axis of a three dimensional space. Single-axis accelerometer 704 has first angle 720 defining a zero degree angle with axis Z. Second single-axis accelerometer 706 is shown with its axis of measurement not in alignment with the axis Z. Second accelerometer 706 has an axis of measurement defined by second angle 730 from the Z axis. This angle may be greater than zero degrees. The measurement axis of second single-axis accelerometer 706 is further defined by angle 731 which defines the measurement axis relative to the X-Y plane. As is shown in the illustrated embodiment, single-axis accelerometers 704 and 706 are configured to be slightly opposed (e.g., single-axis accelerometer 704 is aligned with the Z axis and second single-axis accelerometer 706 is positioned with second angle 730 of thirty degrees and angle 731 of fifteen degrees). In some embodiments, multiple single-axis accelerometers 703 are configured to measure acceleration along the X, Y, and Z axes. In further embodiments, additional single-axis gyroscopes are configured to measure rotation about the X, Y, and Z axes in addition to acceleration along the X, Y, and Z axes. In some embodiments, one or more single-axis inclinometers are substituted for one or more accelerometers or gyroscopes. Single-axis inclinometers may also be used to provide redundant measurements. In some embodiments, the measurements provided by one or more inclinometers are used to verify the orientation of the epidermal electronics device as determined using other data. In some embodiments, single-axis gyroscopes are substituted for one or more accelerometers. Single-axis gyroscopes may also be used to provide redundant measurements. In some embodiments, the accelerometers, inclinometers, and/or gyroscopes include multi-axis accelerometers, multi-axis inclinometers, and/or multi-axis gyroscopes.

In one embodiment, single-axis accelerometer 704 is positioned on an axis. Second single single-axis accelerometer 706 is positioned along the same axis but laterally displaced from accelerometer 704. Single-axis accelerometer 704 and second single single-axis accelerometer 706 are positioned to measure acceleration along the same axis but with opposite signs. Acceleration along the axis will read as positive acceleration to one of the two accelerometers and negative acceleration to the other of the two accelerometers. Therefore, when there is acceleration without rotation, the sum of the acceleration measured by single-axis accelerometer 704 and second single single-axis accelerometer 706 will be zero or approximately zero (e.g., approximately zero accounting for measurement error, etc.). Rotation which is measured by the two accelerometers will result in a net acceleration measured by the two accelerometers. Therefore, two displaced single-axis accelerometers oppositely aligned along the same axis may detect or measure rotation, i.e., angular velocity and/or angular acceleration.

In general terms and with reference to FIGS. 1A-2C, sensors (e.g., accelerometers, inclinometers, gyroscopes, etc.) are positioned and oriented within electronics layer 107 of epidermal electronics device 100 such that angular motion and orientation of the device may be measured. Many configurations are possible and the embodiments described herein are not intended to be limiting. By using opposed or slightly opposed single-axis sensors of the types discussed, epidermal electronics device 100 may be configured to measure the orientation and/or angular motion of the device and therefore the attachment surface 103 to which the epidermal electronics device 100 is attached (e.g., a body part such as a limb, etc.). In some embodiments, a plurality of single-axis sensors are used to measure the orientation of epidermal electronics device 100. For example, six single-axis accelerometers 103 may be used to measure a total of six degrees of freedom. The six single-axis accelerometers may measure X axis acceleration, Y axis acceleration, and Z axis acceleration along with pitch, roll, and yaw angular accelerations about those axes. In some embodiments, combinations of multiple sensor types are used to achieve the same functionality. For example, three single-axis accelerometers may be configured to measure X axis acceleration, Y axis acceleration, and Z axis acceleration with an additional three single-axis gyroscopes configured to measure pitch, roll, and yaw angular velocities about those axes. Other sensors may also be used to measure the orientation, rotation, and/or position of the epidermal electronics device 100 and attachment surface 103. For example, a multi-axis accelerometer measuring X axis acceleration, Y axis acceleration, and Z axis acceleration may be used in conjunction with a multi-axis gyroscope to measure pitch, roll, and yaw angular velocities about those axes.

Figure 3A:
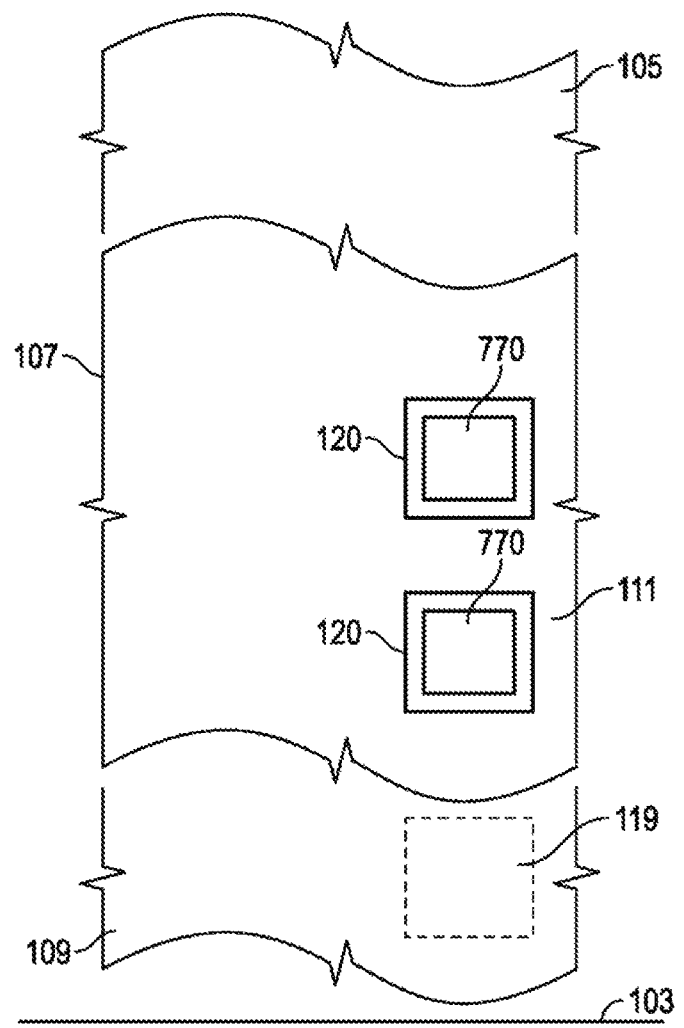
FIG. 3A is an exploded schematic view of an embodiment of the epidermal electronics device showing greater detail.

FIG. 3A illustrates an exploded schematic view of one embodiment of epidermal electronics device 100. This embodiment includes substrate layer 105, electronics layer 107 including layer of material 111, and barrier layer 109. Further included within barrier layer 109 are barrier openings 119.

Substrate layer 105 may provide physical support for electronics layer 107. Substrate layer 105 may also facilitate attachment of the epidermal electronics device 100, including electronics layer 107 and barrier layer 109, to the attachment surface 103. In some embodiments, substrate layer 105 may be discarded or dissolved after the epidermal electronics device 100 has been attached to attachment surface 103.

Electronics layer 107 is illustrated as including components on a layer of material 111. Layer 111 may be used to provide mechanical support to the components of electronics layer 107. It may also be used to facilitate manufacturing of electronics layer 107. In some embodiments, electronics layer 107 is made up only of the electronic components therein (e.g., there is no supporting layer of material). In such a case, electronics layer 107 may be manufactured on substrate layer 105 or barrier layer 109. Substrate layer 105 or barrier layer 109 provides the mechanical support necessary to make and use epidermal electronics device 100.

Substrate layer 105 provides protection to the components of the electronics layer 107. Substrate layer 105 may prevent external forces and elements from interfering with the functions of electronics layer 107. For example, substrate layer 105 may prevent moisture from reaching electronics layer 107. In some embodiments, substrate layer 105 may also prevent physical damage to the components of electronics layer 107. Substrate layer 105 may also shield electronics layer 107 from outside sources of radiation, magnetic fields, light, etc. In some embodiments, barrier layer 109 is permeable or semipermeable. For example, barrier layer 109 may be semipermeable to allow the transfer of drugs through barrier layer 109. Barrier layer 109, as depicted, may include one or more barrier openings 119. In one embodiment, barrier openings 119 correspond to a particular cell or group of cells 120. The barrier openings 119 allow for elements of electronics layer 107 to have direct contact with attachment surface 103. A sensor 770 may have direct contact with attachment surface 103 through barrier opening 119. In some embodiments, epidermal electronics device 100 may be configured with barrier openings 119 in order to better facilitate operation of one or more sensors 770. For example, allowing direct contact with attachment surface 103 may improve the accuracy of an orientation sensor such as an accelerometer. Likewise, a sensor such as a moisture sensor may have improved readings if in contact with attachment surface 103. Barrier openings 119 also facilitate the operation of interaction devices 780. Interaction devices 780 may operate more efficiently if in direct contact with attachment surface 103.

Figure 3B:
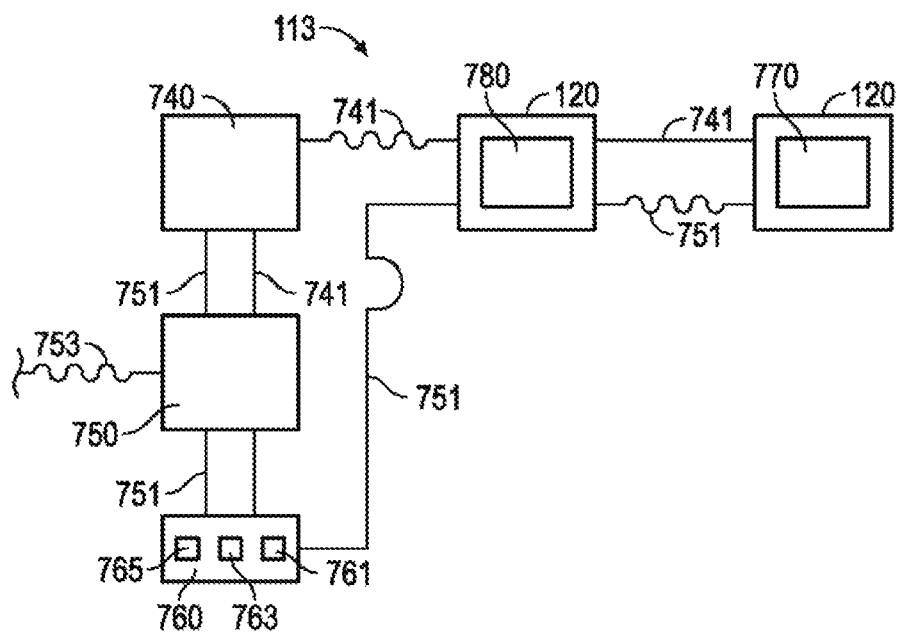
FIG. 3B is a schematic view of an embodiment of the epidermal electronics device showing greater detail of the electronics assembly.

FIG. 3B illustrates electronics assembly 113 according to one embodiment. Electronics assembly 113 includes components which are located in electronics layer 107. As depicted, electronics assembly 113 and the components therein may not be supported by an additional layer of material 111 (e.g., electronics assembly 113 may include only circuits and components without a supporting material or substrate). In some embodiments, electronics assembly 113 is produced on substrate layer 105 (not pictured in FIG. 3B). Electronics assembly 113 may include cells 120, sensors 770, interaction devices 780, power source 740 connected to other components via power connection 741, communications device 750 connected to other components via communications connection 753, control circuit 760, and input/output connection 751. In some embodiments, control circuit 760 further includes memory 761, processor 763, and multiplexer 765.

Interaction device 780 allows epidermal electronics device 100 to interact with attachment surface 103. Interaction device 780 may be configured to provide stimulation to the attachment surface in the form of applied voltage and/or drug delivery. For example, interaction device 780 may be a MEMS drug delivery system. Alternatively, interaction device 780 may be an electrode for delivering an applied voltage to the attachment surface. Interaction device 780 also allows external devices to interact with the epidermal electronics device 100. For example, a camera or motion capture system may monitor the position of the epidermal electronics device. Interaction device 780 may be a passive motion capture marker. Interaction device 780 may also be an active motion capture marker. In some embodiments, interaction device 780 is a light emitting diode (LED) controlled by control circuit 760. The LED may be illuminated intermittently to allow a motion capture system to record the orientation and/or movement of epidermal electronics device 100. This data may be used to calibrate epidermal electronics device 100. It may also be used as a constraint when estimating the orientation and movement of the epidermal electronics device from data gathered by sensors 770. For example, the orientation data from a motion capture system may be used as a boundary or limit when calculating the orientation of a body part using epidermal electronics device 100 (e.g., if a motion capture system determines that an arm has been rotated 30 degrees, a corresponding calculation made by the epidermal electronics device 100 may be limited to 30 degrees). In further embodiments, interaction device 780 includes a physiological sensor. The physiological sensor can be a wearable sensor. The physiological sensor can provide information about a user through contact with the skin of the user or proximity to the skin of the user. For example, the physiological sensor can include a heart rate sensor, a respiratory sensor, a thermal sensor, a blood pressure sensor, a hydration sensor, an oximetry sensor, an electrocardiograph, an electroencephalograph, electroneurograph, electrooculograph, and/or an electromyograph.

Multiple interaction devices 780 may be included in a single electronics layer 107 of epidermal electronics device 100. It is also possible for multiple interaction devices 780 to be located on more than one epidermal electronics device 100. Multiple epidermal electronics devices 100 and corresponding multiple interaction devices 780 may be coordinated and controlled using communication device 750 on each epidermal electronics device 100 as well as control circuit 760 on each epidermal electronics device 100.

Communications device 750 may be included in electronics assembly 113. Communications device 750 provides data transfer to and from the epidermal electronics device 100 through communications connection 753. Communications connection 753 may be a wire or wireless connection between communication device 750 and another source or receiver of data. For example, communications connection 753 may be a connection over a wireless network (e.g., WiFi, Zigbee, Bluetooth, etc.), a wired interface (e.g., Ethernet, USB, Firewire, etc.), or other communications connection (e.g., infrared, optical, ultrasound, etc.). In some embodiments, communications device 750 is a wireless networking device or wired networking device which establishes communication connection 753 and transmits and/or receives data/signals through communications connection 753.

Power connection 741 transfers power from power source 740 to other components in electronics layer 107. Power connection 741 provides power from power source 740 to communication device 750, control circuit 760, cells 120, and the components within cells 120 such as interaction devices 780 and sensors 770. Power connection 741 may be a wired or wireless connection. Power connection 741 may be a conductive wire (e.g., copper, aluminum, etc.). Power connection 741 may be a semiconductor. Where power connection 741 is a wired connection, power connection 741 is configured to maintain mechanical integrity when components of electronics layer 107 move relative to one another. For example, power connection 741 may be a length of wire long enough to allow movement of the components without causing deformation of power connection 741 sufficient to break the connection. Power connection 741 may also be a wireless connection for delivering power (e.g., direct induction, resonant magnetic induction, etc.).

Power source 740 provides electrical power to components within electronics layer 107. In one embodiment, power source 740 is a battery. For example, power source 740 may be a disposable battery, rechargeable battery, and/or removable battery. In some embodiments, power source 740 is configured to allow recharging of power source 740 without removing power source 740 from the electronics layer 107. For example, power source 740 may be a rechargeable battery configured to be recharged through wireless changing (e.g., inductive charging). In other embodiments, power source 740 is configured to receive direct current from a source outside the electronics layer 107. In further embodiments, power source 740 is configured to receive alternating current from a source outside the electronics layer 107. Power source 740 may include a transformer. In some embodiments, power source 740 is configured to receive power from a wireless source (e.g., such that power source 740 is a coil configured to receive power through induction). According to various alternative embodiments, power source 740 can be a capacitor which may be configured to be charged by a wired or wireless source, one or more solar cells, or a metamaterial configured to provide power via microwaves.

With continued reference to FIG. 3B, input/output connection 751 may be a wire connection between cell 120 and control circuit 760. Input/output connection 751 may be configured to allow the connection to flex and deform without suffering mechanical failure. In such a case, input/output connection 751 is configured to maintain the connection between cell 120 and control circuit 760 during deformation of the epidermal electronics device 100 due to movement of the attachment surface 103. In some embodiments, input/output connection 751 allows for deformation while maintaining mechanical integrity by including an additional length of wire which allows for connection points to separate from one another. For example, input/output connection 751 may be a wire with slack to allow two or more components to move relative to one another and not cause mechanical degradation of the input/output connection. In some embodiments, input/output connection 751 is a conductive wire (e.g., copper, aluminum, etc.). Input/output connection 751 may be a semiconductor. In some embodiments, input/output connection 751 is a wireless connection.

Input/output connection 751 allows the components within cell 120 to communicate data to control circuit 760. The component within cell 120 may output data to the control circuit through input/output connection 751. For example, sensor 770 located in cell 120 may output measurement data, in the form of a voltage, across input/output connection 751 to control circuit 760. Input/output connection 751 also allows for the control circuit to communicate with the component within cell 120. Control circuit 760 may send an input to a component within cell 120 through input/output connection 751. For example, control circuit 760 may send an input signal to interaction device 780 which causes interaction device 780 to deliver a drug or chemical to attachment surface 103. Cell 120 may also facilitate communication. Control circuit 760 may also send a calibration signal to sensor 770 or interaction device 780 using input/output connection 751. In some embodiments, power connection 741 and input/output connection 751 are integrated into a single connection. For example, an integrated connection may provide power and input/output through a modulated or otherwise alterable signal.

In some embodiments, electronics assembly 113 includes control circuit 760. Control circuit 760 may further include multiplexer 765, processor 763, and memory 761. Processor 763 may be implemented as a general-purpose processor, an application specific integrated circuit (ASIC), one or more field programmable gate arrays (FPGAs), a digital-signal-processor (DSP), a group of processing components, or other suitable electronic processing components. Memory 761 is one or more devices (e.g., RAM, ROM, Flash Memory, hard disk storage, etc.) for storing data and/or computer code for facilitating the various processes described herein. Memory 761 may be or include non-transient volatile memory or non-volatile memory. Memory 761 may include database components, object code components, script components, or any other type of information structure for supporting the various activities and information structures described herein. Memory 761 may be communicably connected to processor 763 and provide computer code or instructions to processor 763 for executing the processes described herein. Multiplexer 765 may be configured to allow multiple sensors 770 and/or interaction devices 780 to share an input/output connection 751. In some embodiments, cells 120 also facilitate multiplexing of signals from multiple components.

In some embodiments, control circuit 760 is configured to receive data from sensors 770. For example, control circuit 760 may receive acceleration data in the form of a measured voltage from an acceleration sensor. This data may be received by control circuit 760 through multiplexer 765. Control circuit 760 may store sensor data in memory 761. Control circuit 760 may output sensor data to communications device 750. In some embodiments, control circuit 760 is also configured to send control signals to sensors 770. For example, control circuit 760 may calibrate a sensor 770 by sending a control signal to the sensor. Control circuit 760 may also turn sensor 770 off or on. For example, control circuit 760 may send a control signal which causes cell 120 to disconnect sensor 770 from power connection 741. Control circuit 760 may also select which sensors to receive data from using processor 763 and memory 761. Control circuit 760 may receive control signals from communication device 750. In some embodiments, control circuit 760 also generates control signals with processor 763 and memory 761. For example, control circuit 760 may send a control signal to turn off a sensor 770 in response to abnormal data received from the sensor. Control circuit 760 may also send a control signal to turn off a sensor 770 in response to data from other sensors 770. For example, some sensors 770 may be turned off in order to conserve power source 740 if minimal acceleration is detected. When using multiple sensors, one sensor 770 may be maintained in the on position. When increased acceleration activity is detected, control circuit 760 may reactivate, or turn on, the remaining sensors 770.

In some embodiments, control circuit 760 is also configured to receive data from interaction devices 780. For example, control circuit 760 may receive drug delivery data from a drug delivery device. This data may be received by control circuit 760 through multiplexer 765. Control circuit 760 may store this data in memory 761. Control circuit 760 may output interaction device data to communications device 750. In some embodiments, Control circuit 760 is also configured to send control signals to interaction devices 780. For example, control circuit 760 may send a control signal to a drug delivery device causing the device to administer a drug to attachment surface 103. Control circuit 760 may also turn off and on interaction devices 780.

Control circuit 760 may receive signals from other components in electronics layer 107. For example, control circuit 760 may receive signals from communications device 750. Control circuit 760 may also receive signals from power source 740. For example, control circuit 760 may receive a signal from power source 740 indicating how much power is available. Control circuit 760 may use this to take further action. For example, control circuit 760 may communicate this or other information to another device using communications device 750. Control circuit 760 may also take action by controlling components of the electronics layer 107 including cells 120, interaction devices 780, and/or sensors 770. In some embodiments, the functions of control circuit 760 are carried out by the circuitry of cells 120. For example, cells 120 may include transistors and/or additional components which allow cell 120 or a network of cells 120 to perform the above described functions of control circuit 760. In other embodiments, control circuit 760 is located in an area not within electronics layer 107. In one embodiment, communications device 750 may send and receive control signals and data. For example, an external control circuit may perform the above described functions with communications device 750 relaying data between the components of the electronics layer 107 (e.g., sensors 770 and interaction devices 780) and the external control circuit.

Sensors 770 in electronics assembly 113 may include sensors configured to measure orientation data. Orientation data may include data regarding acceleration, orientation, movement, angular motion, and/or rotation of attachment surface 103. For example, sensors 770 may include one or more of single-axis accelerometers, multi-axis accelerometers, single-axis gyroscopes, multi-axis gyroscopes, single-axis inclinometers, or multi-axis inclinometers. In some embodiments, combinations of these sensors are used to measure acceleration, orientation, movement, angular motion, and/or rotation. In some embodiments, sensors 770 include sensors to measure characteristics of attachment surface 103. For example, sensors 770 may be moisture sensors, electrodes, temperature sensors (e.g., thermistors, thermocouples, etc.), light sensors, hydration sensors, etc. Interaction devices 780 may include devices configured to alter attachment surface 103 or provide data to control circuit 760. For example, interaction devices 780 may include drug delivery devices, chemical delivery devices, electrodes, motion capture sensors, LEDs, etc.

Figure 4A:
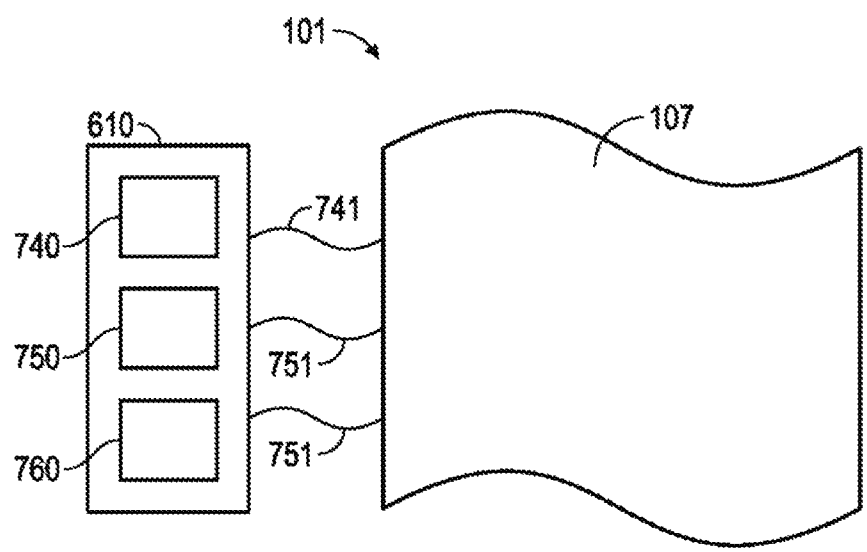
FIG. 4A is a schematic view of an additional embodiment of the epidermal electronics device.

FIG. 4A illustrates an embodiment of another epidermal electronics device shown as epidermal electronics device 101. In some embodiments, epidermal electronics device 101 houses large components in a separate housing from sensors and/or interaction devices in electronics assembly 113. These large components may be located outside of the flexible patch which includes electronics layer 107 and barrier layer 109. This is unlike epidermal electronics device 100 which includes the majority of components within electronics layer 107 (e.g., the majority of components are within the flexible patch). Epidermal electronics device 101 is shown with electronics module 610. Electronics module 610 may hold any or all of power source 740, communications device 750 and/or control circuit 760. In one embodiment, electronics module 610 is separate from electronics layer 107 shown with view 110 (e.g., electronics module 610 may house components outside of electronics assembly 113 and may provide for connection to electronics assembly 113). Electronics module 610 may be a housing containing the above mentioned components. For example, electronics module 610 may be a plastic or polymer housing with access to the components housed within. Electronics module 610 may also be a film or other protective encasement.

In some embodiments, electronics module 610 allows for power source 740, communications device 750 and/or control circuit 760 to be on a larger scale than if they were within electronics layer 107. For example, power source 740 may be a larger battery. Processing circuit 760 may be an integrated circuit or SOC. In some embodiments, electronics module 610 is connected to electronics layer 107 by power connection 741. Electronics module 610 may provide power from power source 740 to components of the electronics layer 107 (e.g., sensors, interaction devices, etc.) through power connection 741. In further embodiments, electronics module 610 is also connected to the electronics layer 107 by input/output connection 751. Electronics module 610 may be connected to electronics layer 107 and/or electronics assembly 113 by one or more input/output connections 751. This may facilitate the use of additional components (e.g., sensors, interactions devices, etc.). The use of multiple input/output connections 751 may reduce the need, partially or completely, for multiplexing.

Figure 4B:
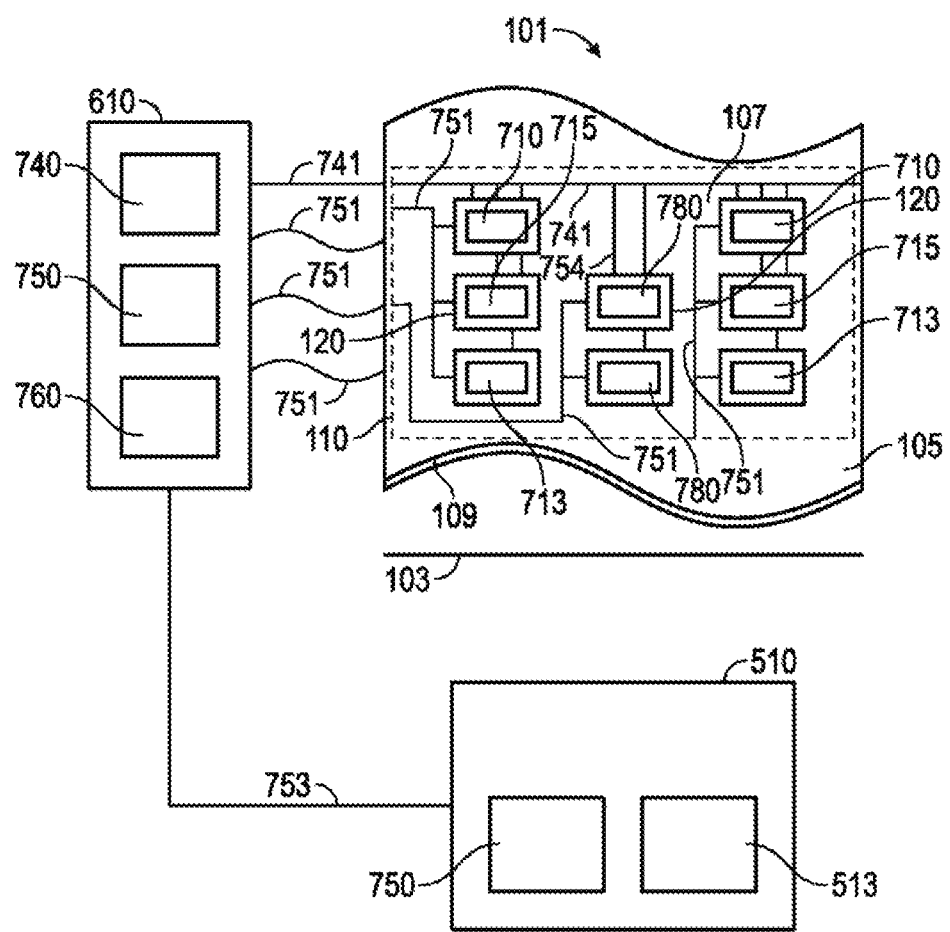
FIG. 4B is a schematic view of the electronics layer of an additional embodiment of the epidermal electronics device.

With reference to FIGS. 4A-4B, epidermal electronics devices 100 and/or 101 may measure the orientation, acceleration, movement, angular motion, rotation, angular velocity, angular acceleration, and/or position (e.g., orientation data) at one point of the attachment surface using a combination of a multi-axis accelerometer 710, multi-axis gyroscope 715, and multi-axis inclinometer 713. Using a combination of these sensors, the orientation, acceleration, movement, angular motion, rotation, angular velocity, angular acceleration, and/or position of the attachment surface may be determined with six degrees of freedom. Multiple combinations of sensors may be used to achieve measurement of six degrees of freedom.

In some embodiments, one type of sensor is used as a constraint on the measurements of another sensor. For example, the data gathered from the multi-axis inclinometer 713 may be used as a constraint on the data gathered by the multi-axis accelerometer 710 or multi-axis gyroscope 715. The angle-relative to gravity measurements of the multi-axis inclinometer may be used as a constraint on accelerometer or gyroscope data integration. In some embodiments, the sensors are integrating accelerometers. In some embodiments, measurements from inclinometers may be used directly (e.g., for angle relative to gravity). Inclinometer measurements may also be used as a check on orientation derived from the integration of data from multi-axis accelerometers 710 or from the integration of data from multi-axis gyroscopes 715. This may be used to limit error propagation. This may also include using inclinometer measurement data to verify data from other sensors and/or verify the orientation of the epidermal electronics device as determined using other data.

Epidermal electronics devices 100 and/or 101 may measure the orientation, acceleration, movement, angular motion, rotation, angular velocity, angular acceleration, and/or position at additional points of the attachment surface using additional sets of sensors. Epidermal electronics devices 100 and/or 101 may use these additional sensors (e.g., multi-axis accelerometer, multi-axis gyroscope 715, and/or multi-axis inclinometer 713) to measure orientation, acceleration, movement, angular motion, rotation, angular velocity, angular acceleration, and/or position at multiple points of the attachment surface 103 with one epidermal electronics device 100.

In some embodiments, orientation, acceleration, movement, angular motion, rotation, angular velocity, angular acceleration, and/or position are measured at multiple points using multiple epidermal electronics devices 100. Measurements from multiple epidermal electronics devices 100 and/or 101 (inter epidermal electronics device measurements) may be used as a constraint on other sensor measurements and integration. Constraints may be applied by the processing circuit 513. In some embodiments, constraints are applied by control circuit 760.

In some embodiments, multiple electronics layers 107, each with its own separate barrier layer 109 and substrate layer 105 (e.g., multiple epidermal electronics patches), connect to the same electronics module 610. This may allow for measurement and interaction at multiple points on attachment surface 103 with a single supporting power source 740, communications device 750, and control circuit 610.

With continued reference to FIG. 4B, electronics module 610 may be connected to data acquisition and processing device 510 via communications connection 753. Data acquisition and processing device 510 includes communications device 750. Communications device 750 allows data acquisition and processing device 510 to receive and send data and/or control signals to communications device 750 in electronics module 610. In some embodiments, communication device 750 in data acquisition and processing device 510 may receive and send data and/or control signals to communications device 750 in electronics layer 107 of an epidermal electronics devices 100 and/or 101.

In some embodiments, data acquisition and processing device 510 also includes processing circuit 513. Processing circuit 513 receives data from epidermal electronics devices 100 and/or 101. Processing circuit 513 analyzes the data. For example, processing circuit 513 may use algorithms to calculate or estimate the orientation, acceleration, movement, rotation, angular velocity, and/or position of the epidermal electronics devices 100 and/or 101. These algorithms may include a Kalman filter, dynamic filter, a customized algorithm, etc. Processing circuit 513 may calculate or estimate the orientation, acceleration, movement, angular motion, angular acceleration, rotation, angular velocity, and/or position of one or more locations on an epidermal electronics device 100 and/or 101 or multiple epidermal electronic devices 100 and/or 101.

In some embodiments, processing circuit 513 also sends control signals to epidermal electronics device 100. For example, processing circuit 513 of data acquisition and processing device 510 may send a control signal to epidermal electronics device 100, using communication devices 750, to calibrate sensor 770. To facilitate the above functions, processing circuit 513 and/or data acquisition and processing device 510 may include one or more of processors and memory.

Data acquisition and processing device 510 may output data, control signals, and/or estimations or calculations regarding orientation, acceleration, movement, angular motion, rotation, angular velocity, angular acceleration, and/or position to additional computing devices. Data acquisition and processing device 510 may also output to one or more epidermal electronics devices 100 and/or 101. This may include outputting data gathered by one epidermal electronics device 100 or 101 to a second epidermal electronics device 100 or 101. In some embodiments, data acquisition and processing device 510 includes a user interface. In other embodiments, data acquisition and processing device 510 is controlled with an additional computer. In some embodiments, data acquisition and processing device 510 may also output data to another computer. In some embodiments, an epidermal electronics device 100 with power source 740, communications device 750, and control circuit 760 integrated in electronics layer 107 is connected to data acquisition and processing device 510.

Figure 5:
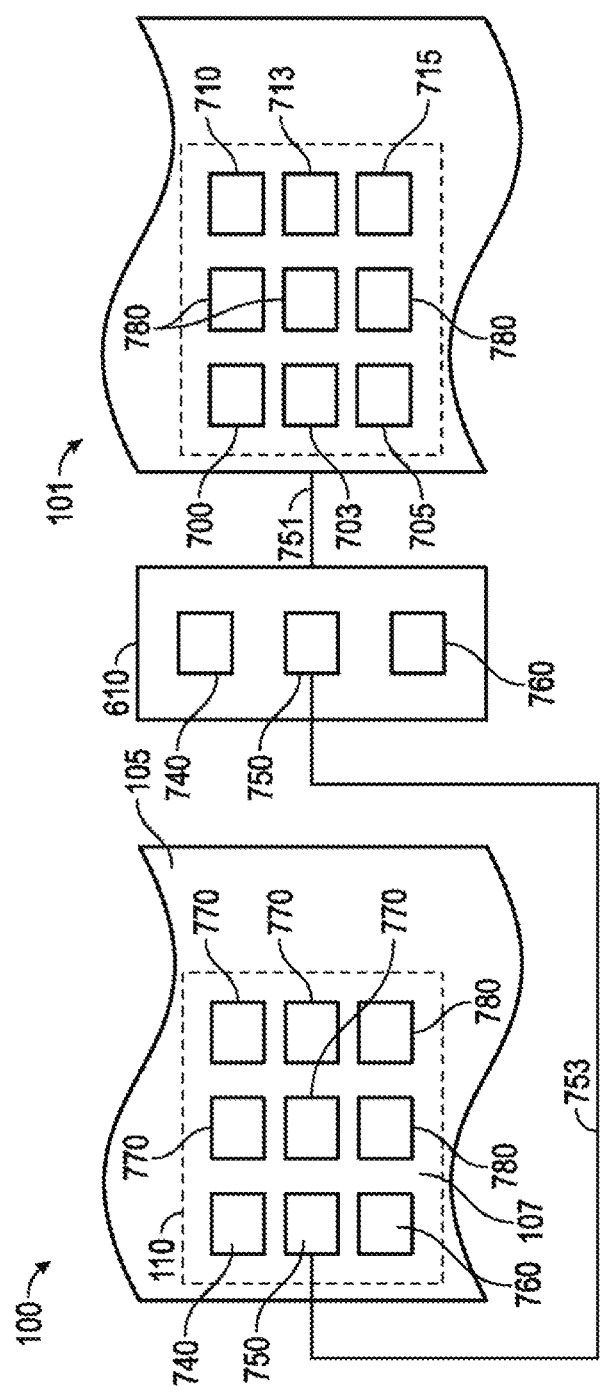
FIG. 5 is a schematic view of two embodiments of the epidermal electronics device in communication with each other.

FIG. 5 illustrates an embodiment of epidermal electronics devices 100 and 101 in communication with one another. Two or more epidermal electronics devices 100 or 101 may communicate with one another through communications connection 753 and communication devices 750. Communications connection 753 may be a wireless connection or a wired one. Multiple epidermal electronics devices 100 may also communicate with data acquisition and processing device 510. Using two or more epidermal electronics devices 100 or 101 allows for multiple points to be measured simultaneously. For example, the orientation, acceleration, movement, rotation, angular velocity, angular acceleration, and/or position of one point may be measured relative to that of another through the use of two or more epidermal electronics devices 100.

Figure 6:
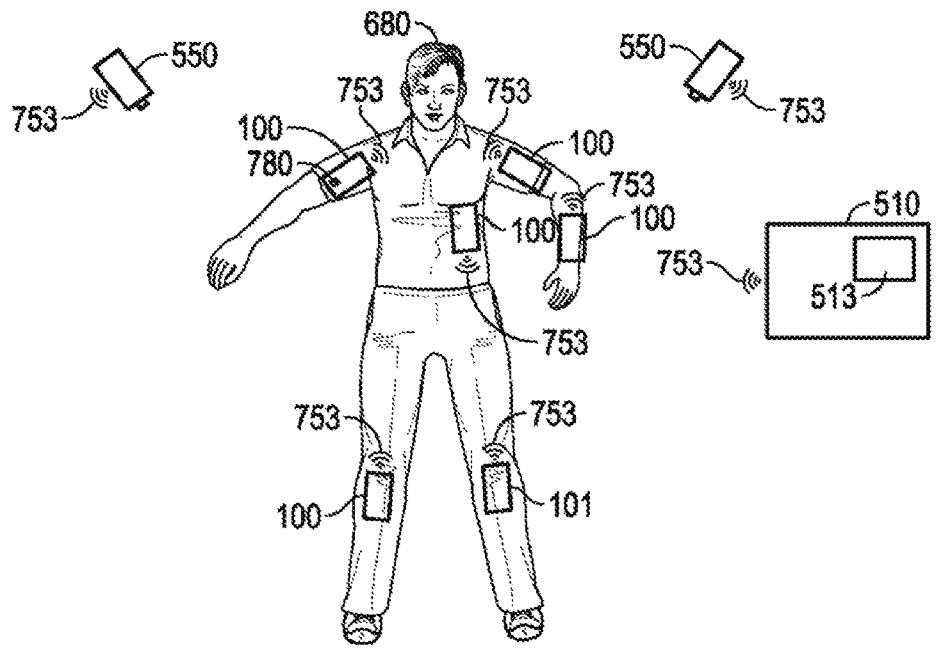
FIG. 6 is a schematic view of an embodiment the epidermal electronics device as used to measure orientation relative to several body parts.

FIG. 6 illustrates one embodiment of multiple epidermal electronics devices 100 used with user 680. In one embodiment, multiple epidermal electronics devices 100 are attached to user 680. Epidermal electronics devices 100 may communicate using wireless communications connection 753. Data may be communicated to data acquisition and processing device 510 which may include processing circuit 513. External sensing devices 550 may also be used to gather information about user 680 and/or epidermal electronics devices 100. External sensing devices 550 may also communicate data with wireless communication connection 753.

In one embodiment, epidermal electronics devices 100 are placed on various body parts of user 680. For example, epidermal electronics devices may be placed on fingers, hands, forearms, upper arms, feet, legs, the head, etc. In some embodiments, the attachment surface 103 of user 680 is his or her skin. Each epidermal electronics device may measure orientation with one of or a combination of single or multi-axis accelerometers, single or multi-axis inclinometers, or single or multi-axis gyroscopes. Epidermal electronics devices 100 may communicate with one another and/or with data acquisition and processing device 510 using communications connection 753 and communications devices 750. In this embodiment, communications connection 753 is illustrated as a wireless connection. In some embodiments, epidermal electronics devices 100 may form a network (e.g., ad hoc network). The network of epidermal electronics devices 100 may communicate data and control signals to other networks of epidermal electronics devices 100. Multiple networks of epidermal electronics devices 100 may share information. This may allow data to be collected from multiple networks (e.g., one network per user, with multiple users) by a single data acquisition and processing device 510.

FIG. 6 further illustrates that two or more epidermal electronics devices 100 may be used to measure attachment surface parameters (e.g., orientation, acceleration, movement, angular motion, rotation, angular velocity, angular acceleration, and/or position) relative to one another. As is illustrated, the attachment surface parameters of a forearm may be measured relative to the attachment surface parameters of an upper arm. This allows epidermal electronics devices 100 and data acquisition and processing device 510 to determine the orientation or movement of the forearm relative to the upper arm. The relative orientation, acceleration, movement, angular motion, rotation, angular velocity, angular acceleration, and/or position of one body part to another may be measured in this way. For further example, the orientation of a finger may be determined relative to a hand. Epidermal electronics devices 100 may also be used to measure a change in attachment surface parameters. Such changes may be used to determine motion of a user, such as gait, gestures, athletic motions (e.g., golf swings, pitching motions, etc.), or the like. This measurement may be made absolutely by a single epidermal electronics device 100 or relative to an additional one or more epidermal electronics device 100. For example, as a user's leg moves, the change in orientation and angular velocity may be measured. This measurement may be made absolutely by epidermal electronics device 100. The measurement may also be made relative to the moving torso of user 680. In that case, measurements are collected by epidermal electronics device 100 on the torso and epidermal electronics device 100 on the leg. The relative orientation and angular velocity may be calculated by data acquisition and processing device 510. In some embodiments, a single epidermal electronics device 100 may be used to measure attachment surface parameters at multiple locations. This may include multiple locations across multiple body parts. For example, a single epidermal electronics device 100 may measure the orientation of the torso and a leg of user 680.

Data acquisition and processing device 510 may use a variety of techniques to determine or estimate the orientation, acceleration, movement, angular motion, rotation, angular velocity, angular acceleration, and/or position of user 680. Data acquisition and processing device 510 may also use the same or other techniques to determine the posture and/or gestures of user 680. These techniques may include applying algorithms, Kalman filters, and/or other dynamic filters to measurements and/or applying constraints provided by one or more epidermal electronics devices 100. For example, a Kalman filter may be used to estimate the orientation of epidermal electronics device 100 attached to a body part of a user. The orientation can be described by various types of state vectors, such as Euler angles, quaternions, etc. Because some of the sensors used by epidermal electronics device 100 measure angular motion (e.g., angular velocity via gyroscopes, angular acceleration via accelerometers) rather than directly measuring orientation (e.g., via inclinometers, field sensors, etc.) physics-based dynamic filters (e.g., Kalman filters) can be used to estimate the orientation. Such filters may incorporate additional state variables (such as angular velocity and/or angular acceleration), which are linked via a state propagation model (e.g., continuous propagation via differential equations, discrete propagation via state transition matrices). The dynamic filter incorporates measurements related to the state variables (e.g., opposed accelerometer measurements for angular acceleration, gyroscope measurements for angular velocity, inclinometer or field measurements for angular orientation, etc.) each of which may depend on a single state variable or multiple ones (e.g., angular motion measurements often also depend on the direction of the sensor, and hence on the orientation). The dynamic filter can include estimates of the noise in such measurements, and hence in the uncertainty in its estimate of each state variable; these uncertainty estimates can be tracked throughout time by the filter. Dynamic filters can readily be formulated to handle different state vector representations (e.g., angles vs quaternions), different measurement types (combinations of direct angular measurements and/or angular velocity and/or angular acceleration), and different sensors (e.g., magnetometers vs inclinometers, rotational vs ring-laser vs vibratory gyroscopes). A comparison of various dynamic filters for use in body sensor networks is presented in "Analysis of Filtering Methods for 3D Acceleration Signals in Body Sensor Network", Wei-zhong Wang, Bang-yu Huang, Lei Wang, Bulletin of Advanced Technology Sensors, Vol 5, No 7, 2011. Presentations of Kalman filters used for 3D orientation estimation include: "Design, Implementation, and Experimental Results of a Quaternion-Based Kalman Filter for Human Body Motion Tracking", Xiaoping Yun, Eric Bachmann, IEEE Transactions on Robotics, Vol 22, No 6, 2006; "Kalman-Filter-Based Orientation Determination Using Inertial/

Magnetic Sensors: Observability Analysis and Performance Evaluation", Angelo Sabatini, Sensors, Sep. 27, 2011; "Using an Extended Kalman Filter for Rigid Body Pose Estimation", Kjartan Halvorsen, et al, Journal of Biomechanical Engineering, Vol 127, p 475 (2005); and "An Extended Kalman Filter for Quaternion-Based Orientation Estimation Using MARG Sensors", Joao Marins, et al, 2001 IEEE/RSJ International Conference on Intelligent Robots and Systems, Maui Oct. 29-Nov. 3, 2001. In some embodiments, constraints are supplied by other sources such as models of human movement, external sensing devices, etc. In some embodiments, constraints may define ranges in which the measurements of epidermal electronics device 100 may be considered valid. Data acquisition and processing device 510 may combine various measurements and/or constraints using a Kalman or other dynamic filter. This may result in a better estimate of unknown variables than one based on one measurement or data point. Additionally, signal noise and inaccuracies may be reduced.

Multiple epidermal electronics devices 100 may also be used to measure the state of user 680. Epidermal electronics devices may be used to measure the posture of user 680. By measuring orientation, acceleration, movement, angular motion, rotation, angular velocity, angular acceleration, and/or position at one or more locations, the user's posture may be determined. For example, it can be determined whether a user 680 is sitting, standing, or lying down using inclinometers and accelerometers measuring various body parts. If a person is sitting, inclinometers on the torso and on a leg will give different readings of the angle relative to gravity. Corresponding accelerometer or gyroscope readings indicating little or no acceleration could indicate that a user 680 is sitting. Alternative configurations and sensors may be used to detect a variety of postures. In some embodiments, the posture measured includes the positioning of one or more body parts during movement or a particular type of movement. For example, epidermal electronics devices 100 may measure the posture of a user 680 while running to ensure proper form or to be used to improve form. For example, epidermal electronics devices 100 may measure the posture of a user 680 while swinging a golf club to ensure proper form or to be used to improve form. In some embodiments, a single epidermal electronics device 100 may be used to measure attachment surface parameters at multiple locations.

Multiple epidermal electronics devices 100 may be used to measure gestures made by user 680. The orientation, acceleration, movement, angular motion, rotation, angular velocity, angular acceleration, and/or position of specific body parts along with the change in the same parameters may be measured. For example, epidermal electronics devices 100 placed on the fingers, hands, and arms may be used to detect gestures made using those body parts. For example, measuring the orientation, acceleration, movement, angular motion, rotation, angular velocity, angular acceleration, and/or position of those body parts along with the change in the same parameters may allow for sign language to be interpreted. In some embodiments, gestures are defined as any particular movement or movements of one or more body parts. Epidermal electronics device 100 may measure movements, and data acquisition and processing device 510 may compare the movements to a library of gestures. The library of gestures may contain the movements comprising gestures. Using the comparison, data acquisition and processing device 510 may estimate or determine if a gesture has been made.

In determining the posture and/or gestures of user 680, a human model may be used in conjunction with one or more epidermal electronics devices 100 and data acquisition and processing device 510. A human model may be a computer model of human movement and provide a way of checking measured movements against a model of all possible movements. A human model may include a human connectivity model, a musculoskeletal model, or other model of movement. The human connectivity model may model a human as an interconnected set of rigid bodies with defined shapes, connected via joints with defined angular constraints. Presentations of such models include: "Motion Models for People Tracking", David Fleet, Visual Analysis of Humans, Chapter 10, Springer-Verlag (2011); and "A 3-D Biomechanical Skeleton Model for Posture and Movement Analysis", Moreno D'Amico, et al, Research into Spinal Deformities 5, IOS Press (2006). This system of defined rigid bodies, interconnectivities, and joints can be used to model postures and postural motions based upon orientation sensing epidermal electronics devices on one or more body parts. The model may be generic or may be personalized for an individual user. In some embodiments, a generic or personalized model is adjusted using measurements provided by epidermal electronics device 100. The human model may be used by the data acquisition and processing device to assist in determining or estimating the posture and/or gestures of user 680. For example, a human connectivity model may be used as a constraint on sensor measurements and integration when determining or estimating the orientation, acceleration, movement, angular motion, rotation, angular velocity, angular acceleration, and/or position of a point measured by epidermal electronics device 100. In some embodiments, further constraints include measurements from additional sensors such as inclinometers. The measurements from one or more inclinometers or magnetometers may be used as a check on orientation estimated from an accelerometer. This technique may be used to limit error propagation. In some embodiments, further constraints may also include inter epidermal electronics device measurements.

With continued reference to FIG. 6, one or more external sensing devices 550 may be used in conjunction with epidermal electronics device 100. In some embodiments, external sensing device 550 is a device external to epidermal electronics device 100 used to measure orientation, acceleration, movement, angular motion, rotation, angular velocity, angular acceleration, and/or position. External sensing device 550 may be a camera or motion capture image sensor. External sensing devices 550 may be used to intermittently make measurements to determine posture. For example, images from external cameras may be used to measure the orientation, acceleration, movement, angular motion, rotation, angular velocity, angular acceleration, and/or position of a user 680. In some embodiments, measurements from motion capture image sensors of active or passive interaction devices 780 are used to determine the orientation, acceleration, movement, angular motion, rotation, angular velocity, angular acceleration, and/or position of a user 680. Measurements from one or more external sensing devices 550 may be used to reset epidermal electronics device 100 based determinations. For example, measurements taken from an external sensing device 550 may be used to calibrate the sensors of one or more epidermal electronic devices 100. In some embodiments, the measurements from external sensing devices 550 may be used to update or individualize a human model for a user 680. The human model may also serve as a calibration point for the sensors of one or more epidermal electronics devices 100. Interaction devices 780 may also be calibrated in the same fashion. In some embodiments, external sensing device 550 is connected to data acquisition and processing device 510 via communication connection 753. External sensing device 550 may include communications device 750 to facilitate communication via communication connection 753. In some embodiments, external sensing device 550 may be connected to control circuit 760 via communications connection 753 and communications device 750.

In one embodiment, an epidermal electronics device 100 determines its position and/or movement relative to another location using an antenna and a field source at the other location. Sensors 770 may be or include one or more antennas. For example, the antenna or antennas may be one or more of a dipole antenna, loop antenna, plate antenna, magnetometer, vector magnetometer, and/or other types of antennas. Epidermal electronics device 100 may use one or more antennas to measure a field source. Based on the measurement of one or more field source, epidermal electronics device 100 may estimate the location, orientation, angular motion, rotation, and/or other movement of epidermal electronics device 100 relative to the field source.

The field source may be a source of any measurable field. For example, the field source may be a source of a magnetic field, electromagnetic radiation (e.g., microwaves, radio waves, etc.), and/or other source of a measurable field. The field source may be a microwave generator and/or antenna, radio transmitter and/or antenna, or other combination of hardware configured to generate a measurable field. In some embodiments, a natural field source can be used, for instance epidermal electronics device may use a magnetometer to measure the Earth's magnetic field, and hence determine one or more angular components of its orientation. Epidermal electronics device 100 may include one or more antennas for measuring the type of field generating by the field source. Epidermal electronics device 100 may include additional hardware for the reception and/or measurement of one or more field sources. For example, epidermal electronics device 100 may include a receiver, signal processing hardware, and/or other hardware.

In one embodiment, the field source is emitted by a second epidermal electronics device 100. This may allow the first epidermal electronics device 100 to determine its location, orientation, angular motion, rotation, and/or other movement relative to the second epidermal electronics device 100 which emits the field source. Orientation information may be sent from the other location to epidermal electronics device 100 containing information about the field source, e.g., type, spatial field pattern, frequency, orientation of the source, etc. The field source may be or be included in interaction device 780. In other embodiments, the field source may be fixed. For example, the field source may be a fixed emitter which generates a field encompassing one or more separate epidermal electronics devices 100. As the field source is fixed, one or more epidermal electronics devices 100 may measure individual absolute location, orientation, angular motion, rotation, and/or other movement relative to the fixed field source. The fixed field source may be included in data acquisition and processing device 510 or another fixed device. In some embodiments, one or more epidermal electronics devices 100 may determine their location, orientation, rotation, angular motion, and/or other movement relative to other epidermal electronics devices 100. In some embodiments, the epidermal electronics device may estimate its absolute location, orientation, rotation, angular motion, and/or other movement by combining the relative information with corresponding absolute information for the other epidermal electronics devices.

In one embodiment, an epidermal electronics device 100 determines its position and/or orientation relative to another location (e.g., a second epidermal electronics device) using a range sensor and a range-determination source at the other location. Range sensors may include one or more receivers for detecting a range signal generated by the range-determination source. For example, the range-determination source may generate range signals comprising pulsed ultrasound waves or pulsed electromagnetic waves. The range sensor (an ultrasound or an electromagnetic detector respectively) can detect the incident waves and, based on time-of-arrival, determine the range between the range-determination source and the range sensor. A single range sensor can be used to detect the range itself. However, in some embodiments, epidermal electronics device 100 comprises multiple range sensors, and uses the differential ranges of each from the range-determination source, to determine the orientation of epidermal electronics device relative to the range determination source. Orientation information may be sent from the other location to epidermal electronics device 100 containing information about the range-determination source, e.g., pulse timing, wave frequency, emission pattern, orientation of the source, etc. For example, two range sensors can be used to determine one angular component of the orientation, while three range sensors can be used to determine two angular components of the orientation. In one embodiment, the roles of the range sensor and the range-determination sources can be reversed; here epidermal electronics device 100 can comprise multiple (e.g., 2 or 3) range-determination sources, and another location (e.g., a second epidermal electronics device) can comprise a range sensor. Differential range measurements by the range sensor can be used to determine the orientation of epidermal electronics device 100. In some embodiments, epidermal electronics device 100 comprises both one or more range-determination sources and one or more range sensors, using reflectors (e.g., diffuse, specular, or retro) at another location to return range signals from the range-determination source to the range sensors, allowing determination of the range and/or orientation between epidermal electronics device 100 and the other location.

In further embodiments, a plurality of fields may be used to measure location, orientation, rotation, angular motion, and/or other movement relative to multiple field sources (fixed and/or moving). For example, field sources may have different timings or frequencies in order to allow epidermal electronics devices 100 to distinguish between a plurality of field sources. This may allow for additional techniques for estimating the location, rotation, and/or other movement of one or more epidermal electronics devices. For example, epidermal electronics device 100 may triangulate its location using a plurality of field sources.

In other above described embodiments, the estimation of absolute and/or relative position, orientation, rotation, angular motion, and/or other movement may be calculated by one or more epidermal electronics device 100. For example, calculations may be performed using one or more control circuits on one or more epidermal electronics devices 100. Epidermal electronics devices 100 may communicate information for use in these calculations using one or more of the techniques described herein. In other embodiments, calculations are performed remote from the epidermal electronics devices 100. For example, one or more epidermal electronics devices 100 may communicate information (e.g., field measurements) to data acquisition and processing device 510 which may perform the calculations described herein.

Still referring to FIG. 6, measurements and/or estimates of location, position, orientation, rotation, and/or other movement may be used in performing a variety of actions and/or further calculations. Orientation, motion, and/or location may be used as a parameter to control one or more interaction devices 780. For example, orientation, motion, or location may be used to control a drug delivery system. If user 680 is lying down (e.g., as determined by epidermal electronics device 100 and/or data acquisition and processing device 510), a drug delivery system may be instructed not to deliver pain medication. Conversely, if a user 680 is moving, the drug delivery system may be instructed by data acquisition and processing device 510 and/or control circuit 760 to administer pain medication.

By measuring the orientation, acceleration, movement, angular motion, rotation, angular velocity, angular acceleration, and/or position and/or the change in the foregoing after an interaction device has been triggered, the effect of the interaction may be measured. This may also allow the interaction device 780 to be calibrated. For example, if a measured parameter (e.g., posture of user 680 during movement) does not show improvement, a larger dose of a drug may be used next time the interaction device 780 is activated.

Additionally, orientation, motion, and/or location may be used to control sensors 770. For example, if a user is in a lying down position, sensors 770 and/or interaction devices 780 may be turned off to conserve power. In some embodiments, any of the parameters described herein (e.g., orientation, posture, acceleration, etc.) may be used as the basis of an alert. Epidermal electronics device 100 may provide an alert when a certain parameter or parameters exceeds a threshold. For example, if rapid acceleration in an event such as a car crash is detected, LEDs on the epidermal electronics device may be illuminated, or illuminated in a particular color corresponding to severity, to alert a viewer as to possible injury. This type of configuration may be used in other settings as well (e.g., physical therapy). In some embodiments, the alert is provided by data acquisition and processing device 510. Data acquisition and processing device 510 may provide the alert using a display. Data acquisition and processing device 510 may provide the alert to another device or computer (e.g., provide an alert to a mobile computing device or phone).

Figure 7:
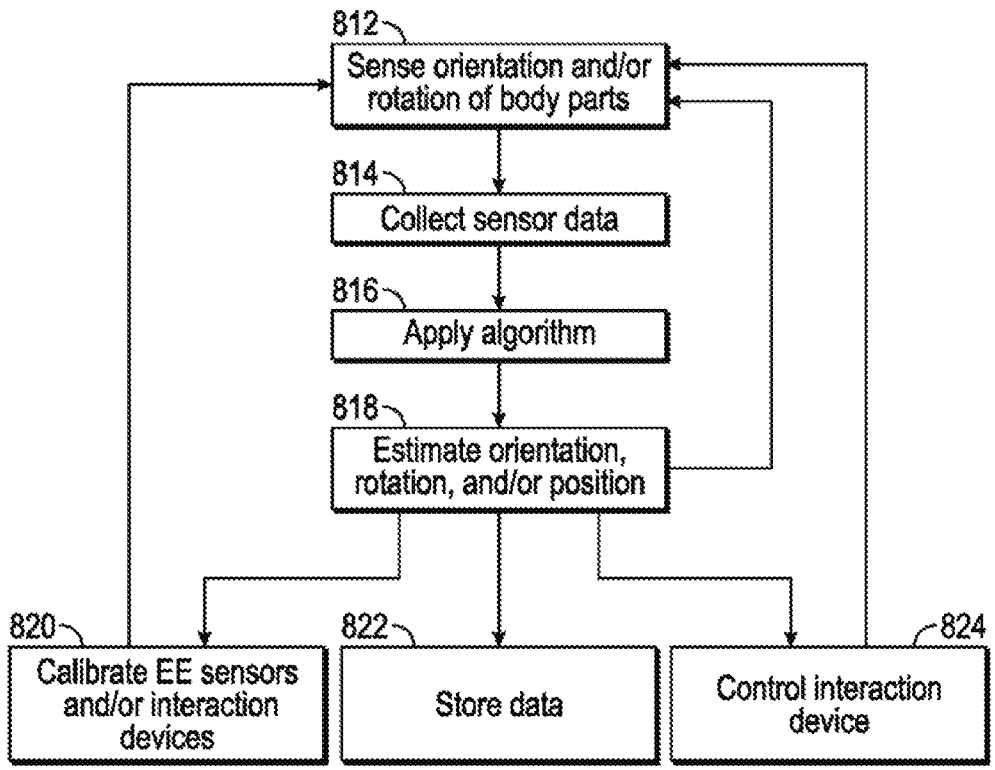
FIG. 7 is a flow chart detailing operation of one embodiment of the epidermal electronics device.

Referring now to FIG. 7, method 810 of using one or more epidermal electronics devices to measure orientation is shown according to one embodiment. Data regarding the orientation and/or angular motion of the surface to which the epidermal electronics device is attached is provided (812). This may be accomplished with any combination of sensors previously described. The sensor data is then collected (814). For example, a control circuit may collect/acquire the data. The control circuit may collect/acquire the data using, in part, a multiplexer. In some embodiments, cells assist in multiplexing. In some embodiments, the sensor data is then communicated to a data acquisition and processing device. This may be done using a combination of the control circuit and the communications device. An algorithm is applied to the sensor data (816). In some embodiments, the data acquisition and processing device applies the algorithm. In other embodiments, the control circuit applies the algorithm. One or more algorithms may be used, and the algorithms may perform a variety of functions. For example, algorithms may be used to reduce signal noise, eliminate extraneous data points, generate constraints for calculating the orientation and/or position of the attachment surface, etc. The algorithms used may include a Kalman filter, dynamic filter, or other custom filter. The orientation, motion, rotation, and/or position of the attachment surface and/or epidermal electronics device is estimated or calculated (818). In some embodiments, the data acquisition and processing device uses the sensor data and/or constraints to estimate or calculate orientation, motion, rotation, and/or position of the attachment surface and/or epidermal electronics device. In other embodiments the control circuit uses the sensor data and/or constraints to estimate or calculate orientation, motion, rotation, and/or position of the attachment surface and/or epidermal electronics device. In further embodiments, one or more algorithms are also used to perform calculations. Posture may be estimated in addition to or instead of orientation, rotation, and/or position of the attachment surface and/or epidermal electronics device. In some embodiments, the location, orientation, motion, and/or rotation of a body part may be referenced to a position in/on the body part which differs from that of the attachment surface and hence epidermal electronics device 100 (for instance, the reference site of a forearm may be at the midpoint of the radius bone while the attachment surface is located on the outer skin surface near the wrist; in such cases, the locations, orientations, motions, and rotations at the two locations may differ by straightforwardly applied offsets. In performing these calculations (e.g., to determine orientation or posture), the data acquisition and processing device may use constraints or checks generated from other sources. For example, constraints may be supplied by the algorithms, additional sensors such as inclinometers, and/or external sensing devices such as motion capture image sensors. Following the estimation or calculation of the orientation, rotation, motion, and/or position of the attachments surface, the epidermal electronics device may begin the cycle again by using sensors to produce data regarding the orientation and/or rotation of the surface to which the epidermal electronics device is attached. In some embodiments, steps (812)-(818) are performed simultaneously as in data pipelining. For example, as a first set of data is being used to calculate orientation, a second set may be filtered using an algorithm, a third set may be collected by the control circuit, and a fourth set may be generated by the sensors.

Simultaneously with the next cycle of steps, additional actions may be taken. In some embodiments the additional actions are taken before the next cycle of steps begins. After the estimation or calculation of the orientation, rotation, and/or position of the attachments surface, the sensors and/or interaction devices may be calibrated (820). The data acquisition and processing device may determine that a sensor and/or interaction device needs to be calibrated. Using data from other sensors onboard the epidermal electronics device, data from external sensing devices, models, and/or calculated constraints, the data acquisition and processing device, in conjunction with the control circuit, may calibrate a sensor or interaction device. In some embodiments, the calibration is done solely by the control circuit. The data acquisition and processing device may be able to override a predetermined calibration algorithm run by the processing circuit. In addition to calibrating sensors and/or interaction devices and/or controlling an interaction device, or in isolation, various types of data may be stored (822). In some embodiments, data is stored by the data acquisition and processing device. In other embodiments, data is stored by the control circuit. The data may be stored locally within the data acquisition and processing device or may be transferred to an additional computer, display device, mobile device, etc. In some embodiments, the results and/or only a portion of the data is stored. In some embodiments, the data is temporarily stored such that a device may display the data and/or a graphical representation of the data. In addition to calibrating sensors and/or interaction devices and/or storing data, or in isolation, one or more interaction devices may be controlled (824). The data acquisition and processing device, in conjunction with the control circuit, may activate one or more interaction devices. For example, upon determining a particular orientation of a user, the data acquisition device and control circuit may activate an interaction device to deliver a drug. In some embodiments, interaction devices are controlled by the control circuit without input from a data acquisition and processing device.

Figure 8:
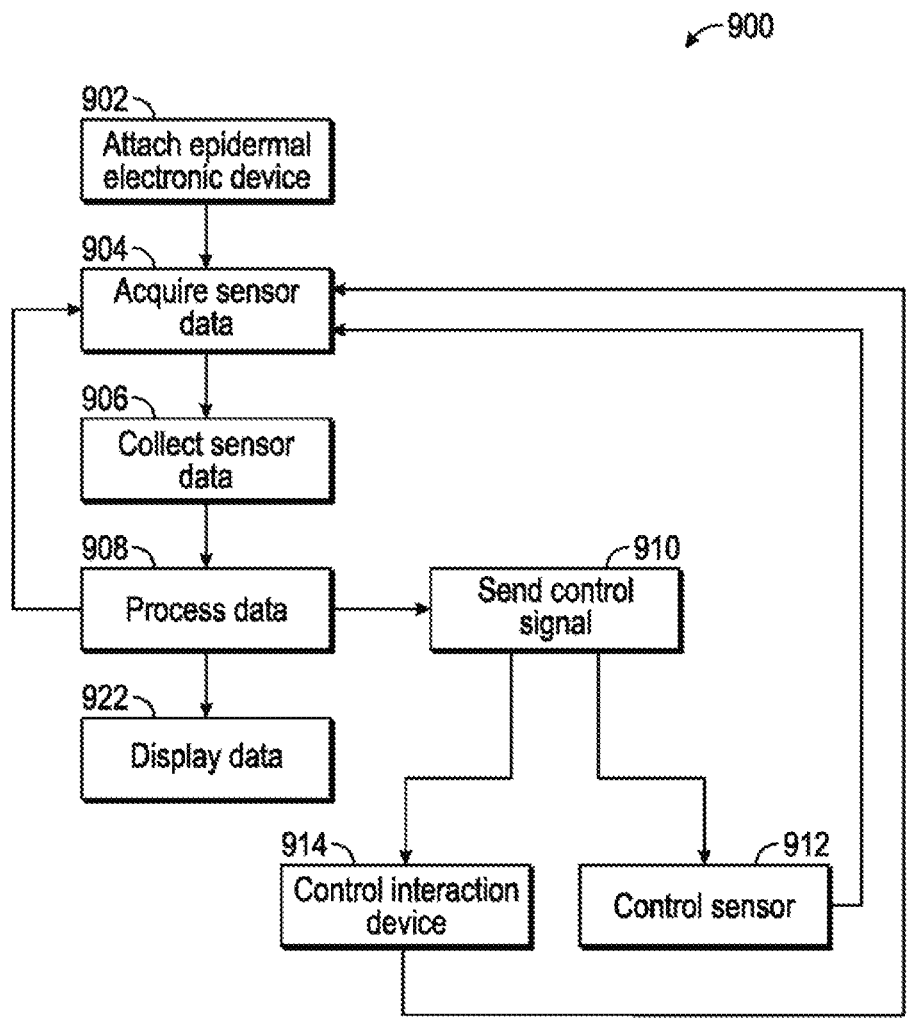
FIG. 8 is a flow chart with additional detail showing the operation on an embodiment of the epidermal electronics device.

Referring now to FIG. 8, method 900 of operation of an epidermal electronics device is shown according to one embodiment. The epidermal electronics device is attached (902). The epidermal electronics device is attached to attachment surface 103 which may include skin, bone, muscle tissue, the heart, the lungs, etc. In some embodiments, attachment surface 103 is a bandage attached or to be attached to the skin or other organ. Sensor data is acquired (904). Acquiring sensor data may include measuring one or more parameters of attachment surface 103. In some embodiments, sensors 770 in epidermal electronics device 100 measure one or more parameters of attachment surface 103. For example, sensors 770 may measure the orientation of attachment surface 103 as approximated by the orientation of electronics layer 107 in epidermal electronics device 100. Sensors 770 may also measure the rate of change in the orientation, acceleration, movement, angular motion, rotation, angular velocity, angular acceleration, and/or position of attachment surface 103. In some embodiments, the rate of change of these parameters is calculated by either control circuit 760 or data acquisition and processing device 510. The sensor data is collected (906). For example, the sensor data is collected by control circuitry. This may be accomplished using multiplexer 765 within control circuit 760. The data is processed (908). For example, control circuit 760 may use processor 763 and memory 761 to calculate the orientation of epidermal electronics device 100. The data may be processed by a variety of techniques to estimate or calculate orientation, acceleration, movement, angular motion, rotation, angular velocity, angular acceleration, and/or position of epidermal electronics device 100. For example, control circuit 760 may use a Kalman filter, dynamic filter, or other algorithm to calculate or estimate the orientation of epidermal electronics device 100. Control circuit 760 may also use constraints in making calculations such as data from other sensors 770 in epidermal electronics device 100, data from another epidermal electronics device 100, data from external sensing devices 550, and/or models. Control circuit 760 may also monitor sensors 770 for irregular measurements.

After acquiring and processing the data, the data is displayed (922). In some embodiments, control circuit 760 sends the data to data acquisition and processing device 510 to be displayed. In other embodiments, data acquisition and processing device 510 displays the data. The data displayed may be one of or a combination of the raw sensor data, constraints, models, processed data, estimated orientation, acceleration, movement, angular motion, rotation, angular velocity, angular acceleration, and/or position of the attachment surface, graphical representations of position, orientation, gait, and/or posture, etc. In some embodiments, the data is displayed on another computer or device to which data acquisition and processing device 510 sends the relevant information. Method 900 may begin again by measuring one or more parameters with sensors 770 of epidermal electronics device 100. In some embodiments, several iterations take place prior to the display of data. In some embodiments, only one iteration of the steps occurs.

In some embodiments, a control signal is sent (910) following the processing of data by control circuit 760. The control signal may be sent to sensor 770 and/or interaction device 780. In the case that the control signal is sent to sensor 770, the sensor 770 is controlled (912). This may include calibrating sensor 770. This may also include turning sensor 770 on or off. In the case that the control signal is sent to interaction device 780, interaction device 780 is controlled (914). This may include activating interaction device 780, for example, delivering a drug with a drug delivery device. Controlling interaction device 780 may also include turning interaction device 780 on or off. After controlling sensor 770 or controlling interaction device 780, the method may begin again by measuring one or more parameters with sensors 770 of epidermal electronics device 100.

In some embodiments, control circuit 760 outputs data using communications device 750 and communications connection 753 after the data has been processed. In other embodiments, the data which is output may not have been previously processed (e.g., control circuit 760 may output measurement data from sensors 770 without estimating or calculating orientation). The data may be output to data acquisition and processing device 510. In some embodiments, the data is output to other devices. For example, data may be output to other epidermal electronics devices 100 or to a computer other than data acquisition and processing device 510. The output data may be acquired and processed. In some embodiments, data is acquired and processed by data acquisition and processing device 510. Data acquisition and processing device 510 may acquire the data through communications device 750 and communications connection 753 with epidermal electronics device 100. The data may be processed by a variety of techniques to estimate or calculate orientation, acceleration, movement, angular motion, rotation, angular velocity, angular acceleration, and/or position of epidermal electronics device 100. For example, data acquisition and processing device 510 may use a Kalman filter, dynamic filter, or other algorithm to calculate or estimate the orientation of epidermal electronics device 100. Data acquisition and processing device 510 may also use constraints in making calculations such as data from other sensors 770 in epidermal electronics device 100, data from another epidermal electronics device 100, data from external sensing devices 550, and/or models. In further embodiments, a control signal may be sent following the acquisition of the data from sensors 770 and processing of the data by data acquisition and processing device 510. Data acquisition and processing device 510 may send the control signal following the acquisition and processing of the data. The control signal may be sent to control circuit 760 using communication device 750 and communication connection 753. In some embodiments, control circuit 760 uses the data or information transferred to send control signals as instructed by data acquisition and processing device 510. Control circuit 760 may also send a control signal to one or more interaction devices 780 and/or one of more sensors 770 based on a calculation by control circuit 760. For example, control circuit 760 may send a calibration control signal to sensor 770 to make a correction following an extraneous measurement detected by control circuit 760.

It should be noted that while FIGS. 7-8 provide various examples of operating epidermal electronics device 100, other steps and/or components may be used, and all such embodiments are within the scope of the present disclosure. For example, the method 810 of using epidermal electronics device 100 may include additional steps or components. Sensors 770 may produce data regarding orientation, acceleration, movement, angular motion, rotation, angular velocity, angular acceleration, and/or position or any other measured characteristic (e.g., moisture). In some embodiments, cells 120 perform the function of multiplexing sensor output. In this case, the functions of control circuit 760 may be performed by cells 120 and/or data acquisition and processing device 510. In some embodiments, the functions of data acquisition and processing device 510 are performed by control circuit 760. For example, control circuit 760 may be configured to apply algorithms to the sensor data and to estimate or calculate orientation, rotation, and/or position of attachments surface 103. In further example, method 900 of operation of an epidermal electronics device may include additional steps or components. The individual steps of method 900 may be performed simultaneously (e.g., as in pipelining). Other steps and components may be used in the methods illustrated in FIGS. 7 and 8 consistent with the disclosure made herein with regards to components and their functions and the functions of the epidermal electronics device.

Systems and methods are also described for monitoring repetitive stress injuries and arthritis. A repetitive stress injury may include damage to tendons, nerves, and other soft tissues that is caused by the repetitive and forceful physical movements or vibrations and sustained positioning of body portions in a biomechanically detrimental position, and may be characterized by numbness, pain, and a wasting and weakening of muscles. The systems and methods include generating sense signals from one or more physiological sensors and motion sensors positioned proximate to a body portion of a subject. In an embodiment, the systems and methods described herein may be used to monitor and treat a medical condition through the generation of sense signals from one or more physiological sensors and motion sensors configured to monitor one or more physiological conditions of a subject and one or more movements or positions of a body portion of the subject and to provide an effect to the body portion through action of one or more effectors. The medical condition can include, but is not limited to, a joint-based non-inflammation condition (e.g., arthralgia, osteo-arthritis), a joint-based inflammation condition (e.g., rheumatoid arthritis, psoriatic arthritis, arthritis, ankylosing spondylitis, juvenile idiopathic arthritis and systemic lupus erythematosus), an enthesis-based condition (e.g., enthesitis), a tendon-based condition (e.g., tendonitis, tenosynovitis), a ligament-based condition (e.g., strain), a nerve entrapment or compression based condition or syndrome (e.g., carpal tunnel entrapment, cubital tunnel entrapment, tarsal tunnel entrapment, radial nerve entrapment, meralgia paresthetica), and the like. For example, carpal tunnel syndrome, a type of carpal tunnel entrapment, relates to compression of the median nerve as it passes through the carpal tunnel into the wrist, and can be related to occupational factors (see, e.g., Palmer, Best Pract Res Clin Rheumatol. February 2011; 25(1): 15-29, which is incorporated herein by reference).

In an embodiment, the systems and methods described herein employ one or more physiological sensors to monitor one or more physiological conditions of a subject and to generate a sense signal in response thereto. The physiological sensors include, but are not limited to, an electromyograph, a strain sensor, a temperature sensor, an optical sensor (e.g., an LED), and an acoustic sensor.

In an embodiment, the systems and methods described herein employ one or more motion sensors to monitor a movement or position of a body portion of a subject and to generate a sense signal in response thereto. The motion sensors include, but are not limited to, sensors configured to measure a repeated motion of a body portion, sensors configured to measure a number of repetitions of a movement of a body portion, sensors configured to measure a speed of a movement of a body portion, sensors configured to measure a duration of movement of a body portion, sensors configured to measure a disposition of a body portion relative to a second body portion, and sensors configured to measure an angle of movement of a body portion.

In an embodiment, the systems and methods described herein employ one or more effectors to affect a body portion responsive to processing of sense signals generated by the sensor assembly. The effectors include, but are not limited to, tactile stimulators (e.g., a tactile stimulator configured to provide a tactile indication regarding a position of a body portion) and nerve stimulators (e.g., a nerve stimulator configured to provide therapeutic stimulation or electrical blockage of nerve conduction).

Figure 9:
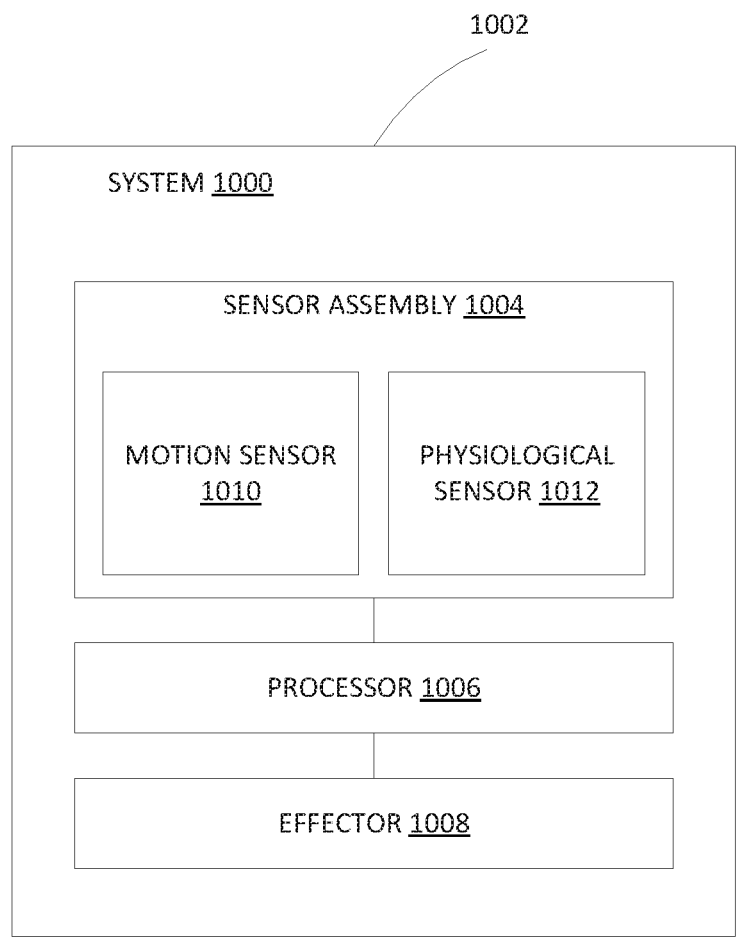
FIG. 9 is a schematic of a system for monitoring, treating, and preventing a repetitive stress injury, arthritis or other medical condition.

In an embodiment, shown in FIG. 9, a system 1000 is configured to monitor and treat a medical condition associated with a repetitive stress injury, arthritis, or other medical condition. The system 1000 includes a substrate 1002, a sensor assembly 1004, a processor 1006, and an effector 1008. In an embodiment, the system 1000 includes epidermal electronic systems (EES) to monitor physiological, positional, and movement conditions for monitoring, preventing, and treating a medical condition associated with a repetitive stress injury, arthritis, or other medical condition. EES describe classes of electronic systems that provide thicknesses, effective elastic moduli, and flexibility suitable for interfacing with a skin surface (see, e.g., Kim et al., Epidermal Electronics, Science, Vol. 333, 838-843 (2011) and Yeo et al., Multifunctional Epidermal Electronics Printed Directly Onto the Skin, Advanced Materials Vol. 25(20), 2773-2778 (2013), which are incorporated herein by reference) and can incorporate sensors (e.g., physiological, temperature, strain) and associated circuitry (e.g., transistors, diodes, photodetectors, radio frequency components, capacitors, oscillators).

The substrate 1002 is a deformable (e.g., flexible, stretchable) substrate configured to interface with a skin surface of a subject. The deformable nature of the substrate 1002 facilitates interaction/interfacing with the skin surface, a generally low-modulus and deformable natural surface. For example, the substrate 1002 can include one or more of an elastomeric polymer, a hydrocolloid film, a nanomembrane (e.g., silicon nanomembrane), or other deformable material. For example, the substrate 1002 can include one or more coating. The substrate 1002 can be positioned in proximity with the skin surface according to various mechanisms including, but not limited to, affixed to the skin via an adhesive material, and held in place by an external pressure, such as pressure provided by a material wrapped around the body portion (e.g., a fabric, a garment, etc.). In an embodiment, the substrate 1002 is configured to reversibly deform to coordinate with a deformation of the skin surface of the body portion upon which the substrate 1002 is mounted. In an embodiment, the substrate 1002 includes a gas-permeable elastomeric sheet on which electronic components of an EES reside (see, e.g., Kim et al., incorporated herein by reference) configured to interface with a skin surface. In an embodiment, the substrate 1002 includes a microfluidic enclosure defined by opposing structured elastomeric substrates between which electronic components of an EES reside (see e.g., Xu et al, Soft Microfluidic Assemblies of Sensors, Circuits, and Radios for the Skin, Science, Vol. 344, 70-74 (2014), which is incorporated herein by reference).

The substrate 1002 can also be configured for interaction with a skin surface of a particular body portion. In example embodiments, the body portion includes one or more of a finger, a hand, a wrist, a toe, a foot, an ankle, an arm, an elbow, a leg, a knee, a shoulder, a hip, a spinal portion (e.g., a region proximate to one or more of a cervical spine, a thoracic spine, a lumbar spine, a sacral spine, and a coccygeal spine), a rib portion (e.g., a region proximate to a rib, such as where the rib attaches the spine), a torso, a neck, and a head region (e.g., face, scalp). For example, the substrate 1002 can conform to a tubular structure to facilitate interaction with a finger or toe (see, e.g., Ying et al., Silicon nanomembranes for fingertip electronics, Nanotechnology, Vol. 23, No. 34, 1-7 (2012) which is incorporated herein by reference). In an embodiment, shown in FIG. 10, the system 1000 is positioned on a wrist 1100 of the subject for monitoring, preventing, and treating a medical condition associated with a repetitive stress injury, arthritis, or other medical condition associated with the wrist or other body portion in close proximity to the wrist, including, but not limited to, the hand, one or more fingers, and the arm.

Referring to FIGS. 9-14, the sensor assembly 1004 includes a motion sensor 1010 and a physiological sensor 1012. The sensor assembly 1004 is configured to generate one or more sense signals based on detection of a movement of a body portion by the motion sensor 1010 and a physiological parameter of the body portion by the physiological sensor 1012. In an embodiment, the motion sensor 1010 includes one or more of an accelerometer (e.g., accelerometer 1400) and a proximity sensor (e.g., proximity sensor 1402) to detect a movement of a body portion and generate a sense signal in response thereto. The proximity sensor can include one or more of an infrared sensor (e.g., infrared sensor 1404) and an optical sensor (e.g., optical sensor 1406). In an embodiment, the proximity sensor is configured to sense a second body portion proximate the body portion on which the system 1000 is positioned. For example, the system 1000 can be positioned on a wrist of a subject and the motion sensor 1010 can include a proximity sensor configured to detect one or more of a presence, a position, an angle, and a movement of another body portion proximate the wrist, such as a hand, a palm, an arm, a finger, a shoulder, and so forth. In an embodiment, the proximity sensor is configured to sense a device interfacing with another portion of the skin surface or with another body portion. For example, the system 1000 can be positioned on a body portion of a subject and a second system 1000 is positioned proximate the body portion or on another body portion, where the proximity sensor of the motion sensor 1010 of the system 1000 can sense one or more of a presence, a position, an angle, and a movement of the second system 1000.

The motion sensor 1010 is configured to detect one or more of a movement of a body portion and a position of the body portion. The body portion can be the portion with which the system 1000 interfaces or can be a portion proximate the portion with which the system 1000 interfaces. In an embodiment, the motion sensor 1010 generates a sense signal based on a repeated motion of the body portion. For example, the system 1000 can be positioned on a wrist of a subject and the motion sensor 1010 measures a repeated flexing or bending of the wrist, such as to move the hand or one or more fingers. In an embodiment, the motion sensor 1010 measures a number of repetitions of a movement of a body portion. For example, the system 1000 can be positioned on a finger of a subject and the motion sensor 1010 measures the number of repetitions that the particular finger is flexed or bent. Measuring the number of repetitions can include, but is not limited to, measuring that zero repetitions have occurred, measuring a finite number of repetitions, measuring the number of repetitions taken over a specified time period, and determining that the number of repetitions exceeds a threshold number (e.g., a threshold at which a subject is at risk for a repetitive strain injury). In an embodiment, the motion sensor 1010 measures a speed of a movement of a body portion. For example, the system 1000 can be positioned on an ankle of a subject and the motion sensor 1010 measures the speed of movement of the ankle, such as one or more of a speed of movement during a flexing of the ankle during a walking motion, a speed of movement relative to a ground surface during a walking motion, or other movement. In an embodiment, the motion sensor 1010 measures a duration of a movement of a body portion. The duration can include one or more of a total duration of movement within a period of time (e.g., duration encompassing multiple repetitions of movement) and a total duration of movement for a single repetition of movement. For example, the system 1000 can be positioned on a finger of a subject and the motion sensor 1010 measures one or more of the duration of motion of bending or flexing the finger over a period of time and the duration of motion of a single repetition of movement of the finger, such as relative to the palm, hand, or wrist. The period of time over which the movement is measured can include, but is not limited to, a minute, an hour, a portion of a day during which a subject is awake and active, a day, or longer duration. In an embodiment, the sensor assembly 1004 is configured to measure the disposition of the body portion over a period of time. For example, the sensor assembly 1004 may measure a disposition of the body portion over time while the body portion is one or more of at rest, while in motion, and while held in a position that is not a rest position (e.g., tensed). In an embodiment, the motion sensor 1010 measures a disposition of a body portion on which the system 1000 is positioned relative to a second body portion during a movement of one or more of the body portion and the second body portion. For example, the system 1000 can be positioned on a phalange of a subject and the motion sensor 1010 measures a disposition of the phalange relative to a wrist or ankle of the subject during motion of the phalange or wrist/ankle. In an embodiment, the motion sensor 1010 measures an angle of movement of a body portion. For example, the system 1000 can be positioned on an arm of a subject and the motion sensor 1010 measures an angle of movement of the arm (e.g., relative to the torso, relative to a rest position of the arm, relative to another body portion, and so forth). Measurement by the motion sensor 1010 of one or more of a repeated motion of a body portion, a number of repetitions of the movement of the body portion, a speed of the movement of the body portion, a duration of the movement of the body portion, a disposition of the body portion relative to a second body portion, and an angle of movement of the body portion provides information that can aid in the determination by the system 1000 of whether the subject has a repetitive stress injury or is at risk for a repetitive stress injury, and can provide data regarding actions to treat or avoid a particular repetitive stress injury with the system 1000.

Figure 13:
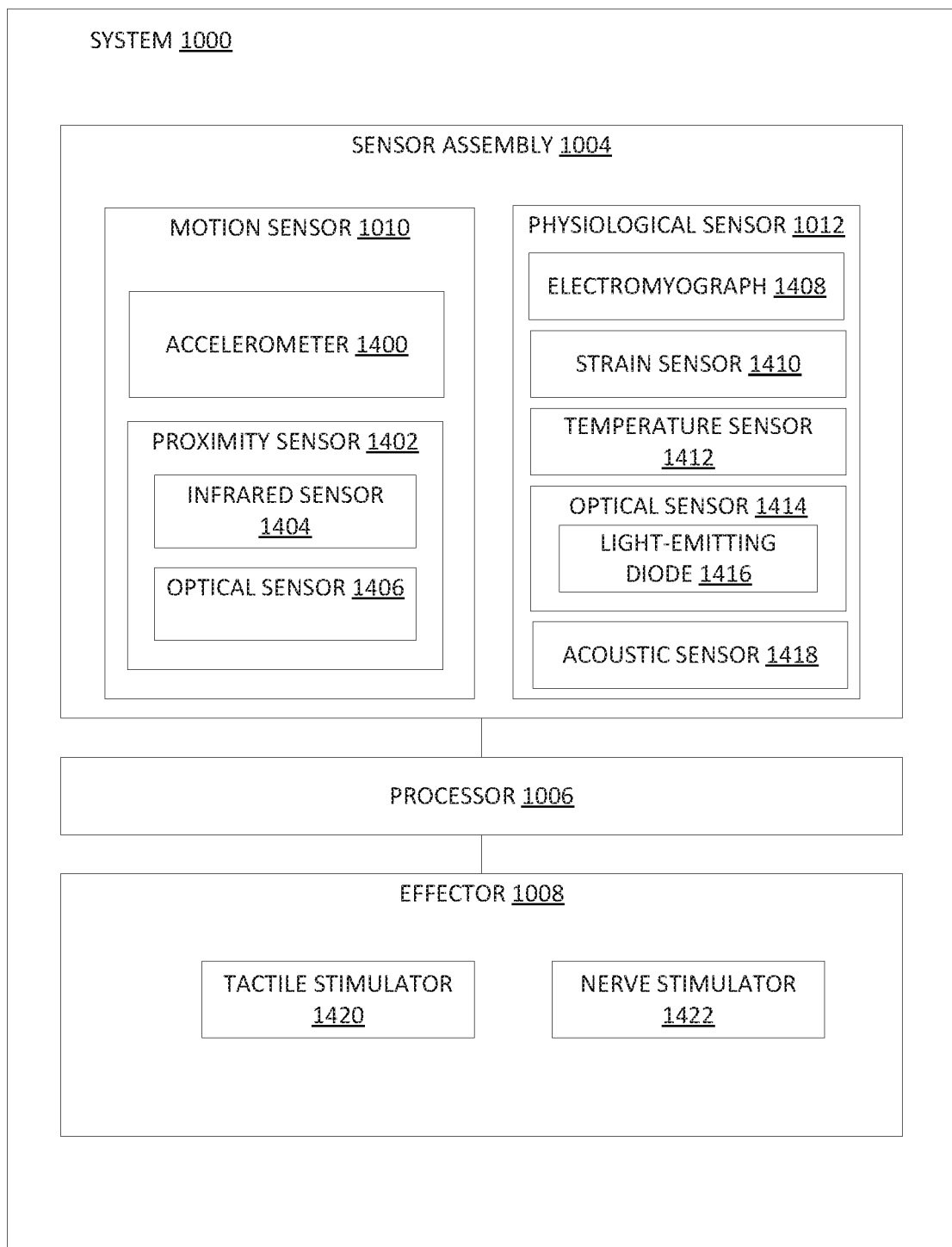
FIG. 13 is a schematic of an embodiment of a system such as shown in FIG. 9.

The physiological sensor 1012 is configured to detect a physiological parameter of the subject on which the system 1000 is positioned. In an embodiment, the physiological sensor 1012 detects a localized physiological parameter provided by one or more of a body portion with which the system 1000 interfaces and a body portion proximate the portion with which the system 1000 interfaces. The physiological sensor 1012 can also be configured to detect systemic physiological parameters of the subject on which the system 1000 is positioned. In an embodiment, the physiological sensor 1012 includes an electromyograph (EMG) (FIG. 13 shows electromyograph 1408), such as sensor electrodes configured to monitor the electrophysiological activity of muscle tissue proximate to the body portion on which the system 1000 is positioned. In an embodiment, the physiological sensor 1012 includes a strain sensor (e.g., strain sensor 1410). For example, the strain sensor may be a silicon nanomembrane-based sensor positioned over the skin surface to measure a strain-based physiological parameter (see, e.g., Son et al., Multifunctional wearable devices for diagnosis and therapy of movement disorders, Nature Nanotechnology, Vol. 9, 397-404 (2014), which is hereby incorporated by reference). In an embodiment, the physiological sensor 1012 includes a temperature sensor (e.g., temperature sensor 1412). For example, the temperature sensor can include, but is not limited to, a single point temperature sensor, a spatial imaging temperature sensor, and a microscale temperature sensor configured as a microscale heating element or actuator, such as one or more microscale temperature sensors incorporating thin serpentine features of thin metal or PIN diodes with nanoscale membranes (see, e.g., Webb et al., Ultrathin conformal devices for precise and continuous thermal characterization of human skin, Nature Materials, Vol. 12, 938-944 (2013), which is incorporated herein by reference). In an embodiment, the physiological sensor 1012 includes an optical sensor (e.g., optical sensor 1414) configured to measure an optical characteristic of a body portion on which the system 1000 is positioned. For example, the optical sensor can include, but is not limited to, a light-emitting diode (LED) (e.g., light-emitting diode 1416), an LED coordinates with a photosensor, an imaging device, such as a camera, and so forth. In an embodiment, the physiological sensor 1012 includes an acoustic sensor (e.g., acoustic sensor 1418). The acoustic sensor may provide data regarding motion of a joint including, but not limited to, a wrist, an elbow, a shoulder, an ankle, a knee, and a hip.

The processor 1006 is configured to receive one or more sense signals from the sensor assembly 1004 and to process the sense signals in order to provide control signals to portions of the system 1000, such as to the effector 1008. In an embodiment, the processor 1006 is a resident device component that is coupled to the substrate 1002. Alternatively, the processor 1006 can be located remotely from the substrate 1002 and can send and receive signals via associated wireless communication methods including, but not limited to acoustic communication signals, optical communication signals, radio communication signals, infrared communication signals, ultrasonic communication signals, and the like. The processor 1006 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGAs having a plurality of programmable logic commands.

The effector 1008 is operably coupled to the processor 1006 and affects a body portion responsive to control by the processor 1006 to one or more of prevent and treat a medical condition associated with a repetitive stress injury, arthritis, or other medical condition. In an embodiment, the effector 1008 includes one or more of a tactile stimulator (e.g., tactile stimulator 1420) and a nerve stimulator (e.g., nerve stimulator 1422). A tactile stimulator can provide a subject an indication regarding a position of a body portion. For example, the sensor assembly 1004 can generate one or more sense signals regarding a position of a body portion on which the system 1000 is positioned, where the processor 1006 receives the sense signals and instructs the effector 1008 (e.g., tactile stimulator) to provide an indication to the user regarding the position, such as by providing a vibrational response to the user. In an embodiment, the processor 1006 determines that the position of the body portion is a biomechanically detrimental position. For example, the processor 1006 can compare the one or more sense signals generated by the sensor assembly 1004 to reference data indicative of a strain injury stored in a resident or remote memory device. The processor 1006 can then instruct the tactile stimulator to affect the body portion, such as by providing a vibrational effect, to provide an indication that the position of the body portion is a biomechanically detrimental position. In an embodiment, the processor 1006 determines that the body portion has maintained the current position for a duration longer than a threshold duration. For example, the processor 1006 can compare the one or more sense signals generated by the sensor assembly 1004 regarding a duration of the body portion in a particular position to a threshold duration stored in a resident or remote memory device. The threshold duration can be based on biomechanical data indicative of when a repetitive stress injury is likely to occur. The processor 1006 can then instruct the tactile stimulator to affect the body portion, such as by providing a vibrational effect, to provide an indication that the body portion has maintained the current position for a duration longer than the threshold duration.

The effector 1008 can include a nerve stimulator configured to provide electrical stimulation to one or more nerves in the subject on which the system 1000 is positioned. In an embodiment, the nerve stimulator generates an electrical current or impulse to therapeutically stimulate a nerve proximate to the body portion on which the system 1000 is positioned. The therapeutic stimulation can be utilized to treat or avoid a repetitive stress injury of the subject. In an embodiment, the nerve stimulator is configured to deliver an excitatory stimulus to a nerve proximate to the body portion on which the system 1000 is positioned. Delivering an excitatory stimulus to a nerve can include delivering a stimulus that results in neural activity (e.g., one or more action potentials), or that changes the resting potential of a nerve membrane so that the nerve is more readily excited to produce or conduct action potentials. Delivering an excitatory stimulus to the nerve induces movement of the body portion or sensation of the body portion. For example, the sensor assembly 1004 generates one or more sense signals based on detection of a movement or position of the body portion by the motion sensor 1010 and a physiological parameter of the body portion by the physiological sensor 1012, where the processor 1006 receives the one or more sense signals and directs the effector 1008 to affect the body portion by generating an electrical current or impulse to deliver an excitatory stimulus to a nerve proximate to the body portion on which the system 1000 is positioned, such as to cause movement of the body portion or to induce a sensation of the body portion. In an embodiment, the nerve stimulator is configured to stimulate the nerve conduction after a threshold period of time during which the body portion is retained in a particular position. For example, the motion sensor 1010 may provide one or more sense signals regarding the position of the body portion over a temporal duration. The system 1000 may infer that the body portion remains within a particular position when the one or more sense signals do not significantly deviate over a period of the temporal duration that corresponds to a threshold duration of time. The threshold duration of time can correspond to a time at which a body portion becomes subject to a risk of strain injury or to an increased risk of strain injury.

In an embodiment, the nerve stimulator is configured to electrically block a nerve conduction of a nerve proximate to the body portion on which the system 1000 is positioned. For example, the nerve stimulator generates an electrical current or impulse to interfere with, block, alter, and the like, a nerve conduction of a nerve. Blocking the nerve conduction can inhibit conduction of pain signals. For example, the sensor assembly 1004 generates one or more sense signals based on detection of a movement of the body portion by the motion sensor 1010 and a physiological parameter of the body portion by the physiological sensor 1012, where the processor 1006 receives the one or more sense signals and directs the effector 1008 affect the body portion by generating an electrical current or impulse to block a nerve conduction of a nerve proximate to the body portion on which the system 1000 is positioned, such as to inhibit a pain receptor of the subject. In an embodiment, the blockage of the nerve conduction can inhibit a movement of the body portion. For example, where the sensor assembly 1004 generates one or more sense signals indicating that the body portion is maintained in a biomechanically detrimental position, the processor 1006 can control the effector 1008 to block a nerve conduction of a nerve proximate to the body portion to inhibit movement of the body portion from maintaining or repositioning into the biomechanically detrimental position. Other indicators for inhibiting the movement of the body portion include, but are not limited to, repetitive movements indicative of a repetitive stress injury, maintaining the body portion in a position that exceeds a threshold duration, and the like.

Figure 11:
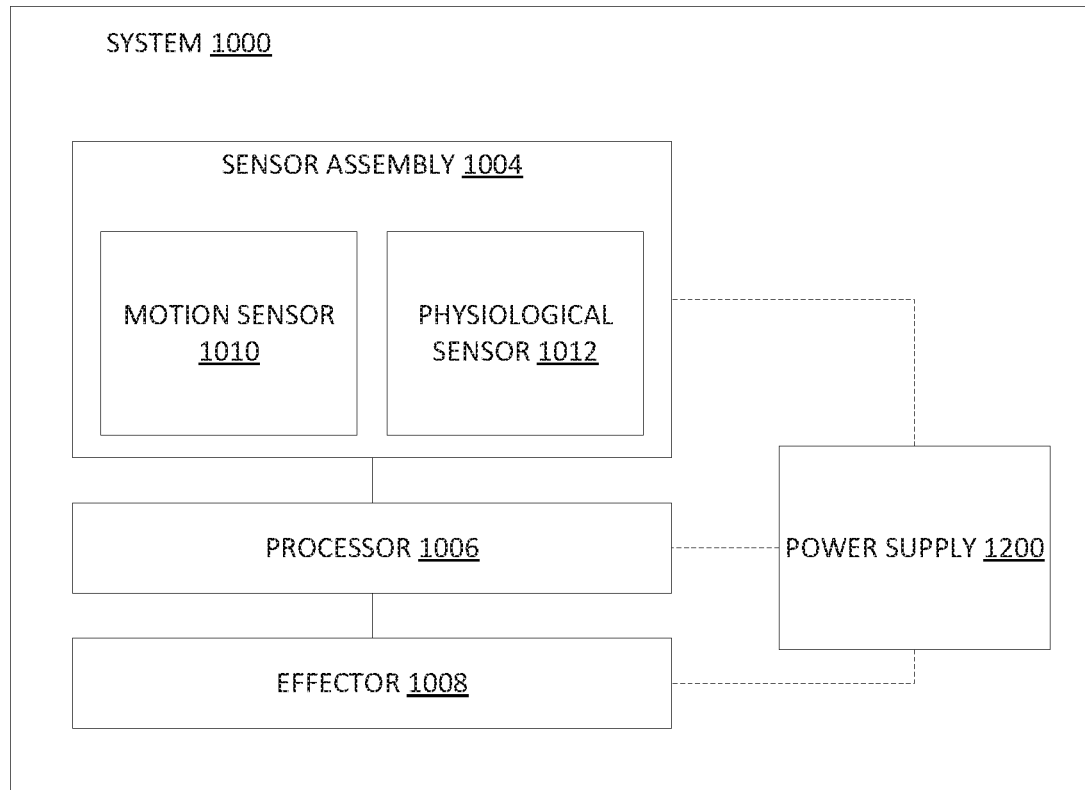
FIG. 11 is a schematic of an embodiment of a system such as shown in FIG. 9.

In an embodiment, as shown in FIG. 11, the system 1000 includes a power supply 1200 configured to provide power to one or more components of the system 1000 including, but not limited to, the sensor assembly 1004, the processor 1006, and the effector 1008. In an embodiment, the power supply 1200 is a resident device component that is coupled to the substrate 1002. Examples of resident device components include, but are not limited to, batteries (e.g., a thin film battery) and solar cells (e.g., silicon-based solar cells) configured to convert light energy into electrical energy for use by the components of the system 1000. In an embodiment, the power supply 1200 includes one or more components positioned remotely from the substrate 1002 that transmit power signals via associated wireless power methods including, but not limited to, inductive coupling of power signals. In such embodiments, the system 1000 includes one or more components positioned on the substrate 1002 configured to one or more of receive, process, and distribute the power signals that originate from components positioned remotely from the substrate 1002. For example, the system 1000 can include a wireless power coil coupled to the substrate 1002 that is configured to receive a remote power signal, such as a remote power signal originating from a remote transmission coil (see, e.g., Kim et al., incorporated herein by reference).

Figure 12:
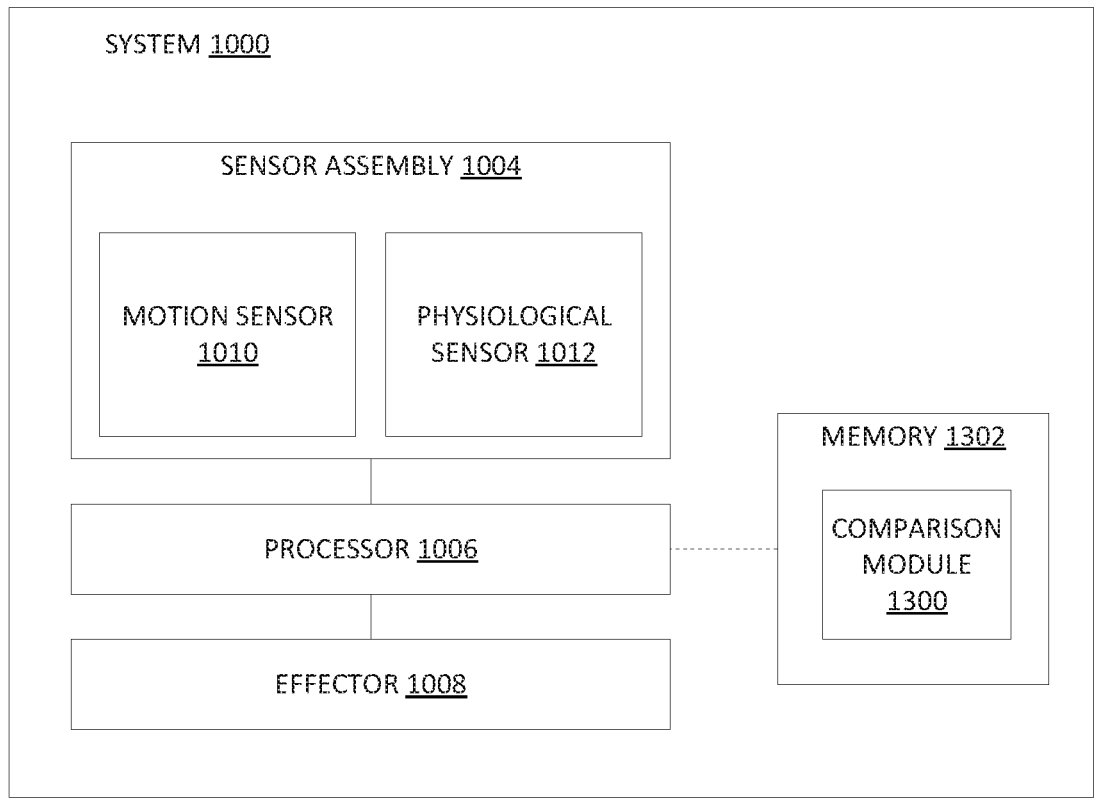
FIG. 12 is a schematic of an embodiment of a system such as shown in FIG. 9.

In an embodiment, as shown in FIG. 12, the system 1000 includes a comparison module 1300 accessible by the processor 1006 to compare the movement of the body portion, detected by the motion sensor 1010 of the sensor assembly 1004, and the physiological parameter of the body portion, detected by the physiological sensor 1012 of the sensor assembly 1004, to reference data indicative of a strain injury. In an embodiment, the processor 1006 accesses the comparison module 1300 by accessing a computer memory 1302, which can include, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the comparison module 1300 and which can be accessed by the processor 1006 or other accessing device. The reference data may be stored by the computer memory 1302 of the system 1000, can be accessible by the processor 1006 via wireless means, or can be available to the processor 1006 through another method. The reference data may include physiological and biomechanical information pertaining to an acute or traumatic injury that include, but is not limited to, a strain, a sprain, or a tear of a muscle or soft tissue (e.g., ligament, tendon, enthesis, or other connective tissue). The reference data may include physiological and biomechanical information pertaining to a long-term or chronic medical condition that can include, but is not limited to, a joint-based non-inflammation condition (e.g., arthralgia, osteo-arthritis), a joint-based inflammation condition (e.g., rheumatoid arthritis, psoriatic arthritis, arthritis, ankylosing spondylitis, juvenile idiopathic arthritis and systemic lupus erythematosus), an enthesis-based condition (e.g., enthesitis), a tendon-based condition (e.g., tendonitis, tenosynovitis), a ligament-based condition (e.g., chronic strain), a nerve entrapment or compression based condition or syndrome (e.g., carpal tunnel entrapment, cubital tunnel entrapment, tarsal tunnel entrapment, radial nerve entrapment, meralgia paresthetica), and the like. By implementing the protocols of the comparison module 1300, the processor 1006 may compare the movement, position, and physiological data pertaining to the body portion obtained by the sensor assembly 1004 to reference data indicative of a strain injury and make a determination regarding the risk or likelihood of a strain injury occurring for the body portion. In an embodiment, the processor 1006 further determines an action to be executed by the effector 1008 based upon the comparison made between the data received from the sensor assembly 1004 and the reference data. For example, where the processor 1006 determines that the body portion is at a relatively high risk for incurring a strain injury, the processor 1006 may control the effector 1008 to take a first action (e.g., electrically affect a nerve conduction), whereas if the processor 1006 determines that the body portion is at a lower risk for incurring a strain injury, the processor 1006 may control the effector 1008 to take a second action (e.g., provide a visible, audible, or tactile warning to the subject).

Figure 14:
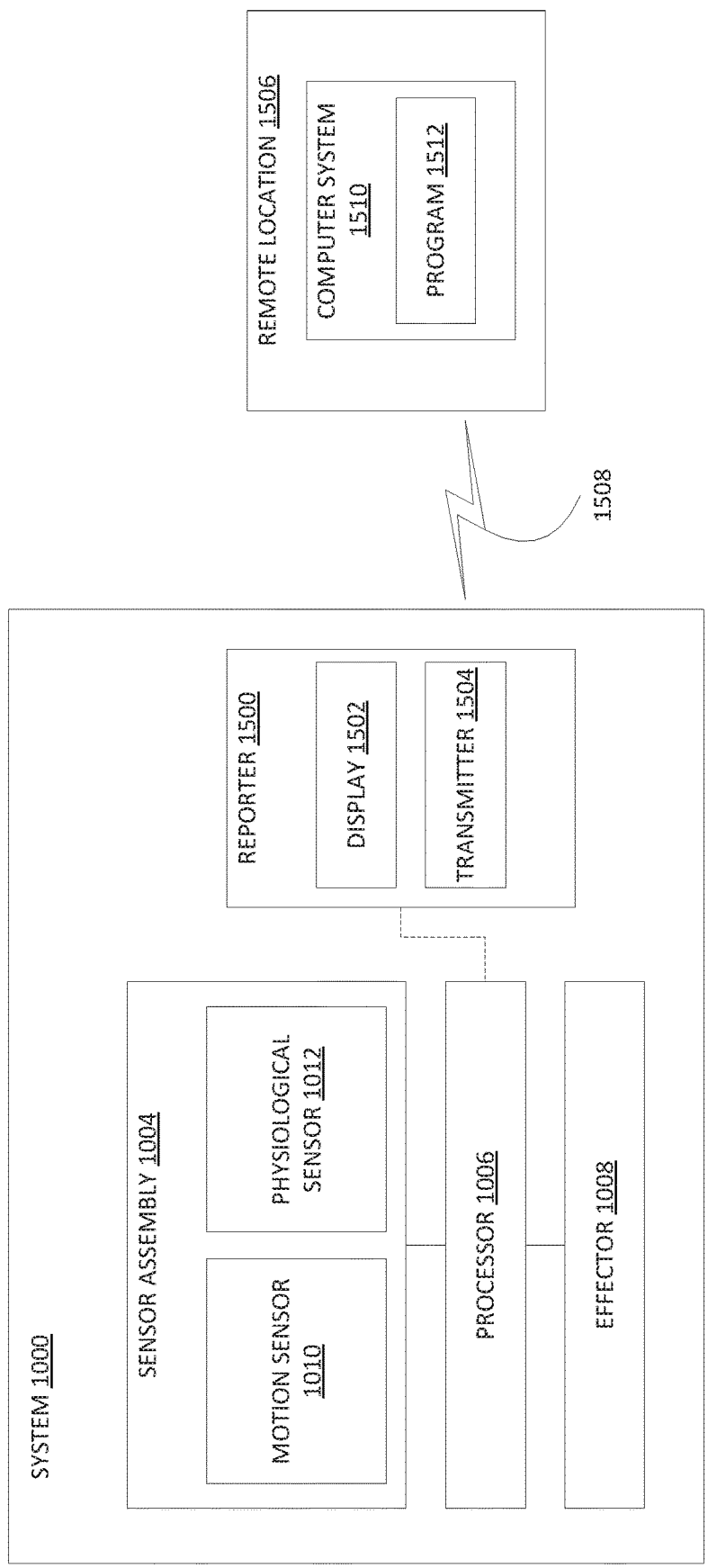
FIG. 14 is a schematic of an embodiment of a system such as shown in FIG. 9.

In an embodiment, as shown in FIG. 14, the system 1000 further includes a reporter 1500 configured to convey information from the system 1000. The information from the reporter 1500 may be provided one or more of visually (e.g., visual information), audibly (e.g., auditory information), and as data (e.g., one or more data signals associated with the information to convey). In an embodiment, the reporter 1500 reports one or more of an actuation of the effector 1008, a detected movement or position of the body portion, and a detected physiological condition. The reporter 1500 can provide warnings or instructions regarding the movement, position, and the physiological condition of the body portion. For example, the reporter 1500 may be configured to report a warning of a risk of a biomechanically detrimental positioning of the body portion. The biomechanically detrimental positioning may influence the risk for a repetitive strain injury (e.g., as determined by the processor 1006 implementing the comparison module 1300). In an embodiment, the reporter 1500 is configured to report an instruction to move the body portion. The reporter 1500 may function in combination with the effector 1008 to provide visual or auditory context to the subject upon action of the effector 1008, such as when a tactile stimulation occurs via a tactile stimulator of the effector 1008. In an embodiment, the reporter 1500 includes a display 1502 configured to report, communicate, or otherwise provide information to the subject utilizing the system 1000. The display 1502 may include, but is not limited to, a graphical user interface (GUI), a touchscreen assembly (e.g., a capacitive touch screen), a liquid crystal display (LCD), a light-emitting diode (LED) display, and a projection-based display. In an embodiment, the reporter 1500 includes a transmitter 1504 configured to transmit information from the system 1000 to a remote location 1506 (e.g., a remote entity, a remote device, and so forth). In an embodiment, the remote location includes a communication device, such as one or more of a mobile communication device and a computer system including, but not limited to, mobile computing devices (e.g., hand-held portable computers, Personal Digital Assistants (PDAs), laptop computers, netbook computers, tablet computers, and so forth), mobile telephone devices (e.g., cellular telephones and smartphones), devices that include functionalities associated with smartphones and tablet computers (e.g., phablets), portable game devices, portable media players, multimedia devices, satellite navigation devices (e.g., Global Positioning System (GPS) navigation devices), e-book reader devices (eReaders), Smart Television (TV) devices, surface computing devices (e.g., table top computers), Personal Computer (PC) devices, and other devices that employ touch-based human interfaces. The reporter 1500 can communicate (e.g., send and receive communication signals) with the remote location 1506 via one or more connected and wireless communication mechanisms (FIG. 14 displays a wireless communication mechanism 1508) including, but not limited to acoustic communication signals, optical communication signals, radio communication signals, infrared communication signals, ultrasonic communication signals, and the like.

In an embodiment, the remote location 1506 includes a computer system configured to store and execute one or more computer-executable programs, whereby the reporter can interact with (e.g., remotely access, execute, and so forth) and modify the programs stored on the computer system. For example, FIG. 14 displays the remote location 1506 including a computer system 610 having a computer-executable program 612 stored thereon. In an embodiment, the information provided to the computer system 610 by the reporter 1500 is used to populate fields of the program, such as fields associated with risks of repetitive stress injury. In an embodiment, the program 612 includes scheduling software configured to provide personnel scheduling functionality, such as to schedule personnel to particular tasks within an organizational structure while considering the risks for repetitive stress injuries associated with the various tasks engaged by the personnel and including actual data, provided by the reporter 1500, of actual risks of repetitive stress injuries of individuals interfacing with the system 1000. For example, the scheduling software can include instructions that, when executed by a computer processor on the computer system 610, causes the computer system 610 to provide real-time personnel scheduling. The reporter 1500 can provide information associated with risks for repetitive stress injuries for one or more individuals interfacing with the system 1000 based on measured movements, positions, and physiological conditions in order for the program 612 to make real-time personnel scheduling assignments, such as to make substantially instantaneous or real-time determinations of personnel assignments to minimize the risk of repetitive stress injuries on an individual basis, an organizational basis, and so forth.

As another example, the scheduling software can include instructions, that when executed by a computer processor on the computer system 610, causes the computer system 610 to provide long-term personnel scheduling. The reporter 1500 can provide information associated with risks for repetitive stress injuries for one or more individuals interfacing with the system 1000 based on measured movements, positions, and physiological conditions in order for the program 612 to make long-term personnel scheduling assignments, such as to make determinations of personnel assignments over time to minimize the risk of repetitive stress injuries on an individual basis, an organizational basis, and so forth.

As another example, the scheduling software can include instructions, that when executed by a computer processor on the computer system 610, causes the computer system 610 to provide personnel tracking. The reporter 1500 can provide information associated with risks for repetitive stress injuries for one or more individuals interfacing with the system 1000 based on measured movements, positions, and physiological conditions in order for the program 612 to track the risks of repetitive stress injuries associated with particular individuals, which can be coordinated with the tracking of the particular assignments of the individual, such as to make determinations of risks of repetitive stress injuries for the individual based on the particular assignments handled by the individual. The information provided by the reporter 1500 can be used to track an individual's propensity for risk of repetitive stress injury as compared to a group of individuals, such as to determine whether the particular individual engages in more biomechanically detrimental activities than the group, to determine whether the particular individual engages in more biomechanically detrimental positioning than the group (e.g., the individual has improper form for performing the various tasks associated with specific job assignments), and so forth.

Figure 15A:
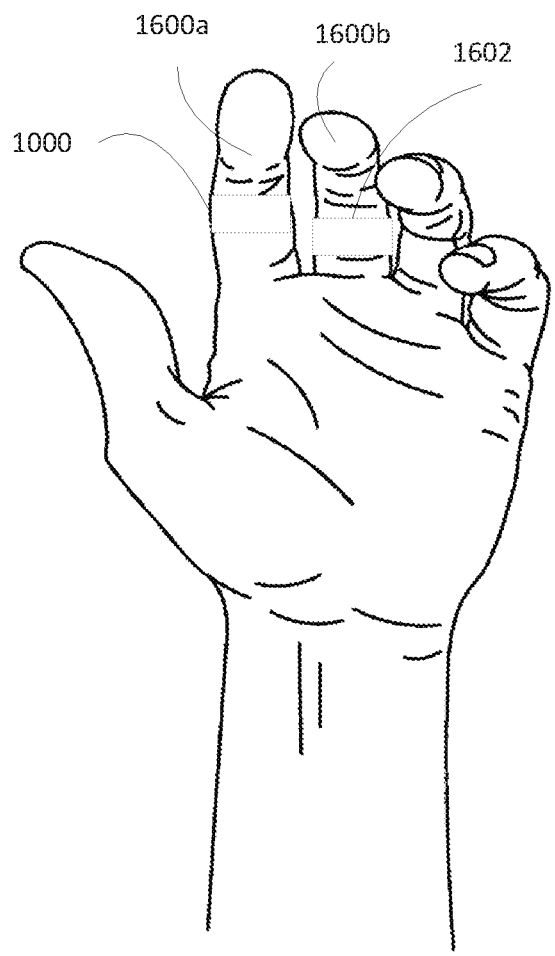
FIG. 15A is a schematic of an embodiment of a system such as shown in FIG. 9.

FIG. 15A illustrates an example environment in which embodiments of the system 1000 may be implemented. As shown, the system 1000 is positioned on a finger 1600a of a subject. In an embodiment, the system 1000 further includes a second device configured to generate one or more sense signals based on detected movements, positions, and physiological parameters of the body portion on which the second device is positioned. The second device can then affect the body portion on which it is positioned, as described herein with respect to the effector 1008 of the system 1000. For example, as shown in FIG. 15A, the system 1000 includes a second device 1602 positioned on another finger 1600b of the same hand of the subject, although other positional configurations can be utilized, including but not limited to, positioning the second device 1602 on a different portion of the same finger 1600a, or positioning the second device 1602 on a hand, a wrist, a toe, a foot, an ankle, an arm, an elbow, a leg, a knee, a shoulder, a hip, a spinal portion (e.g., a region proximate to one or more of a cervical spine, a thoracic spine, a lumbar spine, a sacral spine, and a coccygeal spine), a rib portion (e.g., a region proximate to a rib, such as where the rib attaches the spine), a torso, a neck, and a head region (e.g., face, scalp).

Figure 15B:
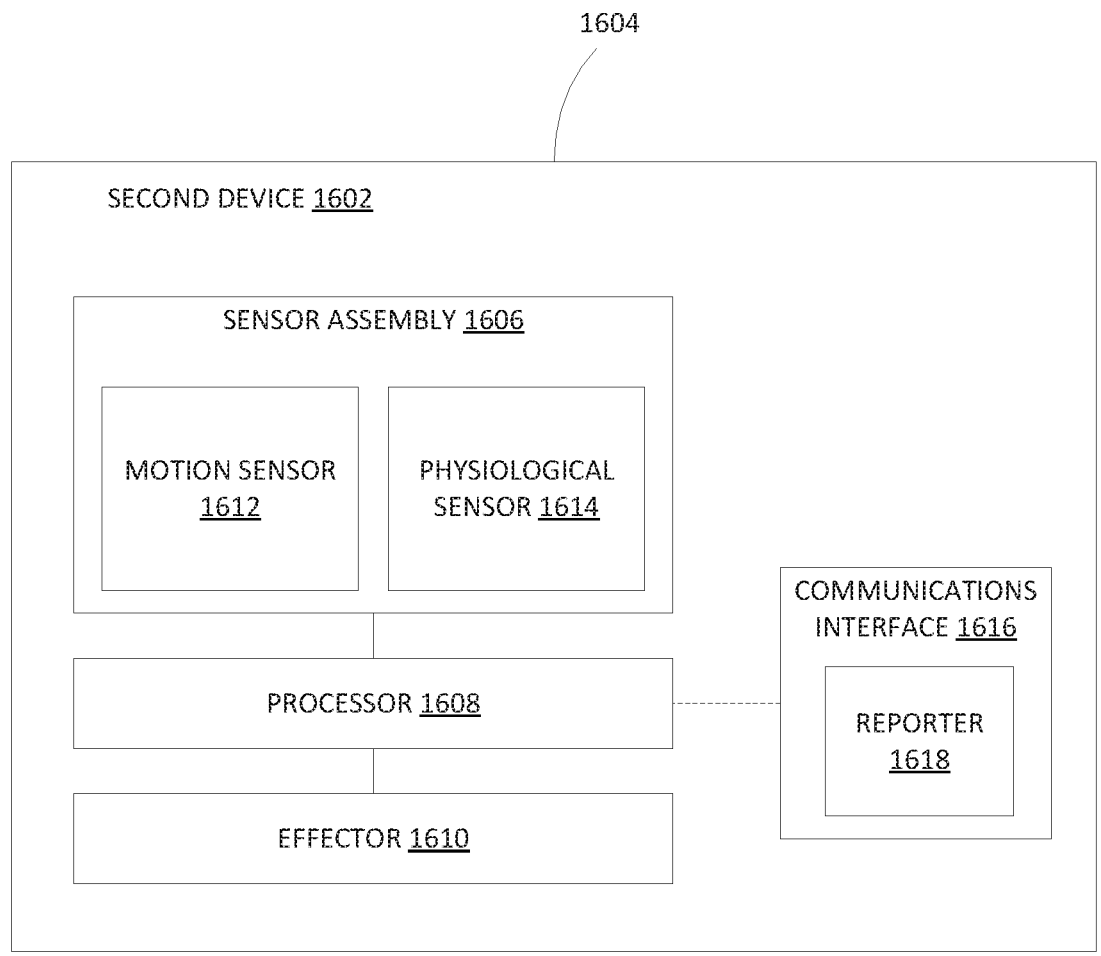
FIG. 15B is a schematic of an embodiment of a system such as shown in FIG. 9.

In an embodiment, an example of which is shown in FIG. 15B, the second device 1602 includes a deformable substrate 1604, a sensor assembly 1606, a processor 1608, and an effector 1610. The second device 1602 incorporates epidermal electronic systems (EES) to monitor physiological, positional, and movement conditions for monitoring, preventing, and treating a medical condition associated with a repetitive stress injury, arthritis, or other medical condition. The deformable substrate 1604 is a deformable (e.g., flexible, stretchable) substrate configured to interface with a skin surface of a subject. The deformable nature of the substrate 1604 facilitates interaction/interfacing with the skin surface, a generally low-modulus and deformable natural surface. In an embodiment, the structure of the substrate 1604 is similar to, or the same as, the structure of the substrate 1002 described herein, with corresponding functionalities.

As shown in FIG. 15B, the sensor assembly 1606 of the second device 1602 includes a motion sensor 1612 and a physiological sensor 1614. The sensor assembly 1606 is configured to generate one or more sense signals based on detection of a movement or position of a body portion by the motion sensor 1612 and a physiological parameter of the body portion by the physiological sensor 1614. In an embodiment, the structures of the sensor assembly 1606, the motion sensor 1612, and the physiological sensor 1614 are similar to, or the same as, the structures of the sensor assembly 1004, the motion sensor 1010, and the physiological sensor 1012, respectively, described herein, including but not limited to, accelerometers, proximity sensors, electromyographs (EMG), strain sensors, temperature sensors, optical sensors, and acoustic sensors, with corresponding functionalities.

The processor 1608 is configured to receive one or more sense signals from the sensor assembly 1606 and to process the sense signals in order to provide control signals to portions of the second device 1602, such as to the effector 1610. In an embodiment, the structure of the processor 1608 is similar to, or the same as, the structure of the processor 1006 described herein, with corresponding functionalities.

The effector 1610 is operably coupled to the processor 1608 and affects a body portion responsive to control by the processor 1608 to one or more of prevent and treat a medical condition associated with a repetitive stress injury, arthritis, or other medical condition. For example, the effector 1610 affects the finger 1600b under the control of the processor 1608, based on the processing of the one or more sense signals from the sensor assembly 1606. In an embodiment, the structure of the effector 1610 is similar to, or the same as, the structure of the effector 1008 described herein, including but not limited to, tactile stimulators and nerve stimulators, with corresponding functionalities.

In an embodiment, one or more components of the system 1000 interact with the second device 1602. One or more components of the system 1000 and the second device 1602 are configured to detect the presence of the respective other of the components of the system 1000 and the second device 1602. For example, the motion sensor 1010 of the system 1000 may sense one or more properties of the second device 1602 to detect a presence of the second device on the finger 1600b, and the motion sensor 1612 of the second device 1602 may sense one or more properties of the system 1000, such as the presence of the substrate 1002 positioned on the finger 1600a, to detect a presence of the system 1000. In an embodiment, the motion sensor 1010 of the system 1000 may sense one or more properties of the finger 1600b to detect one or more of the presence of the finger 1600b, the proximity of the finger 1600b relative to the finger 1600a, and the disposition of the finger 1600b relative to the finger 1600a. In an embodiment, the motion sensor 1612 of the second device may sense one or more properties of the finger 1600a to detect one or more of the presence of the finger 1600a, the proximity of the finger 1600a relative to the finger 1600b, and the disposition of the finger 1600a relative to the finger 1600b.

In an embodiment, as shown in FIG. 15B, the second device 1602 includes a communications interface 1616 to send communication signals from the second device 1602 and to receive communication signals from a remote location or device via one or more connected (e.g., wired connections) and wireless communication mechanisms including, but not limited to acoustic communication signals, optical communication signals, radio communication signals, infrared communication signals, ultrasonic communication signals, and the like. FIG. 15B shows an embodiment where the communications interface 1616 includes a reporter 1618 configured to convey information from the second device 1602. The information from the reporter 1618 may be provided one or more of visually (e.g., visual information), audibly (e.g., auditory information), and as data (e.g., one or more data signals associated with the information to convey). In an embodiment, the structure and functionality of the reporter 1618 is similar to, or the same as, the structure and functionalities of the reporter 1500 described herein.

In an embodiment, the communications interface 1616 of the second device 1602 facilitates communication and interaction between the second device 1602 and other components of the system 1000, including but not limited to, the processor 1006 and the reporter 1500. Accordingly, the communications interface 1616 facilitates the transfer of data between the second device 1602 and other components of the system 1000. The data can include, but is not limited to, data associated with one or more of an actuation of an effector (e.g., effector 1008, effector 1610), a detected movement or position of the body portion (e.g., sensed by motion sensor 1010, motion sensor 1612), a detected physiological condition (sensed by physiological sensor 1012, physiological sensor 1614), warnings or instructions regarding the movement, position, and the physiological condition of the body portion, an indication that warnings or instructions regarding the movement, position, and the physiological condition of the body portion have been reported, a position of a body portion relative to another body portion, and a position of the second device 1602 relative to the position of one or more components of the system 1000.

Figure 16:
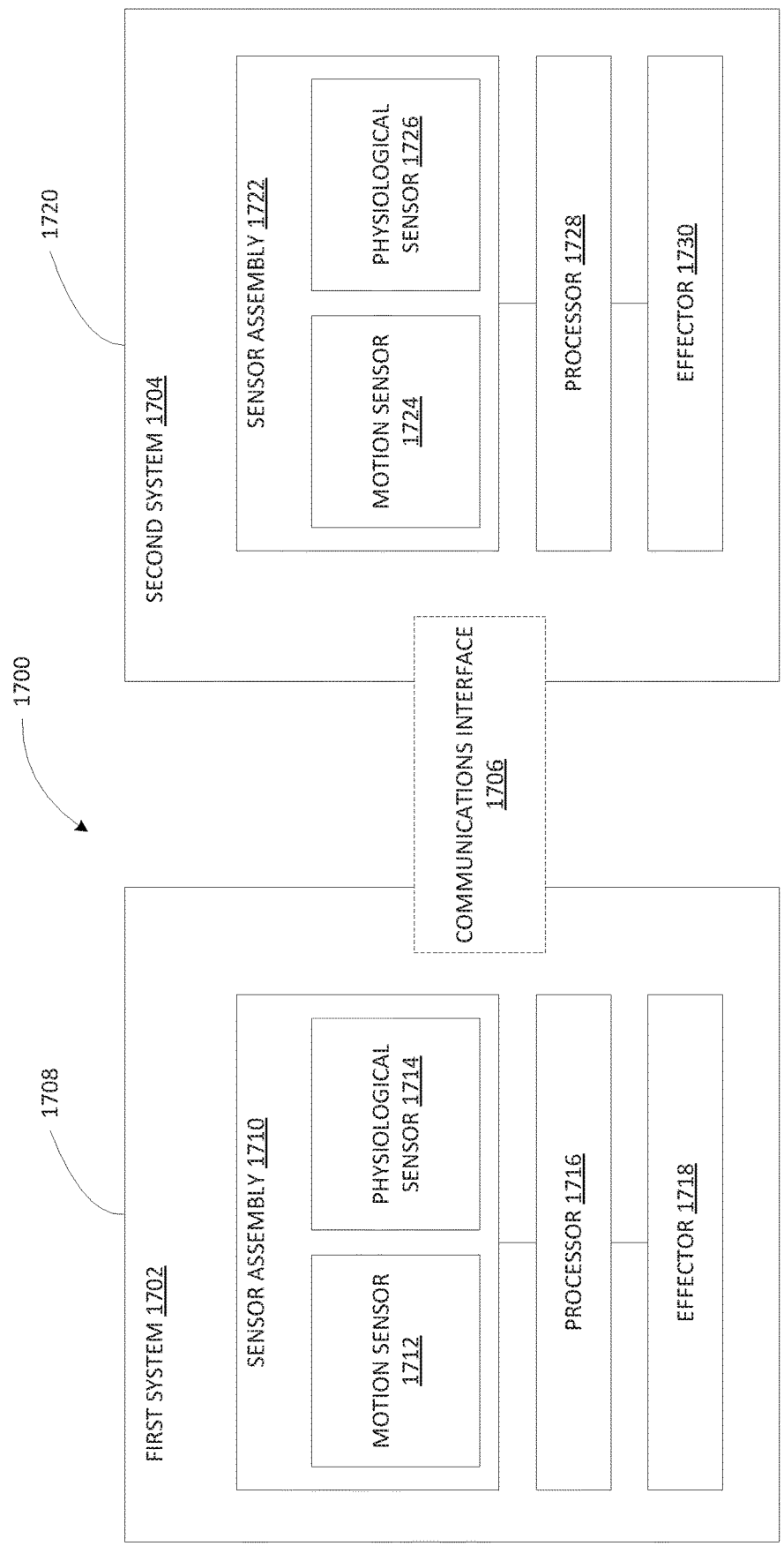
FIG. 16 is a schematic of a system for monitoring, treating, and preventing a repetitive stress injury, arthritis or other medical condition.

Referring now to FIG. 16, an example environment 1700 in which embodiments may be implemented is shown. The environment 1700 includes a first system 1702, a second system 1704, and a communications interface 1706 coupled between the first system 1702 and the second system 1704. The first system 1702 and the second system 1704 are configured to monitor, prevent, and treat a medical condition associated with a repetitive stress injury, arthritis, or other medical condition, and employ epidermal electronic systems (EES) to monitor physiological, positional, and movement conditions for monitoring, preventing, and treating a medical condition associated with a repetitive stress injury, arthritis, or other medical condition. The communications interface 1706 facilitates the transfer of one or more communication signals between the first system 1702 and the second system 1704. As shown, the first system 1702 includes a deformable substrate 1708 configured for interaction with a skin surface of a particular body portion, a sensor assembly 1710 including a motion sensor 1712 and a physiological sensor 1714 configured to generate one or more sense signals based on detection of a movement of a body portion by the motion sensor 1712 and a physiological parameter of the body portion by the physiological sensor 1714, a processor 1716 configured to receive one or more sense signals from the sensor assembly 1710 and to process the sense signals in order to provide control signals to portions of the first system 1702, and an effector 1718 operably coupled to the processor 816 to affect a body portion responsive to control by the processor 1716 to one or more of prevent and treat a medical condition associated with a repetitive stress injury, arthritis, or other medical condition. The substrate 1708, the sensor assembly 1710, the processor 1716, and the effector 1718 may correspond to the substrate 1002, the sensor assembly 1004, the processor 1006, and the effector 1008, respectively. The second system 1704 includes a deformable substrate 1720 configured for interaction with a skin surface of a particular body portion, a sensor assembly 1722 including a motion sensor 1724 and a physiological sensor 1726 configured to generate one or more sense signals based on detection of a movement of a body portion by the motion sensor 1724 and a physiological parameter of the body portion by the physiological sensor 1726, a processor 1728 configured to receive one or more sense signals from the sensor assembly 1722 and to process the sense signals in order to provide control signals to portions of the second system 1704, and an effector 1730 operably coupled to the processor 1728 to affect a body portion responsive to control by the processor 1728 to one or more of prevent and treat a medical condition associated with a repetitive stress injury, arthritis, or other medical condition. The substrate 1720, the sensor assembly 1722, the processor 1728, and the effector 1730 may correspond to the substrate 1604, the sensor assembly 1606, the processor 1608, and the effector 1610, respectively. The communications interface 1706 facilitates communication between the first system 1702 and the second system 1704 and may facilitate communication from one or more of the first system 1702 and the second system 1704 with a remote device or location. In an embodiment, the communications interface 1706 includes a reporter associated with one or more of the first system 1702 and the second system 1704, such as described with reference to the reporter 1500 and the reporter 1618. In an embodiment, the example environment 1700 includes a power supply in power communication with one or more of the first system 1702, the second system 1704, and the communications interface 1706. For example, a power supply may be positioned remotely from the first system 1702, the second system 1704, and the communications interface 1706 and provide one or more wireless power signals to the first system 1702, the second system 1704, and the communications interface 1706.

Figure 17:
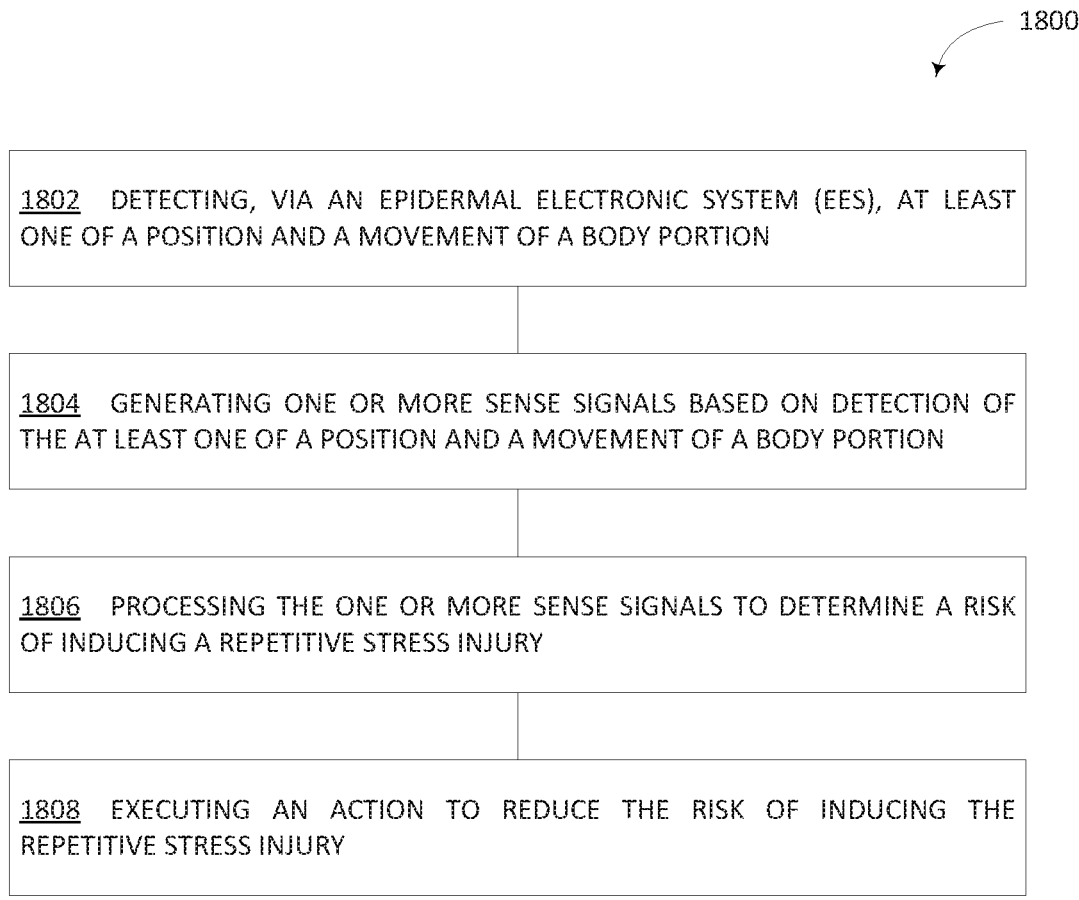
FIG. 17 is a flowchart of a method of monitoring, preventing, and treating a medical condition associated with a repetitive stress injury, arthritis, or other medical condition.
Figure 31:
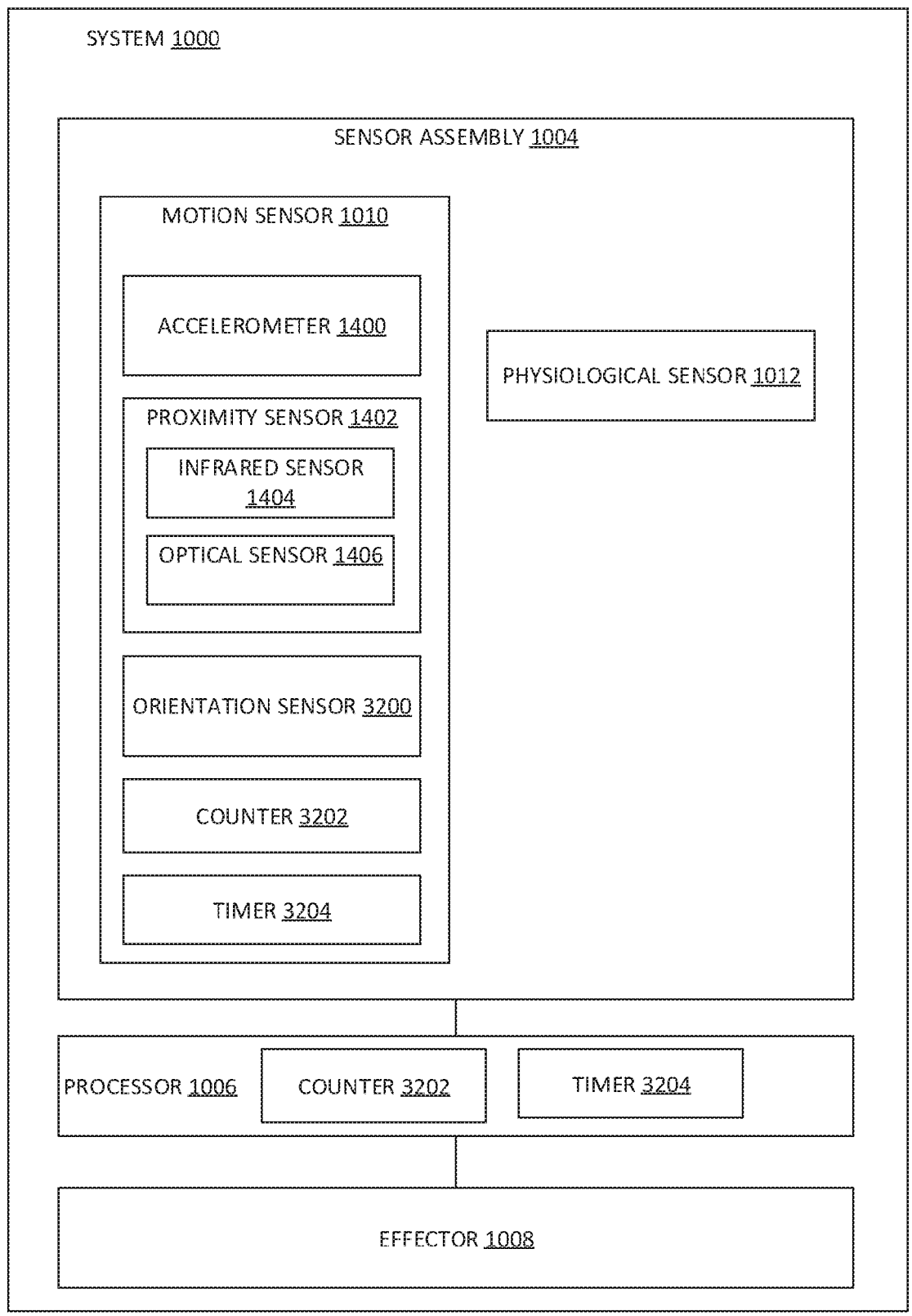
FIG. 31 is a schematic of a system for monitoring and treating a physiological condition of an individual subject, including but not limited to monitoring and treating a pain state of the individual subject.
Figure 32:
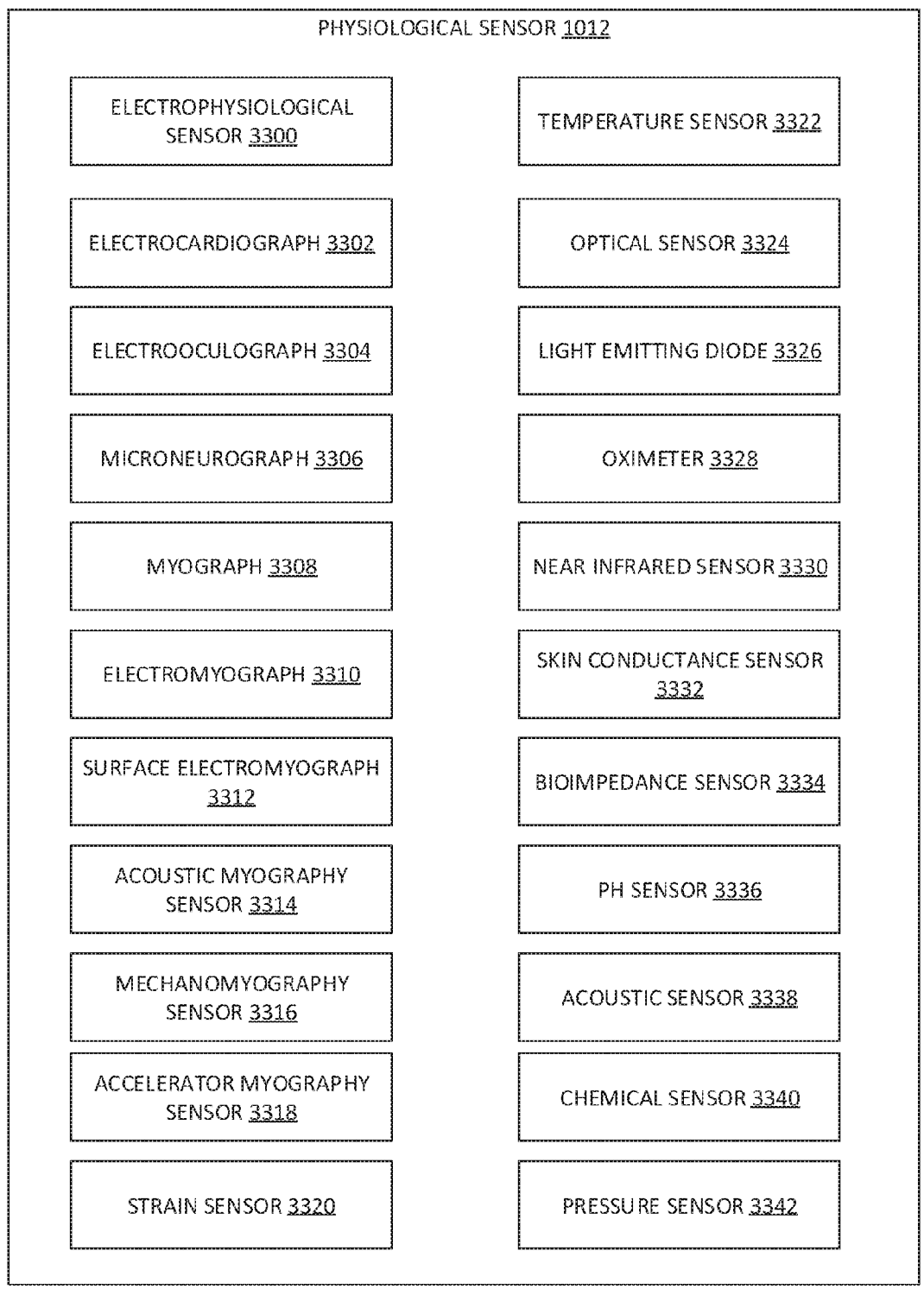
FIG. 32 is a schematic of an embodiment of a system such as shown in FIG. 31.
Figure 33:
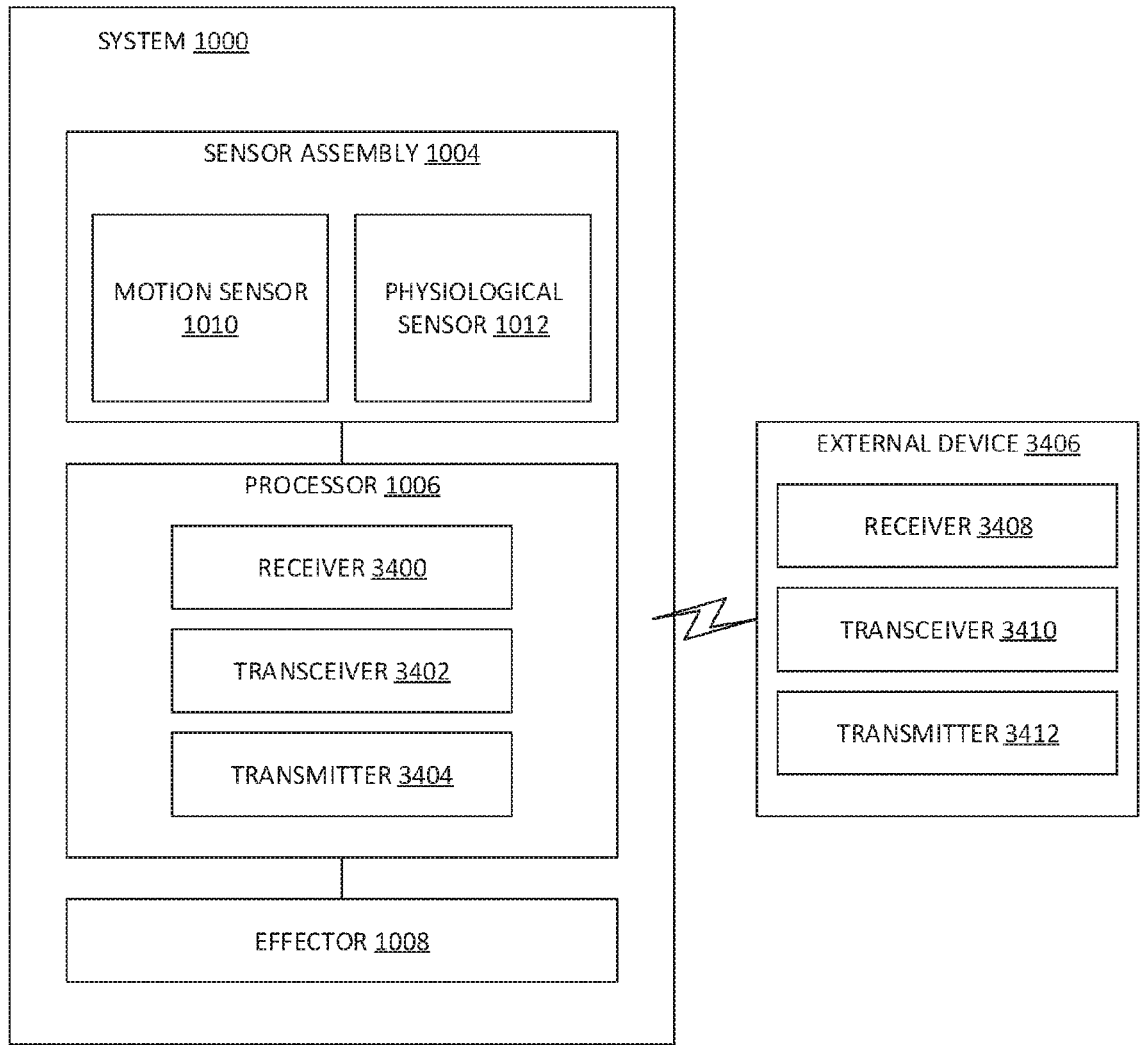
FIG. 33 is a schematic of an embodiment of a system such as shown in FIG. 31.
Figure 34:
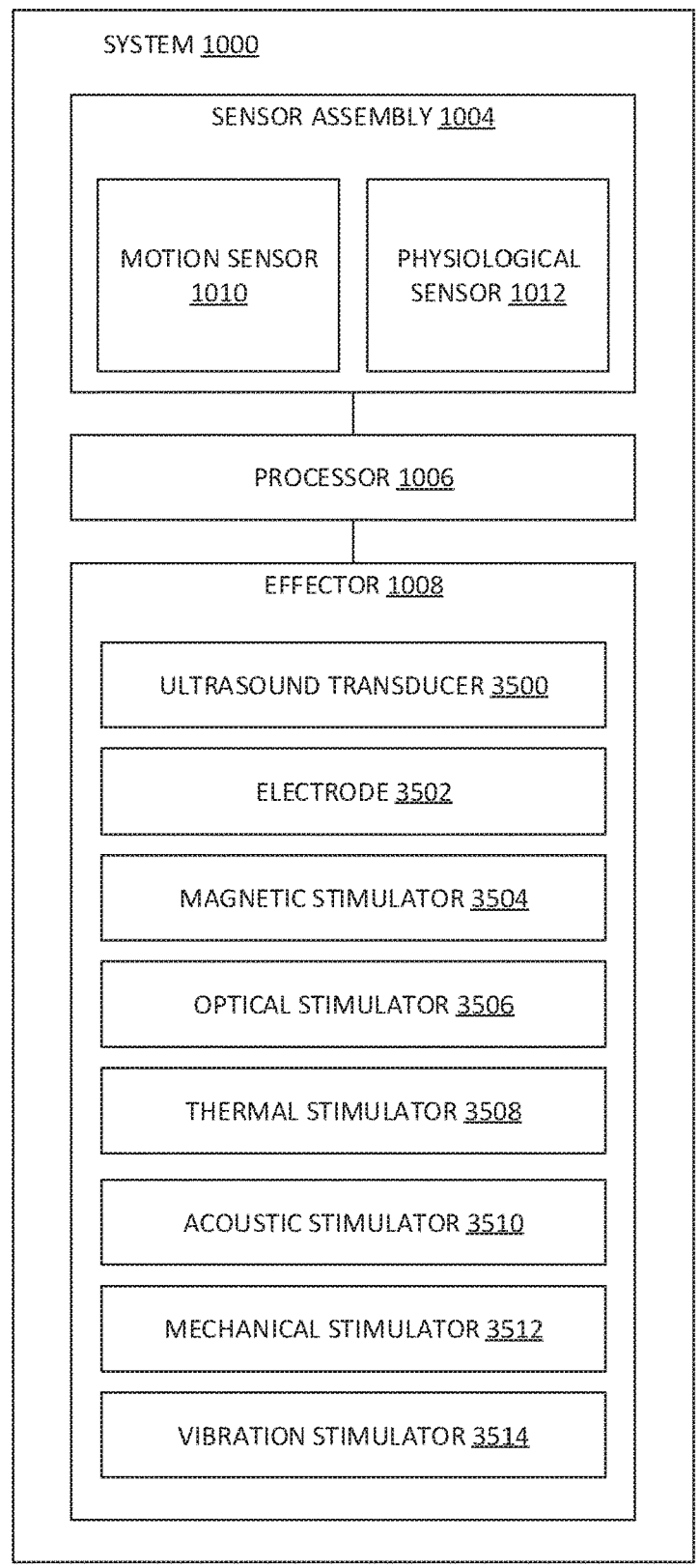
FIG. 34 is a schematic of an embodiment of a system such as shown in FIG. 31.

FIG. 17 illustrates a method 1800 for monitoring, preventing, and treating a medical condition associated with a repetitive stress injury, arthritis, or other medical condition. Method 1800 shows detecting, via an epidermal electronic system (EES), at least one of a position and a movement of a body portion in block 1802. For example, the motion sensor 1010 provided on an EES-based system, such as system 1000, can detect at least one of a position and a movement of a body portion, as described herein. Method 1800 also includes generating one or more sense signals based on detection of the at least one of a position and a movement of a body portion in block 1804. For example, the motion sensor 1010 can generate one or more sense signals based on detecting at least one of a position and a movement of a body portion, as described herein. Method 1800 further includes processing the one or more sense signals to determine a risk of inducing a repetitive stress injury in block 1806. For example, the processor 1006 can receive the one or more sense signals generated from the motion sensor 1010 of the sensor assembly 1004, and can process the one or more sense signals to determine a risk of inducing a repetitive stress injury, such as by accessing and executing the comparison module 1300, as described herein. Method 1800 further includes executing an action to reduce the risk of inducing the repetitive stress injury in block 1808. For example, the processor 1006 can provide one or more control signals to the effector 1008 to affect the body portion to reduce the risk of inducing the repetitive stress injury, as described herein.

FIG. 18 depicts further aspects of the method 1800 illustrated in FIG. 17. Block 1806 shows processing the one or more sense signals to determine a risk of inducing a repetitive stress injury and includes optional block 1900 that shows comparing the one or more sense signals to reference data indicative of a strain injury to determine the risk of inducing the strain injury. For example, the processor 1006 can access and execute the comparison module 1300 to compare the one or more sense signals generated by the sensor assembly 1004 to reference data indicative of a strain injury. Block 1900 also includes optional block 1902 that shows determining the action to execute based upon comparing the one or more sense signals to reference data indicative of a strain injury. For example, the processor 1006 can determine which action for the effector 1008 to take based on a comparison of the one or more sense signals to reference data indicative of a strain injury: where immediate action is warranted, the processor 1006 may determine to deliver an excitatory stimulus to a nerve (e.g., stimulate a nerve conduction) via the effector 1008 to induce movement of the body portion; where the risk of the repetitive stress injury is lesser, the processor 1006 may determine to provide a tactile simulation via the effector 1008.

FIG. 19 depicts further aspects of the method 1800 illustrated in FIG. 17. Block 1806 shows executing an action to reduce the risk of inducing the repetitive stress injury and includes optional block 2000 that shows reporting the determination of the risk of inducing the repetitive strain injury to reduce the risk. Block 2000 includes optional block 2002 that shows providing a tactile indication of the risk. Block 2002 includes optional block 2004, which shows providing a vibration-based indication of the risk and optional block 2006, which shows providing a tactile indication regarding a position of the body portion. Block 2006 includes optional block 2008, which shows providing a tactile indication that the position is a biomechanically detrimental position, and block 2010, which shows providing a tactile indication that the body portion has been in the position longer than a threshold duration.

FIG. 20 depicts further aspects of the method 1800 illustrated in FIG. 19. Block 1806 shows executing an action to reduce the risk of inducing the repetitive stress injury and includes optional block 2000 that shows reporting the determination of the risk of inducing the repetitive strain injury to reduce the risk. Block 2000 includes optional block 2100 that shows providing a visual indication of the risk. Block 2100 includes optional block 2102 that shows providing a visual indication regarding a position of the body portion. Block 2102 includes optional block 2104, which shows providing a visual indication that the position is a biomechanically detrimental position, and optional block 2106, which shows providing a visual indication that the body portion has been in the position longer than a threshold duration.

FIG. 21 depicts further aspects of the method 1800 illustrated in FIG. 19. Block 1806 shows executing an action to reduce the risk of inducing the repetitive stress injury and includes optional block 2000 that shows reporting the determination of the risk of inducing the repetitive strain injury to reduce the risk. Block 2000 includes optional block 2200 that shows providing an auditory indication of the risk. Block 2200 includes optional block 2202 that shows providing an auditory indication regarding a position of the body portion. Block 2202 includes optional block 2204, which shows providing an auditory indication that the position is a biomechanically detrimental position, and optional block 2206, which shows providing an auditory indication that the body portion has been in the position longer than a threshold duration.

FIG. 22 depicts further aspects of the method 1800 illustrated in FIG. 19. Block 1806 shows executing an action to reduce the risk of inducing the repetitive stress injury and includes optional block 2000 that shows reporting the determination of the risk of inducing the repetitive strain injury to reduce the risk. Block 2000 includes optional blocks 2300, 2302, 2304, and 2306. Block 2300 shows reporting at least one of an actuation of an effector configured to execute the action, a detected movement of the body portion, or a detected physiological condition. Block 2302 shows providing a warning of a risk of a biomechanically detrimental positioning of the body portion. Block 2304 shows providing an instruction to move the body portion. Block 2306 shows communicating the determination to a remote location and includes optional block 2308, which shows interacting with a program stored on the computer system, and optional block 2310, which shows modifying a program stored on the computer system.

FIG. 23 depicts further aspects of the method 1800 illustrated in FIG. 17. Block 1808 shows executing an action to reduce the risk of inducing the repetitive stress injury and includes optional block 2400 that shows stimulating a nerve proximate to the body portion. Block 2400 includes optional block 2402 that shows inducing at least one of a movement or a sensation of the body portion by stimulating the nerve conduction of the nerve proximate to the body portion. Block 2402 includes optional block 2404 that shows inducing at least one of a movement or a sensation of the body portion by stimulating a nerve conduction of the nerve after a threshold period of time during which the body portion is retained in a particular position.

FIG. 24 depicts further aspects of the method 1800 illustrated in FIG. 17. Block 1808 shows executing an action to reduce the risk of inducing the repetitive stress injury and includes optional block 2500 that shows electrically blocking a nerve conduction of a nerve proximate to the body portion. Block 2500 includes optional block 2502, which shows electrically blocking a nerve conduction of a nerve proximate to the body portion to inhibit a pain receptor, and optional block 2504, which shows electrically blocking a nerve conduction of a nerve proximate to the body portion to inhibit a movement of the body portion.

FIG. 25 depicts further aspects of the method 1800 illustrated in FIG. 17. Block 1802 shows detecting, via an epidermal electronic system (EES), at least one of a position and a movement of a body portion and includes optional blocks 2600, 2602, 2604, 2606, 2608, and 2610. Block 2600 shows measuring, via an epidermal electronic system (EES), a repeated motion of the body portion. Block 2602 shows measuring, via an epidermal electronic system (EES), a number of repetitions of the movement of the body portion. Block 2604 shows measuring, via an epidermal electronic system (EES), a speed of the movement of the body portion. Block 2606 shows measuring, via an epidermal electronic system (EES), a duration of the movement of the body portion. Block 2608 shows measuring, via an epidermal electronic system (EES), a disposition of the body portion relative to a second body portion. Block 2610 shows measuring, via an epidermal electronic system (EES), an angle of movement of the body portion.

FIG. 26 depicts further aspects of the method 1800 illustrated in FIG. 17 and includes optional block 2700, which shows detecting, via an epidermal electronic system (EES), a physiological parameter of the body portion, and optional block 2702, which shows generating one or more sense signals based on detection of the physiological parameter of the body portion.

FIG. 27 depicts further aspects of the method 1800 illustrated in FIG. 26. Block 2700 shows detecting, via an epidermal electronic system (EES), a physiological parameter of the body portion and includes optional blocks 2800, 2802, 2804, 2806, and 2808. Block 2800 shows detecting a temperature of the body portion. Block 2802 shows detecting a strain of the body portion. Block 2804 shows detecting a blood flow of the body portion. Block 2806 shows detecting a blood oxygenation level of the body portion. Block 2808 shows detecting an electrical activity of the body portion.

FIG. 28 depicts further aspects of the method 1800 illustrated in FIG. 17 and includes optional block 2900, which shows detecting, via an epidermal electronic system (EES), a disposition of the body portion. Block 2900 includes optional block 2902, which shows detecting, via an epidermal electronic system (EES), an angle of a joint proximate the body portion, and optional block 2904, which shows detecting, via an epidermal electronic system (EES), a disposition of the body portion over a period of time.

FIG. 29 depicts further aspects of the method 1800 illustrated in FIG. 17 and includes optional block 3000, which shows detecting, via an epidermal electronic system (EES), a device interfacing with at least one of the body portion and another body portion, and optional block 3002, which shows transmitting a communication signal to the device. Block 3002 includes optional block 3004 that shows transmitting the one or more sense signals generated based on detection of at least one of the position and the movement of the body portion to the device.

FIG. 30 depicts further aspects of the method 1800 illustrated in FIG. 17 and includes optional block 3100, which shows detecting, via an epidermal electronic system (EES), at least one of a position and a movement of a second body portion proximate the body portion.

Systems, devices, and methods are also described for monitoring and treating pain and related disorders. Pain can be attributed to numerous physiological and neurological conditions and can be experienced by an individual subject according to a variety of pain states. In an embodiment, a pain state includes a pain type, a pain level, a pain quality, or combinations thereof. For example, the pain states can include a pain-free state, an onset of pain, a pain pattern, chronic pain, acute pain, mixed pain state, a hyperalgesic pain state, an allodynic pain state, a breakthrough pain state, a neuropathic pain state, a nociceptive pain state, a nonnociceptive pain state, combinations thereof, or the like. Pain types can include, for example, nociceptive pain (e.g., due to mechanical, thermal, and/or chemical interactions), somatic pain, neuropathic pain, visceral pain, superficial pain, and psychogenic pain, where various pain types can be experienced according to particularized biological systems or locations (e.g., musculoskeletal, neuropathic, etc.) or can be nonlocalized. For example, pain types can include spontaneous pain (e.g., occurring in the absence of stimuli), evoked pain (e.g., occurring in response to stimuli), continuous pain, or intermittent pain. For example, pain levels can include intensity, severity, or magnitude of pain. Pain quality can include, but is not limited to, intensity, sharpness, dullness, burning, cold, tenderness, itch, cramping, radiating, tingling, throbbing, aching, tiring, deepness, shocking or electrical, stinging, etc., and combinations thereof. Assessment tools to evaluate a pain state can, for example, include instruments or combinations of instruments and related software designed to monitor physiological responses including chemical changes, biopotentials, muscle activation, and changes thereof. Assessment tools to evaluate a pain state can, for example, include instruments or combinations of instruments (e.g., motion sensor(s), physiological sensor(s), or combinations thereof) and related software designed to monitor autonomic responses as described herein. Assessment tools to evaluate a pain state, for example, can include subjective tools such as the Pain Quality Assessment Scale and the McGill Pain Questionnaire. In an embodiment, the subjective tools can provide the system 1000 with data associated with a baseline or comparative pain level, which in turn can serve as a threshold pain level or other comparative pain indicator.

Pain is prevalent in human and animal populations. As but a few examples, a majority of the human population (60% to 85%) is reported to experience back pain of muscular origin at some point in their lifetime, pain evoked by myofascial trigger points is experienced by approximately 30% of the population, approximately 50 million Americans experience arthritis (such as osteoarthritis or inflammatory arthritis), whereas at least 30% of patients with moderate chronic pain and more than 50% of patients with severe chronic pain fail to achieve adequate pain relief. As such, pain represents a common factor for individuals seeking physician treatment, etc. The costs associated with traditional treatment of pain and the lack of treatment of pain (e.g., lost wages, disability, medical facility costs, etc.) have a large impact on society as a whole. For instance, it is reported that the total economic impact for arthritis alone in 2003 was $128 billion, based on lost wages due to disability and other indirect costs. In addition, pain and movement are intrinsically inter-related. Movement is known to be related to cause, effect, prevention, and therapy of pain and its disorders. The systems, devices, and methods described herein generate sense signals from one or more physiological sensors and motion sensors positioned proximate a body portion of a subject to provide indicators of a physiological state (e.g., a pain state) of the individual subject. In an embodiment, the systems and methods described herein may be used to monitor and treat pain experienced by an individual subject via the generation of sense signals from one or more physiological sensors and motion sensors configured to monitor one or more physiological parameters of the individual subject and one or more movements or positions of a body portion of the individual subject and to provide an effect to the body portion through action of one or more effectors. For example, the systems, devices, and methods can employ an ultrasound transducer as the effector to affect the individual subject, such as to treat the pain associated with movement of the body portion, pain associated with the physiological parameter, or combinations thereof.

In embodiments, movement of the body portion can be indicative of pain experienced by the individual. For example, the conscious or unconscious fear that a motion will induce pain can alter the motion of a body portion, indicating acute or chronic pain. For example, physiological adaptation to acute pain or chronic pain can cause short-term or long-term changes in motor function of a body portion (e.g., increased or inhibited muscle activation), and as such can be indicative of pain. Alterations in movement of a body portion can present, for example, as pronounced minimalization of motion or agitation of affecting a body site (e.g., a muscle), a guarding motion, an awkward gait, a limp, redistribution of activity or stress, modifications in loading, pronounced use of non-dominant limb, reduced force output, lack of use of a body portion, respiratory dysfunction, splinting, etc. For example, conscious or unconscious coping mechanisms (e.g., grimacing, pronounced rubbing or massage of a body portion, etc.) can be indicative of pain. For example, involuntary responses (e.g., reflex, spasm, etc.) can be indicative of pain. In embodiments, movement of the body portion of the individual can be a source of, a cause of, or induce or worsen pain, and, as such, a particular movement can be determined to be associated with the pain. For example, a certain motion can be repeatedly associated temporally with an increase in pain (e.g., as indicated by changes in autonomic responses, measured by chemical sensors, electrophysiological sensors, biopotential sensors, etc. or by subjective reporting). In embodiments, movement of the body portion of the individual can be a preventative treatment or therapeutic treatment of pain. For example, lack of movement or repetition of a movement can be indicative of an increased risk for pain, while sensed and recorded motions indicative of appropriate therapeutic or preventative movements can be indicative of a decreased risk for pain. In an embodiment, muscle fatigue can be associated with, can induce, or can be an indicator of muscle pain.

In an embodiment, the motion of the body portion can provide an indication as to when treatment by the effector can be employed or should be employed. For example, the systems, devices, and methods may employ the effector to provide treatment to the individual subject when the body portion is undergoing motion determined (e.g., previously or simultaneously) to be associated with an increase in pain, e.g., as a palliative treatment. For example, the systems, devices, and methods may employ the effector to provide treatment to the individual subject when there has been a lack of motion in the body portion of the individual subject or the individual subject has been at rest for a time period above a threshold time period. Treatment of the individual subject to induce movement can be a preventative measure (e.g., to induce movement to prevent onset of arthralgia, myalgia, or pressure sores). For example, the systems, devices, and methods may employ the effector to provide treatment to the individual subject when the individual subject is at rest (e.g., not currently undergoing substantial movement, such as exercising, walking, signing, etc.). Treatment of the individual subject during a rest state can provide a convenient and non-interruptive mechanism to treat pain (e.g., chronic or long-term pain) experienced by the individual subject.

In an embodiment, the systems and methods described herein employ one or more physiological sensors to monitor one or more physiological conditions of a subject and to generate a sense signal in response thereto. The physiological sensors can include, but are not limited to, an electrophysiological sensor, an electrocardiograph, an electrooculograph, a microneurograph, a myograph, an electromyograph (e.g., a surface electromyograph), an acoustic myography sensor, a mechanomyography sensor, an accelerometer myography sensor, a strain sensor, a pressure sensor, a temperature sensor, an optical sensor (e.g., an LED, a pulse oximeter, etc.), a near infrared sensor, a skin conductance sensor, a bioimpedance sensor, a pH sensor, an acoustic sensor, or a chemical sensor.

In an embodiment, the systems and methods described herein employ one or more motion sensors to monitor a movement or position of a body portion of an individual subject and to generate a sense signal in response thereto. The motion sensors can include, but are not limited to, an orientation sensor, an accelerometer, a proximity sensor (e.g., an infrared sensor, an optical sensor, etc.), a force sensor, a pressure sensor, sensors configured to measure a repeated motion of a body portion, sensors configured to measure a number of repetitions of a movement of a body portion, sensors configured to measure a speed of a movement of a body portion, sensors configured to measure a duration of movement of a body portion, sensors configured to measure a disposition of a body portion relative to a second body portion, and sensors configured to measure an angle of movement of a body portion. The motion of the body portion can be indicative of pain experienced by the individual, can be indicative of risk of pain, can be indicative of a source of pain, can provide an indication as to when treatment can be employed, or combinations thereof.

In an embodiment, the systems and methods described herein employ one or more effectors to affect a body portion responsive to processing of sense signals generated by the sensor assembly. For example, the one or more effectors can include one or more ultrasound transducers, including, but not limited to, an array of ultrasound transducers, an ultrasound transducer configured to generate low intensity ultrasound signals, an ultrasound transducer configured to generate high intensity focused ultrasound signals, an ultrasound transducer configured to generate ultrasound signals as low dose, high frequency ultrasound signals, an ultrasound transducer configured to generate ultrasound signals on a pulsed basis, an ultrasound transducer configured to generate ultrasound signals on a continuous basis, an ultrasound transducer configured to generate ultrasound signals according to a plurality of treatment patterns, an ultrasound transducer configured to generate ultrasound signals according to a plurality of ultrasound frequencies, ultrasound transducers configured for placement on different locations on the body portion of the individual subject. The one or more effectors can include, but are not limited to, an electrode, a magnetic stimulator, an optical stimulator (e.g., an optical stimulator configured to generate infrared light, an optical stimulator configured to generate low-intensity, pulsed infrared light, etc., and combinations thereof), a thermal stimulator, and combinations thereof.

Figure 10:
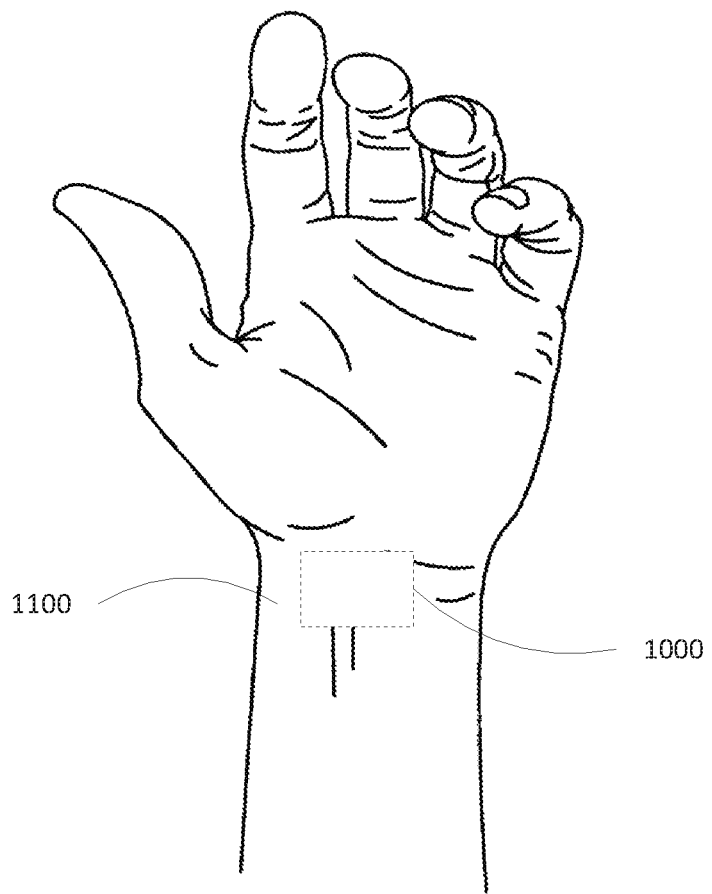
FIG. 10 is a schematic of an embodiment of a system such as shown in FIG. 9.

In an embodiment, referring generally to FIGS. 9-14 and 31-36, the system 1000 (or pain therapy device) is configured for monitoring and treating pain experienced by an individual subject. The system 1000 includes the substrate 1002, the sensor assembly 1004, the processor 1006, and the effector 1008 for placement on the individual subject to monitor the individual subject for indications of pain and for treating the pain through action of the effector 1008. In an embodiment, the system 1000 includes epidermal electronic systems (EES) or devices incorporating epidermal electronics to monitor physiological, positional, and movement conditions for monitoring, preventing, and treating pain experienced by the individual subject. The substrate 1002 is configured to conform to a contour of a body portion of an individual subject (e.g., the curvature of a limb), to interface with a skin surface of the body portion, or combinations thereof. For example, the substrate 1002 can comprise a deformable (e.g., conformable, flexible, stretchable, etc.) material configured to interface with, and conform to, the body portion, including, but not limited to a skin surface of the body portion. The body portion is shown in FIG. 10 as a wrist 1100, however the system 100 can be positioned on any body portion, including but not limited to, an arm, an elbow, a wrist, a hand, a finger, a leg, a hip, a knee, an ankle, a foot, a toe, a facial region, a head region (e.g., proximate one or more cranial muscles of the face or head), an ear region (e.g., via an ear clip configuration, on the ear lobe, pinna, or concha), a neck region, a torso region, a spinal portion, a sacroiliac joint, one or more myofascial trigger points, or the like, or a skin portion thereof. The pliable nature of the substrate 1002 (e.g., flexibility and stretchability) facilitates interaction/interfacing with the body portion, which includes a generally low-modulus and deformable natural skin surface. In an embodiment, the substrate 1002 can include one or more of a stretchable/flexible fabric, paper, or polymer (e.g., a natural or synthetic elastomeric polymer, polyimide, polyvinyl, an organic polymer such as PDMS, xylylene, parylene, an inorganic polymer, a biopolymer, a composite material, or any combination thereof), a film (e.g., a hydrocolloid film), a membrane (e.g., a nanomembrane, such as a silicon nanomembrane), a gas-permeable elastomeric sheet, or other deformable (e.g., stretchable, flexible, pliable) material. The substrate 1002 can be positioned in proximity with the skin surface according to various mechanisms including, but not limited to, affixed to the skin via an adhesive material, held in place by an external pressure, such as pressure provided by a material wrapped around or about a body portion (e.g., a fabric, a garment, a glove, a bandage, etc.), affixed in a textile, fabric, garment, accessory (e.g., a glove, a sock, a finger cot, etc.), or so forth.

In an embodiment, the system 1000 includes at least one flexible or stretchable electronic component. For example, at least one of the sensor assembly 1004 (e.g., motion sensor 1010, physiological sensor 1012, etc. as described herein), the processor (and associated circuitry) 1006, or the effector 1008 can include or be formed of flexible or stretchable electronics coupled to the substrate 1002. For example, interconnects (not illustrated) between these components or within the circuitry can include or be formed of flexible or stretchable electronics (e.g., serpentine conducting tracings allowing for stretchable interconnects) and coupled to the substrate 1002. For example, a power source (e.g., power supply 1200 described herein), can include or be formed of flexible or stretchable electronics and be coupled to the substrate 1002. In an embodiment, the at least one flexible or stretchable electronic component includes at least one of a wavy, bent, mesh (e.g., open mesh), buckled, or serpentine geometry. In an embodiment, the at least one flexible or stretchable electronic component includes at least one nanowire, at least one nanoribbon, or at least one nanomembrane. For example, the system 1000 can include one or more multifunctional electronic units comprising a stretchable/flexible system including a sensor assembly (e.g., sensor assembly 1004), effector (e.g., effector 1008), and power source (e.g., power supply 1200) in communication via associated circuitry (e.g., with processor 1006), including interconnects, residing in or on a deformable substrate (e.g., substrate 1002).

In an embodiment, the system 1000 can include at least one ultrathin electronic component. For example, an ultrathin (e.g., less than 20 micrometers) electronic component can include a thinned wafer (e.g., thinned silicon wafer bonded to a polymer substrate), an ultrathin chip, or the like. For example, ultrathin circuitry can include conductive layers formed on a deformable substrate (e.g., substrate 1002) such as parylene by evaporation deposition with ultraviolet (UV) lithography and etching. For example, at least one of the sensory assembly 1004, the processor 1006, or the effector 1008 can include ultrathin electronics.

In an embodiment, the system 1000 can include at least one electrically conductive thread, yarn, or textile. For example, the sensory assembly 1004, the processor 1006, or the effector 1008 can include at least one electrically conductive thread or yarn. Electrically conductive threads, yarns, or textiles can be configured to provide sufficient current to induce at least one of a wired or wireless coupling, e.g., between electronic components. For example, electronically conductive threads, yarns, or textiles may form the processor 1006 (or circuitry thereof) or other circuitry configured to function in communication between one or more sensor assemblies 1006, one or more effectors 108, or other circuitry of the system 1000. For example, electronically conductive threads, yarns, or textiles may form at least a portion of circuitry configured to function in communication between a plurality of multifunctional electronic units each comprising one or more sensor assemblies 1006, one or more effectors 1008, and processor 1006. Electrically conductive fibers, threads, and yarns can include a metallic material, semi-metallic material, semi-insulative material, semi-conductive material (e.g., silicon and a gallium arsenide), or transparent conductive material (e.g., an indium-tin-oxide (ITO) material). Electrical threads or yarns can be embedded in textiles using weaving, knitting or embroidery, for example, or can be attached using nonwoven production techniques such as adhesion. For example, electrically conductive yarns having curved configuration can be attached to an elastic textile (e.g., by sewing or by adhesion) and can form all or part of a sensor assembly 1004 that measures one or more physical characteristics of an individual, e.g., as the curved configuration is altered, such as due to particular skin topography or the like.

The sensor assembly 1004 is coupled to the substrate 1002 and includes the motion sensor 1010 and the physiological sensor 1012. The sensor assembly 1004 is configured to generate one or more sense signals based on detection of a movement of the body portion by the motion sensor 1010 and upon detection of a physiological parameter of the body portion by the physiological sensor 1012. The one or more sense signals can be associated with one or more movements of the body portion, one or more physiological parameters of the body portion, or combinations thereof. In an embodiment, shown in FIG. 31, the motion sensor 1010 includes one or more of an orientation sensor 3200 (e.g., cells 120 described with reference to FIGS. 1A through 8), an accelerometer (e.g., accelerometer 1400), and a proximity sensor (e.g., proximity sensor 1402) to detect a movement of a body portion and generate a sense signal in response thereto. For example, the orientation sensor 3200 can include one or more of a single-axis accelerometer, a pair of oppositely aligned single-axis accelerometers, an antenna configured to measure a field source, a range sensor, a multi-axis accelerometer, a gyroscope, an inclinometer, or combinations thereof, as described herein, to measure a movement of the body portion based on an orientation or change of orientation of the body portion. The proximity sensor 1402 can include one or more of an infrared sensor (e.g., infrared sensor 1404) and an optical sensor (e.g., optical sensor 1406). In an embodiment, the proximity sensor is configured to sense a second body portion proximate the body portion on which the system 1000 is positioned. For example, the system 1000 can be positioned on a wrist of the individual subject and the motion sensor 1010 can include a proximity sensor configured to detect one or more of a presence, a position, an angle, and a movement of another body portion proximate the wrist, such as a hand, a palm, an arm, a finger, a shoulder, and so forth. In an embodiment, the proximity sensor 1402 is configured to sense a device interfacing with another portion of the skin surface or with another body portion. For example, the system 1000 can be positioned on a body portion of the individual subject and a second system 1000 is positioned proximate the body portion or on another body portion, where the proximity sensor of the motion sensor 1010 of the system 1000 can sense one or more of a presence, a position, an angle, and a movement of the second system 1000. In an embodiment, the motion sensor 1010 includes a pressure sensor, which can be an individual sensor, or incorporated as a component of one or more of the orientation sensor 3200 or the proximity sensor 1402. The pressure sensor can provide an indication (e.g., via sense signals) regarding whether an individual, or a body portion thereof, has been idle for a period of time that exceeds a threshold duration, which in turn can provide an indicator for operation of the effector 1008. For example, treatment of the individual subject to induce movement can be a preventative measure (e.g., to induce movement to prevent onset of arthralgia, myalgia, or pressure sores).

The motion sensor 1010 is configured to detect one or more of a movement of a body portion and a position of the body portion. The movement of the body portion, the position of the body portion, or combinations thereof can be indicative of a pain state of the individual subject. For example, the conscious or unconscious fear that a motion will induce pain can alter the motion of a body portion, indicating acute or chronic pain. For example, physiological adaptation to acute pain or chronic pain can cause short-term or long-term changes in motor function of a body portion (e.g., increased or inhibited muscle activation), and as such can be indicative of pain. Alterations in movement of a body portion can present, for example, as pronounced minimalization of motion or agitation of affecting a body site (e.g., a muscle), a guarding motion, an awkward gait, a limp, redistribution of activity or stress, modifications in loading, pronounced use of non-dominant limb, reduced force output, lack of use of a body portion, respiratory dysfunction, splinting, etc. For example, conscious or unconscious coping mechanisms (e.g., grimacing, pronounced rubbing or massage of a body portion, etc.) can be indicative of pain.

For example, involuntary responses (e.g., reflex, spasm, etc.) can be indicative of pain. In embodiments, movement of the body portion of the individual can be a source of, a cause of, or induce or worsen pain, and, as such, a particular movement can be determined to be associated with the pain. The movement of the body portion, the position of the body portion, or combinations thereof can be indicative of a risk of increased pain experienced by the individual subject, for example, when the movement has been determined to be temporally associated with pain (e.g., as indicated by changes in autonomic responses) or when a movement (e.g., a lack of movement) or repetition of movement indicates a risk of pain. Detection of these movements can facilitate determination by the processor 1006 of a physiological state of the individual subject, which can aid in determining whether to treat the individual subject through action of the effector 1008. Further, the motion of the body portion can provide an indication as to when treatment by the effector 1008 can be employed. For example, the processor 1006 can instruct the effector 1008 (e.g., via one or more control signals, such as electric control signals) to provide treatment to the individual subject when the individual subject is at rest (e.g., not currently undergoing substantial movement, such as exercising, walking, signing, etc.). For example, the processor 1006 can instruct the effector 1008 to provide treatment to the individual subject when the body portion is undergoing motion determined (e.g., previously or simultaneously) to be associated with an increase in pain, e.g., as a palliative treatment. For example, the processor 1006 can instruct the effector 1008 to provide treatment to the individual subject when there has been a lack of motion in the body portion of the individual subject or the individual subject has been at rest for a time period above a threshold time period. Treatment of the individual subject to induce movement can be a preventative measure (e.g., to induce movement to prevent onset of arthralgia, myalgia, or pressure sores).

The body portion can be the portion with which the system 1000 interfaces or can be a portion proximate the portion with which the system 1000 interfaces. In an embodiment, the motion sensor 1010 generates a sense signal based on a repeated motion of the body portion. For example, the system 1000 can be positioned on a wrist of a subject and the motion sensor 1010 measures a repeated flexing or bending of the wrist, such as during movement of the hand or one or more fingers. In an embodiment, the motion sensor 1010 measures a number of repetitions of a movement of a body portion. For example, the system 1000 can be positioned on a finger of a subject and the motion sensor 1010 measures the number of repetitions that the particular finger is flexed or bent. Measuring the number of repetitions can include, but is not limited to, measuring that zero repetitions have occurred, measuring a finite number of repetitions, measuring the number of repetitions taken over a specified time period, and determining that the number of repetitions exceeds a threshold number (e.g., a threshold at which a subject is at risk for pain). The measurement of the number of repetitions can be facilitated by, for example, one or more of a counter 3202 or a timer 3204 present in the motion sensor 1010, in the processor 1006, or combinations thereof. In an embodiment, the motion sensor 1010 measures a speed of a movement of a body portion. For example, the system 1000 can be positioned on an ankle of a subject and the motion sensor 1010 measures the speed of movement of the ankle, such as one or more of a speed of movement during a flexing of the ankle during a walking motion, a speed of movement relative to a ground surface during a walking motion, or other movement. In an embodiment, the motion sensor 1010 measures a duration of a movement of a body portion. The duration can include one or more of a total duration of movement within a period of time (e.g., duration encompassing multiple repetitions of movement) and a total duration of movement for a single repetition of movement. The timer 3204 can facilitate such duration measurements. For example, the system 1000 can be positioned on a cheek or proximate a facial muscle of the individual subject, and the motion sensor 1010 measures the duration of a contraction of the cheek or facial muscle (e.g., such as to indicate a grimace or other pain-related movement of the body portion). The period of time over which the movement is measured can include, but is not limited to, seconds (e.g., 10 seconds, 30 seconds), a minute, 20 minutes, 30 minutes, an hour, a portion of a day during which a subject is awake and active, a portion of a day during which a subject is asleep or otherwise inactive, a day, or longer duration. In an embodiment, the sensor assembly 1004 is configured to measure the disposition of the body portion over a period of time. For example, the sensor assembly 1004 may measure a disposition of the body portion over time while the body portion is one or more of at rest, in motion, and held in a position that is not a rest position (e.g., tensed). In an embodiment, the motion sensor 1010 measures a disposition of a body portion on which the system 1000 is positioned relative to a second body portion during a movement of one or more of the body portion and the second body portion. For example, the system 1000 can be positioned on a phalange of a subject and the motion sensor 1010 measures a disposition of the phalange relative to a wrist or ankle of the subject during motion of the phalange or wrist/ankle. In an embodiment, the motion sensor 1010 measures an angle of movement of a body portion. For example, the system 1000 can be positioned on an arm of a subject and the motion sensor 1010 measures an angle of movement of the arm (e.g., relative to the torso, relative to a rest position of the arm, relative to another body portion, and so forth). Measurement by the motion sensor 1010 of one or more of a repeated motion of a body portion, a number of repetitions of the movement of the body portion, a speed of the movement of the body portion, a duration of the movement of the body portion, a disposition of the body portion relative to a second body portion, and an angle of movement of the body portion provides information that can aid in the determination by the system 1000 of whether the subject is experiencing pain or is at risk of experiencing pain (e.g., delayed onset pain or repetitive injury pain), such as whether the movement is symptomatic of pain or a causal factor of pain.

In an embodiment, the motion sensor 1010 is configured to transmit one or more sense signals to the processor 1006 indicative of a motion state of the individual subject, a rest state of the individual subject, or a duration of a rest state of the individual subject. For example, the motion state of the individual subject can indicate that the individual subject (or body portions thereof) is currently moving, whereas the rest state of the individual subject can indicate that the individual subject (or body portions thereof) are not moving, or are moving at a rate or between orientations that does not exceed a threshold rate. In an embodiment, the processor 1006 determines a rest state of the individual based on the sense signals from the motion sensor 1010. For example, the processor 1006 can compare the sense signals from the motion sensor 1010 to reference data indicative of a body portion at rest to determine whether the body portion of the individual subject is experiencing a rest state (e.g., at or under a motion threshold relative to the reference data) or an active state (e.g., exceeding a motion threshold relative to the reference data). In an embodiment, the processor 1006 is configured to activate the effector 1008 to affect the body portion (e.g., via ultrasound, electric, magnetic, optical, or thermal stimulation, as described further herein) only when the body portion is at rest. For example, the processor 1006 can instruct the effector 1008 (e.g., via one or more electric control signals) to activate to affect the body portion when the sense signals from the motion sensor 1010 indicate that the body portion is experiencing a rest state. As an example, the effector 1008 may operate only when the individual subject, or the particular body portion to treat, is at rest, such as when the individual subject is asleep, resting on furniture, driving or riding in a vehicle, or the like. As another example, the effector 1008 may operate after the individual subject, or the particular body portion to treat, has been at rest, or in the same position, for a period that exceeds a predetermined length of time. In an embodiment, the processor 1006 is configured to activate the effector 1008 to affect the body portion responsive to a predetermined amount of movement of the body portion. For example, the processor 1006 can instruct the effector 1008 (e.g., via one or more electric control signals) to activate to affect the body portion when the sense signals from the motion sensor 1010 indicate that the body portion met or exceeded a predetermined amount of movement, such as by exceeding a threshold distance of travel of the body portion, a threshold period of time of movement of the body portion, a threshold orientation of the body portion, or the like. In an embodiment, the processor 1006 is configured to activate the effector 1008 to affect the body portion responsive to a predetermined type of movement of the body portion. For example, the processor 1006 can instruct the effector 1008 (e.g., via one or more electric control signals) to activate to affect the body portion when the sense signals from the motion sensor 1010 indicate that the body portion experienced a particular type of movement. For example, the sense signals from the motion sensor 1010 might indicate that the body portion experienced a particular type of movement, such as a predetermined high velocity of movement, a high level of force output, a too-rapid step (e.g., indicating tripping), a movement in a particular direction (e.g., indicating a twisting of a joint), or the like, which can indicate an increased risk of pain. For example, the sense signals from the motion sensor 1010 might indicate pronounced minimalization of motion or agitation affecting a body site (e.g., a muscle), e.g., "guarding". For example, the sense signals from the motion sensor 1010 might indicate that the body portion experienced a particular type of movement such as experiencing a predetermined velocity of movement (e.g., the individual subject is slowing down), a grimace, an awkward gait, a limp, pronounced use of non-dominant limb, pronounced rubbing or massage of a body portion (e.g., repeated or deep massage), or the like, which can indicate a level of discomfort or pain experienced by the individual subject. Such occurrences can serve as an indicator to the processor 1006 that the effector 1008 should be activated.

The physiological sensor 1012 is configured to detect one or more physiological parameters of the individual subject on which the system 1000 is positioned, where such physiological parameters can provide an indication as to whether the individual subject is experiencing pain, or to what degree the individual subject is experiencing pain. In an embodiment, the physiological sensor 1012 detects a localized physiological parameter provided by one or more of a body portion with which the system 1000 interfaces and a body portion proximate the portion with which the system 1000 interfaces. The physiological sensor 1012 can also or instead be configured to detect systemic physiological parameters of the subject on which the system 1000 is positioned. In an embodiment, shown in FIG. 32, the physiological sensor 1012 can include an electrophysiological sensor 3300, an electrocardiograph 3302, an electrooculograph 3304, a microneurograph 3306, an electroneurograph, a myograph 3308, an electromyograph (EMG) 3310, a surface electromyograph 3312, an acoustic myography sensor 3314, a mechanomyography sensor 3316, an accelerometer myography sensor 3318, a strain sensor 3320, a temperature sensor 3322, an optical sensor 3324, a light emitting diode (LED) 3326, an oximeter 3328, a near infrared sensor 3330, a skin conductance sensor 3332, a bioimpedance sensor 3334, a pH sensor 3336, an acoustic sensor 3338, a chemical sensor 3340, a pressure sensor 3342, or combinations thereof. For example, the physiological sensor 1012 can include a plurality of sensors, such as a plurality of a single sensor type or a combination of different sensor types, arranged in an array or otherwise communicatively coupled (e.g., via one or more leads and/or wireless coupling, such as between sensor locations).

The electrophysiological sensor 3300 can generate one or more sense signals based upon detection of a physiological parameter of the body portion, for example, by detecting one or more electrical properties associated with biological cells or tissues, and can include one or more of an electroencephalograph (EEG) (e.g., for measuring electrical activity of the brain), an amplified sensor electrode that incorporates silicon metal oxide semiconductor field effect transistors (MOSFETs), the electrocardiograph (ECG) 3302 (e.g., for cardiac electrical activity measurements), the electrooculograph (EOG) 3304 (e.g., for ocular electrical activity measurements), the electromyograph (EMG) 3310 (e.g., for measuring electrical activity of muscle), the surface EMG 3312 (e.g., a noninvasive type of EMG), the microneurograph 3306 (e.g., for electrical activity measurements in nerve fibers), a microneurograph, the skin conductance sensor 3332, the bioimpedance sensor 3334, or the like. For example, an electrophysiological sensor such as an EEG, ECG, EOG, or EMG (e.g., surface EMG) can include one or more capacitive sensors or silicon metal oxide semiconductor field effect transistors (MOSFETs). For capacitive sensing, the electrophysiological sensor 3300 can include a measurement electrode, a reference electrode capacitively coupled with the measurement electrode, and a ground electrode, whereby displacement currents induced in the electrodes provide data associated with ECG, EMG, EOC, etc. In an embodiment, one or more of the electrodes includes a filamentary serpentine mesh structure insulated from the skin surface of the individual, such as with an insulating layer having high permittivity, stretchability, and adhesion (e.g., polydimethylsiloxane). For example, an electrophysiological sensor such as an ECG can include one or more dry electrodes or a conducting polymer comprising adhesive polymer (e.g., polydimethylsiloxane) mixed with a conducting material such as silver microspheres, silver nanowires, or carbon structures (e.g., including carbon nanostructures). For example, the EOG 3304 can be a skin-resident device configured to detect activity in muscles controlling eye and eyelid movement. For example, a surface EMG can include a piezoelectric thin film sensor. In an embodiment, the electrophysiological sensor 3300 can be an array of electrophysiological sensors. In an embodiment, the electrophysiological sensor 3300 measures a muscle activity of a body portion on which the system 1000, such as during a movement of the body portion, during lack of movement, or combinations thereof. For example, the system 1000 can be positioned on a phalange of a subject and the electrophysiological sensor 3300 (e.g., EMG 3310) measures a muscle activity of the phalange during motion or lack of motion of the phalange or wrist/ankle.

The myograph 3308 can generate one or more sense signals based upon detection of a physiological parameter of the body portion, for example by detecting one or more properties associated with one or more muscles, and can include one or more of the EMG 3310, the surface EMG 3312, the acoustic myography sensor 3314 (e.g., for measuring sound in muscle movement), the mechanomyography sensor 3316 (e.g., for measuring oscillations in muscle contraction), the accelerometer myography sensor 3318, or the like. For example, the mechanomyography sensor 3316 can include as a detector a condenser microphone, accelerometer, laser-based instrument, and the like. For example, the acoustic myographic sensor 3314 can include an acoustic transducer. For example, the acoustic myographic sensor 3314 can include an acoustic sensor having a microphone.

In an embodiment, the physiological sensor 1012 includes electrophysiological sensor 3300 (e.g., EEG, ECG 3302), EOG 3304, microneurograph 3306, EMG 3310, surface EMG 3312, acoustic myography sensor 3314, mechanomyography sensor 3316, accelerometer myography sensor 3318, etc.) configured to measure a bioelectrical signal, wherein the bioelectrical signal can be indicative of a pain state of the individual subject. In an embodiment, the electrophysiological sensor 3300 includes an EMG for detecting a bioelectrical signal in a muscle as a localized or systemic indicator of pain. For example, a surface EMG (e.g., surface EMG 3312) positioned on the zygomaticus muscle of the subject's face can detect the bioelectrical signals of the muscle when it contracts as the subject feels pain somewhere in the body, e.g., during a grimace or jaw clenching. For example, a surface EMG positioned on a trapzezius muscle can measure high bioelectrical activity, which is an indication of a high stress level associated with experiencing pain. For example, a surface EMG positioned on a biceps muscle can measure bioelectric activity indicating over use and fatigue associated with pain or the risk of pain. For example, a surface EMG positioned on a muscle during repetitive work can measure bioelectric activity indicative of repetitive injury stress and related pain or risk of pain. For example, a surface EMG positioned on a muscle during exercise can detect bioelectric signal indicative of a sustained muscle contraction (e.g., a muscle spasm or cramp) with associated pain. For example, a surface EMG (e.g., surface EMG 3312) positioned on one or more facial muscles or one or more neck muscles can detect muscle movement associated with audible or nonaudible speech (e.g., pain-related vocalizing). In an embodiment, the electrophysiological sensor 3300 includes an EMG for detecting a bioelectrical signal in a muscle positioned relative to a second body portion during a movement of one or more of the body portion and the second body portion. For example, the system 1000 can be positioned on a wrist of the individual subject and the electrophysiological sensor 3300 can include an electromyograph (not shown) configured to detect movement in one or more fingers.

In an embodiment, the sensor assembly 1004 includes the electrophysiological sensor 3300, microneurograph 3306, or myograph 3308 configured to distinctly measure electrical activity mediated by A delta (AO) nerve fibers (e.g., indicative of sharp, localized pain). In an embodiment, the sensor assembly 1004 includes the electrophysiological sensor 3300, microneurograph 3306, or myograph 3308 configured to distinctly measure electrical activity mediated by C nerve fibers (e.g., indicative of diffuse pain, such as that associated with inflammation). In an embodiment, the electrophysiological sensor 3300, microneurograph 3306, or myograph 3308 is configured to measure electrical activity mediated by A delta (AO) fibers and C fibers, where the one or more sense signals from the sensor assembly 1004 are transmitted to the processor 1006 only when the one of the A delta (AO) fibers or the C fibers are inactive when the other of the A delta (AO) fibers or the C fibers are active. Alternatively, the sensor assembly 1004 can transmit the one or more sense signals when each of the A delta (AO) fibers and C fibers are active, whereby the processor 1006 is configured to disregard portions of the sense signals corresponding to one of the A delta (AO) fibers or the C fibers.

In an embodiment, the physiological sensor 1012 includes a myograph (e.g., EMG 3310, surface EMG 3312, acoustic myography sensor 3314, mechanomyography sensor 3316, the accelerometer myography sensor 3318, etc.) configured to measure a signal (e.g., an acoustic signal or a mechanical signal) associated with a muscle contraction, wherein the signal associated with a muscle contraction can be indicative of a pain state of the individual subject. For example, the acoustic myography sensor 3314 can measure sound waves arising from muscle fiber contractions to assess muscle activity to determine when a muscle or muscle group is being misused, leading to pain and injury.

The strain sensor 3320 can include, but is not limited to, one or more of a metallic stack strain sensor, a silicon nanomembrane strain sensor, a piezoresistor strain sensor, a bonded metallic strain sensor, a wave-structured strain sensor, an open-mesh structured strain sensor, an interlocked metallic-coated nanofiber strain sensor, or the like. In an embodiment, the strain sensor is configured to measure a physiological characteristic of the body portion including, but not limited to, inflammation, swelling, or the like. The metallic stack strain sensor can include a first metallic material positioned on a second metallic material, where differences between electrical resistivity between the first metallic material and the second metallic material experienced during flexing or bending of the materials while mounted to a surface of interest can provide an indication of strain experienced by the surface. For example, in an embodiment, the metallic stack strain sensor includes a titanium/gold stack (Ti/Au) stack with a thickness of 10 nanometers of titanium per 60 nanometers of gold. The Ti/Au stack can provide an electrical resistance of between about 305 ohms and 330 ohms for a strain percentage of between about 0.5% and 3.0%, which can be used to associate the change in electrical resistance of the stack to a strain experienced by the body portion.

The silicon nanomembrane strain sensor can include a thin strip of silicon to provide a thin crystalline semiconductor strip, where changes in the relative resistance of the silicon nanomembrane experienced during flexing or bending of the silicon while mounted to a surface of interest can provide an indication of strain experienced by the surface. For example, in an embodiment, the silicon nanomembrane strain sensor includes a silicon nanomembrane having a thickness from about 100 nm to about 400 nm, a width from about 10 µm to about 100 µm, and a length from about 100 µm to about 1000 µm. Multiple strips of silicon nanomembrane can be utilized to monitor strain associated with the body portion along differing axes, such as by employing a silicon nanomembrane along a longitudinal axis of the body portion and employing a silicon nanomembrane along a transverse axis of the body portion (e.g., the longest dimension of the silicon nanomembrane being parallel to the respective axis). For example, the silicon nanomembranes can be arranged in an array.

The piezoresistor strain sensor can include a material that generates electricity upon deformation. In an embodiment, the piezoresistor strain sensor includes strip of material (e.g., a silicon nanomembrane, semiconducting material, metallic material, etc.) that tapers near a midpoint of the material (e.g., to provide a "dog-bone" shaped structure) that provides a change in electrical resistance upon experiencing mechanical strain (e.g., bending, flexing, etc.). For example, the piezoresistor strain sensor can include a tapered silicon nanomembrane coupled to the body portion to associate the generated electricity of the silicon nanomembrane to a strain experienced by the body portion. In an embodiment, the piezoresistor strain sensor includes a nanoribbon of lead zirconate titanate (PZT) coupled between gold and platinum electrodes, where the nanoribbon generates electricity upon deformation. For example, in an embodiment, the piezoresistor strain sensor includes a lead zirconate titanate nanoribbon coupled to the body portion to associate the generated electricity of the nanoribbon to a strain experienced by the body portion.

The bonded metallic strain sensor can include a metallic material arranged in a grid on a substrate. The metallic material can be structured as a fine wire or foil. In an embodiment, at least a portion of the grid is affixed directly to the body portion. The grid can exhibit a linear change in electrical resistance upon experiencing mechanical strain (e.g., bending, flexing, etc.) For example, in an embodiment, the bonded metallic strain sensor is applied to the body portion to associate the change in electrical resistance of the metallic grid to a strain experienced by the body portion.

The wave-structured strain sensor can include a relatively brittle wave-structured material (e.g., single-crystalline silicon) bonded on an elastic support material. In an embodiment, the wave-structured material includes a substantially planar base layer to mechanically couple to the elastic support material in a substantially continuous manner. In an embodiment, the wave-structured material mechanically couples to elastic support material at discontinuous bonding portions (e.g., at a "valley" of a wave). The wave-structured material can be micro-scale or nano-scale structures (e.g., ribbons, membranes, wires, etc.), where amplitudes and wavelengths of the wave-structure material can change in response to mechanical strains. For example, in an embodiment, the wave-structured strain sensor is applied to the body portion to associate the change in electrical resistance of the wave-structured material to a strain experienced by the body portion.

The open-mesh structured strain sensor includes an open-mesh material having mesh connections at bridging elements, which can provide in-plane rotations of the mesh material(s) upon experiencing mechanical strain (e.g., bending, flexing, etc.). Tensile strains can be applied to ends of the open-mesh material to cause in-plane rotations at the bridging elements, which can alter a shape of the openings within the mesh (e.g., transitioning between open squares and open rhombuses). For example, strains applied in a direction not aligned to connecting bridges of the open-mesh material can lead to rotation of the connecting bridges about the connection points, providing a stretchable strain sensor. In an embodiment, the open-mesh structured strain sensor is applied to the body portion to associate the change in electrical resistance of the open-mesh material to a strain experienced by the body portion.

The interlocked metallic-coated nanofiber strain sensor can include interlocked arrays of metallic-coated nanofibers, each array supported by a substrate material to providing differing levels of interconnection and electric resistance between the arrays when external strains are applied. For example, the interlocked metallic-coated nanofiber strain sensor can include two arrays of high-aspect-ratio platinum-coated polymeric nanofibers each supported on a thin polydimethylsiloxane (PDMS) substrate, where when mechanical strain is applied, the degree of interconnection of the nanofibers and the electrical resistance of the sensor changes in a reversible, directional manner. In an embodiment, the interlocked metallic-coated nanofiber strain sensor is applied to the body portion to associate the change in electrical resistance of the arrays to a strain experienced by the body portion.

In an embodiment, the physiological sensor 1012 includes the temperature sensor 3322. For example, the temperature sensor 3322 can include, but is not limited to, a single point temperature sensor, a spatial imaging temperature sensor, and a microscale temperature sensor configured as a microscale heating element or actuator, such as one or more microscale temperature sensors incorporating thin serpentine features of thin metal or PIN diodes with nanoscale membranes. For example, temperature sensors comprising thermal and/or optical sensors can detect increased tissue temperatures (e.g., in muscle or adjacent skin) associated with delayed onset muscle soreness (DOMS) (sometimes referred to as exercise-induced muscle damage), e.g., within the first 24 hours post-exercise.

In an embodiment, the physiological sensor 1012 includes the acoustic sensor 3338 configured to measure one or more acoustical signatures of a physiological event. For example, the acoustic sensor 3338 can include at least one microphone or acoustic transducer. For example, the acoustic sensor 3338 can be configured to detect an articular noise (e.g., creaking or popping) in an arthritic joint experiencing pain associated with movement. For example, the acoustic sensor 3338 can include an acoustic sensor (e.g., acoustic myographic sensor 3314) configured to detect a musculoskeletal acoustic signature. For example, the acoustic sensor 3338 can be configured to detect a vocal event (e.g., a groan, vocalization, or speech), such as a vocal event indicative of pain. For example, the acoustic sensor 3338 can be configured to detect an acoustic signature of a physiological event indicative of an autonomic response, e.g., a heartbeat, valve closure, blood flow, respiration, etc.

In an embodiment, the physiological sensor 1012 includes the optical sensor 3324 configured to measure an optical characteristic of a body portion on which the system 1000 is positioned. In an embodiment, the optical sensor 3324 is configured to measure a blood flow characteristic associated with the body portion. In an embodiment, the optical sensor 3324 is configured to measure a temperature characteristic associated with the body portion. In an embodiment, the optical sensor 3324 is configured to measure a pressure, strain, or deformation characteristic associated with the body portion (e.g., in swollen tissue). In an embodiment, the optical sensor 3324 is configured to measure a heart rate or respiratory rate. In an embodiment, the optical sensor 3324 is configured to measure at least one of transmitted light or reflected light. For example, the optical sensor 3324 can include, but is not limited to, a photodiode, a light-emitting diode (LED) (e.g., light-emitting diode 3326), an LED coordinated with a photosensor (e.g., photodetector), a fiber optic sensor (e.g., fiber optic strand, fiber Bragg Grating sensors, fluoroptic sensors, etc.), a flexible photonic sensor, an oximeter 3328 (e.g., pulse oximeter, near-infrared oximeter, etc.), an imaging device, such as a camera, or combinations thereof. The fiber optic sensor can include intrinsic fiber optic sensors (e.g., the fiber optic sensor represents the sensing element) and extrinsic fiber optic sensors (e.g., conveyor of light whose characteristics are affected or modulated by the measurand to be received by a separate detector) and can provide measurement of physical parameters such as, but not limited to, temperature, force, torque, strain, position, and the like. In an embodiment, the fiber optic sensor is configured for measurement of one or more of cardiac tissue or respiratory tissue, such as for sensing of temperature, strain, deformation (e.g., swelling) of the respective tissue, which can serve as an indicator for pain. For example, the fiber optic sensor (e.g., single fiber optic line, multiple fiber optic lines in parallel, multiple fiber optic lines in matrix, spiral, honeycomb or other configuration, etc., or combinations thereof) can be supported relative to the body portion, such as via a textile, tape, or ribbon, whereby light emitted from the fiber optics can be collected by a controller as reflections or transmissions (e.g., from the body portion, from the textile, etc.) for determination of the light characteristics thereof (e.g., wavelength, intensity, etc.). Comparison between such characteristics at different time periods can provide an indication as to a change in the physiological state of the body portion, such as via a temperature change, a strain, tissue deformation, or the like. In an embodiment, the optical sensor 3324 includes one or more optoelectronics to generate one or more sense signals based on measurement or sensing of one or more physical characteristics of the individual subject. For example, the optoelectronics can include, but are not limited to, one or more polymer light-emitting diodes (PLEDs), one or more organic photodetectors (OPDs), or combinations thereof. In an embodiment, the optoelectronics include a plurality of polymer light-emitting diodes (PLEDs) configured to emit light of differing wavelengths (e.g., green, red, blue, etc.), which in combination with one or more organic photodetectors (e.g., having an active layer of poly(3-hexylthiophene) (P3HT):(6,6)-phenyl-C61-butyric acid methyl ester (PCBM)) are arranged as an ultraflexible reflective pulse oximeter.

In an embodiment, the physiological sensor 1012 includes the near infrared sensor 3300 configured to measure a physiological characteristic of the body portion such as, but not limited to, tissue oxygenation, a blood analyte, such as oxygen, carbon monoxide, methemoglobin, total hemoglobin, glucose, a protein, or a lipid, or to measure brain activity (prefrontal cortex activity associated with nociception). For example, hypoxemia in muscle, detectable by NIR oximetry, is associated with activation of nerve receptors and increased pain. For example, the physiological sensor 1012 can measure oxygenation in an earlobe, such as by configuring the substrate 1002 to wrap around the earlobe or other portion of the ear, whereby the physiological sensor can measure oxygenation via transmittance. For example, decreased blood flow in skin resulting in hypoxemia or ischemia as detected by the oximeter 3328 can be an indication of or associated with pain or a risk of pain, e.g., from pressure sores. In an embodiment, the pressure sensor 3342 is configured to sense one or more of swelling or rigor of the body portion, which can be associated with pain. For example, at least one of the physiological sensor 1012 or the processor 1006 includes circuitry configured to determine a risk of ischemia for the body portion, such as through a comparison of the one or more sense signals (e.g., from pressure sensor 3342 or other physiological sensor) to reference data indicative of ischemic risk factors. For example, at least one of the physiological sensor 1012 or the processor 1006 includes circuitry configured to determine a risk of prolonged pressure exerted on the body portion, such as through a comparison of the one or more sense signals (e.g., from pressure sensor 3342 or other physiological sensor) to reference data indicative of pressure-based risk factors. In an embodiment, the pressure sensor 3342 can stimulate the body portion with one or more of pressure (e.g., via a mechanical probe) or electrical signal (e.g., via electrode operation) to measure a tenderness or rigidity of the body portion, which can be associated with pain.

In an embodiment, the physiological sensor 1012 is configured to detect changes in one or more physiological parameters indicative of autonomic nervous system responses, including, but not limited to changes in biopotentials, electrophysiological signals, heart rate, heart rate variability, arterial blood pressure, plethysmograph wave amplitude, skin conductance level, number of skin conductance fluctuations and their time derivatives, etc. Changes in the autonomic nervous system, including changes in biopotentials and electrophysiological signals, can be indicators of the presence of pain. For example, ECG 3302 can be configured to measure heart rate variability; a reduction of the heart rate variability power in the high frequency band (i.e., 0.15-0.4 Hz) can be indicative of pain onset. For example, the oximeter 3328 (e.g., a pulse oximeter or photo-plethysmograph) can be configured to assess vasoconstriction; a reduction in the photo-plethysmographic waveform amplitude caused by peripheral vasoconstriction and detectable by the oximeter 3328 can be indicative of pain. For example, skin conductance sensor 3320 can be configured to detect changes in skin conductance; changes in electro-galvanic skin properties, which can be measured by changes in the level and number of skin conductance fluctuations, can be indicative of the presence of pain. For example surface EMG 3312 can be configured to detect changes in the bioelectric signal in the corrugator muscle; changes in muscle tone, which are directed by the autonomic nervous system, can be indicative of the presence of pain.

In an embodiment, one or more of the sensor assembly 1004 or the processor 1006 can be configured to extract information from the detected signal, e.g., a detected electrophysiological signal, such as to process, analyze, receive, or transmit a subset of the total information included in the detected signal. For example, ECG 3302 can capture an electrophysiological signal from the heart and the signal includes features such as heart rate, interbeat interval, and heart rate variability that can be independently assessed; e.g., a reduction of the heart rate variability can be indicative of pain onset. For example, EMG 3312 can capture a signal from the corrugator muscle, and the signal includes such features as amplitudes, frequency, etc. that can be independently assessed; e.g., changes in the amplitude and entropy of an EMG signal can be indicative of the presence of pain.

In an embodiment, one or more physiological sensors 1012 are configured to combine two or more physiological parameters (e.g., autonomic response parameters) and provide a single multi-parameter sense signal. In an embodiment one or more physiological sensors 1012 are configured to provide signals on two or more physiological parameters to the processor 1006 and the processor 1006 combines the information into a single multi-parameter signal. In an embodiment, the system 1000 is configured to assess a multi-parameter composite of autonomic signals to determine an indication of the presence of pain. In an embodiment, the physiological sensor 1012 is configured to detect changes in one or more physiological parameters indicative of responses in the autonomic nervous system for use in quantifying a pain state. For example, quantifiable changes in biopotentials and electrophysiological signals can be indicators of pain intensity. For example, higher skin conductance levels, as measured by skin conductance sensor 3320, can be indicative of high intensity pain.

In an embodiment, the physiological sensor 1012 includes the chemical sensor 3340 configured to measure an analyte, where such analyte can be indicative of a pain state of the individual subject. In an embodiment, the chemical sensor 3340 can include a sensor for detecting an analyte in sweat. For example, the chemical sensor 3340 can include a sensor for detecting increased levels in sweat of a saccharide such as glucose, of a salt such as lactate or glutamate. For example, the chemical sensor 3340 can include a sensor for detecting a hormone (e.g., cortisol or adrenaline). For example, the chemical sensor 3340 can include a sensor for detecting inflammatory mediators (e.g., a prostaglandin (e.g., PGE2), bradykinin, serotonin, adenosine triphosphate, pyruvate, etc.) or a pro-inflammatory cytokine (IL-1α, IL-β, IL-6, TNFα, IL-8). For example, the chemical sensor 3340 can include a sensor for detecting a change in pH. For example, the chemical sensor 3340 can include a sensor for detecting an ion or electrolyte (e.g., hydrogen, sodium, potassium, chloride, calcium, magnesium, phosphate, etc.). In an embodiment, the chemical sensor 3340 includes a multiplexed sweat sensor array fabricated on a mechanically flexible polyethylene terephthalate (PET) substrate. The multiplexed sweat sensor array can include an amperometric glucose sensor, an amperometric lactate sensor, or combinations thereof, which can include glucose oxidase and lactate oxidase immobilized within a permeable film (e.g., a film of polysaccharide chitosan) with a silver/silver chloride (Ag/AgCl) electrode to facilitate a reference electrode and counter electrode for the amperometric glucose sensor, the amperometric lactate sensor, or combinations thereof. The sensors can generate current signals proportional to the abundance of the metabolites (e.g., glucose, lactate, etc.) between the working electrode and the silver/silver chloride reference electrode. The multiplexed sweat sensor array can additionally or alternatively include ion-selective electrodes (e.g., for determination of sodium and potassium levels) with a reference electrode, which can include a polyvinyl butyral (PVB)-coated electrode. The multiplexed sweat sensor array can additionally or alternatively include a temperature sensor, including but not limited to a resistance-based temperature sensor (e.g., a chromium/gold (Cr/Au) microwires supported by an insulating layer, such as a parylene layer). In an embodiment, the chemical sensor 3340 includes a graphene-based sweat sensor having a serpentine bilayer of gold mesh and gold-doped graphene (e.g., gold-doped graphene fabrication through chemical vapor deposition (CVD)). The graphene-based sweat can also include a water-proof film (e.g., a silicone layer), a humidity sensor (e.g., a poly(3,4-ethylenedioxythiophene electrode), a glucose sensor (e.g., a Prussian blue charge-based transfer sensor), a pH sensor (e.g., polyaniline), a counter electrode (e.g., Ag/AgCl), a tremor sensor (e.g., graphene), a sweat uptake layer (e.g., a Nafion layer), or combinations thereof. For example, the chemical sensor 3340 can include a sensor for detecting in sweat a protein (e.g., of a pro-inflammatory cytokine, inflammatory mediator, hormone, etc.) or peptide thereof. In an embodiment, the chemical sensor 3340 can include a transdermal sensor for sensing an analyte in tissue fluids (e.g., blood). For example, the chemical sensor 3340 can include a sensor configured for reverse iontophoresis (e.g., reverse iontophoretic extraction) to draw an analyte (e.g., glucose) from an interstitial space without puncturing the skin. For example, the chemical sensor 3340 can include microneedles to access a tissue space.

The chemical sensor 3340 can facilitate determination of a pain state of the individual subject. For example, changes in levels of physiological chemicals have been associated with increased muscle use or the presence of a pain condition. For instance, increases in lactate levels or in glucose levels (e.g., in response to released hormones), measurable in sweat or bodily tissues (e.g., interstitial tissues), have been associated with increased muscle use or the presence of pain. For example, increased levels of one or more hormones (e.g., cortisol, pregnenolone, DHEA, adrenocorticotrophic hormone (ACTH), a catcholamine (e.g., adrenaline or noradrenaline) testosterone, progesterone, estrogen, thyroid releasing hormone (TRH), triiodothyronine (T3), thyroxine (T4)) released in response to pain are measurable in sweat or other bodily fluids. For example, neuropeptides (e.g., neuropeptide Y, substance P and calcitonin-gene-related peptide (CGRP)) or other neurotransmitters (e.g., glutamate), which are released in response to pain are measurable in sweat or other bodily fluids. For example, pain (e.g., tenderness, allodynia, and hyperalgesia) is associated with sensitization of muscle nociceptors by endogenous mediators such as bradykinin and PGE2 released during movement or exercise. For example, increases or imbalances in levels of adenosine triphosphate (ATP), and electrolytes, as well as low pH generally can be associated with increased pain experienced by the individual subject; ATP and hydrogen ions are irritants that activate nerve endings by binding to receptor molecules, and pathological and pathophysiological changes of skeletal muscle are accompanied by a drop in pH. For example, increased tissue metabolism during exercise leads to decreased oxygen levels (detectable by oximetry), causing a drop in pH and accumulation of hydrogen atoms (detectable as above), which in turn can activate nerve endings to induce pain. For example, muscle spasm (persistent, involuntary muscle contraction) is accompanied by muscle ischemia, which leads to a drop in pH and the release of pain-producing substances such as bradykinin, ATP, and hydrogen ions. For example, an alteration in the levels of an electrolyte might be associated with an ion channel (e.g., Transient Receptor Potential family members) in the activation of nociceptive receptors.

In an embodiment, the chemical sensor 3340 includes an electrochemical sensor. For example, the electrochemical sensor can include, but is not limited to, an amperometric enzymatic electrode, which utilizes glucose oxidase to detect glucose or lactate oxidase to detect lactate, or one or more ion-selective electrodes (e.g., potentiometric), which can detect electrolytes (e.g., sodium, potassium) and can be utilized for pH monitoring. In an embodiment, the electrochemical sensor utilizes reverse iontophoresis. For example, the electrochemical can include a pair of reverse iontophoresis electrodes (e.g., Ag/AgCl), a reference electrode (Ag/AgCl), and a working electrode (e.g., Prussian Blue) that can be modified for selective amperometric biosensing (e.g., treated with glucose oxidase). In an embodiment, the electrochemical sensor includes a ligand, such as an aptamer. For example, a gold nanoparticle/aptamer-modified electrode can be used to detect a protein. In an embodiment, the chemical sensor 3340 includes microfluidic fluid transport, such as through microfluid channels (e.g., formed in or by the substrate 1002 or other supporting substrate). For example, the microfluid channels can transport an analyte of interest from the body portion to a detector positioned on the substrate 1002, or for containment by the system 1000 for subsequent remote analysis. In embodiments, the system 1000 can include one or more of a dolorimeter or algesiometer. For example, the physiological sensor 1012 can include one or more of a dolorimeter or algesiometer to provide indications as to pain experienced by the individual subject (e.g., as a result of operation of the dolorimeter or algesiometer, in comparison to pain experienced independent of the operation of the dolorimeter or algesiometer, or the like).

The processor 1006 is configured to receive one or more sense signals (e.g., from the sensor assembly 1004) associated with one or more of detection of the movement of the body portion by the motion detector 1010, or detection of one or more physiological parameters of the individual subject on which the system 100 is positioned by the physiological sensor 1012, and provide analysis of the one or more sense signals. For example, the processor 1006 includes circuitry configured to identify a physiological state (e.g., a pain state) of the individual subject based on analysis of the one or more sense signals. In an embodiment, the processor 1006 includes circuitry configured to identify a physiological state (e.g., a pain state) of the individual subject based on the movement of the body portion detected by the motion sensor 1010. In an embodiment, the processor 1006 includes circuitry configured to identify a physiological state (e.g., a pain state) of the individual subject based on the one or more physiological parameters detected by the one or more physiological sensor 1012. In an embodiment, the processor 1006 includes circuitry configured to identify a physiological state (e.g., a pain state) of the individual subject based on each of the movement of the body portion detected by the motion sensor 1010 and the one or more physiological parameters detected by the physiological sensor 1012. For example, in an embodiment, the processor 1006 is operably coupled to the sensor assembly 1004 such that the processor 1006 is configured to receive the one or more sense signals from one or more of the motion detector 1010 or the physiological sensor 1012.

In an embodiment, shown in FIG. 12, the system 1000 includes a comparison module 1300 accessible by the processor 1006 to compare one or more of the movement of the body portion, detected by the motion sensor 1010 of the sensor assembly 1004, or the one or more physiological parameters of the body portion, detected by the one or more physiological sensors 1012 of the sensor assembly 1004, to reference data indicative of a physiological state. In an embodiment, the physiological state includes at least one of a pain state, a pain type, a pain level, or a pain quality. For example, the reference data can include one or more of motion data or physiological parameter data, where such data can be associated with, but not limited to, a pain state, such as a pain-free state, an onset of pain, a pain pattern, chronic pain, acute pain, mixed pain state, a hyperalgesic pain state, an allodynic pain state, a breakthrough pain state, a neuropathic pain state, a nociceptive pain state, a non-nociceptive pain state, combinations thereof, or the like. For example, the reference data can include one or more of motion reference data indicative of short-term or long-term changes in motor function of a body portion (e.g., increased or inhibited muscle activation as a result of physiological adaptation to acute pain or chronic pain), a guarding motion, a grimace, an awkward gait, a limp, redistribution of activity or stress, modifications in loading, pronounced use of non-dominant limb, pronounced minimalization of motion or agitation of affecting a body site (e.g., a muscle), pronounced rubbing or massage of a body portion (e.g., repeated or deep massage), reduced force output, lack of use of a body portion, respiratory dysfunction, splinting, involuntary responses (e.g., reflex, spasm, etc.), or the like, or combinations thereof, or physiological reference data including, but not limited to, heart rate (including changes in heart rate or heart rate variation indicative of pain), blood pressure (including changes in blood pressure indicative of pain), electrophysiological data (including, but not limited to, electrical activity of the heart, electrical activity of the eye (e.g., corneo-retinal standing potential, pupil diameter, etc.)), nerve impulses, muscular-skeletal pressure forces or electrical activity (including, but not limited to, electric potential generated by muscle cells, muscular-skeletal acoustic or mechanical properties (e.g., vibrations), etc.), strain data (e.g., associated with muscle), temperature (including changes in temperature indicative of pain), blood oxygenation data (including changes in blood oxygenation indicative of pain), skin conductance data (including changes in skin conductance indicative of pain), bioimpedance data (including changes in bioimpedance indicative of pain), pH data (including changes in pH indicative of pain), or chemical data (including changes in concentrations of chemical analytes indicative of pain) including but not limited to, analytes of sweat, analytes of tissue, a saccharide (e.g., glucose), a salt (e.g., sodium chloride), lactate, an electrolyte (e.g., sodium, chloride, potassium, etc.), a hormone (e.g., cortisol, adrenaline, pregnenolone, DHEA, testosterone, progesterone, estrogen, triiodothyronine (T3), and thyroxine (T4)), a neuropeptide (e.g., neuropeptide Y, substance P and calcitonin-gene-related peptide (CGRP)), a peptide, a protein, or a nucleotide or modified nucleotide (e.g., adenosine triphosphate), an inflammatory mediator (e.g., a prostaglandin (e.g., PGE2), bradykinin, serotonin, adenosine triphosphate, pyruvate, etc.), a pro-inflammatory cytokine (IL-1α, IL-β, IL-6, TNFα, IL-8), or other motion or physiological factor provided herein. In an embodiment, the reference data can include one or more of motion data or physiological parameter data associated with pain types, where such data can be associated with, but not limited to, nociceptive pain (e.g., due to mechanical, thermal, and/or chemical interactions), somatic pain, neuropathic pain, visceral pain, superficial pain, and psychogenic pain. In an embodiment, the reference data can include one or more of motion data or physiological parameter data associated with pain levels, where such data can be associated with, but not limited to, pain intensity, pain severity, or magnitude of pain. In an embodiment, the reference data can include one or more of motion data or physiological parameter data associated with pain quality or pain quantity, where such data can be associated with, but not limited to, a subjective characteristic of the pain (e.g., a subjective pain threshold or tolerance threshold), such as those identified by the individual subject. Pain types can also include spontaneous pain (e.g., occurring in the absence of stimuli), evoked pain (e.g., occurring in response to stimuli), continuous pain, or intermittent pain. In an embodiment, the motion sensor 1010, the physiological sensor 1012, or combinations thereof, can include a stimulator for evaluating evoked responses from the individual subject. For example, the stimulator can include an electrical stimulator, a thermal stimulator, an optical stimulator, or the like. Pain types can also include cephalalgia or headache, which can include, but are not limited to, tension headaches, cervicogenic headaches, migraines, or combinations thereof.

In an embodiment, the reference data can include user-specific threshold or tolerance information. For example, the individual can indicate to the system 1000 (e.g., via user interface 3600 described herein) when the individual feels pain. The system 1000 can then take a snapshot of one or more of the individual's physiological state, motion state, positional state, etc. to set a threshold pain level, to link a physiological or motion parameter to pain experienced by the individual, or the like, which can serve as a comparator to autonomic parameters experienced by the individual. The system 1000 can monitor the individual and receive additional individual input regarding whether the pain intensifies, dissipates, differs in type, location, chronology, etc.

In an embodiment, the processor 1006 is configured to activate the effector 1008 to affect the body portion responsive to the physiological state corresponding to a pain state experienced by the individual subject. For example, the system 1000 can identify (via the processor 1006, the sensor assembly 1004, or combinations thereof) a physiological state of the individual subject, where a physiological state corresponding to a particular pain state is used as a trigger for the processor 1006 to activate the effector 1008 to treat the body portion. For example, the processor 1006 can compare the physiological state to reference data indicative of a trigger condition to activate the effector 1008, where such trigger condition can be a specified pain state, including but not limited to, a pain-free state, an onset of pain, a pain pattern, chronic pain, acute pain, mixed pain state, a hyperalgesic pain state, an allodynic pain state, a breakthrough pain state, a neuropathic pain state, a nociceptive pain state, a non-nociceptive pain state, combinations thereof. In an embodiment, the processor 1006 is configured to activate the effector 1008 responsive to the physiological state corresponding to a pain level experienced by the individual subject, a pain type experienced by the individual subject, a pain quality experienced by the individual subject, or combinations thereof. For example, the processor 1006 can compare the physiological state to reference data indicative of a trigger condition to activate the effector 1008, where such trigger condition can be a specified pain level, pain type, or pain quality, including but not limited to nociceptive pain (e.g., due to mechanical, thermal, and/or chemical interactions), somatic pain, neuropathic pain, visceral pain, superficial pain, psychogenic pain, pain intensity, pain severity, magnitude of pain, myofascial pain syndrome or condition, sharpness, dullness, burning, cold, tenderness, itch, cramping, radiating, tingling, throbbing, aching, tiring, deepness, shocking or electrical, stinging, or combinations thereof. In an embodiment, the processor 1006 is configured to activate the effector 1008 to affect the body portion responsive to information from the physiological sensor 1012 regarding the location of the pain on the body portion. For example, the processor 1006 can activate the effector 1008 responsive to information from one or more EMG 3310 or surface EMG 3312 to determine activation in a specific muscle, e.g., a muscle known anatomically or historically to induce a regional pain. For example, the processor 1006 can activate the effector 1008 responsive to information from a subset of two or more EMG 3310 or surface EMG 3312 sensors indicative of which muscle is experiencing pain.

In an embodiment, the processor 1006 accesses one or more of the comparison module or the reference data by accessing computer memory 1302 which can include, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the comparison module 1300 or memory manager and which can be accessed by the processor 1006 or other associated accessing device.

The processor 1006 includes components to process the one or more sense signals from the sensor assembly 104 and to provide instruction to one or more components of the system 1000, such as the effector 1008. For example, the processor 1006 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an embodiment, the processor 1006 includes one or more ASICs having a plurality of predefined logic components. In an embodiment, the processor 1006 includes one or more FPGAs having a plurality of programmable logic commands. The computer memory device can be integrated with the system 1000, can be associated with an external device and accessible by the system 1000 through wireless or wired communication protocols, or a combination thereof. For example, the reference data can be stored by the computer memory 1302 coupled to the substrate 1002 of the system 1000, can be accessible by the processor 1006 via wireless means, can be available to the processor 1006 through another method, such as through a remote network, a cloud network, and so forth, or combinations thereof. In an embodiment, shown in FIG. 33, the processor 1006 includes, or is operably coupled to, a receiver 3400 or transceiver 3402 (e.g., antenna, etc.), or combinations thereof, to receive the reference data information or other information (e.g., correspondence threshold information, programming information) to facilitate operation or control of the system 1000 through wireless or wired communication protocols. For example, the receiver 3400 can receive one or more communication signals from an external device 3406 associated with but not limited to, control programming, reference data, a query (e.g., a query to transmit information from the system 1000 to the external device 3406, a query to determine a motion state of the individual subject, a query to determine a current physiological state (e.g., pain state) of the individual subject, etc.), or combinations thereof. In embodiments, the processor 1006 can additionally or alternatively include a transmitter 3404 or transceiver 3402 (e.g., antenna, etc.) to send information amongst components of the system 1000 or to components external the system, such as to communicate with the external device 3406. Such communication can include, for example, indications that the processor 1006 is accessing one or more databases or memory devices storing reference or programming data, computational protocols, system updates, or the like. The external device 3406 can include one or more of a receiver 3408, a transceiver 3410, or a transmitter 3412 to facilitate communications with the components of the system 1000. For example, the external device 3406 can include but is not limited to, a communication device or electronic equipment, such as one or more of a mobile communication device or a computer system including, but not limited to, one or more mobile computing devices (e.g., hand-held portable computers, Personal Digital Assistants (PDAs), laptop computers, netbook computers, tablet computers, or so forth), mobile telephone devices (e.g., cellular telephones and smartphones), devices that include functionalities associated with smartphones and tablet computers (e.g., phablets), wearable or portable devices (e.g., including sensors positioned on the same body portion as system 1000, sensors positioned on different body portions than system 1000, sensors positioned remotely from the individual subject, sensors positioned on different individual subjects, etc.), portable game devices, portable media players, multimedia devices, augmented or virtual reality (VR) systems (e.g., VR headsets, VR immersive experience systems, etc.) satellite navigation devices (e.g., Global Positioning System (GPS) navigation devices), e-book reader devices (eReaders), Smart Television (TV) devices, surface computing devices (e.g., table top computers), Personal Computer (PC) devices, and other devices that employ touch-based human interfaces. The system 1000 and the external device 3406 can communicate respective each other (e.g., send and receive communication signals) via the receivers 3400, 3408, the transceivers 3402, 3410, and the transmitters 3404, 3412, such as through one or more connected and wireless communication mechanisms including, but not limited to acoustic communication signals, optical communication signals, radio communication signals, infrared communication signals, ultrasonic communication signals, and the like. In an embodiment, the system 1000 can utilize communications from the external device 3406 as an operational indicator (e.g., when to engage the effector 1008, when to begin sensing via the sensor assembly 1004, etc.).

The processor 1006 can coordinate operations of the system 1000 based on the one or more sense signals and identification of a physiological state (e.g., pain state) of the individual subject based on the one or more sense signals. For example, the processor can coordinate operation of the effector 1008 based upon identification of the physiological state (e.g., pain state) of the individual subject and conditions experienced by the individual subject (e.g., rest state, motion state, etc.). The effector 1008 is operably coupled to the processor 1006 and is configured to effect a body portion of the individual subject responsive to control by the processor 1006. In an embodiment, shown in FIG. 34, the effector can include, but is not limited to, an ultrasound transducer 3500, an electrode 3502, a magnetic stimulator 3504, an optical stimulator 3506, a thermal stimulator 3508, an acoustic stimulator 3510, a mechanical stimulator 3512, a vibration stimulator 3514, or combinations thereof.

The ultrasound transducer 3500 generates ultrasound waves (or signals) directed toward the body portion of the individual subject, such as for therapeutic treatment of the body portion. In an embodiment, the effector 1008 includes an array of ultrasound transducers. For example, the effector 1008 can include a first ultrasound transducer configured for placement on a first location on the body portion of the individual subject and a second ultrasound transducer configured for placement on a second location on the body portion of the individual subject. The array of ultrasound transducers can provide localized treatment based on differing locations of the transducers, based on differing patterns of ultrasound waves generated by the ultrasound transducers, or the like. In an embodiment, the ultrasound transducer 3500 is configured to generate low intensity ultrasound waves (e.g., low intensity therapeutic ultrasound (LITUS); low intensity, long duration ultrasound therapy). For example, the ultrasound transducer 3500 can generate ultrasound waves from about 30 to about 1000 mW/cm$^2$, where such low intensity can be applied to the body portion of the individual subject for up to about eight hours. As another example, the ultrasound transducer 3500 can include a diverging-wave transducer that operates from about 2.5 to about 3 MHz with about 0.03 to about 2 W/cm$^2$ ultrasound intensity for less than about 18 hours of treatment. In an embodiment, the low intensity ultrasound waves correspond to a spatial temporal average intensity of about 90 mW/cm$^2$ at the transducer face, where a one-hour treatment provides about 1795 J of ultrasonic energy to the body portion, and where a six-hour treatment provides about 9596 J of ultrasonic energy to the body portion. In general, greater acoustic energy deposition can provide better clinical outcomes, where it has been found that deposition of an average of 4228 J per treatment session provided clinically significant outcomes, whereas deposition of an average of 2019 J did not provide statistically or clinically significant differences from a control or sham treatment. In an embodiment, the ultrasound transducer 3500 includes a power controller and two ultrasound transducers, having 3 MHz frequency, 0.132 W/cm$^2$ intensity per transducer providing a cumulative ultrasound energy deposition of about 18720 J for a four-hour treatment session. In an embodiment, the ultrasound transducer 3500 includes a divergent lens to scatter the ultrasound waves to a divergent acoustic treatment field. In an embodiment, the ultrasound transducer 3500 is configured to generate high intensity focused ultrasound waves (e.g., HIFU). For example, the ultrasound transducer 3500 can generate the high intensity focused ultrasound waves at about 2.5 to about 3 MHz at about 1900 to about 2810 W/cm$^2$ for a duration from about 3 to about 15 seconds. In an embodiment, the high intensity focused ultrasound waves can provide a nerve conduction block. At intensity levels greater than about 1000 W/cm$^2$, a treatment can lead to localized coagulative necrosis and structural disruption in tissue, such that a focused treatment area of the HIFU ultrasound transducer 3500 can confine the biological effects to a particular, targeted region of the body portion for treatment (e.g., to provide a nerve conduction block, etc.). In an embodiment, the focused treatment area is about 1 mm×10 mm. In an embodiment, the effector 1008 includes an imaging device to facilitate targeting of the targeted region of the body portion. The imaging device can include, for example, an ultrasound imaging transducer with a broadband frequency of about 5 to about 10 MHz to provide a hyperechoic region at the focus of the ultrasound transducer 3500 during synchronous operation with the ultrasound imaging transducer, which can facilitate viewing of the target region via a bright or light region. In an embodiment, the ultrasound transducer 3500 is configured to generate low dose, high frequency ultrasound. For example, the ultrasound transducer 3500 can generate low dose, high frequency ultrasound between about 0.5 to about 3 W/cm$^2$ at about 1 MHz frequency with a pulsed pattern of about 1:4. In an embodiment, the treatment duration for low dose, high frequency ultrasound includes a five minute treatment per day, for about 20 sessions. In an embodiment, the ultrasound transducer 3500 is operated at a frequency of about 8 MHz at about 0.15 W/cm$^2$ for a period of about 15 seconds, with a duty cycle of about 0.01% and a target region of the posterior frontal cortex. In an embodiment, the ultrasound transducer 3500 is operated at a frequency of about 0.5 MHz at about 5.9 W/cm$^2$ for a period of about 500 milliseconds, with a duty cycle of about 36% and a target region of the primary somatosensory cortex S1. In an embodiment, the ultrasound transducer 3500 is operated at a frequency of about 0.25 MHz at about 0.3 to about 2.5 W/cm$^2$ for a period of about 300 milliseconds, with a duty cycle of about 50% and a target region of the primary somatosensory cortex S1. In an embodiment, the ultrasound transducer 3500 is configured to generate ultrasound signals on a pulsed basis, a continuous basis, or combinations thereof.

In an embodiment, the ultrasound transducer 3500 is configured to generate ultrasound signals according to at least a first treatment pattern and a second treatment pattern. The treatment pattern can relate to a spatial pattern (e.g., varying the location of the treatment, varying the depth of treatment, etc.), a timing pattern, an intensity pattern, or the like. For example, in an embodiment, the processor 1006 directs the ultrasound transducer 3500 to alternate generation of the ultrasound signals according to the first treatment pattern and the second treatment pattern on a dynamic basis. In an embodiment, the first treatment pattern differs from the second treatment pattern according to at least one of a target site of the body portion of the individual subject (e.g., a site on the body or limb, such as a position on the skin surface) or a target depth of the body portion of the individual subject. In an embodiment, the ultrasound transducer 3500 generates ultrasound signals according to a plurality of ultrasound frequencies, where the frequency can be tuned or adjusted responsive to control by the processor 1006 or internal ultrasound transducer controller. In an embodiment, the effector 1008 includes a first ultrasound transducer 3500 configured for placement on a first location on the body portion of the individual subject and a second ultrasound transducer 3500 configured for placement on a second location on the body portion of the individual subject. For example, the first ultrasound transducer 3500 and the second ultrasound transducer 3500 can be spaced apart relative to each other (e.g., on different body portions, on different regions of the same body portion, on opposing sides of the same body portion, etc.), where the transducers can receive different sourced frequencies to provide treatment to the individual subject.

In an embodiment, the optical stimulator 3506 is configured to generate infrared light. For example, the optical stimulator 3506 can generate the infrared light as low-intensity, pulsed infrared light. In embodiment, the optical stimulator 3506 generates light at about 0.3 to about 0.4 J/cm$^2$, which is about two and a half times less than a threshold at which histological tissue damage can occur (e.g., about 0.8 to about 1.0 J/cm$^2$). The optical stimulator 3506 can include a laser to facilitate treatment, where the laser can include, but is not limited to, a Holmium:yttrium aluminum garnet laser (2.12 μm), a free electron laser (2.1 μm), an alexandrite laser (750 nm), a solid-state laser (1.87 μm), or combinations thereof. In an embodiment, the optical stimulator 3506 generates light to provide a skin surface temperature increase of about 6 to about 10 degrees centigrade (e.g., to provide stimulation of a peripheral nerve). For example, the processor 1006 can direct the optical stimulator 3506 to generate light to provide a photothermal effect from transient tissue heating (e.g., having a temporally and spatially mediated temperature gradient at the axon level of about 3.8 to about 6.4 degrees centigrade).

In an embodiment, the effector 1008 and stimulations therefrom (e.g., vibration stimulation, ultrasound stimulation, mechanical stimulation, optical stimulation, electrical stimulation, etc.) can engage proprioceptors, mechanoreceptors, or light touch receptors; stimulating such nerves can produce sensations to the nervous system that compete with signals from pain receptors (e.g., nociceptors) and thereby decrease pain nerve perception by the individual. In an embodiment, the effector 1008 and stimulations therefrom can engage body portions in or on the ear (e.g., vagal stimulation). In an embodiment, the effector 1008 and stimulations therefrom can engage one or more myofascial trigger points.

In an embodiment, the processor 1006 is configured to activate the effector 1008 when the individual subject is in a rest state (e.g., seated, prone, or the like while sleeping, reading, watching TV or other electronic device, etc.). For example, the effector 1008 can include the ultrasound transducer 3500 configured for high-power pain threshold ultrasound (HPPTUS) to desensitize latent myofascial trigger points (e.g., pathlogical alteration of muscle fibers that evoke local and referred pain, and does not elicit spontaneous local pain) for pain therapy. In an embodiment, a plurality of HPPTUS applications are applied to the body portion in a treatment session (e.g., while the individual subject is stationary or at rest). For example, the number of HPPTUS applications can include, but are not limited to, three to ten treatments at the latent myofascial trigger point(s). For example, a single HPPTUS application can include, but is not limited to, application of ultrasound energy at 1 MHz, 0.5 to 1.2 W/cm$^2$, continuous wave for about five minutes.

Figure 35:
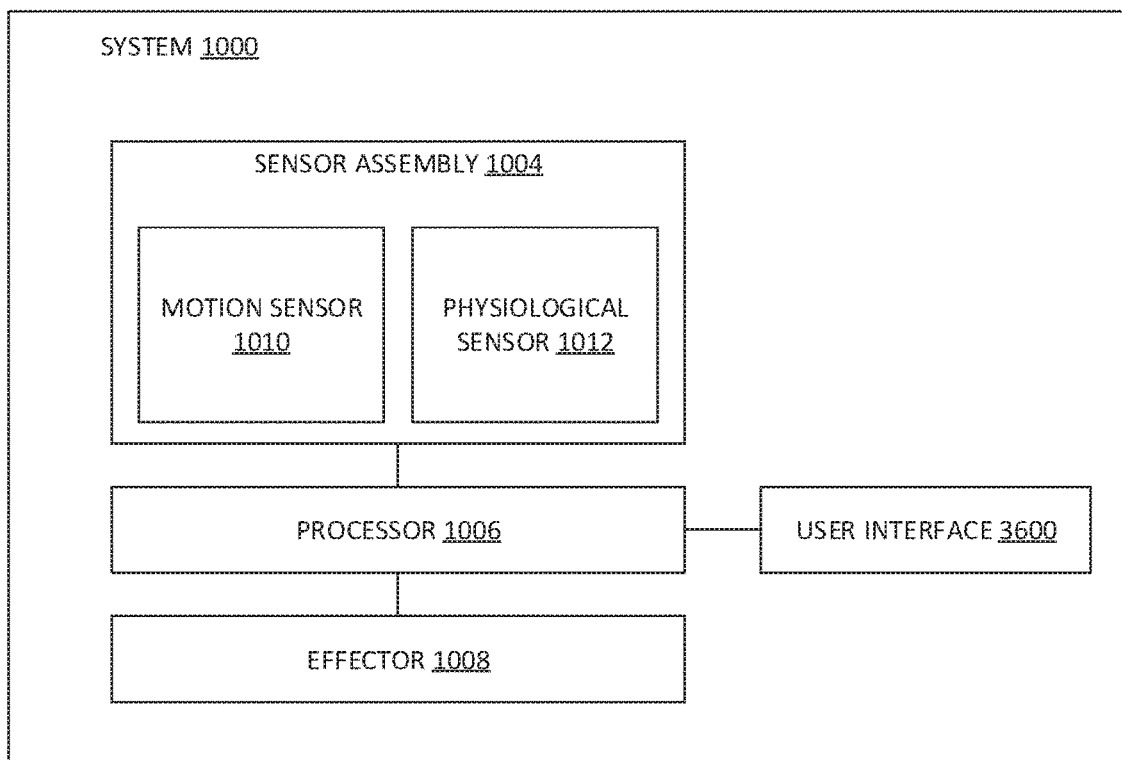
FIG. 35 is a schematic of an embodiment of a system such as shown in FIG. 31.

In an embodiment, shown in FIG. 35, the system 1000 also includes a user interface 3600. The user interface 3600 can be operably coupled to the processor 1006 to facilitate operations of the system 1000. For example, in an embodiment, the processor 1006 is operably coupled to the user interface 3600 and is configured to generate one or more communication signals for display by the user interface 3600. The communication signals for display can include, for example, a request for user input regarding an operation state of the effector 1008. For instance, the system 1000 can seek approval or disapproval by a user (e.g., the individual on which the system 1000 is positioned, a health care professional, etc.) to operate certain functionalities of the system, including but not limited to the functionalities of the effector 1008. In an embodiment, the processor 1006 is configured to prevent activation of the effector 1008 responsive to a user command via the user interface 3600. For example, the processor 1006 can direct the user interface 3600 to display a request for user input regarding whether the effector 1008 should activate. The user can select a deny activation command to prevent the effector 1008 from activating at that time. In an embodiment, the processor 1006 is configured to activate the effector 1008 responsive to a user command via the user interface 3600. For example, the processor 1006 can direct the user interface 3600 to display a request for user input regarding whether the effector 1008 should activate. The user can select an activate or allow activation command to allow the effector 1008 to activate at that time, or to schedule a time or motion state during which the effector 1008 is permitted to activate. For example, the individual can direct a user command via the user interface 3600 to activate the effector 1008 only during a rest period, such as when the individual subject would be sleeping or resting. The user interface 3600 can include, but is not limited to, a graphical user interface (GUI), a touchscreen assembly (e.g., a capacitive touch screen), a liquid crystal display (LCD), a light-emitting diode (LED) display, or projection-based display, or combinations thereof.

Figure 36:
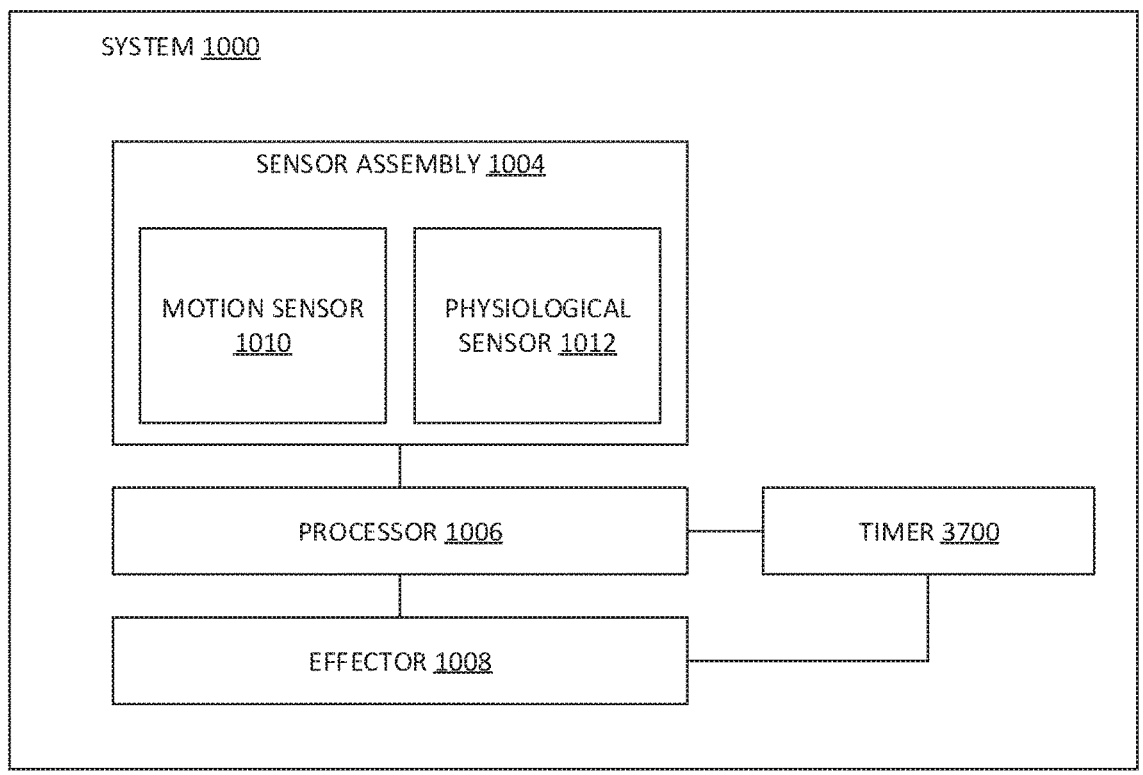
FIG. 36 is a schematic of an embodiment of a system such as shown in FIG. 31.
Figure 37:
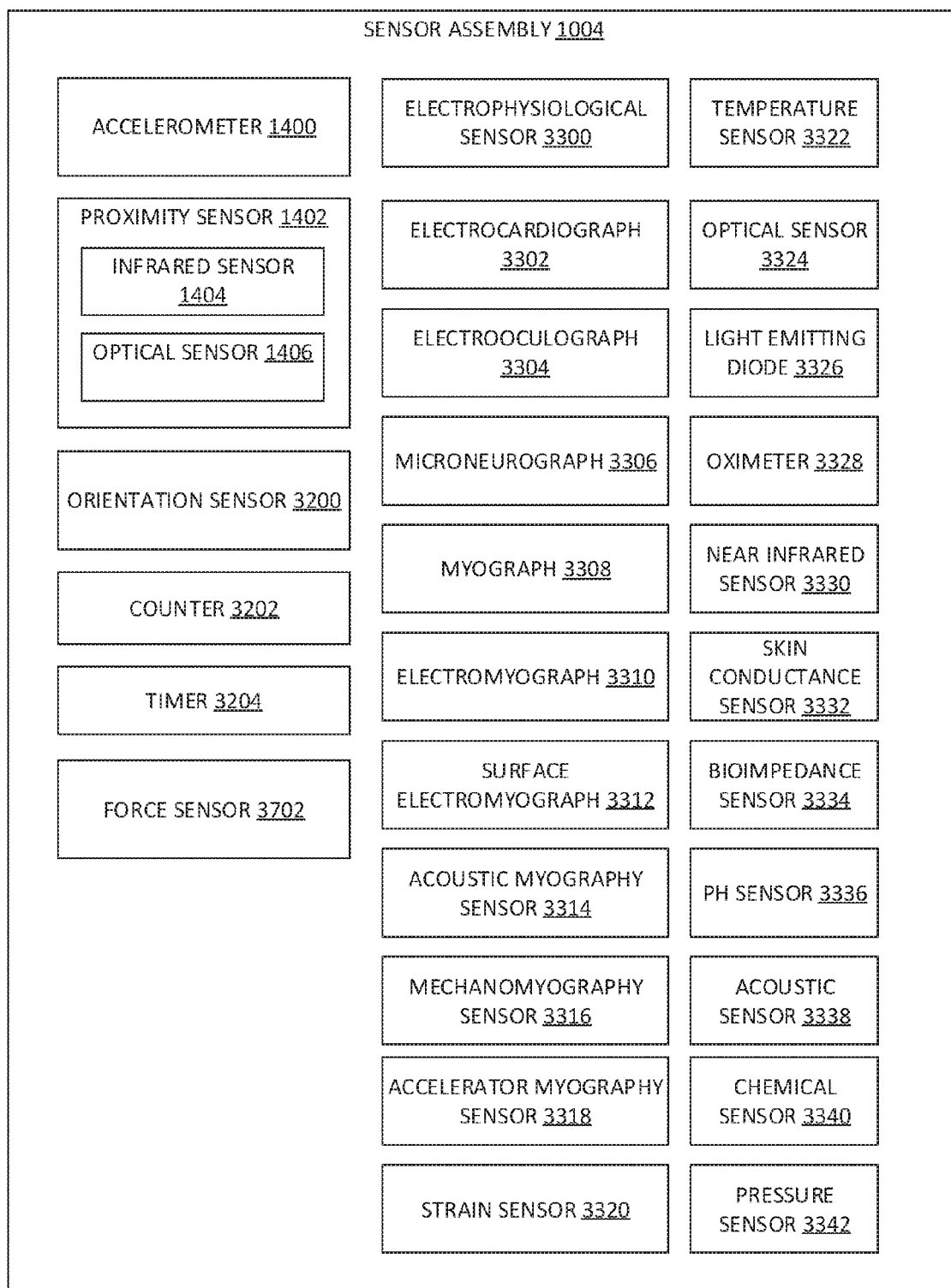
FIG. 37 is a schematic of an embodiment of a sensor assembly for a system for monitoring an individual subject and facilitating a motion regimen of the individual subject.

In an embodiment, shown in FIG. 36, the system 1000 includes a timer 3700 operably coupled to the effector 1008, the processor 1006, or combinations thereof. In an embodiment, the processor 1006 is configured to stop activation of the effector 1008 responsive to a duration of treatment by the effector. For example, the processor 1006 can access a maximum duration reference time (e.g., stored in memory 1302, or otherwise accessible by the processor 1006), whereby the processor 1006 can compare a time of treatment tracked by the timer 3700. When the time of treatment tracked by the timer 3700 meets the maximum duration reference time, the processor 1006 directs the effector 1008 to cease activation. In an embodiment, the processor 1006 is configured to stop activation of the effector 1008 responsive to an intensity of treatment by the effector 1008. For example, the processor 1006 can access a maximum intensity of treatment reference intensity (e.g., stored in memory 1302, or otherwise accessible by the processor 1006), whereby the processor 1006 can compare an intensity of treatment provided by operation of the effector 1008 (e.g., during a single treatment session, over multiple treatment sessions, etc.), which can depend on the power output of the effector 1008, the duration of treatment by the effector 1008, the frequency of treatment by the effector 1008, or the like. When the intensity of treatment determined by the processor 1006 meets the maximum intensity of treatment reference intensity, the processor 1006 directs the effector 1008 to cease activation.

In an embodiment, the effector 1008 is configured to affect the body portion for treatment of at least one of arthritis (e.g., osteoarthritis, rheumatoid arthritis, psoriatic arthritis, etc.), arthralgia, myalgia, neuralgia, enthesitis, myalgia, fibromyalgia, cephalalgia, or traumatic pain. In an embodiment, the effector 1008 is configured to affect the body portion with an active treatment. For example, the processor 1006 can direct the effector 1008 to affect the body portion when the individual subject is experiencing a pain state. In an embodiment, the effector 1008 is configured to affect the body portion with a preventative treatment. For example, the processor 1006 can direct the effector 1008 to affect the body portion prior to the individual subject experiencing a pain state, when the pain state of the individual subject is less than a threshold pain state, or to induce individual subject to move to prevent a pain state. In an embodiment, the effector 1008 is configured to affect the body portion with a palliative treatment.

In an embodiment, the system 1000 is configured to determine or receive an identification of the individual subject on which the system 1000 is positioned to determine whether to provide or enable certain functionalities. For example, the system 1000 can be configured to operate only for certain authorized individuals, whereby certain features or functionalities are disabled if an unidentified or unauthorized individual attempts to use the system 1000. In an embodiment, the system 1000 is configured to identify the individual subject on which the system 1000 is positioned, whereby the system 1000 permits operation of certain system components upon a positive identification of an individual authorized to use the particular system 1000. For example, the sensor assembly 1004 can detect physical characteristics of the individual subject on which the system 1000 is positioned to generate one or more identity sense signals associated with the physical characteristic. The physical characteristics can include, but are not limited to, skin topography features (e.g., pattern of skin surface, follicle pattern, pore pattern, pigmentation, etc.), vascular properties or layouts (e.g., arterial patterns, properties, or layouts; vein patterns, properties, or layouts; etc.), electric current pattern (e.g., photovoltaic current pattern), or skin resistivity measurement. In an embodiment, the processor 1006 or other system component compares the identity sense signals to reference data associated with individual(s) authorized to use the system 1000. When the identity sense signals have a positive correspondence to the reference data, the system 1000 can permit operation of certain system functionalities including, but not limited to, permitting operation of the sensor assembly 1004 for pain monitoring, permitting operation of the effector 1008 (e.g., only upon positive association of an individual, such that the individual becomes authorized to operate the system 1000), selecting a particular treatment protocol (e.g., the reference data can include a correspondence between an identity and a particular treatment protocol, whereby upon confirmation of an identity, the particular treatment protocol is selected for operation of the effector 1008), permitting the transmission of information associated with operation of the system 1000 or the status of the individual subject to a record (e.g., an electronic health record or other health diary), or the like.

Systems, devices, and methods are also described for monitoring an individual subject and facilitating a motion regimen of the individual subject. The individual subject can be monitored for one or more of a movement, such as a movement of a particular body portion, or a physiological parameter, such as a muscle activity or one or more indicators of pain. Such monitoring can provide a basis for effecting a predetermined motion of a motion regimen, providing instructions to the individual subject or external device regarding compliance or non-compliance with the motion regimen (e.g., with target thresholds thereof), providing recommendations to the individual subject or external device regarding the motion regimen or the individual's performance thereof (e.g., the individual subject is exceeding a recommended threshold of muscle activity and should reduce effort of the motions, the individual subject has incorrectly performed one or more motions of the motion regimen and should review a particular section of the motion regimen, etc.), or the like. The motion regimen can include one or more choreographed motions attributed to activities associated with learning or improving skills, such as movement-based skills, rehabilitating, strengthening, or improving flexibility of muscles, interacting with external objects (e.g., interaction between a foot and a floor, dance floor, treadmill, etc.; interaction between a hand and a tool, etc.), or the like. The skills can include fine motor skills, for example playing an instrument, typing, first aid skills, surgical skills (e.g., learned while practicing on a model), writing, calligraphy; use of a limb or body portion, including training muscle memory, for example for use in sports or other activities (e.g., use of arm, torso, legs in tennis or golf swings, use of wrist for table tennis, Ping-Pong, etc.), skiing (e.g., use of knees for bending, use of arms), martial arts, occupational therapy, skills for activities of daily living, or combinations thereof. For example, the motion regimen can include a rehabilitation regimen (e.g., rehabilitation of one or more muscle groups or one or more nerves following debilitating medical condition, or rehabilitation of one or more skills following a stroke), a physical therapy regimen (e.g., rehabilitation, flexibility, or strengthening of one or more muscle groups following injury), a training regimen (e.g., muscle memory training), a motor skills regimen (e.g., fine motor skills training), or combinations thereof. The systems, devices, and methods described herein can include an effector to effect a predetermined motion (e.g., choreographed motion) of a body portion of the individual subject responsive to monitoring one or more of the motion of the body portion or a physiological parameter of the individual subject. For example, a muscle activity of the individual can be compared against a target activity associated with the motion regimen, whereby the effector can induce movement in the body portion to cause a subsequent motion to bring muscle activity within the target activity. For instance, when engaged in a strengthening workout as the motion regimen, one or more muscle activities of the individual's legs can be monitored and compared against target activities to effect an increase or decrease in the muscle activity of the individual. As another example, a movement of the body portion (e.g., an angle of movement, speed of movement, velocity of motion, acceleration of movement, etc., or combinations thereof) can be compared against a target movement associated with the motion regimen, whereby the effector can induce movement in the body portion to cause a subsequent motion to bring the movement within the target movement, to induce a next movement in the choreographed movements of the motion regimen, or the like. For instance, when learning a dance as the motion regimen, the individual's movements during the dance can be monitored and compared against one or more target motions to effect a next step in the dance, a next motion of the dance, a recommendation associated with the dance, etc. As another example, a pain state of the individual subject (e.g., determined via at least one of a movement of the body portion or at least one physiological parameter of the body portion, as described herein) can be compared against a target pain state associated with the motion regimen, whereby the individual subject can be informed to alter their effort level to increase or decrease the pain state to within the target pain state, or the effector can induce movement to increase or decrease the pain state to fall within the target pain state. The target values of the motion regimen can be individual-specific or generalized thresholds. For example, the target values (e.g., muscle activity, pain state, motion thresholds, etc.) can depend on a personal history of the individual, such as whether the individual has experienced a joint disorder, cardiovascular condition, other health condition, or the like; can depend on a feedback from the monitored movement/physiological parameter(s) (e.g., whereby detected movements or physiological parameters can result in the target value being adjusted to compensate for the detected values); or can depend on generalized health or fitness considerations (e.g., height, weight, body mass index, caloric needs or preferences, general health or fitness levels, etc.).

In an embodiment, the systems, devices, and methods described herein employ a sensor assembly to generate one or more sense signals based on detection of at least one of a movement of the body portion of the individual subject or at least one physiological parameter of the body portion. For example, the sensor assembly can include one or more motion sensors to monitor a movement or position of a body portion of an individual subject and to generate a sense signal in response thereto. The motion sensors can include, but are not limited to, an orientation sensor, an accelerometer, a proximity sensor (e.g., an infrared sensor, an optical sensor, etc.), a force sensor, a pressure sensor, sensors configured to measure a repeated motion of a body portion, sensors configured to measure a number of repetitions of a movement of a body portion, sensors configured to measure a speed of a movement of a body portion, sensors configured to measure a duration of movement of a body portion, sensors configured to measure a disposition of a body portion relative to a second body portion, and sensors configured to measure an angle of movement of a body portion. The motion of the body portion can provide an indication of whether the individual subject is adhering to the motion regimen, can be indicative of pain experienced by the individual, can be indicative of risk of pain, can be indicative of a source of pain, can provide an indication as to when the effector should be employed to provide corrective treatment, or combinations thereof. As another example, the sensor assembly can include one or more physiological sensors to monitor one or more physiological parameters of a subject and to generate a sense signal in response thereto. The physiological sensors can include, but are not limited to, an electrophysiological sensor, an electrocardiograph, an electrooculograph, a microneurograph, an electroneurograph, a myograph, an electromyograph (e.g., a surface electromyograph), an acoustic myography sensor, a mechanomyography sensor, an accelerometer myography sensor, a strain sensor, a pressure sensor, a temperature sensor, an optical sensor (e.g., an LED, a pulse oximeter, etc.), a near infrared sensor, a skin conductance sensor, a bioimpedance sensor, a pH sensor, an acoustic sensor, a chemical sensor, or combinations thereof.

In an embodiment, the systems, devices, and methods described herein employ one or more effectors to effect at least one predetermined motion of the body portion of the individual subject responsive to processing of sense signals generated by the sensor assembly. For example, the one or more effectors can include an electric stimulator having at least one electrode (e.g., to stimulate at least one nerve or muscle of the individual subject), an ultrasonic stimulator having at least one ultrasound transducer (e.g., to stimulate at least one nerve or muscle of the individual subject), or other stimulator configured to facilitate movement of the body portion through the motion regimen including, but not limited to, a magnetic stimulator, an optical stimulator, a thermal stimulator, an acoustic stimulator, a mechanical stimulator, a vibrational stimulator, and combinations thereof. In an embodiment, the one or more effectors deliver a stimulus providing stochastic resonance to the individual subject.

In an embodiment, the systems, devices, and methods described herein employ a communicator configured to generate one or more communication signals responsive to instruction by the processor. The one or more communication signals from the communicator are associated with comparison between at least one of the pain state of the individual subject, the movement of the body portion, or the at least one physiological parameter to one or more threshold target values. For example, the communicator can provide communication signals to the individual subject, to an external device, or to an effector to manage a pain state of the individual during the motion regimen.

In an embodiment, referring generally to FIGS. 9-14 and 31-41C, the system 1000 is configured for monitoring an individual subject and facilitating a motion regimen of the individual subject. The system 1000 includes the substrate 1002, the sensor assembly 1004, the processor 1006, and the effector 1008 for placement on the individual subject to monitor the individual subject for indications of a physiological state (e.g., motion state, pain state, etc.) and for effecting a predetermined motion of a body portion of the individual subject through action of the effector 1008. In an embodiment, the system 1000 includes conformal electronics (e.g., epidermal electronic systems (EES) or devices incorporating epidermal electronics) to monitor physiological, positional, and movement conditions for monitoring movement and/or physiological parameters of the individual subject. The substrate 1002 is configured to conform to a contour of a body portion of an individual subject (e.g., the curvature of a limb), to interface with a skin surface of the body portion, or combinations thereof. For example, the substrate 1002 can comprise a deformable (e.g., conformable, flexible, stretchable, etc.) material configured to interface with, and conform to, the body portion, including, but not limited to a skin surface of the body portion. The body portion is shown in FIG. 10 as a wrist 1100, however the system 1000 can be positioned on any body portion, including but not limited to, an arm, an elbow, a wrist, a hand, a finger, a leg, a hip, a knee, an ankle, a foot, a toe, a facial region, a head region (e.g., proximate one or more cranial muscles of the face or head), an ear region (e.g., via an ear clip configuration, on the ear lobe), a neck region, a torso region, a spinal portion, a sacroiliac joint, one or more myofascial trigger points, or the like, or a skin portion thereof. The substrate 1002 can be positioned in proximity with the body portion of the individual subject according to various mechanisms including, but not limited to, affixed to the skin via an adhesive material, held in place by an external pressure, such as pressure provided by a material wrapped around or about a body portion (e.g., a fabric, a garment, a glove, a bandage, etc.), affixed in a textile, fabric, garment, accessory (e.g., a glove, a sock, a finger cot, a wrap, a brace, etc.), or so forth.

The pliable nature of the substrate 1002 (e.g., flexibility and stretchability) facilitates interaction/interfacing with the body portion during movement of the body portion as the individual subject executes the motion regimen, where the body portion includes a generally low-modulus and deformable natural skin surface. In an embodiment, the substrate 1002 can include one or more of a stretchable/flexible fabric, paper, or polymer (e.g., a natural or synthetic elastomeric polymer, polyimide, polyvinyl, an organic polymer such as PDMS, xylylene, parylene, an inorganic polymer, a biopolymer, a composite material, or any combination thereof), a film (e.g., a hydrocolloid film), a membrane (e.g., a nanomembrane, such as a silicon nanomembrane), a gas-permeable elastomeric sheet, or other deformable (e.g., stretchable, flexible, pliable) material.

In an embodiment, the system 1000 includes at least one flexible or stretchable electronic component. For example, at least one of the sensor assembly 1004 (e.g., motion sensor 1010, physiological sensor 1012, etc. as described herein), the processor (and associated circuitry) 1006, or the effector 1008 can include or be formed of flexible or stretchable electronics coupled to the substrate 1002 to provide movement amongst the components of the system 1000 during the motion regimen by the individual subject. For example, interconnects (not illustrated) between these components or within the circuitry can include or be formed of flexible or stretchable electronics (e.g., serpentine conducting tracings allowing for stretchable interconnects) and coupled to the substrate 1002. For example, a power source (e.g., power supply 1200 described herein), can include or be formed of flexible or stretchable electronics and be coupled to the substrate 1002. In an embodiment, the at least one flexible or stretchable electronic component includes at least one of a wavy, bent, mesh (e.g., open mesh), buckled, or serpentine geometry. In an embodiment, the at least one flexible or stretchable electronic component includes at least one nanowire, at least one nanoribbon, or at least one nanomembrane. For example, the system 1000 can include one or more multifunctional electronic units comprising a stretchable/flexible system including a sensor assembly (e.g., sensor assembly 1004), effector (e.g., effector 1008), and power source (e.g., power supply 1200) in communication via associated circuitry (e.g., with processor 1006), including interconnects, residing in or on a deformable substrate (e.g., substrate 1002), such as to provide movement amongst the components of the system 1000 during the motion regimen by the individual subject without compromising the functionality of the components.

In an embodiment, the system 1000 can include at least one ultrathin electronic component. For example, an ultrathin (e.g., less than 20 micrometers) electronic component can include a thinned wafer (e.g., thinned silicon wafer bonded to a polymer substrate), an ultrathin chip, or the like. For example, ultrathin circuitry can include conductive layers formed on a deformable substrate (e.g., substrate 1002) such as parylene by evaporation deposition with ultraviolet (UV) lithography and etching. For example, at least one of the sensory assembly 1004, the processor 1006, or the effector 1008 can include ultrathin electronics.

In an embodiment, the system 1000 can include at least one electrically conductive thread, yarn, or textile. For example, the sensory assembly 1004, the processor 1006, or the effector 1008 can include at least one electrically conductive thread or yarn. Electrically conductive threads, yarns, or textiles can be configured to provide sufficient current to induce at least one of a wired or wireless coupling, e.g., between electronic components. For example, electronically conductive threads, yarns, or textiles may form the processor 1006 (or circuitry thereof) or other circuitry configured to function in communication between one or more sensor assemblies 1006, one or more effectors 108, or other circuitry of the system 1000. For example, electronically conductive threads, yarns, or textiles may form at least a portion of circuitry configured to function in communication between a plurality of multifunctional electronic units each comprising one or more sensor assemblies 1006, one or more effectors 1008, and processor 1006. Electrically conductive fibers, threads, and yarns can include a metallic material, semi-metallic material, semi-insulative material, semi-conductive material (e.g., silicon and a gallium arsenide), or transparent conductive material (e.g., an indium-tin-oxide (ITO) material). Electrical threads or yarns can be embedded in textiles using weaving, knitting or embroidery, for example, or can be attached using nonwoven production techniques such as adhesion. For example, electrically conductive yarns having curved configuration can be attached to an elastic textile (e.g., by sewing or by adhesion) and can form all or part of a sensor assembly 1004 that measures one or more movements or physical characteristics of an individual, e.g., as the curved configuration is altered, such as due to particular skin topography or the like during execution of the motion regimen.

The sensor assembly 1004 is coupled to the substrate 1002 and is configured to generate one or more sense signals based on detection of at least one of a movement of the body portion or at least one physiological parameter of the body portion (e.g., during execution of the motion regimen by the individual subject). In an embodiment, the sensor assembly includes one or more of the motion sensor 1010 (e.g., to generate one or more sense signals based on detection of movement of the body portion) or the physiological sensor 1012 (e.g., to generate one or more sense signals based on detection of at least one physiological parameter of the body portion). In an embodiment, shown in FIG. 37, the sensor assembly 1004 includes one or more of an orientation sensor 3200 (e.g., cells 120 described with reference to FIGS. 1A through 8), an accelerometer (e.g., accelerometer 1400), a proximity sensor (e.g., proximity sensor 1402), a force sensor (e.g., force sensor 3702), or a strain sensor (e.g., strain sensor 3320) to detect a movement of a body portion of the individual subject on which the system 1000 is positioned and generate a sense signal in response thereto. For example, the orientation sensor 3200 can include one or more of a single-axis accelerometer, a pair of oppositely aligned single-axis accelerometers, an antenna configured to measure a field source, a range sensor, a multi-axis accelerometer, a gyroscope, an inclinometer, or combinations thereof, as described herein, to measure a movement of the body portion based on an orientation or change of orientation of the body portion. In an embodiment, the force sensor 3702 measures a force associated with movement of the body portion. In an embodiment, one or more of the force sensor 3702 or the processor 1006 includes circuitry configured to determine a risk of strain of the body portion (e.g., based on the force associated with movement of the body portion). The proximity sensor 1402 can include one or more of an infrared sensor (e.g., infrared sensor 1404) and an optical sensor (e.g., optical sensor 1406). In an embodiment, the proximity sensor is configured to sense a second body portion proximate the body portion on which the system 1000 is positioned. For example, the system 1000 can be positioned on a wrist of the individual subject and the sensor assembly 1004 can include a proximity sensor (e.g., proximity sensor 1402) configured to detect one or more of a presence, a position, an angle, and a movement of another body portion proximate the wrist, such as a hand, a palm, an arm, a finger, a shoulder, and so forth. The presence or proximity of a second body portion relative to the body portion on which the system 1000 is positioned can provide an indication as to whether the movement by the individual subject corresponds to the motion regimen or deviates therefrom.

In an embodiment, the proximity sensor 1402 is configured to sense a device interfacing with another portion of the skin surface or with another body portion. For example, the system 1000 can be positioned on a body portion of the individual subject and a second system 1000 is positioned proximate the body portion or on another body portion, where the proximity sensor 1402 of the system 1000 can sense one or more of a presence, a position, an angle, and a movement of the second system 1000. In an embodiment, the sensor assembly 1004 includes a pressure sensor (e.g., pressure sensor 3342), which can be an individual sensor, or incorporated as a component of one or more of the orientation sensor 3200 or the proximity sensor 1402. The pressure sensor can generate sense signals indicative of a pressure experienced by the body portion, which can indicate, for example, a grip strength of the individual subject over time (e.g., gripping a tool, sports equipment, surgical implement, musical instrument, etc.), a pressure of another body portion on the body portion over time, a pressure of a support on the body portion over time (e.g. a chair or a bed), or the like. In an embodiment, the sensor assembly 1004 (e.g., via one or more motion sensors, such as motion sensor 1010) can sense spastic motions, repetitive motions (e.g., associated with a risk of stress, repetitive stress injury, and the like), or tremors, such as those associated with a movement disorder or pathology (e.g., spasticity, palsy, autism, Parkinson's disease, etc.). For example, the sensor assembly 1004 (e.g., via one or more motion sensors, such as motion sensor 1010) can sense in an autistic person jerking motion, rocking, etc., which can be a sign of stress. In an embodiment, the system 1000 can be used to provide to an autistic person exhibiting signs of stress, stimulus such as tactile, vibration, electrical, etc. (e.g., via the effector 1008), which can calm the autistic person and can train self-calming skills. In an embodiment, the system 1000 can be used to train and calm spastic muscles. In an embodiment, the sensor assembly 1004 (e.g., via one or more motion sensors, such as motion sensor 1010) can sense muscle rigidity, and the effector 1008 can be used to relax the muscles and train the muscles to be less rigid.

Figure 38:
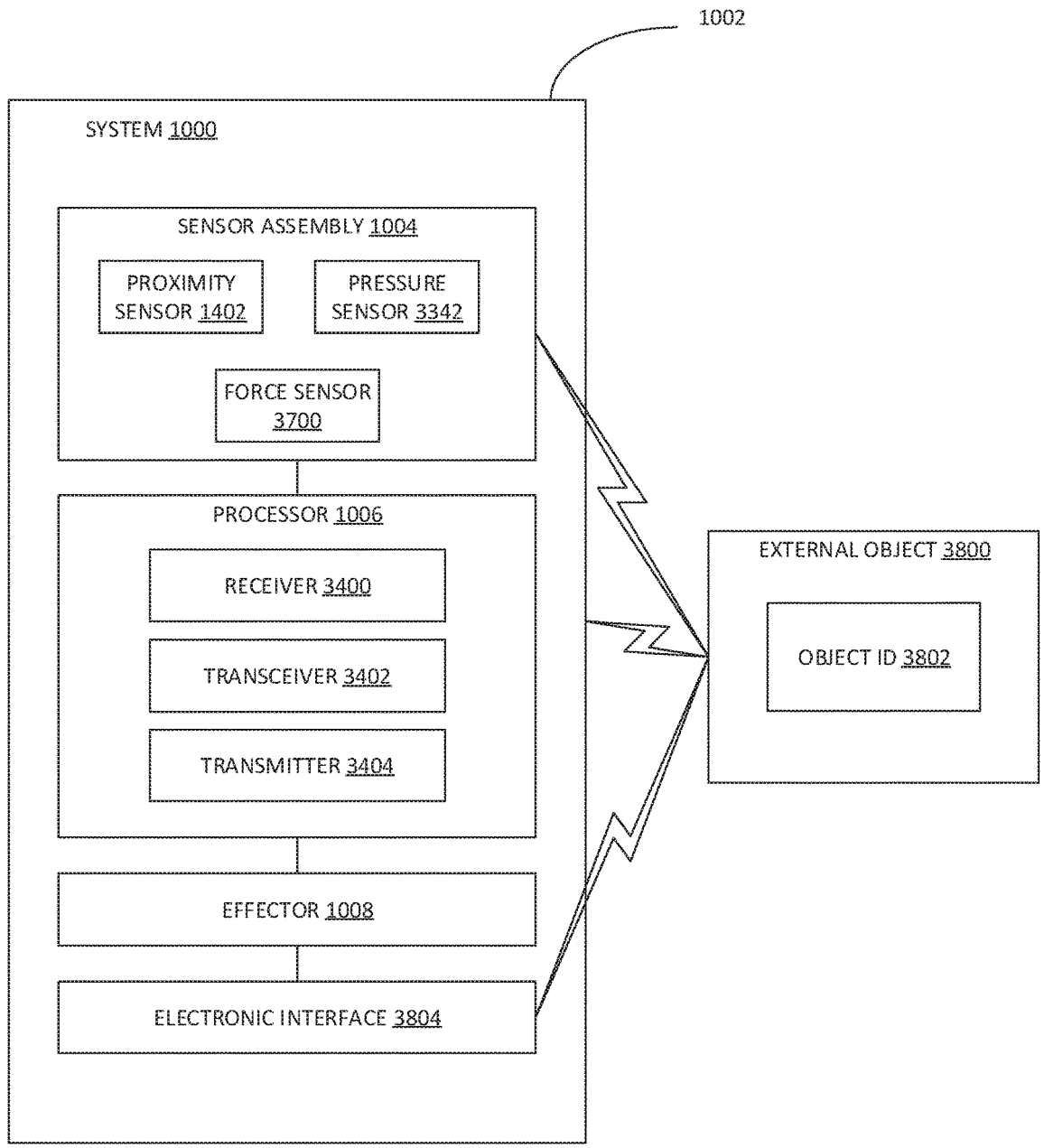
FIG. 38 is a schematic of an embodiment of a system for monitoring an individual subject and facilitating a motion regimen of the individual subject.

In an embodiment, shown in FIG. 38, the sensor assembly 1004 is configured to detect interaction with an external object 3800. For example, the sensor assembly 1004 can include one or more of the proximity sensor 1402, the pressure sensor 3342, or the force sensor 3702 to detect an interaction between the individual subject (e.g., via the body portion on which the system 1000 is positioned, via a different body portion, or combinations thereof) and the external object 3800. For example, the external object can include, but is not limited to, external device 3406, a floor surface, a tool, an article of sports equipment, a surgical implement, a musical instrument, a treadmill, a keyboard, a rehabilitation device, a therapy device, or the like. In an embodiment, the interaction between the external object 3800 and the individual subject provides a basis for control of the effector 1008 (e.g., via the processor 1006) to proceed through a choreographed movement of the motion regimen. For example, the sensor assembly 1004 generates one or more sense signals based upon detection of interaction between a body portion and the external object 3800 (e.g., via one or more of the proximity sensor 1402, the pressure sensor 3342, or the force sensor 3702), whereby the processor 1006 determines whether the interaction is within a target or threshold interaction (e.g., threshold duration of interaction, threshold force of interaction, threshold angle of interaction, etc.). In an implementation, such determination by the processor 1006 can be implemented via execution of the comparison module 1300 or other processor function. Following analysis of the interaction by the processor 1006, the processor 1006 can generate control signals to control operation of the effector 1008. For example, if the body portion is not scheduled to contact the external object 3800 (e.g., as scheduled in the motion regimen), a determination that the body portion and the external object 3800 interacted can lead to generation of control signals to the effector 1008 to effect the body portion to proceed to a choreographed movement to avoid interacting with the external object 3800 (e.g., how large a step to take, how far to move a limb, how much force to use during a movement (e.g., step, strike, hand grip, toe grip), etc.). Monitoring the interaction between the individual subject and the external object 3800 can also include proximity signaling, such that the system 1000 can monitor whether the body portion is approaching an intended object (e.g., an object prescribed for interaction with the body portion by the motion regimen) or an unintended object (e.g., an object not prescribed for interaction with the body portion by the motion regimen, or prescribed for interaction with the body portion at a different point in time than an existing or expected interaction). For example, the processor 1006 can determine whether the body portion is approaching a correct or intended control interface (e.g., an "engage" switch) of a control panel at a prescribed time during the motion regimen or an incorrect or unintended control interface (e.g., a "disengage" switch) of the control panel. In an embodiment, the system 1000 is configured to receive information associated with the external object 3800. For example, the external object 3800 can include an object identifier 3802 having identifying information (e.g., object name, size, weight, model, etc.) associated with the external object 3800 stored therein. The external object 3800 can transmit the identifying information to the system 1000 (e.g., received by receiver 3400 or transceiver 3402), for example when queried by the system 1000 (e.g., based upon proximity between the system 1000 and the external object 3800). In an embodiment, the object identifier 3802 includes a tag (e.g., RFID tag) having a unique identity of the external object 3800, where the unique identity is associated with the identifying information, for example, stored in a database accessible by the system 1000. In an embodiment, the system 1000 includes an electronic interface 3804 to operably couple to electronics of an external device (e.g., external object 3800, external device 3406, etc.), including but not limited to electronics of an external object or equipment or external simulator (e.g., simulated, practice, or real control panel such as a flight panel; exercise equipment; simulator for skiing, simulator for surgery, etc., motion capture device) or virtual environment so as to be informed as to what movements to choreograph (e.g., via operation of the effector 1008). The electronic interface 3804 is configured to receive one or more control signals, one or more communication signals, and the like, from the external device. For example, in an embodiment, at least one of the motion regimen or the predetermined motion (e.g., choreographic movement or motion) is based at least in part on information from the external device received via the electronic interface 3804.

In an embodiment, the sensor assembly 1004 includes an accelerometer (e.g., accelerometer 1400, an accelerometer of the orientation sensor 3200, etc.) to provide sense signals associated with an acceleration of the body portion, where the processor 1006 can interpret the sense signals to determine whether the body portion is moving at a speed or velocity that corresponds to a scheduled movement of the motion regimen. For example, the accelerometer can provide sense signals to the processor 1006 for the determination as to whether the body portion is moving at a speed or velocity that corresponds to a scheduled movement of the motion regimen; such body movements can be further analyzed together with the sense signals from one or more of the proximity sensor 1402, the pressure sensor 3342, or the force sensor 3702 to determine whether the speed or velocity of movement of the body portion is associated with a proper or improper interaction or expected interaction with an external object (e.g., external object 3800).

The body portion monitored for movement or physiological parameters by the system 1000 can be the body portion with which the system 1000 interfaces (e.g., the body portion on which the system 1000 is positioned) or can be a body portion proximate or distal the body portion with which the system 1000 interfaces. In an embodiment, the sensor assembly 1004 generates a sense signal based on a repeated motion of the body portion. For example, the system 1000 can be positioned on a wrist of a subject, and the sensor assembly 1004 measures changes in the position of finger flexor tendons during movement of one or more fingers. In an embodiment, the sensor assembly 1004 measures a number of repetitions of a movement of a body portion. For example, the system 1000 can be positioned on a finger of a subject and the sensor assembly 1004 measures the number of repetitions that the particular finger is flexed or bent. Measuring the number of repetitions can include, but is not limited to, measuring that zero repetitions have occurred, measuring a finite number of repetitions, measuring the number of repetitions taken over a specified time period, and determining that the number of repetitions exceeds a threshold number (e.g., a threshold associated with the motion regimen). The measurement of the number of repetitions can be facilitated by, for example, one or more of the counter 3202 or the timer 3204 present in the sensor assembly 1004, in the processor 1006, or combinations thereof. In an embodiment, the sensor assembly 1004 measures a speed of a movement of a body portion. For example, the system 1000 can be positioned on an ankle of a subject and the sensor assembly 1004 measures the speed of movement of the ankle, such as one or more of a speed of movement during a flexing of the ankle during a walking motion of the motion regimen, a speed of movement relative to a ground surface during a walking motion of the motion regimen, or other movement. In an embodiment, the sensor assembly 1004 measures a duration of a movement of a body portion. The duration can include one or more of a total duration of movement within a period of time (e.g., duration encompassing multiple repetitions of movement) and a total duration of movement for a single repetition of movement. The timer 3204 can facilitate such duration measurements. In an embodiment, the sensor assembly 1004 is configured to measure the disposition of the body portion over a period of time. For example, the sensor assembly 1004 may measure a disposition of the body portion over time while the body portion is one or more of at rest, in motion, and held in a position that is not a rest position (e.g., tensed). In an embodiment, the sensor assembly 1004 measures a disposition of a body portion on which the system 1000 is positioned relative to a second body portion during a movement of one or more of the body portion and the second body portion. For example, the system 1000 can be positioned on a phalange of a subject and the motion sensor 1010 measures a disposition of the phalange relative to a wrist or ankle of the subject during motion of the phalange or wrist/ankle. In an embodiment, the sensor assembly 1004 measures an angle of movement of a body portion. For example, the system 1000 can be positioned on an arm of a subject and the sensor assembly 1004 measures an angle of movement of the arm (e.g., relative to the torso, relative to a rest position of the arm, relative to another body portion, and so forth). Measurement by the sensor assembly 1004 of one or more of a repeated motion of a body portion, a number of repetitions of the movement of the body portion, a speed of the movement of the body portion, a duration of the movement of the body portion, a disposition of the body portion relative to a second body portion, and an angle of movement of the body portion provides information that can aid in the determination by the system 1000 of whether the subject is adhering to the motion regimen, whether the effector 1008 should alter the stimulation provided to the body portion, whether the effector 1008 should cease stimulation provided to the body portion, whether the effector 1008 should initiate stimulation to the body portion or the like.

In an embodiment, the sensor assembly 1004 is configured to transmit one or more sense signals to the processor 1006 indicative of one or more of a motion state of the individual subject, a rest state of the individual subject, or a duration of a rest state of the individual subject. For example, the motion state of the individual subject can indicate that the individual subject (or body portion thereof) is currently moving, whereas the rest state of the individual subject can indicate that the individual subject (or body portion thereof) is not moving, or is moving at a rate or between orientations that does not exceed a threshold rate. In an embodiment, the processor 1006 determines a rest state of the individual based on the sense signals from the sensor assembly 1004. For example, the processor 1006 can compare the sense signals from the sensor assembly 1004 to reference data indicative of a body portion at rest to determine whether the body portion of the individual subject is experiencing a rest state (e.g., at or under a motion threshold relative to the reference data) or an active state (e.g., exceeding a motion threshold relative to the reference data). In an embodiment, the processor 1006 is configured to activate the effector 1008 to affect the body portion (e.g., via ultrasound stimulation, electric stimulation, thermal stimulation, mechanical stimulation, vibrational stimulation, optical stimulation, as described further herein) when the body portion is at rest (e.g., at the beginning of the motion regimen). For example, the processor 1006 can instruct the effector 1008 (e.g., via one or more electric control signals) to activate to affect the body portion when the sense signals from the sensor assembly 1004 indicate that the body portion is experiencing a rest state. As another example, the effector 1008 may operate after the individual subject, or the particular body portion, has been at rest, or in the same position, for a period that exceeds a predetermined length of time (e.g., permitting a rest period for the individual subject after the individual subject has exerted themselves by following the motion regimen). In an embodiment, the processor 1006 is configured to activate the effector 1008 to affect the body portion responsive to a predetermined amount of movement of the body portion. For example, the processor 1006 can instruct the effector 1008 (e.g., via one or more electric control signals) to activate to affect the body portion when the sense signals from the sensor assembly 1004 indicate that the body portion met or exceeded a predetermined amount of movement, such as by exceeding a threshold distance of travel of the body portion, a threshold period of time of movement of the body portion, a threshold orientation of the body portion, or the like, where such thresholds can correspond to the choreographed movements of the motion regimen. In an embodiment, the processor 1006 is configured to activate the effector 1008 to affect the body portion responsive to a predetermined type of movement of the body portion. For example, the processor 1006 can instruct the effector 1008 (e.g., via one or more electric control signals) to activate to affect the body portion when the sense signals from the sensor assembly 1004 indicate that the body portion experienced a particular type of movement. For example, the sense signals from the sensor assembly 1004 might indicate that the body portion experienced a particular type of movement, such as a predetermined high velocity of movement, a high level of force output, a too-rapid step (e.g., indicating tripping), a movement in a particular direction (e.g., indicating a twisting of a joint), or the like, which can indicate a pain state of the individual or non-compliance with the motion regimen. For example, the sense signals from the sensor assembly 1004 might indicate pronounced minimalization of motion or agitation affecting a body site (e.g., a muscle), e.g., "guarding". For example, the sense signals from the sensor assembly 1004 might indicate that the body portion experienced a particular type of movement such as experiencing a predetermined velocity of movement (e.g., the individual subject is slowing down), a grimace, an awkward gait, a limp, pronounced use of non-dominant limb, pronounced rubbing or massage of a body portion (e.g., repeated or deep massage), or the like, which can indicate a level of discomfort or pain experienced by the individual subject. Such occurrences can serve as an indicator to the processor 1006 that the effector 1008 should be activated, deactivated, or altered. In an embodiment, the processor 1006 is configured to activate the effector 1008 to affect the body portion responsive to completion of a portion of the motion regimen (e.g., responsive to completion of one choreographed movement of the motion regimen). For example, the processor 1006 can instruct the effector 1008 (e.g., via one or more electric control signals) to activate to affect the body portion when the sense signals from the sensor assembly 1004 indicate that the body portion executed a portion of the motion regimen. For example, the sense signals from the sensor assembly 1004 might indicate that the body portion executed a first choreographed movement of the motion regimen, whereby the processor 1006 can instruct one or more effectors 1008 to activate to effect the next choreographed movement of the motion regimen. The choreographed movements of the motion regimen can be stored in a memory device accessible by the processor 1006 to implement the motion regimen via action of one or more effectors 1008. Stimulation provided by the one or more effectors 1008 can be altered via control by the processor 1006 to maintain motion by the individual subject consistent with the motion regimen, or to cause the motion by the individual subject to return to the thresholds of the motion regimen.

The sensor assembly 1004 is configured to detect one or more physiological parameters of the individual subject on which the system 1000 is positioned, where such physiological parameters can provide an indication as to whether the individual subject is experiencing pain (e.g., due to an exercise program of the motion regimen, due to motion outside the target values of the motion regimen, etc.), or to what degree the individual subject is experiencing pain (e.g., providing an indication whether to cease, alter, or initiate effector 1008 activation). In an embodiment, the sensor assembly 1004 detects a localized physiological parameter provided by one or more of a body portion with which the system 1000 interfaces and a body portion proximate the portion with which the system 1000 interfaces. The sensor assembly 1004 can also or instead be configured to detect systemic physiological parameters of the subject on which the system 1000 is positioned. In an embodiment, shown in FIG. 37, the sensor assembly 1004 can include one or more of the electrophysiological sensor 3300, the electrocardiograph 3302, the electrooculograph 3304, the microneurograph 3306, an electroneurograph, the myograph 3308, the electromyograph (EMG) 3310, the surface electromyograph 3312, the acoustic myography sensor 3314, the mechanomyography sensor 3316, the accelerometer myography sensor 3318, the strain sensor 3320, the temperature sensor 3322, the optical sensor 3324, the light emitting diode (LED) 3326, the oximeter 3328, the near infrared sensor 3330, the skin conductance sensor 3332, the bioimpedance sensor 3334, the pH sensor 3336, the acoustic sensor 3338, the chemical sensor 3340, the pressure sensor 3342, or combinations thereof; the functionalities and associated pain state, pain type, and pain level determinations thereof are provided herein. In an embodiment, the sensor assembly 1004 can include a plurality of sensors (e.g., of those shown in FIG. 37 or in addition to those shown in FIG. 37), such as a plurality of a single sensor type or a combination of different sensor types, arranged in an array or otherwise communicatively coupled (e.g., via one or more leads and/or wireless coupling, such as between sensor locations). Further, one or more components of the sensor assembly 1004 can provide sense signals directed to a plurality of detection schemes. For example, the acoustic sensor 3338 can operate as proximity sensor to sense a proximity between the body portion and another body portion, between the body portion and an external device or external object, or the like, such as through echolocation; the acoustic sensor can operate as one or more of a motion sensor or a physiological sensor by measuring one or more acoustical signatures of a motion event or physiological event. For example, the acoustic sensor 3338 can include at least one microphone or acoustic transducer. For example, the acoustic sensor 3338 can be configured to detect an articular noise (e.g., crepitus), such as an articular noise associated with movement (e.g., creaking or popping) or an articular noise (e.g., friction or grinding) in an arthritic joint experiencing pain associated with movement. For example, the acoustic sensor 3338 can include an acoustic sensor (e.g., acoustic myographic sensor 3314) configured to detect musculoskeletal acoustic signature. For example, the acoustic sensor 3338 can be configured to detect a vocal event (e.g., a groan, vocalization, or speech), such as a vocal event indicative of movement or pain. For example, the acoustic sensor 3338 can be configured to detect an acoustic signature of a physiological event indicative of an autonomic response, e.g., a heartbeat, valve closure, blood flow, respiration, etc.

The processor 1006 is configured to receive one or more sense signals (e.g., from the sensor assembly 1004) associated with one or more of detection of the movement of the body portion (e.g., by the motion detector 1010), or detection of one or more physiological parameters of the individual subject on which the system 1000 is positioned (e.g., by the physiological sensor 1012), to provide analysis of the one or more sense signals and to provide control of the components of the system 1000 (e.g., control of the effector 1008). For example, the processor 1006 includes circuitry configured to identify a physiological state (e.g., a pain state, a motion state, etc.) of the individual subject based on analysis of the one or more sense signals. In an embodiment, the processor 1006 includes circuitry configured to identify a physiological state (e.g., a pain state, a motion state, etc.) of the individual subject based on the movement of the body portion detected by the sensor assembly 1004 (e.g., via one or more of accelerometer 1400, proximity sensor 1402, orientation sensor 3200, force sensor 3702, etc.). In an embodiment, the processor 1006 includes circuitry configured to identify a physiological state (e.g., a pain state, a motion state, etc.) of the individual subject based on the one or more physiological parameters detected by the sensor assembly 1004 (e.g., via one or more of the electrophysiological sensor 3300, the electrocardiograph 3302, the electrooculograph 3304, the microneurograph 3306, an electroneurograph, the myograph 3308, the electromyograph (EMG) 3310, the surface electromyograph 3312, the acoustic myography sensor 3314, the mechanomyography sensor 3316, the accelerometer myography sensor 3318, the strain sensor 3320, the temperature sensor 3322, the optical sensor 3324, the light emitting diode (LED) 3326, the oximeter 3328, the near infrared sensor 3330, the skin conductance sensor 3332, the bioimpedance sensor 3334, the pH sensor 3336, the acoustic sensor 3338, the chemical sensor 3340, the pressure sensor 3342). In an embodiment, the processor 1006 includes circuitry configured to identify a physiological state (e.g., a pain state, a motion state, etc.) of the individual subject based on each of the movement of the body portion detected by the motion sensor 1010 and the one or more physiological parameters detected by the physiological sensor 1012. For example, in an embodiment, the processor 1006 is operably coupled to the sensor assembly 1004 such that the processor 1006 is configured to receive the one or more sense signals from the sensor assembly (e.g., from one or more of the motion detector 1010 or the physiological sensor 1012).

In an embodiment, shown in FIG. 12, the system 1000 includes a comparison module 1300 accessible by the processor 1006 to compare one or more of the movement of the body portion, detected by the sensor assembly 1004 (e.g., via motion sensor 1010), or the one or more physiological parameters of the body portion, detected by the sensor assembly 1004 (e.g., via one or more physiological sensors 1012), to one or more target values associated with the motion regimen. In an embodiment, the target values include reference data associated with a physiological state, where the physiological state includes at least one of a pain state, a pain type, a pain level, a pain quality, or a motion state. For example, the reference data can include one or more of motion data or physiological parameter data, where such data can be associated with, but not limited to, a motion state, such as a rest state, an in-motion state, a duration of motion state, or the like, a pain state, such as a pain-free state, an onset of pain, a pain pattern, chronic pain, acute pain, mixed pain state, a hyperalgesic pain state, an allodynic pain state, a breakthrough pain state, a neuropathic pain state, a nociceptive pain state, a non-nociceptive pain state, combinations thereof, or the like, described herein. In an embodiment, the one or more target values include a predefined target for one or more limb motions. For example, the target values can include one or more targets for leg motions, for arm motions, for foot motions, for hand motion, for finger motion, etc. (e.g., for a martial arts choreographed motion regimen, for a dance choreographed motion regimen, for a surgical skills training choreographed motion regimen, or the like). In an embodiment, the one or more target values include a predefined target for an activity of one or more muscles. For example, the target values can include one or more targets for muscle activity for abdominal muscles, for leg muscles, for back muscles, etc. (e.g., for a cardiovascular exercise choreographed motion).

In an embodiment, the one or more target values (or reference data thereof) can include user-specific information, such as user-specific threshold or tolerance information. For example, the individual can indicate to the system 1000 (e.g., via user interface 3600 described herein) when the individual feels pain. The system 1000 can then take a snapshot of one or more of the individual's physiological state, motion state, positional state, etc. to set a threshold pain level, to link a physiological or motion parameter to pain experienced by the individual, or the like, which can serve as a comparator to autonomic parameters experienced by the individual. The system 1000 can monitor the individual and receive additional individual input regarding whether the pain intensifies, dissipates, differs in type, location, chronology, etc. The reference data can include user-specific personal history information, such as whether the individual has experienced a joint disorder, cardiovascular condition, other health condition, or the like, can depend on a feedback from monitored movement/physiological parameter(s) (e.g., whereby detected movements or physiological parameters can result in the target value being adjusted to compensate for the detected values), or can depend on generalized health or fitness considerations of the individual (e.g., height, weight, body mass index, caloric needs or preferences, general health or fitness levels, etc.).

In an embodiment, the processor 1006 provides a motion determination related to the individual subject responsive to comparison of at least one of the movement of the body portion or the at least one physiological parameter of the body portion to one or more target values associated with the motion regimen. The motion determination can include, for example, a determination regarding whether the individual subject is moving correctly (e.g., within the threshold or target values of the motion regimen) or incorrectly (e.g., outside of the threshold or target values of the motion regimen). For example, the processor 1006 receives the one or more sense signals from the sensor assembly 1004 and accesses the comparison module 1300 to compare the sense signals to the target values of the motion regimen. When the sense signals are outside of the target values (e.g., when the sense signals are outside of a threshold range, when the sense signals differ by statistically significant factors, etc., such as by moving too quickly or too slowly, by having too high/low muscle activity, by having too high/low pain state, by moving a body portion outside of a preferred orientation, or the like), the processor 1006 can provide a motion determination that the individual subject is not in compliance with the motion regimen. When the sense signals are within the target values, the processor can provide a determination that the individual subject is in compliance with the motion regimen. In an embodiment, the processor 1006 determines whether to initiate a next motion of the body portion in a motion sequence effected by the effector 1008 responsive to comparison of at least one of the movement of the body portion or the at least one physiological parameter of the body portion to one or more target values associated with the motion regimen. For example, the processor 1006 receives the one or more sense signals from the sensor assembly 1004 and accesses the comparison module 1300 to compare the sense signals to the target values of the motion regimen. When the sense signals are outside of the target values, the processor 1006 can cease activation of the effector 1006, or can alter activation of the effector 1008 (e.g., to bring the sense signals within the target values). When the sense signals are within the target values, the processor 1006 can continue activation of the effector 1006 to initiate the next motion of the motion sequence (e.g., choreographed motion sequence) of the motion regimen. In an embodiment, the processor 1006 generates a stop instruction (e.g., provided via visual, audio, and/or tactile display) responsive to comparison of at least one of the movement of the body portion or the at least one physiological parameter of the body portion to one or more target values associated with the motion regimen. The stop instruction can be provided to one or more of the individual subject or an external device (e.g., external device 3406). For example, when the sense signals are outside of the target values, the processor 1006 can generate the stop instruction provided to one or more of the individual subject or the external device 3406, such as via display 1502, transmission via transceiver 3402 or transmitter 3404, or the like.

The processor 1006 can coordinate operations of the system 1000 based on the one or more sense signals and identification of a physiological state (e.g., pain state, motion state, etc.) of the individual subject based on the one or more sense signals. For example, the processor can coordinate operation of the effector 1008 based upon identification of the physiological state (e.g., pain state, motion state, etc.) of the individual subject and conditions experienced by the individual subject (e.g., rest state, motion state, within range of target values of motion regimen, outside range of target values of motion regimen, etc.). The effector 1008 is operably coupled to the processor 1006 and is configured to effect at least one predetermined motion of the body portion of the individual subject responsive to control by the processor 1006, where such at least one predetermined motion corresponds to a motion regimen (e.g., one or more choreographed movements of the motion regimen).

Figure 39:
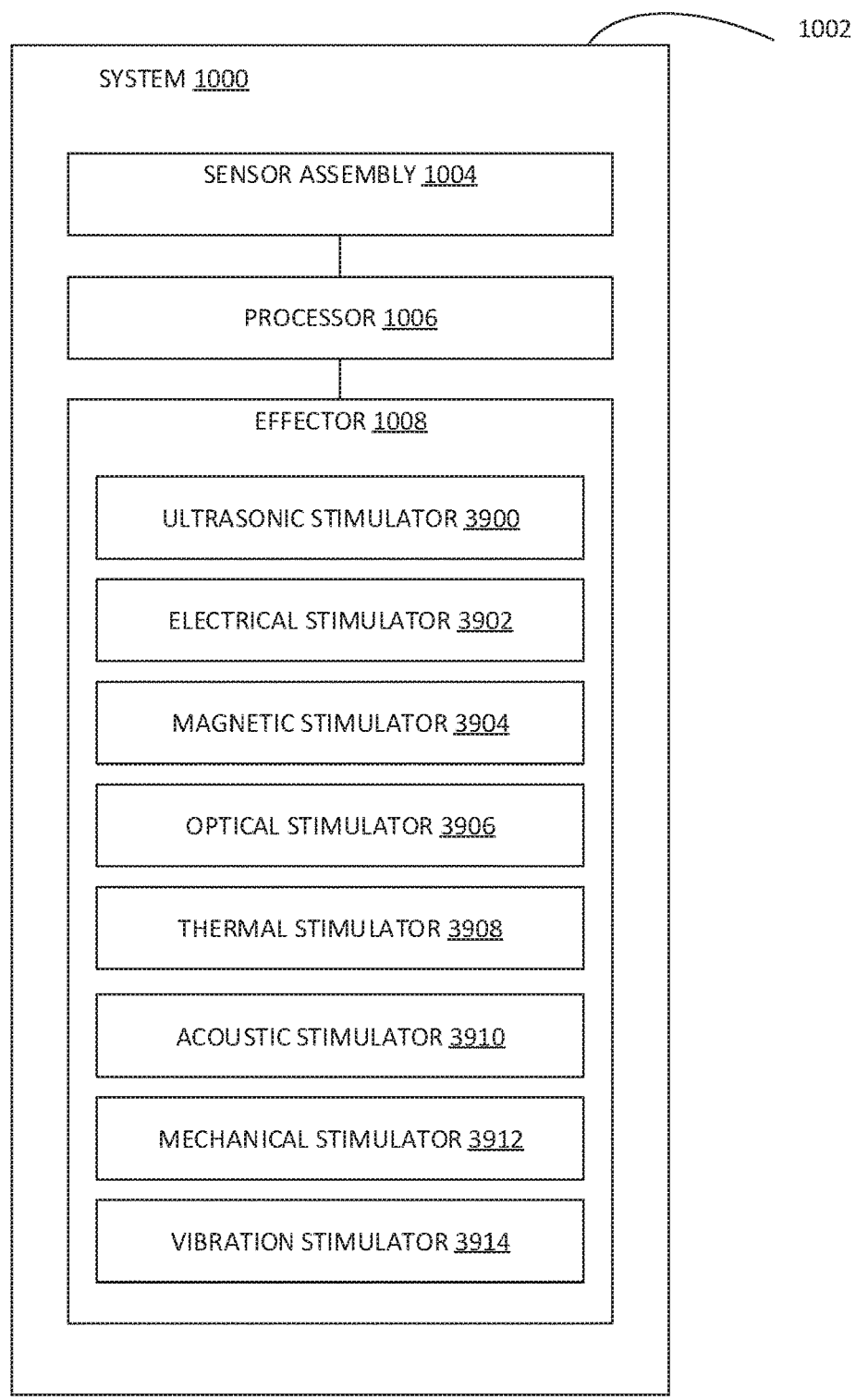
FIG. 39 is a schematic of an embodiment of a system for monitoring an individual subject and facilitating a motion regimen of the individual subject.

In an embodiment, shown in FIG. 39, the effector 1008 can include, but is not limited to, an ultrasonic stimulator 3900 (e.g., ultrasound transducer 3500), an electric stimulator 3902 having at least one electrode (e.g., electrode 3502), a magnetic stimulator 3904 (e.g., magnetic stimulator 3504), an optical stimulator 3906 (e.g., optical stimulator 3506), a thermal stimulator 3908 (e.g., thermal stimulator 3508), an acoustic stimulator 3910 (e.g., acoustic stimulator 3510), a mechanical stimulator 3912 (e.g., mechanical stimulator 3512), a vibration stimulator 3914 (e.g., vibration stimulator 3514), or combinations thereof.

In an embodiment, the effector 1008 includes the electric stimulator 3902 having at least one electrode (e.g., electrode 3502), where the electric stimulator 3902 stimulates at least one nerve or muscle of the individual subject to induce the at least one predetermined motion of the body portion. For example, the electric stimulator 3902 can generate one or more electric stimulation signals via the at least one electrode to electrically stimulate at least one nerve or muscle of the individual subject to induce the at least one predetermined motion of the body portion responsive to control by the processor 1006. In an embodiment, the electric stimulator 3902 is configured to deliver an electric excitatory stimulus to a nerve proximate to the body portion on which the system 1000 is positioned (e.g., to electrically stimulate a nerve conduction, to electrically block or inhibit nerve conduction, etc.) to induce a choreographed movement of the motion regimen. Inducing the choreographed movement can include, but is not limited to, altering a velocity, direction, speed, angle, etc. of the body portion or other body portion, inducing a null movement (e.g., stopping motion, maintaining a stopped motion, etc.), or other change or maintenance of movement. For example, the electric stimulator 3902 generates an electrical current or impulse to activate, trigger, interfere with, block, alter, or the like a nerve conduction of a nerve. In an embodiment, the blockage of the nerve conduction can inhibit a movement of the body portion. For example, where the sensor assembly 1004 generates one or more sense signals indicating that the body portion is moving in positions, directions, speeds, or the like that are not within the target values of the motion regimen, the processor 1006 can control the effector 1008 (e.g., the electric stimulator 3902) to block a nerve conduction of a nerve proximate to the body portion to inhibit movement of the body portion from maintaining or repositioning into the motions not associated with the motion regimen. In an embodiment, the electric stimulator 3902 is configured to electrically stimulate one or more muscle fibers of one or more muscle groups proximate to the body portion on which the system 1000 is positioned to induce a choreographed movement of the motion regimen. For example, the electric stimulator 3902 generates an electrical current or impulse to directly activate, trigger, interfere with, block, alter, or the like an activation (e.g., contraction) or deactivation (e.g., relaxation) of one or more muscle fibers.

In an embodiment, the effector 1008 (e.g., the electric stimulator 3902) can stimulate at least one nerve that drives an effect (e.g., movement in a muscle) distal from the body portion to induce the at least one predetermined motion. In embodiments, the effector 1008 delivers an excitatory stimulus to generate activity or one or more action potentials, delivers a blocking or inhibiting stimulus to block conduction of action potentials or other neural activity on a nerve or nerve fiber, or combinations thereof. For example, the electric stimulator 3902 can stimulate a nerve (e.g., the radial nerve) of the lower arm to induce a predetermined motion (e.g., extension) in a wrist, finger, or thumb.

In an embodiment, the system 1000 includes one or more effectors 1008 for placement on the individual subject to effect the choreographed motions of one or more body portions of the individual subject according to the motion regimen through action of the one or more effectors 1008. When more than one effector 1008 is utilized, the effectors 1008 can be coupled to the same deformable substrate 1002, to different deformable substrates 1002 operably coupled to the processor 1006 for coordination of activities, or otherwise coordinated to effect the choreographed movements (e.g., included as different systems (e.g., system 1000, second system 1000, system 1704, etc.) in communication with each other), or the like. The processor 1006 can coordinate activation of the various effectors 1008 to effect the choreographed motions of one or more body portions of the individual subject according to the motion regimen. Such coordination can include activating multiple effectors 1006 simultaneously, in sequence, or combinations thereof. For example, the processor 1006 can activate a first effector 1008 and a second effector 1008 to effect a first movement of one or more body portions of the motion regimen. For example, the first and second effectors 1008 can affect the same body portion or different body portions. The processor 1006 can then cease activation of the first effector 1008 while resuming or altering activation (e.g., increasing stimulation, decreasing stimulation, etc.) of the second effector 1008 to effect a second movement of the motion regimen. The processor 1006 can then cease activation of each of the first effector 1008 and the second effector 1008 to halt movement of the body portion(s) upon which the first and second effectors 1008 act, and can activate a third effector 1008 to effect a third movement of the motion regimen, such as a motion by a different body portion than the portion(s) affected by the first and second effectors 1008.

In an embodiment, the effector 1008 includes the magnetic stimulator 3904, where the magnetic stimulator 3904 stimulates at least one nerve or muscle of the individual subject to induce the at least one predetermined motion of the body portion. For example, the magnetic stimulator 3904 (e.g., a micromagnetic stimulator comprising microcoils) can generate one or more magnetic stimulation signals to stimulate at least one nerve or muscle of the individual subject to induce the at least one predetermined motion of the body portion responsive to control by the processor 1006. In an embodiment, the magnetic stimulator 3904 is configured to deliver a magnetic excitatory stimulus to a nerve proximate to the body portion on which the system 1000 is positioned (e.g., to magnetically stimulate a nerve conduction, to magnetically block or inhibit a nerve conduction, etc.) to induce a choreographed movement of the motion regimen. For example, the magnetic stimulator 3904 generates an magnetic field to activate, trigger, interfere with, block, alter, or the like, a nerve conduction of a nerve.

In an embodiment, the effector 1008 includes the optical stimulator 3906, where the optical stimulator 3906 stimulates at least one nerve or muscle of the individual subject to induce the at least one predetermined motion of the body portion. For example, the optical stimulator 3906 (e.g. an infrared or near-infrared light source) can generate one or more stimulation signals (e.g., infrared or near infrared light) to stimulate at least one nerve or muscle of the individual subject to induce the at least one predetermined motion of the body portion responsive to control by the processor 1006. In an embodiment, the optical stimulator 3906 is configured to deliver an optical excitatory stimulus to a nerve proximate to the body portion on which the system 1000 is positioned (e.g., to optically stimulate a nerve conduction, to optically block or inhibit a nerve conduction, etc.) to induce a choreographed movement of the motion regimen. For example, the optical stimulator 3906 generates an infrared light to activate, trigger, interfere with, block, alter, or the like a nerve conduction of a nerve.

In an embodiment, the effector 1008 includes the ultrasonic stimulator 3900, where the ultrasonic stimulator 3900 stimulates at least one nerve or muscle of the individual subject to induce the at least one predetermined motion of the body portion. For example, the ultrasonic stimulator 3900 can generate one or more ultrasonic stimulation signals via an ultrasound transducer to acoustically stimulate at least one nerve or muscle of the individual subject to induce the at least one predetermined motion of the body portion responsive to control by the processor 1006. In an embodiment, the ultrasonic stimulator 3900 is configured to deliver an acoustic excitatory stimulus to a nerve proximate to the body portion on which the system 1000 is positioned (e.g., to acoustically stimulate a nerve conduction, to acoustically block or inhibit a nerve conduction, etc.) to induce a choreographed movement of the motion regimen. For example, the ultrasonic stimulator 3900 generates an ultrasonic signal or impulse to activate, trigger, interfere with, block, alter, and the like a nerve conduction of a nerve. In an embodiment, the ultrasonic stimulator 3900 is configured to electrically stimulate one or more muscle fibers of one or more muscle groups proximate to the body portion on which the system 1000 is positioned to induce a choreographed movement of the motion regimen. For example, the ultrasonic stimulator 3900 generates an ultrasonic signal or impulse to activate, trigger, interfere with, block, alter, and the like an activation (e.g., contraction) or deactivation (e.g., relaxation) of one or more muscle fibers.

In an embodiment, the effector 1008 is configured to deliver a stimulus providing stochastic resonance to a tissue of the body part of the individual subject. For example, the effector 1008 (e.g., the vibration stimulator 3914) can stimulate (e.g., with mechanical or acoustic vibration) as a sub-sensory input that can enhance the response of the nervous system of the individual subject to other sensory inputs, such as the response of stimulation provided by one or more effectors 1008 used to induce the movements of the motion regimen. For example, an effector (e.g., one or more effectors 1008) can apply vibratory stimuli to one portion of a muscle (e.g., belly) or tendon to influence responsiveness of another portion of the muscle (e.g., spindles) or tendon (e.g., Golgi tendon organ). In an embodiment, the effector 1008 can stimulate (e.g., with vibration, such as with vibration stimulator 3914) to provide stochastic resonance to the stimulation for a muscle regimen (e.g., a muscle training regimen, a fine motor skills regimen, etc.). For example, the system 1000 can include a vibration effector (e.g., vibration stimulator 3914) to provide Gaussian noise stimulation (e.g., at 0-300 Hz) to improve motor performance during choreographed movement of the motion regimen. For example, the system 1000 can include a vibration effector (e.g., vibration stimulator 3914) in a glove worn by a person with decreased sensation in fingers, or an individual who desires enhanced sensation (e.g., surgeon, explosives technician, laboratory technician, musician, etc.), such as to provide training of a skill. For example, the vibration effector can be added to an instrument/tool/device to enhance sensitivity to tactile inputs described herein, while working in stroke rehabilitation. For example, a vibrating effector can provide stimulations at a similar frequency to that of the effector 1008 effecting the motion regimen to improve response. In an embodiment, the effector 1008 is configured to deliver a stimulus to the body portion of the individual subject providing stochastic resonance to a distal tissue. For example, an effector (e.g., one or more effectors 1008) can apply vibratory stimuli to a proximal body portion (e.g., a wrist) to influence responsiveness of a laterally distal body portion (e.g., one or more fingers). For example, an effector (e.g., one or more effectors 1008) can apply vibratory stimuli to one portion of a body portion, such as the dorsal portion of a body portion (e.g., a top of a hand or a finger), to influence responsiveness of another portion of the body portion, such as the ventral portion of the body portion (e.g., the palmar portion of a hand or finger).

In an embodiment, the system 1000 includes a computer memory device (e.g., computer memory 1302) accessible by the processor 1006 to store information associated with operation of the system 1000, including use of the system 1000 by one or more individual subjects during execution of one or more motion regimens. In an embodiment, the processor 1006 accesses the computer memory 1302, which can include, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the comparison module 1300 and which can be accessed by the processor 1006 or other accessing device. The information (e.g., reference data, program data, individual subject data, etc.) may be stored by the computer memory 1302 of the system 1000, and can be accessible by the processor 1006 via wireless means, or can be available to the processor 1006 through another method. In an embodiment, the processor 1006 stores data associated with the movement of the body portion on the computer memory 1302. The data associated with the movement of the body portion can be detected by the sensor assembly 1004 and stored by the processor 1006, can be acquired from an external device or object (e.g., external device 3406, external object 3800, etc.) such as via the receiver 3400 or transceiver 3402 and stored by the processor 1006, and the like. In an embodiment, the processor 1006 stores data associated with muscle activity of the individual subject on the computer memory 1302. The data associated with muscle activity of the individual subject can be detected by the sensor assembly 1004 and stored by the processor 1006, can be acquired from an external device or object (e.g., external device 3406, external object 3800, etc.) such as via the receiver 3400 or transceiver 3402 and stored by the processor 1006, and the like. In an embodiment, the processor 1006 stores data associated with the at least one physiological parameter of the body portion (e.g., detected by the sensor assembly 1004) on the computer memory 1302. In an embodiment, the processor 1006 stores data associated with pain experienced by the individual subject on the computer memory 1302. The data associated with pain experienced by the individual subject can be detected by the sensor assembly 1004 and stored by the processor 1006, can be acquired from an external device or object (e.g., external device 3406, external object 3800, etc.) such as via the receiver 3400 or transceiver 3402 and stored by the processor 1006, can be acquired from the individual subject or other person via the user interface 3600, and the like. In an embodiment, the processor 1006 stores data associated with operation of the effector 1008 on the computer memory 1302. The data associated with operation of the effector 1008 can include, for example, duration of motion regimen, time and duration of operation, type of stimulation provided, on which body portion(s) the effector 1008 is positioned to effect, target nerve(s), target muscle(s), and the like. In an embodiment, the system 1000 includes a reporter (e.g., reporter 1500) configured to generate one or more communication signals responsive to control by the processor 1006. For example, the processor 1006 can instruct the reporter 1500 to generate a report based on information stored in the computer memory 1302. The report can include, but is not limited to, one or more of a summary of data stored on the computer memory 1302, compliance or non-compliance of the individual subject with the motion regimen, historical progress of the individual subject, and the like. In an embodiment, the processor 1006 can instruct the reporter 1500 to generate a report based on data sent directly from the processor 1006, such as a summary of data processed by the processor, compliance or non-compliance of the individual subject with the motion regimen, or historical progress of the individual subject.

As described herein, the movement of the body portion, the position of the body portion, or combinations thereof can be indicative of a pain state of the individual subject. For example, the one or more sense signals from the sensor assembly 1004 (e.g., associated with one or more of motion or physiological parameter(s)) can be associated with pain responsive to muscle activity. Since pain and pain thresholds can differ from individual to individual, the motion regimen can be user-specific, such as by being tailored to the individual characteristics of each individual subject. In an embodiment, the motion regimen includes one or more motion thresholds (e.g., target values) responsive to the one or more sense signals associated with pain. For example, the one or more motion thresholds can be user-specific and dependent on a pain signal associated with muscle activity of the individual subject during execution of the motion regimen. For example, an individual can utilize the system 1000 during an exercise motion regimen. When the sensor assembly 1004 measures one or more physiological parameters of muscle activity indicative of pain that exceeds a motion threshold (e.g., target value) for the exercise regimen, the processor 1006 can deactivate the effector 1008, can cause the effector 1008 to initiate a therapeutic operation to reduce the pain, or can provide other instructions to the effector 1008 responsive to the pain experienced by the individual subject. For example, in an embodiment, the processor 1006 is configured to activate the effector 1008 to reduce a pain state of the individual subject, described herein. For example, the effector 1008 can include at least one of the ultrasound transducer 3500, the electrode 3502, the magnetic stimulator 3504, the optical stimulator 3506, the thermal stimulator 3508, the acoustic stimulator 3510, the mechanical stimulator 3512, or the vibration stimulator 3514 to treat the individual subject to reduce a pain state of the individual subject, as described herein.

In an embodiment, the effector 1008 includes one or more of a neural stimulator or a muscle stimulator. In an embodiment, the effector 1008 provides stimulation according to one or more stimulation sequences. In an embodiment, the effector 1008 provides stimulation according to one or more stimulation patterns that induce the body portion and the individual subject to move. For example, the system 1000 can include a plurality of effectors 1008, such as one or more effectors 1008 positioned on each finger of the individual subject, whereby a subset of the effectors 1008 activate to stimulate one or more nerves of a particular finger to press a specific key of a keyboard (e.g., while the letter associated with the key is displayed on a display device). In an embodiment, the effector 1008 can stimulate (e.g., activate, trigger, interfere with, block, alter, etc.) at least one of a peripheral nerve, a motor nerve, a cutaneous nerve, a proprioceptor, a mechanoreceptor, for example. In an embodiment, the effector 1008 can stimulate (e.g., inhibit or block) a nociceptor. In an embodiment, the effector 1008 can stimulate (e.g., with vibration stimulus) nerves associated with a particular skin distribution (e.g., a dermatome). In an embodiment, the motion regimen includes one or more motion thresholds dependent on a personal history of the individual subject. The personal history can include, for example, an age of the individual subject, a general activity level of the individual subject (e.g., sedentary lifestyle, highly active, etc.), whether the individual subject has or has had a joint disorder, whether the individual subject has or has had an injured joint, whether the individual subject has previously performed the motion regimen, etc. In an embodiment, the motion regimen includes one or more motion thresholds at a higher threshold when the personal history lacks a joint disorder than when the personal history includes a joint disorder. In an embodiment, the motion regimen includes one or more motion thresholds at a higher threshold when the personal history includes a history of having previously performed the motion regimen. In an embodiment, the one or more motion thresholds are programmable (e.g., via the user interface 3600), where a user can identify the one or more motion thresholds before, during, or after execution of the motion regimen, such as to provide a goal threshold (e.g., identification of the one or more motion thresholds before execution of the motion regimen), to alter a goal threshold (e.g., identification of the one or more motion thresholds before execution of the motion regimen, such as to make the motion regimen more difficult, easier, etc.), or to plan for a future motion regimen (e.g., identification of the one or more motion thresholds after execution of the motion regimen).

In an embodiment, the individual subject can interact with the system 1000 to alter the parameters of the motion regimen, such as to customize the motion regimen to user preferences. For example, the individual can modify one or more features (e.g., motion thresholds, target values, choreographed movements, etc.) via a user interface. In an embodiment, the processor 1006 modifies the motion regimen responsive to a user input via the user interface (e.g., user interface 3600). For example, the individual subject or other user can add or remove choreographed movements to the motion regimen, can add or modify motion thresholds or target values of the motion regimen, and the like. In an embodiment, the processor 1006 selects the motion regimen for execution responsive to a user input via the user interface (e.g., user interface 3600). For example, the computer memory 1302 can include a plurality of motion regimens, whereby the processor 1006 selects which of the plurality of motion regimens to execute responsive to user input from the user interface 3600. In an embodiment, the motion regimen includes one or more choreographed motions attributed to activities associated with learning or improving skills, such as movement-based skills; rehabilitating, strengthening, or improving flexibility of muscles; interacting with external objects (e.g., interaction between a foot and a floor, dance floor, treadmill, etc.); or the like. The skills can include fine motor skills, for example playing an instrument, typing, first aid skills, surgical skills (e.g., learned while practicing on a model, simulation, or robotic interface), writing, calligraphy; use of a limb or body portion, including training muscle memory, for example for use in sports or other activities (e.g., use of arm, torso, legs in tennis or golf swings, use of wrist for table tennis, Ping-Pong, etc.), skiing (e.g., use of knees for bending, use of arms), martial arts; or combinations thereof. For example, the motion regimen can include a rehabilitation regimen (e.g., rehabilitation of one or more muscle groups following debilitating medical condition), a physical therapy regimen (e.g., rehabilitation, flexibility, or strengthening of one or more muscle groups following injury), an occupational therapy regimen (e.g., learning skills for activities of daily living), a training regimen (e.g., muscle memory training), a motor skills regimen (e.g., fine motor skills training), or combinations thereof.

In an embodiment, the system 1000 includes at least one of a receiver a transceiver, or a transmitter configured to at least one of receive one or more communication signals from an external device or transmit one or more communication signals to the external device. For example, the system 1000 can include one or more of the receiver 3400, the transceiver 3402, or the transmitter 3404 to send and receive communication signals via the receivers from an external device, such as external device 3406, external object 3800, or other device. The communication signals can be sent and received through one or more connected and wireless communication mechanisms including, but not limited to acoustic communication signals, optical communication signals, radio communication signals, infrared communication signals, ultrasonic communication signals, and the like. In an embodiment, the processor 1006 activates the effector 1008 to affect the body portion (e.g., effect the predetermined motion of the motion regimen, provide pain treatment, etc.) responsive to receiving one or more communication signals from the external device. In an embodiment, the processor 1006 prevents activation or disables activation of the effector 1008 responsive to receiving one or more communication signals from the external device. In an embodiment, the external device (e.g., external device 3406, external object 3800, etc.) includes a display. For example, the external device (e.g., external device 3406, external object 3800, etc.) can includes at least one of an LCD display, OLED display, a flexible display, a projected display, or a three dimensional display. In an embodiment, the external device (e.g., external device 3406, external object 3800, etc.) includes at least one of a virtual reality display device or an augmented reality display device. For example, the virtual reality display device or the augmented reality display device can display an image responsive to receiving one or more communication signals from the system 1000. In an embodiment, the external device (e.g., external device 3406, external object 3800, etc.) includes at least one of a haptic feedback device, an audio feedback device, or a visual feedback device. For example, the external device 3406 or external object 3800 can provide feedback to the individual subject as one or more of haptic feedback (e.g., via a haptic feedback device), audio feedback (e.g., via an audio feedback device), or visual feedback (e.g., via a visual feedback device) responsive to one or more communication signals from the system 1000. For example, the system 1000 can send one or more communication signals to the external device 3406 or external object 3800 indicating that the individual subject is in compliance with the motion regimen (e.g., performing the choreographed motions within the motion thresholds or target values, performing the choreographed motions according to a predetermined schedule of performance dates or frequencies, etc.), whereby the external device 3406 or external object 3800 can provide at least one of haptic feedback (e.g., a vibration-based message), audio feedback (e.g., an audio message or signal), or visual feedback (e.g., a visually-displayed message, an image of a virtual reality or augmented reality display device, etc.) to the individual subject or other user of the system 1000 (e.g., a trainer, a coach, a healthcare professional, etc.). In an embodiment, the system 1000 influences the motions of the individual subject (e.g., via operation of one or more effectors 1008) in a manner specific to the particular external object 3800 with which the individual is interacting (or should avoid interacting). For example, the system 1000 can include one or more sensors configured to identify the external object 3800 (e.g., via one or more sensors of the sensor assembly 1004), where, upon identification, a particular motion regimen is selected for operation by the system 1000. For example, upon identification of a particular tool, the system 1000 can operate one or more effectors 1008 causing the individual subject to grasp the object once a certain proximity between the individual subject's hand and the object (or portion of the object) is reached. In an embodiment, the system 1000 is configured to prevent contact between the body portion of the individual subject and the external object 3800, such as when the motion regimen has not scheduled such interaction, or when such interaction is unsafe, or when such interaction is scheduled for a later interaction time, and the like. As another example, the effector 1008 can stimulate one or more muscle groups of the individual subject to repel the body portion from a particular region of the external object (e.g., avoiding interaction between a hand and the blade of a knife), while providing a signal when the body portion approaches a different region of the external object (e.g., causing one or more muscles of the hand to contract when the body portion approaches the handle of the knife). The motions regimen can provide multiple contextual queues to the muscles of the individual subject during interaction with the external object 3800 to facilitate execution of the desired motion regimen (e.g., a motion regimen specific to the external object 3800).

In an embodiment, the system 1000 can receive one or more feedback signals from an external device or object based on the one or more sense signals from the sensor assembly 1004. For example, the sensor assembly 1004 can generate one or more sense signals based on detection of at least one of a movement of the body portion or at least one physiological parameter of the body portion, where the processor 1006 instructs the system 1000 to transmit one or more communication signals (e.g., the one or more sense signals) to the external device or object (e.g., external device 3406, external object 3800, etc.) for processing by the external device or object. The processing by the external device or object can involve determining whether the one or more sense signals provide an indication that the individual subject is in compliance with the motion regimen, is not in compliance with the motion regimen, is in a pain state within the target values of the motion regimen, is in a pain state exceeding the target values of the motion regimen, has a muscle activity that is within the target values of the motion regimen, has a muscle activity that exceeds the target values of the motion regimen, or the like. The external device or object can then generate one or more feedback signals for transmission to the system 1000, where the processor 1006 can direct control of the effector 1008 responsive to the feedback signals to determine the stimulation settings for the effector 1008 (e.g., to bring the individual subject in compliance with the motion regimen based on the feedback signals, to reduce a pain state of the individual subject based on the feedback signals, to increase a pain state of the individual subject based on the feedback signals, to increase a muscle activity of the individual subject based on the feedback signals, to decrease a muscle activity of the individual subject based on the feedback signals, etc.).

In an embodiment, the system 1000 is configured to determine or receive an identification of the individual subject on which the system 1000 is positioned to determine whether to provide or enable certain functionalities. For example, the system 1000 can be configured to operate only for certain authorized individuals, whereby certain features or functionalities are disabled if an unidentified or unauthorized individual attempts to use the system 1000. In an embodiment, the system 1000 is configured to identify the individual subject on which the system 1000 is positioned, whereby the system 1000 permits operation of certain system components upon a positive identification of an individual authorized to use the particular system 1000. For example, the sensor assembly 1004 can detect physical characteristics of the individual subject on which the system 1000 is positioned to generate one or more identity sense signals associated with the physical characteristic. The physical characteristics can include, but are not limited to, skin topography features (e.g., pattern of skin surface, follicle pattern, pore pattern, pigmentation, etc.), vascular properties or layouts (e.g., arterial patterns, properties, or layouts; vein patterns, properties, or layouts; etc.), electric current pattern (e.g., photovoltaic current pattern), or skin resistivity measurement. In an embodiment, the processor 1006 or other system component compares the identity sense signals to reference data associated with individual(s) authorized to use the system 1000 (e.g., via comparison module 1300). When the identity sense signals have a positive correspondence to the reference data, the system 1000 can permit operation of certain system functionalities including, but not limited to, permitting operation of the sensor assembly 1004 for motion and physiological parameter monitoring, permitting operation of the effector 1008 (e.g., only upon positive association of an individual, such that the individual becomes authorized to operate the system 1000), selecting a particular motion regimen (e.g., the reference data can include a correspondence between an identity and a particular motion regimen, whereby upon confirmation of an identity, the particular motion regimen is selected for operation of the effector 1008), permitting the transmission of information associated with operation of the system 1000 or the status of the individual subject to a record (e.g., an electronic health record or other health diary), or the like.

Figure 40:
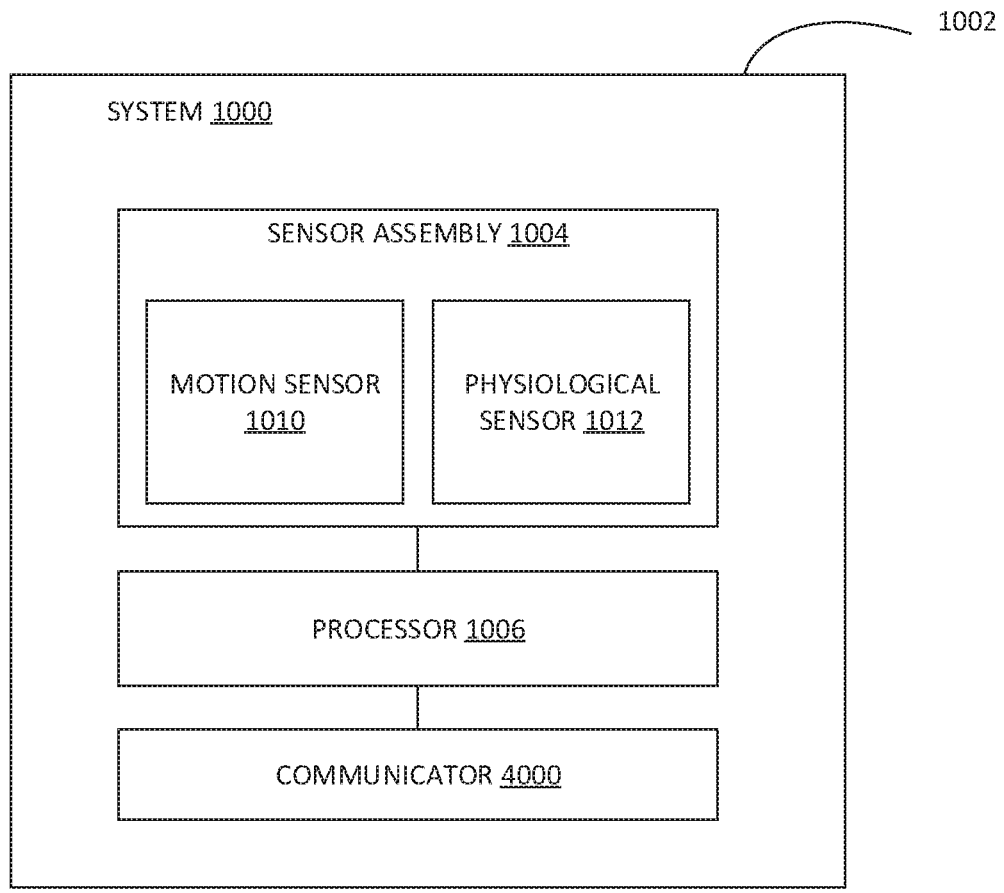
FIG. 40 is a schematic of an embodiment of a system for monitoring an individual subject and facilitating a motion regimen of the individual subject.

In an embodiment, shown in FIG. 40, the system 1000 includes the deformable substrate 1002, the sensor assembly 1004 (including the motion sensor 1010 and the physiological sensor 1012), the processor 1006, and a communicator 4000 for placement on the individual subject to monitor the individual subject for indications of a pain state during a motion regimen executed by the individual subject. The functionalities of the system 1000 can be varied dependent upon the pain state of the individual subject. For example, the system 1000 can provide training messages to the individual subject dependent on the pain state, the system 1000 can provide information to or receive information from an external device dependent on the pain state, the system 1000 can activate or deactivate an effector dependent on the pain state, and the like. The sensor assembly 1004 is coupled to the deformable substrate and generates one or more sense signals based on detection of a movement of the body portion by the motion sensor 1010 and at least one physiological parameter of the body portion by the physiological sensor 1012 during the motion regimen executed by the individual subject. The processor 1006 is coupled to the sensor assembly 1004 to receive the one or more sense signals. The processor 1006 includes circuitry configured to identify a pain state of the individual subject based on at least one of the movement of the body portion or the at least one physiological parameter. For example, the processor 1006 includes circuitry that includes or accesses the comparison module to compare the one or more sense signals to reference data indicative of a pain state, where such reference data can include, for example, one or more of motion reference data indicative of short-term or long-term changes in motor function of a body portion (e.g., increased or inhibited muscle activation as a result of physiological adaptation to acute pain or chronic pain), a guarding motion, a grimace, an awkward gait, a limp, redistribution of activity or stress, modifications in loading, pronounced use of non-dominant limb, pronounced minimalization of motion or agitation of affecting a body site (e.g., a muscle), pronounced rubbing or massage of a body portion (e.g., repeated or deep massage), reduced force output, lack of use of a body portion, respiratory dysfunction, splinting, involuntary responses (e.g., reflex, spasm, etc.), or the like, or combinations thereof, or physiological reference data including, but not limited to, heart rate (including changes in heart rate or heart rate variation indicative of pain), blood pressure (including changes in blood pressure indicative of pain), electrophysiological data (including, but not limited to, electrical activity of the heart, electrical activity of the eye (e.g., corneo-retinal standing potential, pupil diameter, etc.)), nerve impulses, muscular-skeletal pressure forces or electrical activity (including, but not limited to, electric potential generated by muscle cells, muscular-skeletal acoustic or mechanical properties (e.g., vibrations), etc.), strain data (e.g., associated with muscle), temperature (including changes in temperature indicative of pain), blood oxygenation data (including changes in blood oxygenation indicative of pain), skin conductance data (including changes in skin conductance indicative of pain), bioimpedance data (including changes in bioimpedance indicative of pain), pH data (including changes in pH indicative of pain), or chemical data (including changes in concentrations of chemical analytes indicative of pain) including but not limited to, analytes of sweat, analytes of tissue, a saccharide (e.g., glucose), a salt (e.g., sodium chloride), lactate, an electrolyte (e.g., sodium, chloride, potassium, etc.), a hormone (e.g., cortisol, adrenaline, pregnenolone, DHEA, testosterone, progesterone, estrogen, triiodothyronine (T3), and thyroxine (T4)), a neuropeptide (e.g., neuropeptide Y, substance P and calcitonin-gene-related peptide (CGRP)), a peptide, a protein, or a nucleotide or modified nucleotide (e.g., adenosine triphosphate), an inflammatory mediator (e.g., a prostaglandin (e.g., PGE2), bradykinin, serotonin, adenosine triphosphate, pyruvate, etc.), a pro-inflammatory cytokine (IL-1$\alpha$, IL-$\beta$, IL-6, TNF$\alpha$, IL-8), or other motion or physiological factor provided herein. In an embodiment, the reference data can include one or more of motion data or physiological parameter data associated with pain types, where such data can be associated with, but not limited to, nociceptive pain (e.g., due to mechanical, thermal, and/or chemical interactions), somatic pain, neuropathic pain, visceral pain, superficial pain, and psychogenic pain. In an embodiment, the reference data can include one or more of motion data or physiological parameter data associated with pain levels, where such data can be associated with, but not limited to, pain intensity, pain severity, or magnitude of pain. In an embodiment, the reference data can include one or more of motion data or physiological parameter data associated with pain quality or pain quantity, where such data can be associated with, but not limited to, a subjective characteristic of the pain (e.g., a subjective pain threshold or tolerance threshold), such as those identified by the individual subject. Pain types can also include spontaneous pain (e.g., occurring in the absence of stimuli), evoked pain (e.g., occurring in response to stimuli), continuous pain, or intermittent pain. In an embodiment, the motion sensor 1010, the physiological sensor 1012, or combinations thereof, can include a stimulator for evaluating evoked responses from the individual subject. For example, the stimulator can include an electrical stimulator, a thermal stimulator, an optical stimulator, or the like. Pain types can also include cephalalgia or headache, which can include, but are not limited to, tension headaches, cervicogenic headaches, migraines, or combinations thereof. In an embodiment, the reference data can include user-specific threshold or tolerance information. For example, the individual can indicate to the system 1000 (e.g., via user interface 3600 described herein) when the individual feels pain. The system 1000 can then take a snapshot of one or more of the individual's physiological state, motion state, positional state, etc. to set a threshold pain level, to link a physiological or motion parameter to pain experienced by the individual, or the like, which can serve as a comparator to autonomic parameters experienced by the individual. The system 1000 can monitor the individual and receive additional individual input regarding whether the pain intensifies, dissipates, differs in type, location, chronology, etc.

When the processor 1006 identifies a pain state, the processor 1006 compares at least one of the pain state of the individual subject, the movement of the body portion, or the at least one physiological parameter to one or more threshold target values. The threshold target values can be stored in a computer memory device (e.g., computer memory 1302) accessible by the processor 1006 for comparison to at least one of the pain state of the individual subject, the movement of the body portion, or the at least one physiological parameter to one or more threshold target values. For example, the threshold target values can provide a guideline for the individual subject to achieve during execution of the motion regimen, such as by providing a pain state threshold to reach during an exercise training regimen to provide a fitness goal while avoiding undue pain or risk for injury. In an embodiment, the one or more threshold target values are associated with a personal history of the individual subject. For example, the one or more threshold target values can be associated with a prior execution of the motion regimen by the individual subject, such as to provide a baseline or comparative performance guideline. In an embodiment, the one or more threshold target values correspond to a minimum activity level during execution of the motion regimen. For example, the one or more target values can provide a guideline for an expected level of effort to be output by the individual subject during execution of the motion regimen, such as a minimum expected effort (e.g., to meet a particular fitness goal, etc.). In an embodiment, the minimum activity level includes at least one of a minimum pain level, a minimum anatomical parameter, a minimum movement (e.g., detected by the motion sensor 1010), a minimum physiological parameter (e.g., detected by the physiological sensor 1012), or a minimum historical activity level of the individual subject. For example, the minimum activity level can correspond to a minimum muscle activity, a minimum tendon activity, a minimum ligament activity, a minimum cardiovascular activity, a minimum caloric reduction, and the like. In an embodiment, the one or more threshold target values correspond to a maximum activity level during execution of the motion regimen. For example, the one or more target values can provide a guideline for an expected level of effort to be output by the individual subject during execution of the motion regimen, such as a maximum expected effort (e.g., prior to being at risk for injury, etc.). In an embodiment, the maximum activity level includes at least one of a maximum pain level, a maximum anatomical parameter, a maximum movement (e.g., detected by the motion sensor 1010), a maximum physiological parameter (e.g., detected by the physiological sensor 1012), or a maximum historical activity level of the individual subject. For example, the maximum activity level can correspond to a maximum muscle activity, a maximum tendon activity (e.g., without risking strain), a minimum ligament activity (e.g., without risking sprain), a maximum cardiovascular activity, a maximum caloric reduction, and the like.

In an embodiment, the one or more threshold target values correspond to a maximum activity level during execution of the motion regimen and a minimum activity level during execution of the motion regimen. For example, the system 1000 can operate to determine whether the individual subject should expend more or less effort, such as by comparing at least one of the pain state of the individual subject, the movement of the body portion, or the at least one physiological parameter to the maximum activity level and the minimum activity level. The processor 1006 then provides control signals to the communicator 4000 to generate one or more communication signals to direct the at least one of the pain state of the individual subject, the movement of the body portion, or the at least one physiological parameter between the maximum activity level and the minimum activity level, according to one or more of displaying information about the activity level, transmitting information about the activity level, or controlling activation of an effector (e.g., effector 1008). For example, the communicator 4000 can include circuitry configured to generate the one or more communication signals to provide control instructions to one or more components of the system 1000 or external device (e.g., external device 3406, external object 3800, etc.), to provide information (e.g., via reporting) to one or more components of the system 1000 or external device (e.g., external device 3406, external object 3800, etc.), to provide other functionalities, or combinations thereof.

Figure 41A:
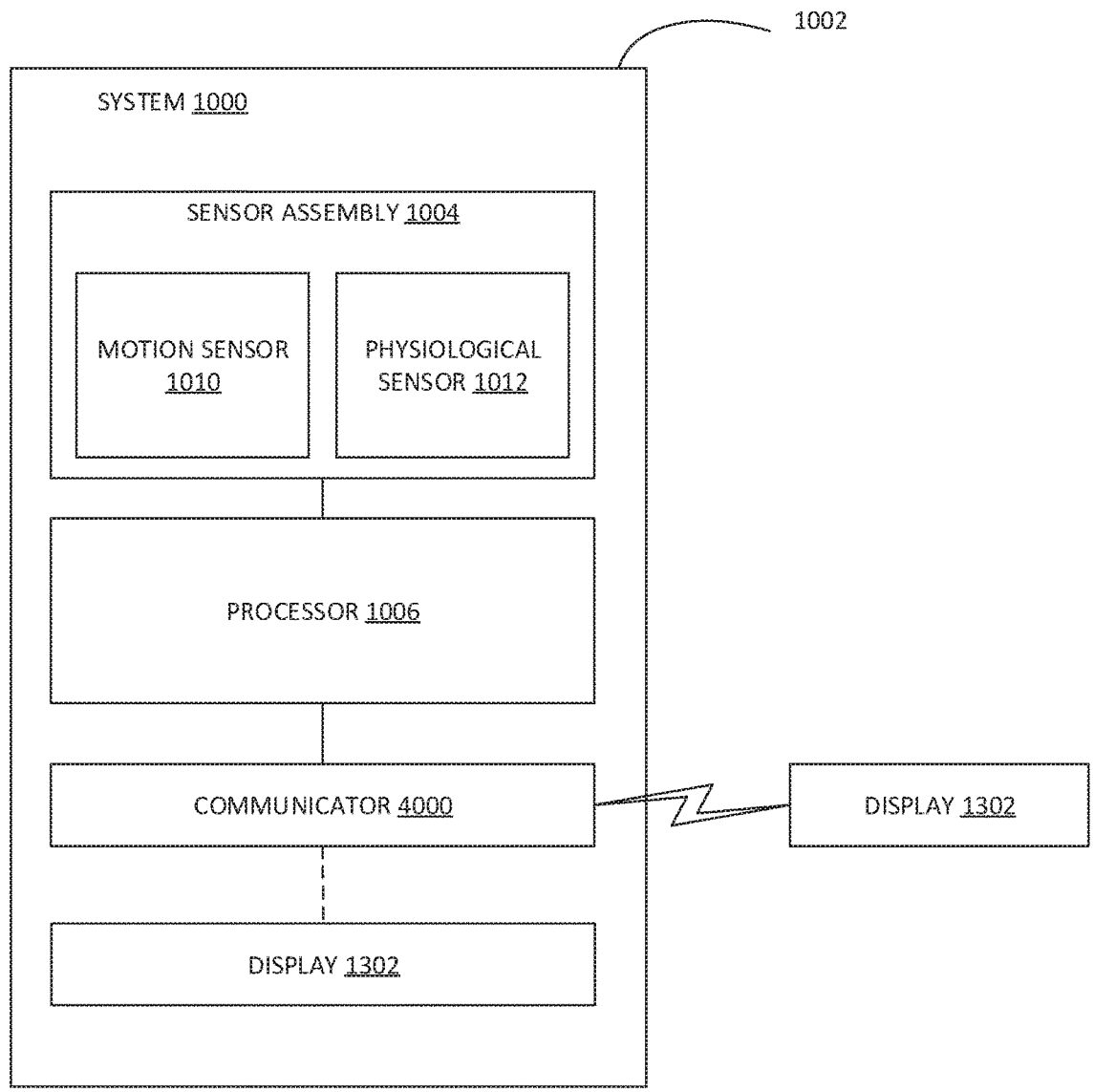
FIG. 41A is a schematic of an embodiment of a system such as shown in FIG. 40.
Figure 41B:
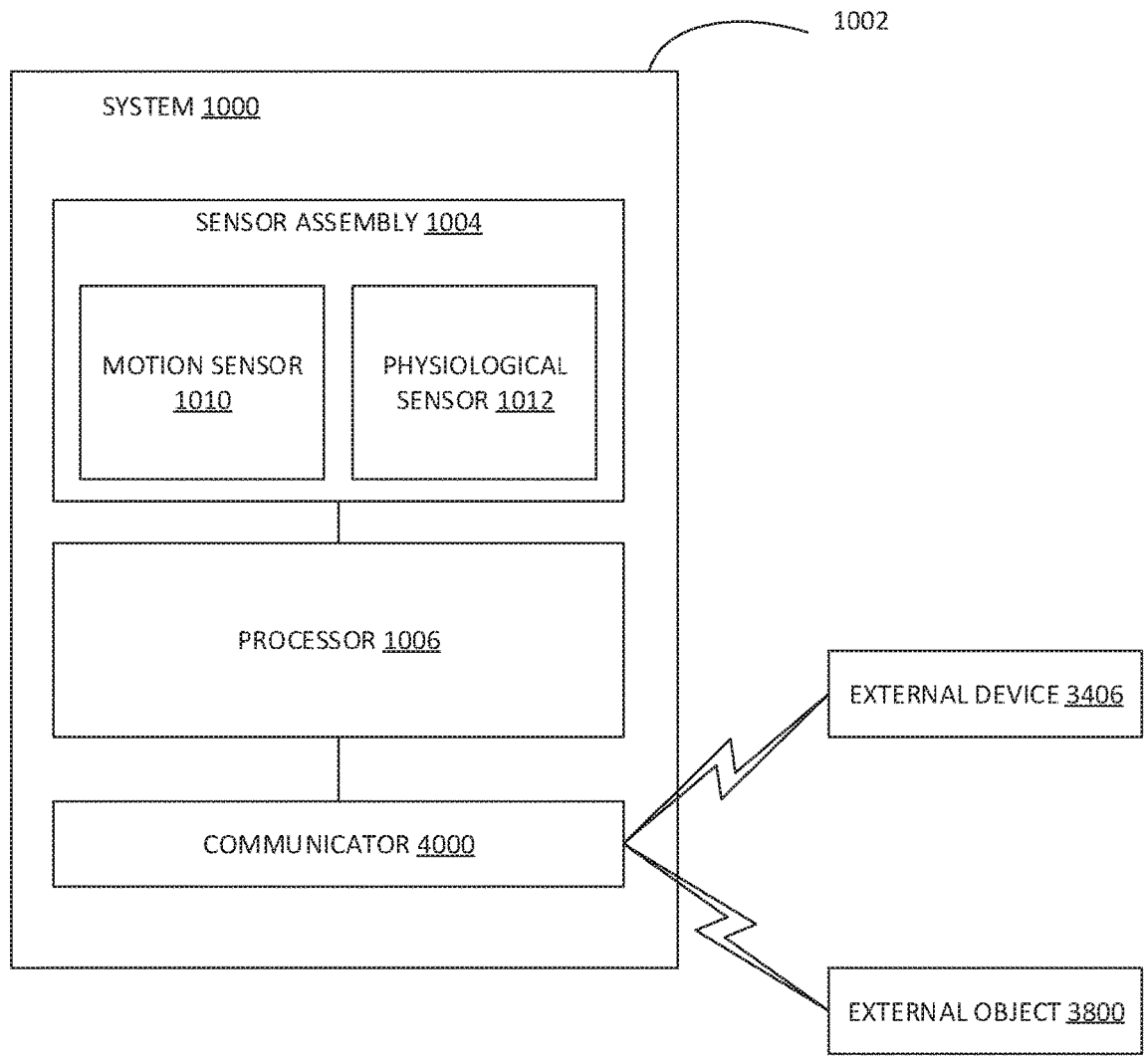
FIG. 41B is a schematic of an embodiment of a system such as shown in FIG. 40.
Figure 41C:
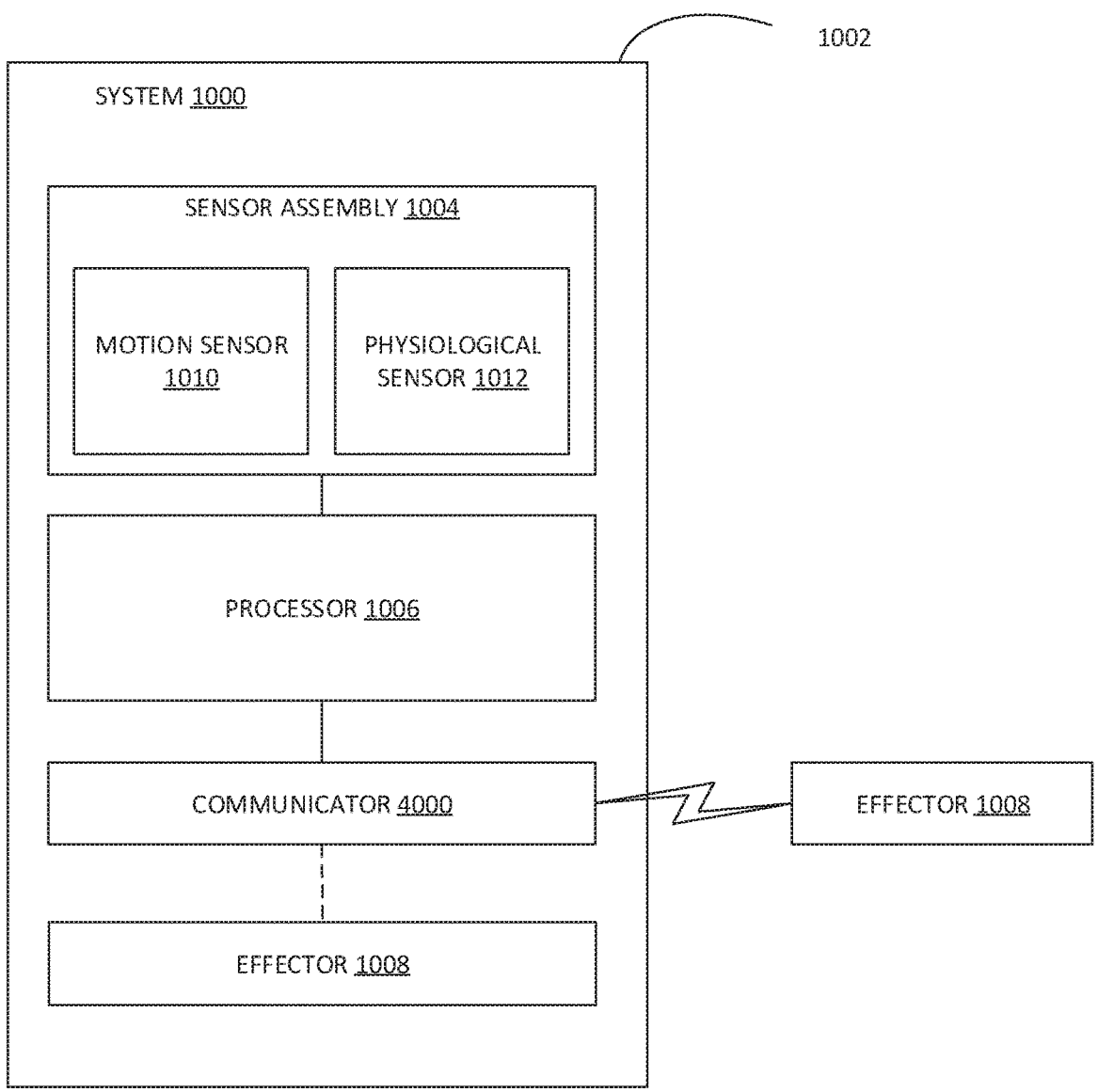
FIG. 41C is a schematic of an embodiment of a system such as shown in FIG. 40.

For example, referring to the embodiments shown in FIGS. 41A-41C, the communicator 4000 is configured to direct the one or more communication signals to one or more of a display device (e.g., display 1502), shown in FIG. 41A, an external device (e.g., external device 3406, external object 3800, etc.), shown in FIG. 41B, or an effector (e.g., effector 1008), shown in FIG. 41C, to manage a pain state of the individual subject, such as to bring the activity level of the individual subject during execution of the motion regimen to between the maximum activity level and the minimum activity level.

In an embodiment, shown in FIG. 41A, the communicator 4000 is configured to direct the one or more communication signals to the display 1502, such as to provide visual, audio, or haptic instructions to the individual subject to manage a pain state of the individual subject, such as to bring the activity level of the individual subject during execution of the motion regimen to between the maximum activity level and the minimum activity level. The display 1502 can be coupled to the deformable substrate 1002, or provided as an external display. For example, the one or more communication signals can include instructions to the individual subject to increase activity until the pain state attains the maximum activity level. For example, the one or more communication signals include instructions to the individual subject to decrease activity until the pain state is less than the maximum activity level. For example, the one or more communication signals are associated with instructions to the individual subject to increase activity until the pain state exceeds the minimum activity level. In an embodiment, the one or more communication signals are associated with instructions for the individual subject to cease activity responsive to comparison by the processor 1006 between the at least one physiological parameter (e.g., detected by the physiological sensor 1012) with reference data associated with injury to the body portion. For example, the reference data associated with injury to the body portion can include physiological inflammation data.

In an embodiment, shown in FIG. 41B, the communicator 4000 is configured to direct the one or more communication signals to one or more external devices, such as external device 3406 or external object 3800 to manage a pain state of the individual subject, such as to bring the activity level of the individual subject during execution of the motion regimen to between the maximum activity level and the minimum activity level. For example, the one or more communication signals can indicate (e.g., to a third party, such as a trainer, a coach, a healthcare professional, etc.) that the individual subject should increase activity until the pain state attains the maximum activity level. For example, the one or more communication signals can indicate (e.g., to a third party, such as a trainer, a coach, a healthcare professional, etc.) that the individual subject should decrease activity until the pain state is less than the maximum activity level. For example, the one or more communication signals can indicate (e.g., to a third party, such as a trainer, a coach, a healthcare professional, etc.) that the individual subject should increase activity until the pain state exceeds the minimum activity level. In an embodiment, the one or more communication signals are can indicate (e.g., to a third party, such as a trainer, a coach, a healthcare professional, etc.) that the individual subject should cease activity responsive to comparison by the processor 1006 between the at least one physiological parameter (e.g., detected by the physiological sensor 1012) with reference data associated with injury to the body portion. For example, the reference data associated with injury to the body portion can include physiological inflammation data. In an embodiment, the processor 1006 is configured to activate the communicator 4000 responsive to one or more communication signals from the external device (e.g., external device 3406, external object 3800, etc.). In an embodiment, the processor 1006 is configured to prevent activation of the communicator 4000 responsive to one or more communication signals from the external device (e.g., external device 3406, external object 3800, etc.). In an embodiment, the external device (e.g., external device 3406, external object 3800, etc.) includes at least one of a virtual reality display device or an augmented reality display device. For example, the virtual reality display device or the augmented reality display device can display an image responsive to receiving one or more communication signals from the communicator 4000. In an embodiment, the external device (e.g., external device 3406, external object 3800, etc.) includes at least one of a haptic feedback device, an audio feedback device, or a visual feedback device. For example, the external device 3406 or external object 3800 can provide feedback to the individual subject as one or more of haptic feedback (e.g., via a haptic feedback device), audio feedback (e.g., via an audio feedback device), or visual feedback (e.g., via a visual feedback device) responsive to one or more communication signals from the communicator 4000. For example, the communicator 4000 can send one or more communication signals to the external device 3406 or external object 3800 indicating that the individual subject is in compliance with the motion regimen (e.g., performing the choreographed motions within the motion thresholds or target values, performing the choreographed motions according to a predetermined schedule of performance dates or frequencies, etc.), whereby the external device 3406 or external object 3800 can provide at least one of haptic feedback (e.g., a vibration-based message), audio feedback (e.g., an audio message or signal), or visual feedback (e.g., a visually-displayed message, an image of a virtual reality or augmented reality display device, etc.) to the individual subject or other user of the system 1000 (e.g., a trainer, a coach, a healthcare professional, etc.).

In an embodiment, shown in FIG. 41C, the communicator 4000 is configured to direct the one or more communication signals to at least one effector (e.g., effector 1008, an effector remote from the deformable substrate 1002, etc.) to effect at least one predetermined motion of the motion regimen responsive to the one or more communication signals to manage a pain state of the individual subject, such as to bring the activity level of the individual subject during execution of the motion regimen to between the maximum activity level and the minimum activity level. For example, the one or more communication signals can include instructions to the effector 1008 to induce activity of the individual subject until the pain state attains the maximum activity level. For example, the one or more communication signals can include instructions to the effector 1008 to decrease activity of the individual subject until the pain state is less than the maximum activity level. For example, the one or more communication signals can include instructions to the effector 1008 to increase activity of the individual subject until the pain state exceeds the minimum activity level. In an embodiment, the one or more communication signals are associated with instructions for the effector 1008 to cease activity responsive to comparison by the processor 1006 between the at least one physiological parameter (e.g., detected by the physiological sensor 1012) with reference data associated with injury to the body portion. For example, the reference data associated with injury to the body portion can include physiological inflammation data.

In an embodiment, the motion sensor 1010 includes one or more of the accelerometer 1400, the proximity sensor 1402 (e.g., infrared sensor 1404, optical sensor 1406), the orientation sensor 3200, the force sensor 3702, the pressure sensor 3342, the strain sensor 3320, or another sensor (e.g., a sensor described with reference to FIG. 37) or combinations thereof, the functionalities and associated movement detection of the body portion are provided herein. In an embodiment, physiological sensor 1012 can include one or more of the electrophysiological sensor 3300, the electrocardiograph 3302, the electrooculograph 3304, the microneurograph 3306, an electroneurograph, the myograph 3308, the electromyograph (EMG) 3310, the surface electromyograph 3312, the acoustic myography sensor 3314, the mechanomyography sensor 3316, the accelerometer myography sensor 3318, the strain sensor 3320, the temperature sensor 3322, the optical sensor 3324, the light emitting diode (LED) 3326, the oximeter 3328, the near infrared sensor 3330, the skin conductance sensor 3332, the bioimpedance sensor 3334, the pH sensor 3336, the acoustic sensor 3338, the chemical sensor 3340, the pressure sensor 3342, or combinations thereof, the functionalities and associated pain state, pain type, and pain level determinations thereof are provided herein. In an embodiment, the sensor assembly 1004 can include a plurality of sensors (e.g., of those shown in FIG. 37 or in addition to those shown in FIG. 37), such as a plurality of a single sensor type or a combination of different sensor types, arranged in an array or otherwise communicatively coupled (e.g., via one or more leads and/or wireless coupling, such as between sensor locations). Further, one or more components of the sensor assembly 1004 can provide sense signals directed to a plurality of detection schemes. For example, the acoustic sensor 3338 can operate as proximity sensor to sense a proximity between the body portion and another body portion, between the body portion and an external device or external object, or the like, such as through echolocation; the acoustic sensor can operate as one or more of a motion sensor or a physiological sensor by measuring one or more acoustical signatures of a motion event or physiological event. For example, the acoustic sensor 3338 can include at least one microphone or acoustic transducer. For example, the acoustic sensor 3338 can be configured to detect an articular noise, such as an articular noise associated with movement or an articular noise (e.g., creaking or popping) in an arthritic joint experiencing pain associated with movement. For example, the acoustic sensor 3338 can include an acoustic sensor (e.g., acoustic myographic sensor 3314) configured to detect a musculoskeletal acoustic signature. For example, the acoustic sensor 3338 can be configured to detect a vocal event (e.g., a groan, vocalization, or speech), such as a vocal event indicative of movement or pain. For example, the acoustic sensor 3338 can be configured to detect an acoustic signature of a physiological event indicative of an autonomic response, e.g., a heartbeat, valve closure, blood flow, respiration, etc.

In an embodiment, the processor 1006 (e.g., via circuitry thereof) is configured to identify the pain state of the individual subject responsive to a determination that the movement of the body portion exceeds the one or more threshold target values. For example, the processor can compare (e.g., via the comparison module 1300) the one or more sense signals from the motion sensor 1010 to the one or more threshold target values for movement to determine that the individual subject is experiencing a particular pain level, pain state, or pain type. For example, the one or more sense signals can correspond to a movement of the body portion of the individual subject where the movement corresponds to at least one of a reduction in velocity of the body portion (e.g., the individual subject is beginning to slow down during the motion regimen), a reduction in muscle activity of a muscle of the body portion (e.g., the individual subject is beginning to favor a muscle or muscle group due to pain, thereby activating the muscle less), or an erratic motion of the body portion (e.g., the individual subject is limping, having a guarding motion, etc.).

In an embodiment, the system 1000 is configured to determine or receive an identification of the individual subject on which the system 1000 is positioned to determine whether to provide or enable certain functionalities. For example, the system 1000 can be configured to operate only for certain authorized individuals, whereby certain features or functionalities are disabled if an unidentified or unauthorized individual attempts to use the system 1000. In an embodiment, the system 1000 is configured to identify the individual subject on which the system 1000 is positioned, whereby the system 1000 permits operation of certain system components upon a positive identification of an individual authorized to use the particular system 1000. For example, the sensor assembly 1004 can detect physical characteristics of the individual subject on which the system 1000 is positioned to generate one or more identity sense signals (e.g., via the physiological sensor 1012) associated with the physical characteristic. The physical characteristics can include, but are not limited to, skin topography features (e.g., pattern of skin surface, follicle pattern, pore pattern, pigmentation, etc.), vascular properties or layouts (e.g., arterial patterns, properties, or layouts; vein patterns, properties, or layouts; etc.), electric current pattern (e.g., photovoltaic current pattern), or skin resistivity measurement. In an embodiment, the processor 1006 or other system component compares the identity sense signals to reference data associated with individual(s) authorized to use the system 1000 (e.g., via comparison module 1300). When the identity sense signals have a positive correspondence to the reference data, the system 1000 can permit operation of certain system functionalities including, but not limited to, permitting operation of the sensor assembly 1004 for motion and physiological parameter monitoring, permitting operation of the effector 1008 (e.g., only upon positive association of an individual, such that the individual becomes authorized to operate the system 1000), permitting operation of the communicator 4000 to generate and/or transmit one or more communication signals, selecting a particular motion regimen (e.g., the reference data can include a correspondence between an identity and a particular motion regimen, whereby upon confirmation of an identity, the particular motion regimen is selected for operation of the effector 1008), permitting the transmission of information associated with operation of the system 1000 or the status of the individual subject to a record (e.g., an electronic health record or other health diary), or the like.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the systems and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

Those skilled in the art will recognize that at least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

Those skilled in the art will recognize that at least a portion of the systems and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

This disclosure has been made with reference to various example embodiments. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system; e.g., one or more of the steps may be deleted, modified, or combined with other steps.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, an article, or an apparatus that comprises a list of elements does not include only those elements but may include other elements not expressly listed or inherent to such process, method, system, article, or apparatus.

In an embodiment, the system is integrated in such a manner that the system operates as a unique system configured specifically for function of the system for monitoring an individual subject and facilitating a motion regimen of the individual subject (e.g., system 1000), and any associated computing devices of the system operate as specific use computers for purposes of the claimed system, and not general use computers. In an embodiment, at least one associated computing device of the system operates as a specific use computer for purposes of the claimed system, and not a general use computer. In an embodiment, at least one of the associated computing devices of the system is hardwired with a specific ROM to instruct the at least one computing device. In an embodiment, one of skill in the art recognizes that the system for monitoring an individual subject and facilitating a motion regimen of the individual subject (e.g., system 1000) effects an improvement at least in the technological field of monitoring and effecting body movements.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
   a deformable substrate configured to conform to a body portion of an individual subject;
   a sensor assembly coupled to the deformable substrate, the sensor assembly configured to generate one or more sense signals based on detection of at least one of a movement of the body portion or at least one physiological parameter of the body portion;
   a processor operably coupled to the sensor assembly and configured to receive the one or more sense signals, the processor including circuitry configured to identify a physiological state of the individual subject based on at least one of the movement of the body portion or the at least one physiological parameter of the body portion;
   a memory device accessible by the processor and storing a motion regimen having a plurality of choreographed movements of at least the body portion; and
   an effector configured to conform to the body portion and operably coupled to the processor and configured to effect at least one predetermined motion of the body portion corresponding to the motion regimen responsive to control by the processor, wherein the processor is configured to control the effector to effect a second choreographed movement of the body portion of the motion regimen upon determination that the body portion executed a first choreographed movement of the motion regimen based at least on the one or more sense signals from the sensor assembly.

2. The system of claim 1, wherein the effector is configured to deliver a stimulus providing stochastic resonance to a tissue of the body portion of the individual subject.

3. The system of claim 1, wherein the sensor assembly is configured to generate one or more sense signals based on detection of at least one of a movement of a second body portion distal to the body portion or at least one physiological parameter of the second body portion.

4. The system of claim 1, wherein the sensor assembly includes at least one orientation sensor configured to detect the movement of the body portion.

5. The system of claim 1, further including a reporter coupled to the deformable substrate, the reporter configured to generate one or more communication signals responsive to instruction by the processor.

6. The system of claim 5, wherein the one or more communication signals are associated with at least one of a summary of data processed by the processor, compliance or non-compliance of the individual subject with the motion regimen, or historical progress of the individual subject.

7. The system of claim 1, wherein the one or more sense signals include one or more sense signals associated with pain responsive to muscle activity.

8. The system of claim 1, wherein the processor is configured to activate the effector to reduce a pain state of the individual subject.

9. The system of claim 1, including at least one of a receiver, a transceiver, or a transmitter configured to at least one of receive one or more communication signals from an external device or transmit one or more communication signals to the external device.

10. The system of claim 9, wherein the external device includes at least one of a virtual reality display device or an augmented reality display device, wherein the at least one of a virtual reality display device or an augmented reality display device is configured to display an image responsive to receiving the one or more communication signals.

11. The system of claim 9, wherein the one or more communication signals from the external device are feedback signals responsive to one or more communication signals associated with the at least one of a movement of the body portion or at least one physiological parameter of the body portion transmitted to the external device.

12. The system of claim 1, wherein the effector includes at least one of an electric stimulator including at least one electrode, an ultrasonic stimulator including at least one ultrasound transducer, a magnetic stimulator, or an optical stimulator.

13. The system of claim 1, including a user interface coupled to the deformable substrate, wherein the processor is configured to at least one of modify the motion regimen responsive to a user input via the user interface or select the motion regimen for execution responsive to a user input via the user interface.

14. The system of claim 9, wherein the processor is configured to at least one of activate the effector to affect the body portion responsive to the one or more communication signals from the external device or prevent activation of the effector responsive to the one or more communication signals from the external device.

15. The system of claim 1, wherein the sensor assembly is configured to generate one or more identity sense signals associated with at least one physical characteristic of the individual subject, and wherein the processor is configured to at least one of transmit information to a record when the one or more identity sense signals correspond to an authorized individual or permit operation of one or more of the sensor assembly or the effector only when the one or more identity sense signals correspond to an authorized individual.

16. The system of claim 1, further including a second effector configured to conform to a second body portion of the individual subject and operably coupled to the processor, wherein the processor is configured to cease activation of the first effector upon determination that the body portion executed the second choreographed movement of the motion regimen.

17. The system of claim 16, wherein the processor is configured to control the second effector to effect a third choreographed movement of the motion regimen to move the second body portion upon determination that the body portion executed the second choreographed movement of the motion regimen based at least on the one or more sense signals from the sensor assembly.

* * * * *